US009624499B2

(12) United States Patent
Kuhn et al.

(10) Patent No.: US 9,624,499 B2
(45) Date of Patent: Apr. 18, 2017

(54) PROMOTERS FOR REGULATING EXPRESSION IN PLANTS

(75) Inventors: Josef Martin Kuhn, Ludwigshafen (DE); Holger Schultheiss, Boehl-Iggelheim (DE); Julia Verena Hartig, Neustadt (DE); Linda Patricia Loyall, Limburgerhof (DE); Elke Duwenig, Limburgerhof (DE); Marc Saric, Malsch (DE); Maarten Hendrik Stuiver, Neustadt (DE); Oliver Oswald, Lautertal (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 574 days.

(21) Appl. No.: 14/005,402

(22) PCT Filed: Mar. 15, 2012

(86) PCT No.: PCT/IB2012/051239
§ 371 (c)(1),
(2), (4) Date: Sep. 16, 2013

(87) PCT Pub. No.: WO2012/127373
PCT Pub. Date: Sep. 27, 2012

(65) Prior Publication Data
US 2014/0007289 A1    Jan. 2, 2014

Related U.S. Application Data

(60) Provisional application No. 61/453,970, filed on Mar. 18, 2011.

(51) Int. Cl.
C12N 15/82    (2006.01)
(52) U.S. Cl.
CPC ..... *C12N 15/8216* (2013.01); *C12N 15/8222* (2013.01); *C12N 15/8223* (2013.01); *C12N 15/8225* (2013.01); *C12N 15/8239* (2013.01)
(58) Field of Classification Search
None
See application file for complete search history.

(56) References Cited

FOREIGN PATENT DOCUMENTS

| CN | 101914534 | | 12/2010 |
|---|---|---|---|
| EP | 1666599 | | 6/2006 |
| WO | WO 2009/099580 | * | 8/2009 |
| WO | WO 2011023537 | | 3/2011 |
| WO | WO 2011023539 | | 3/2011 |
| WO | WO 2012/077020 A1 | * | 6/2012 |
| WO | WO 2012077020 | | 6/2012 |

OTHER PUBLICATIONS

Fourgoux-Nicol et al., Plant Mol Biol 40:857-72 (1999).*
Potenza et al., In Vitro Cell Dev Biol Plant 40:1-22 (2004).*
Saha et al., In Silico Biol 7:(1)7-19 (2007).*
Donald & Cashmore, EMBO J 9:1717-26 (1990).*
Kim et al., Plant Mol Biol 24:105-17 (1994).*
Dolferus et al., Plant Physiol 105:1075-87 (1994).*
Rodriquez-Trelles et al., Int J Dev Biol $7:665-73 (2003).*
Cooper & Brown, Genome Res 18:201-05 (2008).*
Schmutz et al., Nature 463:178-83 (2010).*
Office action for U.S. Appl. No. 10/925,392, mailed Feb. 22, 2006.*
European Search Report, issued in EP 12761445.1, dated Aug. 20, 2014.
Database EMBL [on-line], "GM_WBb0014N09.f GM_WbB Glycine Max Genomic Clone GM_WBb0014N09 5', Genomic Survey Sequence," (Nov. 1, 2006), XP002728279.
Database EMBL [on-line], "454GmaGlobSeed521407 Soybean Seeds Containing Globular-Stage Embryos Glycine max cDNA, mRNA Sequence," (Oct. 2, 2008), XP002728280.
Li et al., "Cloning and Preliminary Analysis of Promoter of Soybean Receptor-Like Protein Kinase," Journal of Plant Physiology and Molecular Biology, vol. 32, No. 3, (2006), pp. 387-394.
International Search Report, issued in PCT/IB2012/051239, dated Jul. 26, 2012.
GenBank [online], "Soybean Clone JCVI-FLGm-15M12 Unknown mRNA," (Aug. 6, 2009), Database Accession No. BT096166.1.
GenBank [online], "Predicted Protein [Populus Trichocarpa]," Database Accession No. XP_002321177.1.

* cited by examiner

*Primary Examiner* — Amjad Abraham
*Assistant Examiner* — Russell Boggs
(74) *Attorney, Agent, or Firm* — Marshall, Gerstein & Borun LLP

(57) ABSTRACT

Isolated nucleic acid molecules capable of regulating expression in plants, as well as expression [cassettes, vectors and transgenic plants comprising the same are provided.

10 Claims, No Drawings

PROMOTERS FOR REGULATING EXPRESSION IN PLANTS

This application is a National Stage application of International Application No. PCT/IB2012/051239, filed Mar. 15, 2012, which claims the benefit of U.S. Provisional Application No. 61/453,970, filed Mar. 18, 2011.

FIELD OF THE INVENTION

The present invention relates to isolated nucleic acid molecules capable of regulating expression in plants as well as expression cassettes, vectors and transgenic plants comprising the same.

BACKGROUND OF THE INVENTION

Manipulation of plants to alter and/or improve phenotypic characteristics (such as productivity, quality or pest resistance) requires the expression of heterologous genes in plant tissues. Such genetic manipulation relies on the availability of a means to drive and to control gene expression as required. For example, genetic manipulation relies on the availability and use of suitable promoters which are effective in plants and which regulate gene expression so as to give the desired effect(s) in the transgenic plant. For numerous applications in plant biotechnology a tissue-specific expression profile is advantageous, since beneficial effects of expression in one tissue may have disadvantages in others. For example, promoters driving expression in the plant epidermis, such as epidermis-preferential or epidermis-specific promoters are useful for expressing genes that prevent pathogens such as fungi or bacteria from infecting a plant through the epidermis. It is advantageous to have the choice of a variety of different promoters so that the most suitable promoter may be selected for a particular gene, construct, cell, tissue, plant or environment. Moreover, the increasing interest in transforming plants with multiple plant transcription units (PTU) and the potential problems associated with using common regulatory molecules for these purposes merit having a variety of promoter molecules available.

There is, therefore, a constant need in the art for the identification of novel molecules that can be used for expression of selected transgenes in economically important plants. It is thus an objective of the present invention to provide new and alternative expression cassettes for expression of transgenes in various tissues of plants, for example in the epidermis. The objective is solved by the present invention.

SUMMARY OF THE INVENTION

A first embodiment of the invention relates to an isolated nucleic acid molecule capable of regulating expression in plants selected from the list comprising i) a molecule described by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89, and ii) a fragment of at least 250 consecutive bases of a molecule described by any of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89 and iii) a nucleotide molecule of at least 250 consecutive bases with a sequence identity of at least 60% to a transcription regulating nucleotide molecule described by any of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89, and iv) a nucleotide molecule with a sequence identity of at least 60% to a transcription regulating nucleotide molecule described by any of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89, and v) a nucleotide molecule of at least 250 bases capable of hybridizing under conditions equivalent to hybridization in 7% sodium dodecyl sulfate (SDS), 0.5 M NaPO$_4$, 1 mM EDTA at 50° C. with washing in 0.1×SSC, 0.1% SDS at 50° C. to a transcription regulating nucleotide molecule described by any of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89, or the complement thereof;

vi) a nucleotide molecule of at least 250 bases capable of hybridizing under conditions equivalent to hybridization in 7% sodium dodecyl sulfate (SDS), 0.5 M NaPO$_4$, 1 mM EDTA at 50° C. with washing in 0.1×SSC, 0.1% SDS at 50° C. to a nucleic acid comprising 250 or more consecutive nucleotides of a transcription regulating nucleotide molecule described by any of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89, or the complement thereof;

vii) a nucleotide molecule which is the complement or reverse complement of any of the previously mentioned nucleotide sequences under i) to vi).

In another embodiment the isolated nucleic acid molecules having a sequence as defined above under i), ii), iii), iv) v), vi) and vii) are capable for driving constitutive expression in plants, or expression in plant epidermis or mesophyll. In another embodiment, the expression derived from the isolated nucleic acid molecules as defined above under i), ii), iii), iv) v), vi) and vii) is inducible in plant epidermis and/or mesophyll by pathogen infection, for example by infection with a fungus.

In a preferred embodiment, the isolated nucleic acid molecules capable of regulating expression in plants having a sequence as defined above under ii) comprise a minimal promoter, preferably the minimal promoter of the respective isolated nucleic acid molecule.

The isolated nucleic acid molecule may be obtained or is obtainable from plant genomic DNA from a gene (e.g., from plant genomic DNA) encoding a polypeptide comprising an amino acid sequence which has at least 80% amino acid sequence homology to a polypeptide selected from the group described by SEQ ID NO: 221, 223, 225, 227, 229, 231, 233, 235, 237, 239, 241, 243, 245, 247, 249, 251, 253 and 255.

The isolated nucleic acid molecule may be obtained or is obtainable from plant genomic DNA from a gene which has at least 80% sequence identity to a nucleic acid molecule selected from the group described by SEQ ID NO: 220, 222, 224, 226, 228, 230, 232, 234, 236, 238, 240, 242, 244, 246, 248, 250, 252 and 254.

In one embodiment the isolated nucleic acid molecules having a sequence as specified above are capable of modifying transcription in a plant, or part thereof, for example in a plant cell. More specifically, the isolated nucleic acid molecules having a sequence as specified above are capable of modifying transcription constitutively, in epidermis and or mesophyll of a plant or a plant cell derived from such tissue.

It is also an embodiment of the invention at hand that the isolated nucleic acid molecules as defined above having the sequences specified under ii), iii), iv) v), vi) and vii) have substantially the same transcription regulating activity as the corresponding transcription regulating nucleotide molecule described by SEQ ID NO: 1, 2, 3, 4, 5, 6, 7, 8, 9, 10, 11, 12, 13, 14, 15, 16, 17 and 18 they are derived from.

Preferably, the isolated nucleic acid molecule is selected from the group of molecules described by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 and 89 or any homolog or fragment thereof. More preferably the transcription regulating nucleotide molecule is selected from the group of molecules consisting of:

i) the molecule described by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 and 89, and ii) a fragment of at least 250 consecutive bases, preferably at least 300 consecutive bases, more preferably at least 400 consecutive bases, even more preferably at least 500 consecutive bases, most preferably at least 750 consecutive bases of a molecule described by any of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 and 89 and iii) a nucleotide molecule of at least 250 consecutive bases, preferably at least 300 consecutive bases, more preferably at least 400 consecutive bases, even more preferably at least 500 consecutive bases, most preferably at least 750 consecutive bases with a sequence identity of at least 60%, 65% or 70%, preferably at least 75%, 80% or 85%, more preferably at least 90% or 95%, even more preferably at least 96% or 97%, most preferably at least 98% or 99% to a transcription regulating nucleotide molecule described by any of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89, and iv) a nucleotide molecule having a sequence identity of at least 60%, 65% or 70%, preferably at least 75%, 80% or 85%, more preferably at least 90% or 95%, even more preferably at least 96% or 97%, most preferably at least 98% or 99% to an isolated nucleic acid molecule capable of regulating expression in plants described by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89, and v) a nucleotide molecule of at least 250 bases, preferably at least 300 bases, more preferably at least 400 bases, even more preferably at least 500 bases, most preferably at least 750 bases capable of hybridizing preferably under conditions equivalent to hybridization in 7% sodium dodecyl sulfate (SDS), 0.5 M NaPO$_4$, 1 mM EDTA at 50° C. with washing in 0.1×SSC, 0.1% SDS at 50° C., more desirably in 7% SDS, 0.5 M NaPO$_4$, 1 mM EDTA at 50° C. with washing in 0.1×SSC, 0.1% SDS at 65° C. to an isolated nucleic acid molecule capable of regulating expression in plants described by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89, or the complement thereof;

vi) a nucleotide molecule of at least 250 bases, preferably at least 300 bases, more preferably at least 400 bases, even more preferably at least 500 bases, most preferably at least 750 bases capable of hybridizing preferably under conditions equivalent to hybridization in 7% sodium dodecyl sulfate (SDS), 0.5 M NaPO$_4$, 1 mM EDTA at 50° C. with washing in 0.1×SSC, 0.1% SDS at 50° C., more desirably in 7% SDS, 0.5 M NaPO$_4$, 1 mM EDTA at 50° C. with washing in 0.1×SSC, 0.1% SDS at 65° C. to a nucleic acid comprising at least 250 preferably at least 300, more preferably at least 400, even more preferably at least 500, most preferably at least 750 consecutive nucleotides of an isolated nucleic acid molecule capable of regulating expression in plants described by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89, or the complement thereof;

vii) an isolated nucleic acid molecule capable of regulating expression in plants which is the complement or reverse complement of any of the previously mentioned nucleic acid molecules under i) to vi).

In a preferred embodiment, the isolated nucleic acid molecules capable of regulating expression in plants having a sequence as defined above under ii) comprise a minimal promoter, preferably the minimal promoter of the respective isolated nucleic acid molecule.

Another embodiment of the invention is an expression cassette for regulating expression in plants comprising a) at least one isolated nucleic acid molecule capable of regulating expression in plants as defined above, and functionally linked thereto b) at least one nucleic acid molecule which is heterologous in relation to said transcription regulating nucleotide molecule which is to be expressed in a plant or part thereof.

The heterologous nucleotide molecule to be expressed in a plant or part thereof is preferably furthermore operably linked to introns, having expression enhancing effects, NEE-NAs (WO2011023537, WO2011023539), 5' and or 3'-untranslated regions, transcription termination and/or polyadenylation signals. 3'-untranslated regions are suitable to stabilize mRNA expression and structure. This can result in prolonged presence of the mRNA and thus enhanced expression levels. Termination and polyadenylation signals are suitable to stabilize mRNA expression (e.g., by stabilization of the RNA transcript and thereby the RNA level) to ensure constant mRNA transcript length and to prevent read-through transcription. Especially in multigene expression constructs this is an important feature. Furthermore correct termination of transcription is linked to re-initiation of transcription from the regulatory 5' nucleotide sequence resulting in enhanced expression levels. The above-mentioned signals can be any signal functional in plants and can for example be isolated from plant genes, plant virus genes or other plant pathogens. However, in a preferred embodiment the 3'-untranslated regions, transcription termination and polyadenylation signals are from the genes employed as the source for the promoters of this invention.

The transcription regulating molecules of the invention can be utilized to express any kind of nucleic acid molecule. For example, expression of the nucleic acid molecule can result in expression of a protein, or expression of an antisense RNA, sense or double-stranded RNA. Preferably, expression of the nucleic acid molecule confers to the plant an agronomically valuable trait.

Another embodiment of the invention relates to a vector comprising an isolated nucleic acid molecule or an expression cassette of the invention. Yet another embodiment of the invention relates to a transgenic host cell or non-human organism comprising an expression cassette or a vector of the invention. Yet another embodiment of the invention relates to a transgenic plant or plant cell comprising an expression cassette or a vector of the invention. Preferably, said plant or plant cell is from a dicotyledonous plant, preferably of the family Fabacea, more preferably of the genus *Glycine*, most preferably the species *Glycine max*.

A further embodiment of the invention is a method for the production of an expression cassette as defined above or a vector as defined above comprising the steps of
a. providing an isolated nucleic acid molecule capable of regulating expression in plants as defined above and
b. functionally linking said isolated nucleic acid molecule to at least one nucleic acid molecule heterologous to said isolated nucleic acid molecule.

An additional embodiment of the invention is a method for the production of a transgenic plant comprising the steps of
a. providing an expression cassette as defined above or a vector as defined above and
b. transforming said expression cassette or vector into a plant part or plant cell and
c. regenerating a plant from said transformed plant part or plant cell.

An additional embodiment of the invention is a method for providing an expression cassette comprising an isolated nucleic acid molecule capable of regulating expression in plants comprising the steps of
a) isolating a first nucleic acid molecule from plant genomic DNA be using at least 15 consecutive bp, preferably at least 20 consecutive by of a sequence described by SEQ ID NO: 1, 2, 3, 4, 5, 6, 7, 8, 9, 10, 11, 12, 13, 14, 15, 16, 17 or 18 or 220, 222, 224, 226, 228, 230, 232, 234, 236, 238, 240, 242, 244, 246, 248, 250, 252 and 254 and
b) functionally linking the first nucleic acid molecule obtained in step a) to at least one additional nucleic acid molecule heterologous to said first nucleic acid molecule.

DEFINITIONS

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention, which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower).

As used herein, the word "or" means any one member of a particular list and also includes any combination of members of that list.

The term "gene" is used broadly to refer to any segment of nucleic acid associated with a biological function. Thus, genes include coding sequences and/or the regulatory molecules required for their expression. For example, gene refers to a nucleic acid fragment that expresses mRNA or functional RNA, or encodes a specific protein, and which includes regulatory molecules. Genes also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

The term "native" or "wild type" gene refers to a gene that is present in the genome of an untransformed cell, i.e., a cell not having a known mutation.

A "marker gene" encodes a selectable or screenable trait.

The term "chimeric gene" refers to any gene that contains
1) DNA sequences, including regulatory and coding sequences, that are not functionally linked together in nature, or
2) sequences encoding parts of proteins not naturally adjoined, or
3) parts of promoters that are not naturally adjoined.

Accordingly, a chimeric gene may comprise regulatory molecules and coding sequences that are derived from different sources, or comprise regulatory molecules, and coding sequences derived from the same source, but arranged in a manner different from that found in nature.

A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

An "oligonucleotide" corresponding to a nucleotide sequence of the invention, e.g., for use in probing or amplification reactions, may be about 30 or fewer nucleotides in length (e.g., 9, 12, 15, 18, 20, 21, 22, 23, or 24, or any number between 9 and 30). Generally specific primers are upwards of 14 nucleotides in length. For optimum specificity and cost effectiveness, primers of 16 to 24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

The terms "polypeptide", "peptide", "oligopeptide", "gene product", "expression product" and "protein" are used interchangeably herein to refer to a polymer or oligomer of consecutive amino acid residues. As used herein, the term "amino acid sequence" or a "polypeptide sequence" refers to a list of abbreviations, letters, characters or words representing amino acid residues. Amino acids may be referred to herein by either their commonly known three letter symbols or by the one-letter symbols recommended by the IUPAC-IUB Biochemical Nomenclature Commission. The abbreviations used herein are conventional one letter codes for the amino acids: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid (see L. Stryer, Biochemistry, 1988, W. H. Freeman and Company, New York. The letter "x" as used herein within an amino acid sequence can stand for any amino acid residue.

"Coding sequence" refers to a DNA or RNA molecule that codes for a specific amino acid molecule and excludes the non-coding sequences. It may constitute an "uninterrupted coding sequence", i.e., lacking an intron, such as in a cDNA or it may include one or more introns bounded by appropriate splice junctions. An "intron" is a molecule of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, microRNA, siRNA, ribozyme, or other RNA that is not translated.

The term "RNA transcript" refers to the product resulting from RNA polymerase catalyzed transcription of a DNA molecule. When the RNA transcript is a perfect complementary copy of the DNA molecule, it is referred to as the primary transcript or it may be a RNA molecule derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Isolated nucleic acid molecule capable of regulating expression", "transcription regulating nucleotide molecule", "regulatory molecule", or "suitable regulatory molecules", each refer to nucleotide molecules influencing the transcription, RNA processing or stability, or translation of the associated (or functionally linked) nucleotide molecules to be transcribed. The transcription regulating nucleotide molecule may have various localizations with respect to the nucleotide molecules to be transcribed. The transcription regulating nucleotide molecule may be located upstream (5' non-coding sequences), within, or downstream (3' non-coding sequences) of the molecule to be transcribed (e.g., a coding sequence). The transcription regulating nucleotide molecule may be selected from the group comprising enhancers, promoters, translation leader sequences, introns, 5'-untranslated sequences, 3'-untranslated sequences, and polyadenylation signal sequences. They include natural and synthetic molecules as well as molecules, which may be a combination of synthetic and natural molecules. As is noted above, the term "transcription regulating nucleotide molecule" is not limited to promoters. However, preferably a transcription regulating nucleotide molecule of the invention comprises at least one promoter molecule (e.g., a molecule localized upstream of the transcription start of a gene capable to induce transcription of the downstream molecules). In one preferred embodiment the transcription regulating nucleotide molecule of the invention comprises the promoter molecule of the corresponding gene and—optionally and preferably—the native 5'-untranslated region of said gene. Furthermore, the 3'-untranslated region and/or the polyadenylation region of said gene may also be employed. As used herein, the term "cis-element" or "promoter motif" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element. The promoters of the present invention desirably contain cis-elements that can confer or modulate gene expression. Cis-elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequent manipulation.

"5' non-coding sequence" or "5'-untranslated sequence" or "-region" refers to a sequence of a nucleotide molecule located 5' (upstream) to the coding sequence. It is present in the fully processed mRNA upstream of the initiation codon and may affect processing of the primary transcript to mRNA, mRNA stability or translation efficiency.

"3' non-coding sequence" or "3'-untranslated sequence" or "-region" refers to a sequence of a nucleotide molecule located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., 1989.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide. The term "transit peptide" as used herein refers part of an expressed polypeptide (preferably to the amino terminal extension of a polypeptide), which is translated in conjunction with the polypeptide forming a precursor peptide and which is required for its entrance into a cell organelle (such as the plastids (e.g., chloroplasts) or mitochondria). The term "transit sequence" refers to a nucleotide sequence that encodes the transit peptide.

"Promoter" refers to a nucleotide molecule, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA box and other sequences that serve to specify the site of transcription initiation, to which regulatory elements are added for control of expression. "Promoter" also refers to a nucleotide molecule that includes a minimal promoter plus regulatory elements that is capable of controlling the expression of a coding sequence or functional RNA. This type of promoter molecule consists of proximal and more distal upstream elements, the latter elements often referred to as enhancers. Accordingly, an "enhancer" is a DNA molecule, which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements, derived from different promoters found in nature, or even be comprised of synthetic DNA segments. A promoter may also contain DNA sequences that are involved in the binding of protein factors, which control the effectiveness of transcription initiation in response to physiological or developmental conditions. A person skilled in the art is aware of methods for rendering a unidirectional to a bidirectional promoter and of methods to use the complement or reverse complement of a promoter sequence for creating a promoter having the same promoter specificity as the original sequence. Such methods are for example described for constitutive as well as inducible promoters by Xie et al. (2001) "Bidirectionalization of polar promoters in plants" nature biotechnology 19 pages 677-679. The authors describe that it is sufficient to add a minimal promoter to the 5' prime end of any given promoter to receive a promoter controlling expression in both directions with same promoter specificity.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Constitutive promoter" refers to a promoter that is able to express the open reading frame (ORF) that it controls in all or nearly all of the plant tissues during all or nearly all developmental stages of the plant. Each of the transcription-activating elements do not exhibit an absolute tissue-specificity, but mediate transcriptional activation in most plant parts at a level of at least 1% of the level reached in the part of the plant in which transcription is most active.

"Regulated promoter" refers to promoters that direct gene expression not constitutively, but in a temporally- and/or spatially-regulated manner, and includes both tissue-specific and inducible promoters. It includes natural and synthetic molecules as well as molecules which may be a combination of synthetic and natural molecules. Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysone-inducible systems.

"Tissue-specific promoter" refers to regulated promoters that are not expressed in all plant cells but only in one or more cell types in specific organs (such as leaves or seeds), specific tissues (such as epidermis, green tissue, embryo or cotyledon), or specific cell types (such as leaf parenchyma or seed storage cells). These also include promoters that are temporally regulated, such as in early or late embryogenesis, during leaf expansion fruit ripening in developing seeds or fruit, in fully differentiated leaf, or at the onset of senescence.

"Inducible promoter" refers to those regulated promoters that can be turned on in one or more cell types or that cause increased expression upon an external stimulus, such as a chemical, light, hormone, stress, or a pathogen.

"Operably-linked" or "functionally linked" refers preferably to the association of nucleic acid molecules on single nucleic acid fragment so that the function of one is affected by the other. For example, a regulatory DNA molecule is said to be "operably linked to" or "associated with" a DNA molecule that codes for an RNA or a polypeptide if the two molecules are situated such that the regulatory DNA molecule affects expression of the coding DNA molecule (i.e., that the coding sequence or functional RNA is under the transcriptional control of the promoter). Coding sequences can be operably-linked to regulatory molecules in sense or antisense orientation.

"Expression" refers to the transcription and/or translation of an endogenous gene, ORF or portion thereof, or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

"Specific expression" is the expression of gene products, which is limited to one or a few plant tissues (spatial limitation) and/or to one or a few plant developmental stages (temporal limitation). It is acknowledged that hardly a true specificity exists: promoters seem to be preferably switch on in some tissues, while in other tissues there can be no or only little activity. This phenomenon is known as leaky expression. However, with specific expression in this invention is meant preferable expression in one or a few plant tissues.

The "expression pattern" of a promoter (with or without enhancer) is the pattern of expression levels, which shows where in the plant and in what developmental stage transcription is initiated by said promoter. Expression patterns of a set of promoters are said to be complementary when the expression pattern of one promoter shows little overlap with the expression pattern of the other promoter. The level of expression of a promoter can be determined by measuring the 'steady state' concentration of a standard transcribed reporter mRNA. This measurement is indirect since the concentration of the reporter mRNA is dependent not only on its synthesis rate, but also on the rate with which the mRNA is degraded. Therefore, the steady state level is the product of synthesis rates and degradation rates. The rate of degradation can however be considered to proceed at a fixed rate when the transcribed molecules are identical, and thus this value can serve as a measure of synthesis rates. When promoters are compared in this way techniques available to those skilled in the art are hybridization S1-RNAse analysis, northern blots and competitive RT-PCR. This list of techniques in no way represents all available techniques, but rather describes commonly used procedures used to analyze transcription activity and expression levels of mRNA. The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter molecules that the sequence surrounding the initiation site (initiator) plays an important role in determining the level of RNA expression directed by that specific promoter. This includes also part of the transcribed sequences. The direct fusion of promoter to reporter molecules would therefore lead to suboptimal levels of transcription. A commonly used procedure to analyze expression patterns and levels is through determination of the 'steady state' level of protein accumulation in a cell. Commonly used candidates for the reporter gene, known to those skilled in the art are beta-glucuronidase (GUS), chloramphenicol acetyl transferase (CAT) and proteins with fluorescent properties, such as green fluorescent protein (GFP) from *Aequora victoria*. In principle, however, many more proteins are suitable for this purpose, provided the protein does not interfere with essential plant functions. For quantification and determination of localization a number of tools are suited. Detection systems can readily be created or are available which are based on, e.g., immunochemical, enzymatic, fluorescent detection and quantification. Protein levels can be determined in plant tissue extracts or in intact tissue using in situ analysis of protein expression. Generally, individual transformed lines with one chimeric promoter reporter construct will vary in their levels of expression of the reporter gene. Also frequently observed is the phenomenon that such transformants do not express any detectable product (RNA or protein). The variability in expression is commonly ascribed to 'position effects', although the molecular mechanisms underlying this inactivity are usually not clear.

"Overexpression" refers to the level of expression in transgenic cells or organisms that exceeds levels of expression in normal or untransformed (non-transgenic) cells or organisms.

"Antisense inhibition" refers to the production of antisense RNA transcripts capable of suppressing the expression of protein from an endogenous gene or a transgene.

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species homologous to the affected genes (English 1996). Gene silencing includes virus-induced gene silencing (Ruiz et al. 1998).

The terms "heterologous DNA molecule", "exogenous DNA segment" or "heterologous nucleic acid," as used herein, each refer to a molecule that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA molecule. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA molecule is a DNA molecule that is naturally associated with a host cell into which it is introduced.

"Homologous to" in the context of nucleotide sequence identity refers to the similarity between the nucleotide sequences of two nucleic acid molecules or between the amino acid sequences of two protein molecules. Estimates of such homology are provided by either DNA-DNA or DNA-RNA hybridization under conditions of stringency as is well understood by those skilled in the art (as described in Haines and Higgins (eds.), Nucleic Acid Hybridization, IRL Press, Oxford, U.K.), or by the comparison of sequence similarity between two nucleic acids or proteins.

The term "substantially similar" or "similar" refers to nucleotide and amino acid sequences that represent functional and/or structural equivalents or orthologs of *Arabidopsis thaliana* or *Glycine max* sequences disclosed herein.

In its broadest sense, the term "substantially similar" or "similar" when used herein with respect to a nucleotide sequence means that the nucleotide sequence is part of a gene which encodes a polypeptide having substantially the same structure and function as a polypeptide encoded by a gene for the reference nucleotide sequence, e.g., the nucleotide sequence comprises a promoter from a gene that is the ortholog of the gene corresponding to the reference nucleotide sequence, as well as promoter sequences that are structurally related the promoter sequences particularly exemplified herein, i.e., the substantially similar promoter sequences hybridize to the complement of the promoter sequences exemplified herein under high or very high stringency conditions. For example, altered nucleotide sequences, which simply reflect the degeneracy of the genetic code but nonetheless encode amino acid sequences that are identical to a particular amino acid sequence are substantially similar to the particular sequences. The term "substantially similar" also includes nucleotide sequences wherein the sequence has been modified, for example, to optimize expression in particular cells, as well as nucleotide sequences encoding a variant polypeptide having one or more amino acid substitutions relative to the (unmodified) polypeptide encoded by the reference sequence, which substitution(s) does not alter the activity of the variant polypeptide relative to the unmodified polypeptide.

In its broadest sense, the term "substantially similar" or "similar" when used herein with respect to polypeptide or nucleic acids means that the polypeptide or nucleic acid has substantially the same structure and function as the reference polypeptide. In addition, amino acid sequences or nucleic acids that are substantially similar to a particular sequence are those wherein overall amino acid or nucleic acid identity is at least 90% or greater to the instant sequences. Modifications that result in equivalent nucleotide or amino acid sequences are well within the routine skill in the art. The percentage of amino acid or nucleic acid sequence identity between the substantially similar and the reference polypeptide or nucleic acid is at least 90% or more, e.g., 91%, 92%, 93%, 94%, 95%, 96%, 97%, 98%, up to at least 99%, wherein the reference polypeptide is an polypeptide encoded by a gene with a promoter having any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89, a nucleotide sequence comprising an open reading frame comprised in SEQ ID NOs: 220, 222, 224, 226, 228, 230, 232, 234, 236, 238, 240, 242, 244, 246, 248, 250, 252 or 254, which encodes a polypeptide described by SEQ ID NOs: 221, 223, 225, 227, 229, 231, 233, 235, 237, 239, 241, 243, 245, 247, 249, 251, 253 or 255. One indication that two polypeptides are substantially similar to each other, besides having substantially the same function, is that an agent, e.g., an antibody, which specifically binds to one of the polypeptides, also specifically binds to the other.

Sequence comparisons maybe carried out using a Smith-Waterman sequence alignment algorithm (see e.g., Waterman (1995)). The localS program, version 1.16, is preferably used with following parameters: match: 1, mismatch penalty: 0.33, open-gap penalty: 2, extended-gap penalty: 2.

Moreover, a nucleotide sequence that is "substantially similar" or "similar" to a reference nucleotide sequence is said to be "equivalent" to the reference nucleotide sequence. The skilled artisan recognizes that equivalent nucleotide sequences encompassed by this invention can also be defined by their ability to hybridize, under low, moderate and/or stringent conditions (e.g., 0.1×SSC, 0.1% SDS, 65° C.), with the nucleotide sequences that are within the literal scope of the instant claims.

What is meant by "substantially the same activity" or "the same activity" when used in reference to a polynucleotide fragment or a homolog is that the fragment or homolog has at least 90% or more, e.g., 91%, 92%, 93%, 94%, 95%, 96%, 97%, 98%, up to at least 99% of the expression regulating activity of the full length polynucleotide.

"Target gene" refers to a gene on the replicon that expresses the desired target coding sequence, functional RNA, or protein. The target gene is not essential for replicon replication. Additionally, target genes may comprise native non-viral genes inserted into a non-native organism, or chimeric genes, and will be under the control of suitable regulatory sequences. Thus, the regulatory sequences in the target gene may come from any source, including the virus. Target genes may include coding sequences that are either heterologous or homologous to the genes of a particular plant to be transformed. However, target genes do not include native viral genes. Typical target genes include, but are not limited to genes encoding a structural protein, a seed storage protein, a protein that conveys herbicide resistance, and a protein that conveys insect resistance. Proteins encoded by target genes are known as "foreign proteins". The expression of a target gene in a plant will typically produce an altered plant trait.

The term "altered plant trait" means any phenotypic or genotypic change in a transgenic plant relative to the wildtype or non-transgenic plant host.

"Replication gene" refers to a gene encoding a viral replication protein. In addition to the ORF of the replication protein, the replication gene may also contain other overlapping or non-overlapping ORF(s), as are found in viral sequences in nature. While not essential for replication, these additional ORFs may enhance replication and/or viral DNA accumulation. Examples of such additional ORFs are AC3 and AL3 in ACMV and TGMV geminiviruses, respectively.

"Chimeric trans-acting replication gene" refers either to a replication gene in which the coding sequence of a replication protein is under the control of a regulated plant promoter other than that in the native viral replication gene, or a modified native viral replication gene, for example, in which a site specific sequence(s) is inserted in the 5' transcribed but untranslated region. Such chimeric genes also include insertion of the known sites of replication protein binding between the promoter and the transcription start site that attenuate transcription of viral replication protein gene.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms". Examples of methods of transformation of plants and plant cells include *Agrobacterium*-mediated transformation (De Blaere 1987) and particle bombardment technology (U.S. Pat. No. 4,945,050). Whole plants may be regenerated from transgenic cells by methods well known to the skilled artisan (see, for example, Fromm 1990).

"Transformed," "transgenic," and "recombinant" refer to a host organism such as a bacterium or a plant into which a heterologous nucleic acid molecule has been introduced. The nucleic acid molecule can be stably integrated into the genome generally known in the art and are disclosed (Sambrook 1989; Innis 1995; Gelfand 1995; Innis & Gelfand 1999. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" plants or calli have been through the transformation process and contain a foreign gene integrated into their chromosome. The term "untransformed" refers to normal plants that have not been through the transformation process.

"Transiently transformed" refers to cells in which transgenes and foreign DNA have been introduced (for example, by such methods as *Agrobacterium*-mediated transformation or biolistic bombardment), but not selected for stable maintenance.

"Stably transformed" refers to cells that have been selected and regenerated on a selection media following transformation.

"Transient expression" refers to expression in cells in which a virus or a transgene is introduced by viral infection or by such methods as *Agrobacterium*-mediated transformation, electroporation, or biolistic bombardment, but not selected for its stable maintenance.

"Genetically stable" and "heritable" refer to chromosomally-integrated genetic elements that are stably maintained in the plant and stably inherited by progeny through successive generations.

"Primary transformant" and "T0 generation" refer to transgenic plants that are of the same genetic generation as the tissue which was initially transformed (i.e., not having gone through meiosis and fertilization in between).

"Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

Wild-type: The term "wild-type", "natural" or "natural origin" means with respect to an organism, polypeptide, or nucleic acid sequence, that said organism is naturally occurring or available in at least one naturally occurring organism which is not changed, mutated, or otherwise manipulated by man.

The terms "genome" or "genomic DNA" is referring to the heritable genetic information of a host organism. Said genomic DNA comprises the DNA of the nucleus (also referred to as chromosomal DNA) but also the DNA of the plastids (e.g., chloroplasts) and other cellular organelles (e.g., mitochondria). Preferably the terms genome or genomic DNA is referring to the chromosomal DNA of the nucleus.

The term "chromosomal DNA" or "chromosomal DNA-sequence" is to be understood as the genomic DNA of the cellular nucleus independent from the cell cycle status. Chromosomal DNA might therefore be organized in chromosomes or chromatids, they might be condensed or uncoiled. An insertion into the chromosomal DNA can be demonstrated and analyzed by various methods known in the art like e.g., polymerase chain reaction (PCR) analysis, Southern blot analysis, fluorescence in situ hybridization (FISH), and in situ PCR.

The term "nucleic acid" refers to deoxyribonucleotides or ribonucleotides and polymers thereof in either single- or double-stranded form, composed of monomers (nucleotides) containing a sugar, phosphate and a base, which is either a purine or pyrimidine. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer 1991; Ohtsuka 1985; Rossolini 1994). A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that, by the hand of man, exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5%

(by dry weight) of chemical precursors or non-protein of interest chemicals. The nucleotide sequences of the invention include both the naturally occurring sequences as well as mutant (variant) forms. Such variants will continue to possess the desired activity, i.e., either promoter activity or the activity of the product encoded by the open reading frame of the non-variant nucleotide sequence.

The term "variant" or "homolog" with respect to a sequence (e.g., a polypeptide or nucleic acid sequence such as—for example—a transcription regulating nucleotide molecule of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence.

"Expression cassette" as used herein means a DNA sequence capable of directing expression of a particular nucleotide sequence in an appropriate host cell, comprising a promoter operably linked to a nucleotide sequence of interest, which is—optionally—operably linked to termination signals and/or other regulatory elements. An expression cassette may also comprise sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one, which is naturally occurring but has been obtained in a recombinant form useful for heterologous expression. An expression cassette may be assembled entirely extracellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby becomes functionally linked and controlled by said promoter sequences. Likewise, a nucleic acid sequence to be expressed may be placed (or inserted) downstream of an endogenous promoter sequence thereby forming an expression cassette. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development. In a preferred embodiment, such expression cassettes will comprise the transcriptional initiation region of the invention linked to a nucleotide sequence of interest. Such an expression cassette is preferably provided with a plurality of restriction sites for insertion of the gene of interest to be under the transcriptional regulation of the regulatory regions. The expression cassette may additionally contain selectable marker genes. The cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such, as the octopine synthase and nopaline synthase termination regions and others described below (see also, Guerineau 1991; Proudfoot 1991; Sanfacon 1991; Mogen 1990; Munroe 1990; Ballas 1989; Joshi 1987).

"Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

A "transgenic plant" is a plant having one or more plant cells that contain an expression vector or recombinant expression construct.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full length cDNA or gene sequence or isolated nucleic acid sequence capable of regulating expression in plants, preferably the complete cDNA or gene sequence or isolated nucleic acid sequence capable of regulating expression in plants is the reference sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. In a preferred embodiment the comparison window defining the homology of sequence consists of the entire query sequence. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similarity-method of Pearson and Lipman 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described (Higgins 1988, 1989; Corpet 1988; Huang 1992; Pearson 1994). The ALIGN program is based on the algorithm of Myers and Miller, supra. The BLAST programs of Altschul et al., 1990, are based on the algorithm of Karlin and Altschul, supra. Multiple aligments (i.e. of more than 2 sequences) are preferably performed using the Clustal W algorithm (Thompson 1994; e.g., in the software VectorNTI™, version 9; Invitrogen Inc.) with the scoring matrix BLOSUM62 MT2 with the default settings (gap opening penalty 15/19, gap extension penalty 6.66/0.05; gap separation penalty range 8; % identity for alignment delay 40; using residue specific gaps and hydrophilic residue gaps).

Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. 1997. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). See www.ncbi.nlm.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, preferably the complete query or reference sequence as defined by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) (i) The term "substantial identity" of polynucleotide sequences means that a polynucleotide comprises a sequence that has at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 90%, 95%, and most preferably at least 98%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(ii) The term "substantial identity" in the context of a peptide indicates that a peptide comprises a sequence with at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with anti-bodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. The reference sequences of the invention are defined by the sequences comprised in the sequence protocol, preferably SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 and 89, 220, 222, 224, 226, 228, 230, 232, 234, 236, 238, 240, 242, 244, 246, 248, 250, 252 and 254, 221, 223, 225, 227, 229, 231, 233, 235, 237, 239, 241, 243, 245, 247, 249, 251, 253 and 255. Preferably the reference sequence comprises the complete sequence as defined by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89 or 220, 222, 224, 226, 228, 230, 232, 234, 236, 238, 240, 242, 244, 246, 248, 250, 252 or 254 or 221, 223, 225, 227, 229, 231, 233, 235, 237, 239, 241, 243, 245, 247, 249, 251, 253 or 255, more preferably the reference sequence consists of the complete sequence as defined by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89 or 220, 222, 224, 226, 228, 230, 232, 234, 236, 238, 240, 242, 244, 246, 248, 250, 252 or 254 or 221, 223, 225, 227, 229, 231, 233, 235, 237, 239, 241, 243, 245, 247, 249, 251, 253 or 255.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984:

$$T_m = 81.5° C. + 16.6(\log_{10} M) + 0.41(\% GC) - 0.61(\% \text{form}) - 500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, 4, 5, 6, 7, 8, 9, or 10° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4 to 6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

"DNA shuffling" is a method to introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA preferably encodes a variant polypeptide modified with respect to the polypeptide encoded by the template DNA, and may have an altered biological activity with respect to the polypeptide encoded by the template DNA.

"Recombinant DNA molecule" is a combination of DNA sequences that are joined together using recombinant DNA technology and procedures used to join together DNA sequences as described, for example, in Sambrook et al., 1989.

The word "plant" refers to any plant, particularly to agronomically useful plants (e.g., seed plants), and "plant cell" is a structural and physiological unit of the plant, which comprises a cell wall but may also refer to a protoplast. The plant cell may be in form of an isolated single cell or a cultured cell, or as a part of higher organized unit such as, for example, a plant tissue, or a plant organ differentiated into a structure that is present at any stage of a plant's development. Such structures include one or more plant organs including, but are not limited to, fruit, shoot, stem, leaf, flower petal, etc. Preferably, the term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruits (the mature ovary), plant tissues (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous. Included within the scope of the invention are all genera and species of higher and lower plants of the plant kingdom. Included are furthermore the mature plants, seed, shoots and seedlings, and parts, propagation material (for example seeds and fruit) and cultures, for example cell cultures, derived therefrom. Preferred are plants and plant materials of the following plant families: Amaranthaceae, Brassicaceae, Carophyllaceae, Chenopodiaceae, Compositae, Cucurbitaceae, Labiatae, Leguminosae, Papilionoideae, Liliaceae, Linaceae, Malvaceae, Rosaceae, Saxifragaceae, Scrophulariaceae, Solanaceae, Tetragoniaceae. Annual, perennial, monocotyledonous and dicotyledonous plants are preferred host organisms for the generation of transgenic plants. The use of the recombination system, or method according to the invention is furthermore advantageous in all ornamental plants, forestry, fruit, or ornamental trees, flowers, cut flowers, shrubs or turf. Said plant may include—but shall not be limited to—bryophytes such as, for example, Hepaticae (hepaticas) and Musci (mosses); pteridophytes such as ferns, horsetail and clubmosses; gymnosperms such as conifers, cycads, ginkgo and Gnetaeae; algae such as Chlorophyceae, Phaeophpyceae, Rhodophyceae, Myxophyceae, Xanthophyceae, Bacillariophyceae (diatoms) and Euglenophyceae. Plants for the purposes of the invention may comprise the families of the Rosaceae such as rose, Ericaceae such as rhododendrons and azaleas, Euphorbiaceae such as *poinsettias* and *croton*, Caryophyllaceae such as pinks, Solanaceae such as *petunias*, Gesneriaceae such as African violet, Balsaminaceae such as touch-me-not, Orchidaceae such as orchids, Iridaceae such as *gladioli, iris, freesia* and *crocus*, Compositae such as marigold, Geraniaceae such as *geraniums*, Liliaceae such as *Drachaena*, Moraceae such as *ficus*, Araceae such as *philodendron* and many others. The transgenic plants according to the invention are furthermore selected in particular from among dicotyledonous crop plants such as, for example, from the families of the Leguminosae such as pea, alfalfa and soybean; the family of the Umbelliferae, particularly the genus *Daucus* (very particularly the species *carota* (carrot)) and *Apium* (very particularly the species *graveolens* var. *dulce* (celery)) and many others; the family of the Solanaceae, particularly the genus *Lycopersicon*, very particularly the species *esculentum* (tomato) and the genus *Solanum*, very particularly the species *tuberosum* (potato) and *melongena* (aubergine), tobacco and many others; and the genus *Capsicum*, very particularly the species *annum* (pepper) and many others; the family of the Leguminosae, particularly the genus *Glycine*, very particularly the species *max* (soybean) and many others; and the family of the Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli); and the genus *Arabidopsis*, very particularly the species *thaliana* and many others; the family of the Compositae, particularly the genus *Lactuca*, very particularly the species *sativa* (lettuce) and many others. The transgenic plants according to the invention may be selected among monocotyledonous crop plants, such as, for example, cereals such as wheat, barley, sorghum and millet, rye, triticale, maize, rice or oats, and sugarcane. Further preferred are trees such as apple, pear, quince, plum, cherry, peach, nectarine, apricot, papaya, mango, and other woody species including coniferous and deciduous trees such as poplar, pine, sequoia, cedar, oak, etc. Especially preferred are *Arabidopsis thaliana, Nicotiana tabacum*, oilseed rape, soybean, corn (maize), wheat, *Linum usitatissimum* (linseed and flax), *Camelina sativa, Brassica juncea*, potato and tagetes.

"Significant increase" is an increase that is larger than the margin of error inherent in the measurement technique, preferably an increase by about 2-fold or greater.

"Significantly less" means that the decrease is larger than the margin of error inherent in the measurement technique, preferably a decrease by about 2-fold or greater.

DETAILED DESCRIPTION OF THE INVENTION

The present invention thus provides for isolated nucleic acid molecules comprising a plant nucleotide sequence that directs transcription in epidermis of an operably linked nucleic acid fragment in a plant or part thereof.

The present invention further provides for isolated nucleic acid molecules comprising a plant nucleotide sequence that directs transcription in epidermis of an operably linked nucleic acid fragment in a plant or part thereof upon induction by a pathogen, preferably a fungal pathogen.

The present invention further provides for isolated nucleic acid molecules comprising a plant nucleotide sequence that directs constitutive transcription of an operably linked nucleic acid fragment in a plant or part thereof.

The present invention further provides for isolated nucleic acid molecules comprising a plant nucleotide sequence that directs mesophyll specific or mesophyll preferable transcription of an operably linked nucleic acid fragment in a plant or part thereof.

The present invention further provides for isolated nucleic acid molecules comprising a plant nucleotide sequence that directs mesophyll and epidermis specific or mesophyll and epidermis preferable transcription of an operably linked nucleic acid fragment in a plant or part thereof upon induction by a pathogen, preferably a fungal pathogen.

In addition, the present invention provides transgenic expression cassettes for regulating expression in plant epidermis, inducible expression in plant epidermis and/or mesophyll or constitutive expression comprising a) at least one transcription regulating nucleotide molecule derived from any of the *Glycine max* genes described by the GenBank *Glycine max* genome loci Glyma11g14950, Glyma14g06680, Glyma02g47670, Glyma14g02930, Glyma17g27610, Glyma13g44640, Glyma08g37270, Glyma04g40860.1, Glyma01g33070.2, Glyma15g05820.1, Glyma01g42660.1, Glyma17g14320 or Glyma01g01510.1 or their orthologous genes and functionally linked thereto b) at least one nucleic acid molecule which is heterologous in relation to said transcription regulating nucleotide molecule.

In addition, the present invention provides transgenic expression cassettes for regulating expression in plant mesophyll comprising a) at least one transcription regulating nucleotide molecule derived from any of the *Arabidopsis thaliana* genes described by the GenBank *Arabidopsis thaliana* genome loci At1g49750, At3g62410, At1g61520, At1g30380 or At1g65490 or their orthologous genes and functionally linked thereto b) at least one nucleic acid molecule which is heterologous in relation to said transcription regulating nucleotide sequence.

"tissue-specific transcription" in the context of this invention means the transcription of a nucleic acid molecule by a transcription regulating nucleic acid molecule in a way that transcription of said nucleic acid molecule in said tissue contribute to more than 90%, preferably more than 95%, more preferably more than 99% of the entire quantity of the RNA transcribed from said nucleic acid molecule in the entire plant during any of its developmental stage. The transcription regulating nucleotide molecules specifically disclosed herein are considered to be tissue-specific transcription regulating nucleotide molecules.

"tissue-preferential transcription" in the context of this invention means the transcription of a nucleic acid molecule by a transcription regulating nucleic acid molecule in a way that transcription of said nucleic acid sequence in the said tissue contribute to more than 50%, preferably more than 70%, more preferably more than 80% of the entire quantity of the RNA transcribed from said nucleic acid sequence in the entire plant during any of its developmental stage.

"substantially the same transcription regulating activity" in the context of this invention means the transcription of a nucleic acid molecule by a transcription regulating nucleic acid molecule which is a fragment or a homolog or a variant of any of SEQ ID NO: 1, 2, 3, 4, 5, 6, 7, 8, 9, 10, 11, 12, 13, 14, 15, 16, 17 or 18 has the same tissue specific or tissue preferential transcription as the transcription regulating nucleic acid molecule it is derived from and has at least 50% preferably at least 60%, more preferably at least 80% or 90%, even more preferably at least 95%, most preferably the same expression strength as the transcription regulating nucleic acid molecule it is derived from.

Preferably a transcription regulating nucleotide molecule of the invention comprises at least one promoter sequence of the respective gene (e.g., a sequence localized upstream of the transcription start of the respective gene capable to induce transcription of the downstream sequences). Said transcription regulating nucleotide molecule may comprise the promoter sequence of said genes but may further comprise other elements such as the 5'-untranslated sequence, enhancer, introns etc. Preferably, said promoter sequence directs transcription of an operably linked nucleic acid segment in a plant epidermis or plant epidermis cell e.g., a linked plant DNA comprising an open reading frame for a structural or regulatory gene.

As specified above in the DEFINITION section, identities between nucleotide sequences are preferably measured by the BLASTN program using default parameters with a wordlength (W) of 11, an expectation (E) of 10, a cutoff of 100, M=5, N=−4, and a comparison of both strands. For measuring identity between amino acid sequences, the BLASTP program is used with default parameters with a wordlength (W) of 3, an expectation (E) of 10, and the BLOSUM62 scoring matrix (see Henikoff & Henikoff, 1989). The BLAST Program version 1.4.7 or later is used.

Preferably, such homolog or fragment of said isolated nucleotide sequence (e.g., the sequences specified under ii), iii), iv) v), vi) and vii) above) is capable to modify transcription in a plant cell or organism, more preferably said homolog or fragment (e.g., the sequences specified under ii), iii), iv) v) and vi) above) has substantially the same transcription regulating activity as the transcription regulating nucleotide molecule described by SEQ ID NO: 1, 2, 3, 4, 5, 6, 7, 8, 9, 10, 11, 12, 13, 14, 15, 16, 17 or 18. Preferably, the homolog or fragment (e.g., the sequences specified under iv) or v) above) is hybridizing under stringent conditions (i.e. medium stringent, more preferably high stringent conditions) with the specified target sequence.

Preferably, the transcription regulating nucleotide molecule employed in the expression cassettes of the invention is selected from the group of molecules consisting of the molecules described by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 and 89 or any homolog or fragment thereof. More preferably the transcription regulating nucleotide molecule employed in the expression cassette of the invention is selected from the group of molecules consisting of i) the molecule described by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 and 89, and ii) a fragment of at least 250 consecutive bases, preferably at least 300 consecutive bases, more preferably at least 400 consecutive bases, even more preferably at least 500 consecutive bases, most preferably at least 750 consecutive bases of a molecule described by any of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 and 89 and iii) a nucleotide molecule of at least 250 consecutive bases, preferably at least 300 consecutive bases, more preferably at least 400 consecutive bases, even more preferably at least 500 consecutive bases, most preferably at least 750 consecutive bases with a sequence identity of at least 60%, 65% or 70%, preferably at least 75%, 80% or 85%, more preferably at least 90% or 95%, even more preferably at least 96% or 97%, most preferably at least 98% or 99% to a transcription regulating nucleotide molecule described by any of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89, and iv) a nucleotide molecule having a sequence identity of at least 60%, 65%, 70%, 75% or 80%, preferably at least 85%, more preferably at least 90% or 95%, even more preferably at least 96% or 97%, most preferably at least 98% or 99% to an isolated nucleic acid molecule capable of regulating expression in plants described by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 and 89, and v) a nucleotide molecule of at least 250 bases, preferably at least 300 bases, more preferably at least 400 bases, even more preferably at least 500 bases, most preferably at least 750 bases capable of hybridizing preferably under conditions equivalent to hybridization in 7% sodium dodecyl sulfate (SDS), 0.5 M NaPO$_4$, 1 mM EDTA at 50° C. with washing in 0.1×SSC, 0.1% SDS at 50° C., more desirably in 7% SDS, 0.5 M NaPO$_4$, 1 mM EDTA at 50° C. with washing in 0.1×SSC, 0.1% SDS at 65° C. to an isolated nucleic acid molecule capable of regulating expression in plants described by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 and 89, or the complement thereof;

vi) a nucleotide molecule of at least 250 bases, preferably at least 300 bases, more preferably at least 400 bases, even more preferably at least 500 bases, most preferably at least 750 bases capable of hybridizing preferably under conditions equivalent to hybridization in 7% sodium dodecyl sulfate (SDS), 0.5 M NaPO$_4$, 1 mM EDTA at 50° C. with washing in 0.1×SSC, 0.1% SDS at 50° C., more desirably in 7% SDS, 0.5 M NaPO$_4$, 1 mM EDTA at 50° C. with washing in 0.1×SSC, 0.1% SDS at 65° C. to a nucleic acid comprising at least 250 preferably at least 300, more preferably at least 400, even more preferably at least 500, most preferably at least 750 consecutive nucleotides of an isolated nucleic acid molecule capable of regulating expression in plants described by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 and 89, or the complement thereof;

vii) an isolated nucleic acid molecule capable of regulating expression in plants which is the complement or reverse complement of any of the previously mentioned nucleic acid molecules under i) to vi).

Preferably, such homolog or fragment of the transcription regulating nucleotide molecule to be employed in the expression cassette of the invention (e.g., the sequences specified under ii), iii), iv) v), vi) and vii) above) is capable to modify transcription in a plant cell or organism, more preferably said homolog or fragment (e.g., the sequences specified under ii), iii), iv) v) and vi) above) has substantially the same transcription regulating activity as the transcription regulating nucleotide molecule described by SEQ ID NO: 1, 2, 3, 4, 5, 6, 7, 8, 9, 10, 11, 12, 13, 14, 15, 16, 17 and 18. Preferably, the homolog or fragment (e.g., the sequences specified under iii) above) has a sequence identity of at least 60% or 65%, preferably at least 70%, 75% or 80%, more preferably at least 90% or 95%, most preferably at least 97%, 98% or 99% to a sequence described by SEQ ID NO: 1, 2, 3, 4, 5, 6, 7, 8, 9, 10, 11, 12, 13, 14, 15, 16, 17 and 18. Preferably, the homologs or fragments (e.g., the sequences specified under iv) or vi) above) are hybridizing under stringent conditions (i.e. preferably medium stringent, more preferably high stringent conditions) with the specified target sequence.

In the applications U.S. 61/419,895 and EP 10193800.9 methods for the production of such homologs having the same expression pattern as the reference sequence as defined by SEQ ID NO: 1, 2, 3, 4, 5, 6, 7, 8, 9, 10, 11, 12, 13, 14, 15, 16, 17 and 18 are described.

The homologs or fragments of the transcription regulating nucleotide molecule of the invention (e.g., the sequence described by any of SEQ ID NO: 1, 2, 3, 4, 5, 6, 7, 8, 9, 10, 11, 12, 13, 14, 15, 16, 17 and 18) may be obtained or is obtainable from plant genomic DNA from a gene which is encoding an amino acid sequence having at least 90% amino acid sequence identity, more preferably at least 90% or 95%, most preferably at least 97% or 98% amino acid sequence identity, to a polypeptide as described by SEQ ID NO: 221, 223, 225, 227, 229, 231, 233, 235, 237, 239, 241, 243, 245, 247, 249, 251, 253 and 255.

The activity of a transcription regulating nucleotide molecule is considered equivalent if transcription is initiated in the same tissues as is by the reference molecule. Such expression profile is preferably demonstrated using reporter genes operably linked to said transcription regulating nucleotide sequence. Preferred reporter genes (Schenborn 1999) in this context are green fluorescence protein (GFP) (Chuff 1996; Leffel 1997), chloramphenicol transferase, luciferase (Millar 1992), beta-glucuronidase or beta-galactosidase. Especially preferred is beta-glucuronidase (Jefferson 1987).

Beside this the transcription regulating activity of a functional equivalent homolog or fragment of the transcription regulating nucleotide molecule may vary from the activity of its parent sequence, especially with respect to expression level. The expression level may be higher or lower than the expression level of the parent sequence. Both derivations may be advantageous depending on the nucleic acid sequence of interest to be expressed. Preferred are such functional equivalent sequences, which—in comparison with its parent sequence—does, not derivate from the expression level of said parent sequence by more than 50%, preferably 25%, more preferably 10% (as to be preferably judged by either mRNA expression or protein (e.g., reporter gene) expression). Furthermore preferred are equivalent sequences which demonstrate an increased expression in comparison to its parent sequence, preferably an increase by at least 50%, more preferably by at least 100%, most preferably by at least 500%.

Preferably a functional equivalent of the transcription regulating nucleotide molecule of the invention can be obtained or is obtainable from plant genomic DNA from a gene expressing a mRNA described by a cDNA comprising a sequence which is substantially similar and preferably has at least 90%, preferably at least 92% or 95%, more preferably at least 96% or 97%, most preferably at least 99% sequence identity to a sequence described by any SEQ ID NOs: 220, 222, 224, 226, 228, 230, 232, 234, 236, 238, 240, 242, 244, 246, 248, 250, 252 and 254. Preferably said transcription regulating nucleotide molecule exhibits promoter activity in the same tissue/s as the reference molecule as defined by SEQ ID NO: 1, 2, 3, 4, 5, 6, 7, 8, 9, 10, 11, 12, 13, 14, 15, 16, 17 and 18.

Such functional equivalent of the transcription regulating nucleotide molecule may be obtained from other plant species by using the *Arabidopsis thaliana*, or *Glycine max* promoter sequences described herein as probes to screen for homologous structural genes in other plants by hybridization under low, moderate or stringent hybridization conditions. Regions of the promoter sequences of the present invention which are conserved among species could also be used as PCR primers to amplify a segment from a species other than *Arabidopsis thaliana*, or *Glycine max*, and that segment used as a hybridization probe (the latter approach permitting higher stringency screening) or in a transcription assay to determine promoter activity. Moreover, the promoter sequences could be employed to identify structurally related sequences in a database using computer algorithms.

More specifically, based on the nucleic acid sequences of the present invention, orthologs may be identified or isolated from the genome of any desired organism, preferably from another plant, according to well known techniques based on their sequence similarity to the *Arabidopsis thaliana*, or *Glycine max* nucleic acid sequences, e.g., hybridization, PCR or computer generated sequence comparisons. For example, all or a portion of a particular *Arabidopsis thaliana*, or *Glycine max* nucleic acid sequence is used as a probe that selectively hybridizes to other gene sequences present in a population of cloned genomic DNA fragments or cDNA fragments (i.e., genomic or cDNA libraries) from a chosen source organism. Further, suitable genomic and cDNA libraries may be prepared from any cell or tissue of an organism. Such techniques include hybridization screening of plated DNA libraries (either plaques or colonies; see, e.g., Sambrook 1989) and amplification by PCR using oligonucleotide primers preferably corresponding to sequence domains conserved among related polypeptide or subsequences of the nucleotide sequences provided herein (see, e.g., Innis 1990). These methods are particularly well suited to the isolation of gene sequences from organisms closely related to the organism from which the probe sequence is derived. The application of these methods using the *Arabidopsis thaliana*, or *Glycine max* sequences as probes is well suited for the isolation of gene sequences from any source organism, preferably other plant species. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the sequence of the invention. Methods for preparation of probes for hybridization and for construction of cDNA and genomic libraries are generally known in the art and are disclosed in Sambrook et al. (1989). In general, sequences that hybridize to the sequences disclosed herein will have at least about 50% to 70% and even about 80% 85%, 90%, 95% to 98% or more identity with the disclosed sequences. That is, the sequence similarity of sequences may range, sharing at least about 50% to 70%, and even about 80%, 85%, 90%, 95% to 98% sequence similarity.

The nucleic acid molecules of the invention can also be identified by, for example, a search of known databases for genes encoding polypeptides having a specified amino acid sequence identity or DNA having a specified nucleotide sequence identity. Methods of alignment of sequences for comparison are well known in the art and are described hereinabove.

Hence, the isolated nucleic acid molecules of the invention include the orthologs of the *Arabidopsis thaliana*, or *Glycine max* sequences disclosed herein, i.e., the corresponding nucleotide sequences in organisms other than *Arabidopsis thaliana*, or *Glycine max* including, but not limited to, plants other than *Arabidopsis thaliana*, or *Glycine max*, preferably dicotyledonous plants, e.g., alfalfa, sunflower, rape seed, cotton, peanut, tobacco, or sugar beet, but also cereal plants such as corn, wheat, rye, turfgrass, *sorghum*, millet, sugarcane, barley and banana. An orthologous gene is a gene from a different species that encodes a product having the same or similar function, e.g., catalyzing the same reaction as a product encoded by a gene from a reference organism. Thus, an ortholog includes polypeptides having less than, e.g., 50% amino acid sequence identity, but which ortholog encodes a polypeptide having the same or similar function. Databases such GenBank may be employed to identify sequences related to the *Arabidopsis thaliana*, or *Glycine max* sequences, e.g., orthologs in other dicotyledonous plants. Alternatively, recombinant DNA techniques such as hybridization or PCR may be employed to identify sequences related to the *Arabidopsis thaliana*, or *Glycine max* sequences or to clone the equivalent sequences from different DNAs.

The transcription regulating nucleotide sequences of the invention or their functional equivalents can be obtained or isolated from any plant or non-plant source, or produced synthetically by purely chemical means. Preferred sources include, but are not limited to the plants defined in the DEFINITION section above.

Thus, another preferred embodiment of the invention relates to a method for identifying and/or isolating a transcription regulating nucleotide molecule characterized that said identification and/or isolation utilizes a nucleic acid molecule encoding a polypeptide comprising a sequence as described by SEQ ID NO: 221, 223, 225, 227, 229, 231, 233, 235, 237, 239, 241, 243, 245, 247, 249, 251, 253 and 255, or a part of said nucleic acid sequence. Preferred are nucleic acid molecules comprising nucleic acid sequences described by or comprising any of SEQ ID NO: 220, 222, 224, 226, 228, 230, 232, 234, 236, 238, 240, 242, 244, 246, 248, 250, 252 and 254 or parts thereof. "Part" in this context means a nucleic acid sequence of at least 15 consecutive nucleotides, preferably at least 25 consecutive nucleotides, more preferably at least 50 consecutive nucleotides.

The method for identification and/or isolation can be based on (but is not limited to) the methods described above such as polymerase chain reaction, hybridization or database screening. Preferably, this method of the invention is based on a polymerase chain reaction, wherein said nucleic acid sequence or its part is utilized as oligonucleotide primer. The person skilled in the art is aware of several methods to amplify and isolate the promoter of a gene starting from part of its coding sequence (such as, for example, part of a cDNA). Such methods may include but are not limited to method such as inverse PCR ("iPCR") or "thermal asymmetric interlaced PCR" ("TAIL PCR").

Thus, another embodiment of the invention relates to a method for providing or producing a transgenic expression cassette for heterologous expression in plants comprising the steps of:

I. isolating of a transcription regulating nucleotide molecule of a plant gene utilizing at least one nucleic acid sequence comprising any of SEQ ID NO: 220, 222, 224, 226, 228, 230, 232, 234, 236, 238, 240, 242, 244, 246, 248, 250, 252 and 254, or a part of at least 15, preferably at least 20 consecutive nucleotides of said nucleic acid sequence, and II. functionally linking said transcription regulating nucleotide molecule to another nucleotide molecule of interest, which is heterologous in relation to said transcription regulating nucleotide molecule.

Still another embodiment of the invention relates to a method for providing a transgenic expression cassette for expression comprising the steps of:

I. isolating of a transcription regulating nucleotide molecule utilizing at least one nucleic acid molecule or a part thereof, wherein said molecule is encoding a protein comprising any of SEQ ID NO: 221, 223, 225, 227, 229, 231, 233, 235, 237, 239, 241, 243, 245, 247, 249, 251, 253 and 255, or a part of at least 15 consecutive nucleotides thereof, and II. functionally linking said transcription regulating nucleotide molecule to another nucleotide molecule of interest, which is heterologous in relation to said transcription regulating nucleotide molecule.

Preferably, the nucleic acid molecule employed for the isolation comprises at least 15 consecutive nucleotides, preferably at least 25 consecutive nucleotides, more preferably at least 50 consecutive nucleotides of a nucleic acid molecule comprising a sequence described by any of SEQ ID NO: 220, 222, 224, 226, 228, 230, 232, 234, 236, 238, 240, 242, 244, 246, 248, 250, 252 and 254. Preferably, the isolation of the transcription regulating nucleotide molecule is realized by a polymerase chain reaction utilizing said nucleic acid sequence as a primer. The operable linkage can be realized by standard cloning method known in the art such as ligation-mediated cloning or recombination-mediated cloning.

Preferably, the transcription regulating nucleotide sequences and promoters of the invention include a consecutive stretch of about 250 consecutive bases, preferably at least 300 consecutive bases, more preferably at least 400 consecutive bases, even more preferably at least 500 consecutive bases, most preferably at least 750 consecutive bases, of any one of SEQ ID NOs: 1, 2, 3, 4, 5, 6, 7, 8, 9, 10, 11, 12, 13, 14, 15, 16, 17 and 18, or the promoter orthologs thereof, which include the minimal promoter region.

Preferably, the transcription regulating nucleotide sequences and promoters of the invention include a consecutive stretch of about 250 consecutive bases, preferably at least 300 consecutive bases, more preferably at least 400 consecutive bases, even more preferably at least 500 consecutive bases, most preferably at least 750 consecutive bases, of any one of SEQ ID NOs: 1, 2, 3, 4, 5, 6, 7, 8, 9, 10, 11, 12, 13, 14, 15, 16, 17 and 18, or the promoter orthologs thereof, which include the minimal promoter region. In a particular embodiment of the invention said consecutive stretch of about 250 consecutive bases, preferably at least 300 consecutive bases, more preferably at least 400 consecutive bases, even more preferably at least 500 consecutive bases, most preferably at least 750 consecutive bases, has at least 50% or 60%, preferably at least 70% or 80%, more preferably at least 90% even more preferably at least 95% or 97%, most preferably 98% or 99%, nucleic acid sequence identity with a corresponding consecutive stretch of about 250 consecutive bases, preferably at least 300 consecutive bases, more preferably at least 400 consecutive bases, even more preferably at least 500 consecutive bases, most preferably at least 750 consecutive bases, of any one of SEQ ID NOs: 1, 2, 3, 4, 5, 6, 7, 8, 9, 10, 11, 12, 13, 14, 15, 16, 17 and 18 or the promoter orthologs thereof, which include the minimal promoter region. The above-defined stretch of contiguous nucleotides preferably comprises one or more promoter motifs selected from the group consisting of TATA box, GC-box, CAAT-box and a transcription start site.

The transcription regulating nucleotide sequences of the invention or their functional equivalents are capable of driving expression of a coding sequence in a target cell, particularly in a plant cell. The promoter sequences and methods disclosed herein are useful in regulating expression, respectively, of any heterologous nucleotide sequence in a host plant or part thereof in order to vary the phenotype of that plant. These promoters can be used with combinations of enhancer, upstream elements, and/or activating sequences from the 5' flanking regions of plant expressible structural genes. Similarly the upstream element can be used in combination with various plant promoter sequences.

The transcription regulating nucleotide sequences and promoters of the invention are useful to modify the phenotype of a plant. Various changes in the phenotype of a transgenic plant are desirable, i.e., modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in an alteration in the phenotype of the transformed plant.

Generally, the transcription regulating nucleotide sequences and promoters of the invention may be employed to express a nucleic acid segment that is operably linked to said promoter such as, for example, an open reading frame, or a portion thereof, an anti-sense sequence, a sequence encoding for a double-stranded RNA sequence, or a transgene in plants.

An operable linkage may—for example—comprise an sequential arrangement of the transcription regulating nucleotide molecule of the invention (for example a sequence as described by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 and 89) with a nucleic acid sequence to be expressed, and—optionally—additional regulatory elements such as for example polyadenylation or transcription termination elements, enhancers, introns etc., in a way that the transcription regulating nucleotide molecule can fulfill its function in the process of expressing the nucleic acid sequence of interest under the appropriate conditions. The term "appropriate conditions" means preferably the presence of the expression cassette in a plant cell. Preferred are arrangements, in which the nucleic acid sequence of interest to be expressed is placed downstream (i.e., in 3'-direction) of the transcription regulating nucleotide molecule of the invention in a way, that both sequences are covalently linked. Optionally additional sequences may be inserted in-between the two sequences. Such sequences may be for example linker or multiple cloning sites. Furthermore, sequences can be inserted coding for parts of fusion proteins (in case a fusion protein of the protein encoded by the nucleic acid of interest is intended to be expressed). Preferably, the distance between the nucleic acid sequence of interest to be expressed and the transcription regulating nucleotide molecule of the invention is not more than 200 base pairs, preferably not more than 100 base pairs, more preferably no more than 50 base pairs.

An operable linkage in relation to any expression cassette or of the invention may be realized by various methods known in the art, comprising both in vitro and in vivo procedure. Thus, an expression cassette of the invention or an vector comprising such expression cassette may by realized using standard recombination and cloning techniques well known in the art (see e.g., Maniatis 1989; Silhavy 1984; Ausubel 1987).

An expression cassette may also be assembled by inserting a transcription regulating nucleotide molecule of the invention (for example a sequence as described by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 and 89) into the plant genome. Such insertion will result in an operable linkage to a nucleic acid sequence of interest which as such already existed in the genome. By the insertion the nucleic acid of interest is expressed in a way due to the transcription regulating properties of the transcription regulating nucleotide sequence. The insertion may be directed or by chance. Preferably the insertion is directed and realized by for example homologous recombination. By this procedure a natural promoter may be exchanged against the transcription regulating nucleotide molecule of the invention, thereby modifying the expression profile of an endogenous gene. The transcription regulating nucleotide molecule may also be inserted in a way, that antisense mRNA of an endogenous gene is expressed, thereby inducing gene silencing.

Similar, a nucleic acid sequence of interest to be expressed may by inserted into a plant genome comprising the transcription regulating nucleotide molecule in its natural genomic environment (i.e. linked to its natural gene) in a way that the inserted sequence becomes operably linked to the transcription regulating nucleotide sequence, thereby forming an expression cassette of the invention.

The expression cassette may be employed for numerous expression purposes such as for example expression of a protein, or expression of an antisense RNA, sense or double-stranded RNA. Preferably, expression of the nucleic acid sequence confers to the plant an agronomically valuable trait.

The open reading frame to be linked to the transcription regulating nucleotide molecule of the invention may be obtained from an insect resistance gene, a disease resistance gene such as, for example, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker, a positive selectable marker, a gene affecting plant agronomic characteristics, i.e., yield, standability, and the like, or an environment or stress resistance gene, i.e., one or more genes that confer herbicide resistance or tolerance, insect resistance or tolerance, disease resistance or tolerance (viral, bacterial, fungal, oomycete, or nematode), stress tolerance or resistance (as exemplified by resistance or tolerance to drought, heat, chilling, freezing, excessive moisture, salt stress, or oxidative stress), increased yields, food content and makeup, physical appearance, male sterility, drydown, standability, prolificacy, starch properties or quantity, oil quantity and quality, amino acid or protein composition, and the like. By "resistant" is meant a plant, which exhibits substantially no phenotypic changes as a consequence of agent administration, infection with a pathogen, or exposure to stress. By "tolerant" is meant a plant, which, although it may exhibit some phenotypic changes as a consequence of infection, does not have a substantially decreased reproductive capacity or substantially altered metabolism.

The expression regulating nucleotide sequences specified above may be optionally operably linked to other suitable regulatory sequences, e.g., a transcription terminator sequence, operator, repressor-binding site, transcription factor binding site and/or an enhancer.

The present invention further provides a recombinant vector containing the expression cassette of the invention, and host cells comprising the expression cassette or vector, e.g., comprising a plasmid. The expression cassette or vector may augment the genome of a transformed plant or may be maintained extra-chromosomally. The expression cassette or vector of the invention may be present in the nucleus, chloroplast, mitochondria and/or plastid of the cells of the plant. Preferably, the expression cassette or vector of the invention is comprised in the chromosomal DNA of the plant nucleus. The present invention also provides a transgenic plant prepared by this method, a seed from such a plant and progeny plants from such a plant including hybrids and inbreds. The expression cassette may be operatively linked to a structural gene, the open reading frame thereof, or a portion thereof. The expression cassette may further comprise a Ti plasmid and be contained in an *Agrobacterium tumefaciens* cell; it may be carried on a microparticle, wherein the microparticle is suitable for ballistic transformation of a plant cell; or it may be contained in a plant cell or protoplast. Further, the expression cassette or vector can be contained in a transformed plant or cells thereof, and the plant may be a dicot or a monocot. In particular, the plant may be a dicotyledonous plant. Preferred transgenic plants are transgenic maize, soybean, barley, alfalfa, sunflower, canola, soybean, cotton, peanut, sorghum, tobacco, sugarbeet, rice, wheat, rye, turfgrass, millet, sugarcane, tomato, or potato.

The invention also provides a method of plant breeding, e.g., to prepare a crossed fertile transgenic plant. The method comprises crossing a fertile transgenic plant comprising a particular expression cassette of the invention with itself or with a second plant, e.g., one lacking the particular expression cassette, to prepare the seed of a crossed fertile transgenic plant comprising the particular expression cassette. The seed is then planted to obtain a crossed fertile transgenic plant. The plant may be a monocot or a dicot. In a particular embodiment, the plant is a dicotyledonous plant. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants.

The transcription regulating nucleotide sequences of the invention further comprise sequences which are complementary to one (hereinafter "test" sequence) which hybridizes under stringent conditions with a nucleic acid molecule as described by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 and 89, as well as RNA which is transcribed from the nucleic acid molecule. When the hybridization is performed under stringent conditions, either the test or nucleic acid molecule of invention is preferably supported, e.g., on a membrane or DNA chip. Thus, either a denatured test or nucleic acid molecule of the invention is preferably first bound to a support and hybridization is effected for a specified period of time at a temperature of, e.g., between 55 and 70° C., in double strength citrate buffered saline (SC) containing 0.1% SDS followed by rinsing of the support at the same temperature but with a buffer having a reduced SC concentration. Depending upon the degree of stringency required such reduced concentration buffers are typically single strength SC containing 0.1% SDS, half strength SC containing 0.1% SDS and one-tenth strength SC containing 0.1% SDS. More preferably hybridization is carried out under high stringency conditions (as defined above).

Virtually any DNA composition may be used for delivery to recipient plant cells, e.g., dicotyledonous cells, to ultimately produce fertile transgenic plants in accordance with the present invention. For example, DNA segments or fragments in the form of vectors and plasmids, or linear DNA segments or fragments, in some instances containing only the DNA element to be expressed in the plant, and the like, may be employed. The construction of vectors, which may be employed in conjunction with the present invention, will be known to those of skill of the art in light of the present disclosure (see, e.g., Sambrook 1989; Gelvin 1990).

The nucleotide sequence of interest linked to one or more of the transcription regulating nucleotide sequences of the invention can, for example, code for a ribosomal RNA, an antisense RNA or any other type of RNA that is not translated into protein. In another preferred embodiment of the invention, said nucleotide sequence of interest is translated into a protein product. The transcription regulating nucleotide molecule and/or nucleotide sequence of interest linked thereto may be of homologous or heterologous origin with respect to the plant to be transformed. A recombinant DNA molecule useful for introduction into plant cells includes that which has been derived or isolated from any source, that may be subsequently characterized as to structure, size and/or function, chemically altered, and later introduced into plants. An example of a nucleotide sequence or segment of interest "derived" from a source, would be a nucleotide sequence or segment that is identified as a useful fragment within a given organism, and which is then chemically synthesized in essentially pure form. An example of such a nucleotide sequence or segment of interest "isolated" from a source, would be nucleotide sequence or segment that is excised or removed from said source by chemical means, e.g., by the use of restriction endonucleases, so that it can be further manipulated, e.g., amplified, for use in the invention, by the methodology of genetic engineering. Such a nucleotide sequence or segment is commonly referred to as "recombinant."

Therefore a useful nucleotide sequence, segment or fragment of interest includes completely synthetic DNA, semi-synthetic DNA, DNA isolated from biological sources, and DNA derived from introduced RNA. Generally, the introduced DNA is not originally resident in the plant genotype which is the recipient of the DNA, but it is within the scope of the invention to isolate a gene from a given plant genotype, and to subsequently introduce multiple copies of the gene into the same genotype, e.g., to enhance production of a given gene product such as a storage protein or a protein that confers tolerance or resistance to water deficit.

The introduced recombinant DNA molecule includes but is not limited to, DNA from plant genes, and non-plant genes such as those from bacteria, yeasts, animals or viruses. The introduced DNA can include modified genes, portions of genes, or chimeric genes, including genes from the same or different genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of untransformed plant.

The introduced recombinant DNA molecule used for transformation herein may be circular or linear, double-stranded or single-stranded. Generally, the DNA is in the form of chimeric DNA, such as plasmid DNA that can also contain coding regions flanked by regulatory sequences, which promote the expression of the recombinant DNA present in the resultant plant. Generally, the introduced recombinant DNA molecule will be relatively small, i.e., less than about 30 kb to minimize any susceptibility to physical, chemical, or enzymatic degradation which is known to increase as the size of the nucleotide molecule increases. As noted above, the number of proteins, RNA transcripts or mixtures thereof, which is introduced into the plant genome, is preferably preselected and defined, e.g., from one to about 5-10 such products of the introduced DNA may be formed.

Two principal methods for the control of expression are known, viz.: overexpression and underexpression. Overexpression can be achieved by insertion of one or more than one extra copy of the selected gene. It is, however, not unknown for plants or their progeny, originally transformed with one or more than one extra copy of a nucleotide sequence, to exhibit the effects of underexpression as well as overexpression. For underexpression there are two principle methods, which are commonly referred to in the art as "antisense downregulation" and "sense downregulation" (sense downregulation is also referred to as "cosuppression"). Generically these processes are referred to as "gene silencing". Both of these methods lead to an inhibition of expression of the target gene.

Obtaining sufficient levels of transgene expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed.

It is specifically contemplated by the inventors that one could mutagenize a promoter to potentially improve the utility of the elements for the expression of transgenes in plants. The mutagenesis of these elements can be carried out at random and the mutagenized promoter sequences screened for activity in a trial-by-error procedure. Alternatively, particular sequences which provide the promoter with desirable expression characteristics, or the promoter with expression enhancement activity, could be identified and these or similar sequences introduced into the sequences via mutation. It is further contemplated that one could mutagenize these sequences in order to enhance their expression of transgenes in a particular species.

The means for mutagenizing a DNA segment encoding a promoter sequence of the current invention are well known to those of skill in the art. As indicated, modifications to promoter or other regulatory element may be made by random, or site-specific mutagenesis procedures. The promoter and other regulatory element may be modified by altering their structure through the addition or deletion of one or more nucleotides from the sequence which encodes the corresponding unmodified sequences.

Mutagenesis may be performed in accordance with any of the techniques known in the art, such as, and not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector, which exists in both a single stranded and double stranded form. Typical vectors useful in site-directed mutagenesis include vectors such as the M13 phage. These phages are readily commercially available and their use is generally well known to those skilled in the art. Double stranded plasmids also are routinely employed in site directed mutagenesis, which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the promoter. An oligonucleotide primer bearing the desired mutated sequence is prepared, generally synthetically. This primer is then annealed with the single-stranded vector, and subjected to DNA polymerizing enzymes such as $E.\ coli$ polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as $E.\ coli$ cells, and cells are selected which include recombinant vectors bearing the mutated sequence arrangement. Vector DNA can then be isolated from these cells and used for plant transformation. A genetic selection scheme was devised by Kunkel et al. (1987) to enrich for clones incorporating mutagenic oligonucleotides. Alternatively, the use of PCR with commercially available thermostable enzymes such as Taq polymerase may be used to incorporate a mutagenic oligonucleotide primer into an amplified DNA fragment that can then be cloned into an appropriate cloning or expression vector. The PCR-mediated mutagenesis procedures of Tomic et al. (1990) and Upender et al. (1995) provide two examples of such protocols. A PCR employing a thermostable ligase in addition to a thermostable polymerase also may be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected promoter-encoding DNA segments using site-directed mutagenesis is provided as a means of producing potentially useful species and is not meant to be limiting, as there are other ways in which sequence variants of DNA sequences may be obtained. For example, recombinant vectors encoding the desired promoter sequence may be treated with mutagenic agents, such as hydroxylamine, to obtain sequence variants.

As used herein; the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (see, for example, Watson and Ramstad, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224. A number of template-dependent processes are available to amplify the target sequences of interest present in a sample, such methods being well known in the art and specifically disclosed herein below.

Where a clone comprising a promoter has been isolated in accordance with the instant invention, one may wish to delimit the essential promoter regions within the clone. One efficient, targeted means for preparing mutagenizing promoters relies upon the identification of putative regulatory elements within the promoter sequence. This can be initiated by comparison with promoter sequences known to be expressed in similar tissue-specific or developmentally unique manner. Sequences, which are shared among promoters with similar expression patterns, are likely candidates for the binding of transcription factors and are thus likely elements that confer expression patterns. Confirmation of these putative regulatory elements can be achieved by deletion analysis of each putative regulatory region followed by functional analysis of each deletion construct by assay of a reporter gene, which is functionally attached to each construct. As such, once a starting promoter sequence is provided, any of a number of different deletion mutants of the starting promoter could be readily prepared.

Functionally equivalent fragments of a transcription regulating nucleotide molecule of the invention can also be obtained by removing or deleting non-essential sequences without deleting the essential one. Narrowing the transcription regulating nucleotide molecule to its essential, transcription mediating elements can be realized in vitro by trial-and-error deletion mutations, or in silico using promoter element search routines. Regions essential for promoter activity often demonstrate clusters of certain, known promoter elements. Such analysis can be performed using available computer algorithms such as PLACE ("Plant Cis-acting Regulatory DNA Elements"; Higo 1999), the BIOBASE database "Transfac" (Biologische Datenbanken GmbH, Braunschweig; Wingender 2001) or the database PlantCARE (Lescot 2002).

A method for producing such regulatory nucleic acid molecules with mutated sequences regulating the same expression specificity as the parent sequence or reference sequence is for example defined in U.S. 61/419,895 and EP 10193800.9.

Preferably, functional equivalent fragments of one of the transcription regulating nucleotide sequences of the invention comprises at least 250 base pairs, preferably, at least 300 base pairs, more preferably at least 400 base pairs, even more preferably 500 base pairs, most preferably 750 base pairs of a transcription regulating nucleotide molecule as described by SEQ ID NO: 1, 2, 3, 4, 5, 6, 7, 8, 9, 10, 11, 12, 13, 14, 15, 16, 17 or 18. More preferably this fragment is starting from the 3'-end of the indicated sequences.

Especially preferred are equivalent fragments of transcription regulating nucleotide sequences, which are obtained by deleting the region encoding the 5'-untranslated region of the mRNA, thus only providing the (untranscribed) promoter region. The 5'-untranslated region can be easily determined by methods known in the art (such as 5'-RACE analysis). Accordingly, some of the transcription regulating nucleotide sequences of the invention are equivalent fragments of other sequences.

An expression cassette of the invention may comprise further regulatory elements. The term in this context is to be understood in a broad meaning comprising all sequences, which may influence construction or function of the expression cassette. Regulatory elements may for example modify transcription and/or translation in prokaryotic or eukaryotic organism. In an preferred embodiment the expression cassette of the invention comprised downstream (in 3'-direction) of the nucleic acid sequence to be expressed a transcription termination sequence and—optionally additional regulatory elements—each operably liked to the nucleic acid sequence to be expressed (or the transcription regulating nucleotide sequence).

Additional regulatory elements may comprise additional promoter, minimal promoters, or promoter elements, which may modify the expression regulating properties. For example the expression may be made depending on certain stress factors such water stress, abscisin (Lam 1991) or heat stress (Schoffl 1989). Furthermore additional promoters or promoter elements may be employed, which may realize expression in other organisms (such as *E. coli* or *Agrobacterium*). Such regulatory elements can be found in the promoter sequences or bacteria such as amy and SPO2 or in the promoter sequences of yeast or fungal promoters (such as ADC1, MFa, AC, P-60, CYC1, GAPDH, TEF, rp28, and ADH).

Furthermore, it is contemplated that promoters combining elements from more than one promoter may be useful. For example, U.S. Pat. No. 5,491,288 discloses combining a Cauliflower Mosaic Virus promoter with a histone promoter. Thus, the elements from the promoters disclosed herein may be combined with elements from other promoters. Promoters, which are useful for plant transgene expression include those that are inducible, viral, synthetic, constitutive (Odell 1985), temporally regulated, spatially regulated, tissue-specific, and spatial-temporally regulated.

Where expression in specific tissues or organs is desired, tissue-specific promoters may be used. In contrast, where gene expression in response to a stimulus is desired, inducible promoters are the regulatory elements of choice. Such inducible promoters may additionally be tissue or organ specifically expressed and or induced. Where continuous expression is desired throughout the cells of a plant, constitutive promoters are utilized. Additional regulatory sequences upstream and/or downstream from the core promoter sequence may be included in expression constructs of transformation vectors to bring about varying levels of expression of heterologous nucleotide sequences in a transgenic plant.

A variety of 5' and 3' transcriptional regulatory sequences are available for use in the present invention. Transcriptional terminators are responsible for the termination of transcription and correct mRNA polyadenylation. The 3' nontranslated regulatory DNA sequence preferably includes from about 50 to about 1,000, more preferably about 100 to about 1,000, nucleotide base pairs and contains plant transcriptional and translational termination sequences. Appropriate transcriptional terminators and those which are known to function in plants include the CaMV 35S terminator, the tml terminator, the nopaline synthase terminator, the pea rbcS E9 terminator, the terminator for the T7 transcript from the octopine synthase gene of *Agrobacterium tumefaciens*, and the 3' end of the protease inhibitor I or II genes from potato or tomato, although other 3' elements known to those of skill in the art can also be employed. Alternatively, one also could use a gamma coixin, oleosin 3 or other terminator from the genus *Coix*.

Preferred 3' elements include those from the nopaline synthase gene of *Agrobacterium tumefaciens* (Bevan 1983), the terminator for the T7 transcript from the octopine synthase gene of *Agrobacterium tumefaciens*, and the 3' end of the protease inhibitor I or II genes from potato or tomato.

As the DNA sequence between the transcription initiation site and the start of the coding sequence, i.e., the untranslated leader sequence, can influence gene expression, one may also wish to employ a particular leader sequence. Preferred leader sequences are contemplated to include those, which include sequences, predicted to direct optimum expression of the attached gene, i.e., to include a preferred consensus leader sequence, which may increase or maintain mRNA stability and prevent inappropriate initiation of translation. The choice of such sequences will be known to those of skill in the art in light of the present disclosure. Sequences that are derived from genes that are highly expressed in plants will be most preferred.

Preferred regulatory elements also include the 5'-untranslated region, introns and the 3'-untranslated region of genes. Such sequences that have been found to enhance gene expression in transgenic plants include intron sequences (e.g., from Adh1, bronze1, actin1, actin 2 (WO 00/760067), or other plant introns as disclosed in WO2011/023537, WO2011/023539, WO2006/094976.

Additional preferred regulatory elements are enhancer sequences or polyadenylation sequences.

The heterologous nucleotide sequence to be expressed is preferably furthermore operably linked to 3'-untranslated regions, transcription termination and/or polyadenylation signal. 3'-untranslated regions are suitable to stabilize mRNA expression and structure. This can result in prolonged presence of the mRNA and thus enhanced expression levels. Termination and polyadenylation signals are suitable to stabilize mRNA expression, to ensure constant mRNA transcript length and to prevent read-through transcription. Especially in multigene expression constructs this is an important feature. Furthermore correct termination of transcription is linked to re-initiation of transcription from the regulatory 5' nucleotide sequence resulting in enhanced expression levels. The above-mentioned signals can be any signal functional in plants and can for example be isolated from plant genes, plant virus genes or other plant pathogens. However, in a preferred embodiment the 3'-untranslated regions, transcription termination and polyadenylation signals are from the genes employed as the source for the promoters of this invention.

Preferred polyadenylation sequences are those from plant genes or *Agrobacterium* T-DNA genes (such as for example the terminator sequences of the OCS (octopine synthase) or NOS (nopaline synthase) genes).

Examples of enhancers include elements from the CaMV 35S promoter, octopine synthase genes (Ellis et al., 1987), the rice actin I gene, the maize alcohol dehydrogenase gene (Callis 1987), the maize shrunken I gene (Vasil 1989), TMV Omega element (Gallie 1989) and promoters from non-plant eukaryotes (e.g. yeast; Ma 1988). Vectors for use in accordance with the present invention may be constructed to include the ocs enhancer element. This element was first identified as a 16 bp palindromic enhancer from the octopine synthase (ocs) gene of ulti-lane (Ellis 1987), and is present in at least 10 other promoters (Bouchez 1989). The use of an enhancer element, such as the ocs elements and particularly multiple copies of the element, will act to increase the level of transcription from adjacent promoters when applied in the context of plant transformation.

An expression cassette of the invention (or a vector derived thereof) may comprise additional functional elements, which are to be understood in the broad sense as all elements, which influence construction, propagation, or function of an expression cassette or a vector or a transgenic organism comprising them. Such functional elements may include origin of replications (to allow replication in bacteria; for the ORI of pBR322 or the P15A ori; Sambrook 1989), or elements required for *Agrobacterium* T-DNA transfer (such as for example the left and/or rights border of the T-DNA).

Ultimately, the most desirable DNA segments for introduction into, for example, a dicot genome, may be homologous genes or gene families which encode a desired trait (e.g., increased yield per acre, fungal resistance) and which are introduced under the control of novel promoters or enhancers, etc., or perhaps even homologous or tissue specific (e.g., root-, collar/sheath-, whorl-, stalk-, earshank-, kernel- or leaf-specific) promoters or control elements. Indeed, it is envisioned that a particular use of the present invention will be the expression of a gene in the epidermis or mesophyll or inducible in the epidermis and/or mesophyll.

Additionally, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane.

A particular example of such a use concerns the direction of a herbicide resistance gene, such as the EPSPS gene, to a particular organelle such as the chloroplast rather than to the cytoplasm. This is exemplified by the use of the rbcs transit peptide which confers plastid-specific targeting of proteins. In addition, it is proposed that it may be desirable to target certain genes responsible for male sterility to the mitochondria, or to target certain genes for resistance to phytopathogenic organisms to the extracellular spaces, or to target proteins to the vacuole.

By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. Targeting of certain proteins may be desirable in order to enhance the stability of the protein (U.S. Pat. No. 5,545,818).

It may be useful to target DNA itself within a cell. For example, it may be useful to target introduced DNA to the nucleus as this may increase the frequency of transformation. Within the nucleus itself it would be useful to target a gene in order to achieve site-specific integration. For example, it would be useful to have a gene introduced through transformation replace an existing gene in the cell. Other elements include those that can be regulated by endogenous or exogenous agents, e.g., by zinc finger proteins, including naturally occurring zinc finger proteins or chimeric zinc finger proteins (see, e.g., U.S. Pat. No. 5,789,538, WO 99/48909; WO 99/45132; WO 98/53060; WO 98/53057; WO 98/53058; WO 00/23464; WO 95/19431; and WO 98/54311) or myb-like transcription factors. For example, a chimeric zinc finger protein may include amino acid sequences, which bind to a specific DNA sequence (the zinc finger) and amino acid sequences that activate (e.g., GAL 4 sequences) or repress the transcription of the sequences linked to the specific DNA sequence.

It is one of the objects of the present invention to provide recombinant DNA molecules comprising a nucleotide sequence according to the invention operably linked to a nucleotide segment of interest.

A nucleotide segment of interest is reflective of the commercial markets and interests of those involved in the development of the crop. Crops and markets of interest changes, and as developing nations open up world markets, new crops and technologies will also emerge. In addition, as the understanding of agronomic traits and characteristics such as yield and heterosis increase, the choice of genes for transformation will change accordingly. General categories of nucleotides of interest include, for example, genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in starch, oil, carbohydrate, or nutrient metabolism, as well as those affecting kernel size, sucrose loading, zinc finger proteins, see, e.g., U.S. Pat. No. 5,789,538, WO 99/48909; WO 99/45132; WO 98/53060; WO 98/53057; WO 98/53058; WO 00/23464; WO 95/19431; and WO 98/54311, and the like.

One skilled in the art recognizes that the expression level and regulation of a transgene in a plant can vary significantly from line to line. Thus, one has to test several lines to find one with the desired expression level and regulation. Once a line is identified with the desired regulation specificity of a chimeric Cre transgene, it can be crossed with lines carrying different inactive replicons or inactive transgene for activation.

Other sequences, which may be linked to the gene of interest, which encodes a polypeptide, are those which can target to a specific organelle, e.g., to the mitochondria, nucleus, or plastid, within the plant cell. Targeting can be achieved by providing the polypeptide with an appropriate targeting peptide sequence, such as a secretory signal peptide (for secretion or cell wall or membrane targeting, a plastid transit peptide, a chloroplast transit peptide, e.g., the chlorophyll a/b binding protein, a mitochondrial target peptide, a vacuole targeting peptide, or a nuclear targeting peptide, and the like. For example, the small subunit of ribulose bisphosphate carboxylase transit peptide, the EPSPS transit peptide or the dihydrodipicolinic acid synthase transit peptide may be used, for examples of plastid organelle targeting sequences (see WO 00/12732). Plastids are a class of plant organelles derived from proplastids and include chloroplasts, leucoplasts, amyloplasts, and chromoplasts. The plastids are major sites of biosynthesis in plants. In addition to photosynthesis in the chloroplast, plastids are also sites of lipid biosynthesis, nitrate reduction to ammonium, and starch storage. And while plastids contain their own circular genome, most of the proteins localized to the plastids are encoded by the nuclear genome and are imported into the organelle from the cytoplasm.

Transgenes used with the present invention will often be genes that direct the expression of a particular protein or polypeptide product, but they may also be non-expressible DNA segments, e.g., transposons such as Ds that do no direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to the recipient cells will often depend on the purpose of the transformation. One of the major purposes of transformation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch properties; oil quantity and quality; and the like. One may desire to incorporate one or more genes conferring any such desirable trait or traits, such as, for example, a gene or genes encoding pathogen resistance.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. For example, plasmids bearing the bar and aroA expression units in either convergent, divergent, or colinear orientation, are considered to be particularly useful. Further preferred combinations are those of an insect resistance gene, such as a Bt gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired.

EXAMPLES

Materials and General Methods

Unless indicated otherwise, chemicals and reagents in the Examples were obtained from Sigma Chemical Company (St. Louis, Mo.), restriction endonucleases were from New England Biolabs (Beverly, Mass.) or Roche (Indianapolis, Ind.), oligonucleotides were synthesized by MWG Biotech Inc. (High Point, N.C.), and other modifying enzymes or kits regarding biochemicals and molecular biological assays were from Clontech (Palo Alto, Calif.), Pharmacia Biotech (Piscataway, N.J.), Promega Corporation (Madison, Wis.), or Stratagene (La Jolla, Calif.). Materials for cell culture media were obtained from Gibco/BRL (Gaithersburg, Md.) or DIFCO (Detroit, Mich.). The cloning steps carried out for the purposes of the present invention, such as, for example, restriction cleavages, agarose gel electrophoresis, purification of DNA fragments, transfer of nucleic acids to nitrocellulose and nylon membranes, linking DNA fragments, transformation of *E. coli* cells, growing bacteria, multiplying phages and sequence analysis of recombinant DNA, are carried out as described by Sambrook (1989). The sequencing of recombinant DNA molecules is carried out using ABI laser fluorescence DNA sequencer following the method of Sanger (Sanger 1977).

Example 1

Identification and Validation of Promoters from Soybean Putatively Conferring Constitutive Expression or Expression in Epidermis of a Plant 1.1 Identification of Promoters Putatively Conferring Constitutive Expression or Expression in Epidermis A soybean gene expression profiling analysis was carried out by a commercial supplier of AFLP comparative expression technology (Keygene N. V., P.O. Box 216, 6700 AE Wageningen, The Netherlands) using RNA samples from 34 soybean tissues generated by BASF (Table 1). AFLP bands were selected for constitutive expression in all tissues and expression in epidermis.

TABLE 1

Soybean samples for AFLP screen

| Sample # | Tissue | Source | Stage | Treatment |
|---|---|---|---|---|
| 1 | Leaf - Epidermis | unifoliolate leaf | V2-3 | |
| 2 | Leaf - mesophyll | unifoliolate leaf | V2-3 | |
| 3 | Leaf - Epidermis* | unifoliolate leaf | V2-3 | mock 8 + 16 h |
| 4 | Leaf - Epidermis* | unifoliolate leaf | V2-3 | +ASR 8 hai |
| 5 | Leaf - Epidermis* | unifoliolate leaf | V2-3 | +ASR 16 hai |
| 6 | Leaf - Epidermis* | unifoliolate leaf | V2-3 | +ASR 112 hai |
| 7 | Leaf - Mesophyll* | unifoliolate leaf | V2-3 | mock 8 + 16 h |
| 8 | Leaf - Mesophyll* | unifoliolate leaf | V2-3 | +ASR 16 hai |
| 9 | Leaf - Mesophyll* | unifoliolate leaf | V2-3 | +ASR 112 hai |
| 10 | Leaf | unifoliolate leaves | V2-3 | |
| 11 | Leaf | trifoliolate leaves | V2-3 | |
| 12 | Leaf | trifoliolate leaves | R1-2 | |
| 13 | Leaf | trifoliolate leaves | R7 | |
| 14 | Stem | complete | VC | |
| 15 | Stem | complete | V2-3 | |
| 16 | Stem | complete | R2 | |
| 17 | Shoot tip | complete | VC | |
| 18 | root | complete | VC | |
| 19 | root | complete | R2 | |
| 20 | flowers | buds | R1 | |
| 21 | fowers | complete | R2 | |
| 22 | embryo | 18-20 days | R5 | |
| 23 | embryo | 5-9 mm | R5 | |
| 24 | embryo | complete | R6 | |
| 25 | embryo | complete | R7 | |
| 26 | embryo | complete | R8 | |

TABLE 1-continued

Soybean samples for AFLP screen

| Sample # | Tissue | Source | Stage | Treatment |
|---|---|---|---|---|
| 27 | whole seeds | 14 days | R4 | |
| 28 | endosperm | 14 days | R4 early | |
| 29 | endosperm | complete | R4 late | |
| 30 | endosperm | complete | R5 | |
| 31 | endosperm | complete | R6 | |
| 32 | siliques | seeds | R3 | |
| 33 | siliques | seeds | R4 | |
| 34 | siliques | seeds | R6 | | hai = hours after infection; ASR = Asian Soybean Rust 1.2 Identification of the Genes Corresponding to AFLP Bands Expressed Sequence Tag (EST) sequences of AFLP bands were used as query for BLASTN searching against a soybean sequence database. The corresponding genes are listed in table 2.

TABLE 2

Overview over corresponding genes for *G. max* promoters conferring constitutive expression and expression in the epidermis

| Feature name | SEQ ID # |
|---|---|
| Glyma11g14950_gene | 220 |
| Glyma14g06680_gene | 222 |
| Glyma02g47670_gene | 224 |
| Glyma14g02930_gene | 226 |
| Glyma17g27610_gene | 228 |

1.3 Confirmation of Allele-Specific Expression Pattern Using Quantitative Reverse Transcriptase-Polymerase Chain Reaction (qRT-PCR)

In order to confirm the native expression patterns of the identified soybean genes in an allele-specific manner, quantitative reverse transcription PCR (qRT-PCR) was performed using total RNA isolated from the same materials as were used for the AFLP expression profiling (Table 1).

Primers for qRT-PCR were designed based on the sequences of the isolated EST fragments using the Vector NTI software package (Invitrogen, Carlsbad, Calif., USA). Primers were designed to distinguish individual alleles of the candidate gene in the tetraploid soybean genome. Primers for qRT-PCR are listed in table 3. The tubulin gene served as a control for normalization purposes.

TABLE 3

Primer sequences for qRT-PCR

| Feature name | Primer | Sequence | SEQ ID # |
|---|---|---|---|
| Glyma11g14950 | Loy1294 | CCTTCATAGACCTGAATCAACACACCG | 90 |
| | Loy1296 | GGAGGAGTCATGACTGTGTTGATTCC | 91 |
| Glyma14g06680 | Loy1275 | CGCCGGGTTTATGTGTC | 92 |
| | Loy1278 | CCGGGGCTAAGTCTAAGTGT | 93 |
| Glyma02g47670 | Loy1420 | CGTCTGCTACAGCGTGTGGAAGGACGAGG | 94 |
| | Loy1421 | GAGACGTGGCGGTGCTTCTTGCGGTAATC | 95 |
| Glyma14g02930 | Loy1425 | TGGAATCAAAGACAGGTAGACTGGC | 96 |
| | Loy1427 | CTGCTTTCAGTGTAATGGTTTCCAGA | 97 |
| Glyma17g27610 | Loy1429 | TTGTCTGGTTTGGAAAGAAGAAAGTTGTGA | 98 |
| | Loy1430 | CACACAGAGCACAAGGAATAGTGGCAAT | 99 |
| Tubulin | Loy1145 | TGGGAATCCACTCAACGAAGT | 100 |
| | Loy1146 | CCTGACAGCATCAGCCATGT | 101 | qRT-PCR was performed using QuantiTect Kit (Qiagen, Hilden, Germany) and SYBR Green qPCR Master Mix (Roche Diagnostics, Mannheim, Germany) in a Roche LightCycler (Roche Diagnostics, Mannheim, Germany). cDNA was synthesized using 800 ng of total RNA and 1 µl reverse transcriptase in a 20 µl volume. The cDNA was diluted with 60 µl of RNAse free water to a final volume of 80 µl. 4 µl of diluted cDNA were used in a 10 µl PCR reaction according to manufacturer's instruction. The thermocycling conditions were as follows: Denature at 95° C. for 2 minutes, and run 45 cycles at 95° C. for 10 seconds and 60° C. for 20 seconds and 72° C. for 20 seconds for amplification. After the final cycle of the amplification, the dissociation curve analysis was carried out to verify that the amplification occurred specifically and no primer dimer product was generated during the amplification process. The tubulin gene (primer sequences in table 3) was used as an endogenous reference gene to normalize the calculation using the Comparative Ct (Cycle of threshold) value method. The DeltaCt value was obtained by subtracting the Ct value of tubulin gene from the Ct value of the respective candidate gene, and the relative transcription quantity (expression level) of the candidate gene was expressed as $2^{-DeltaCt}$.

1.4 Identification of the Promoter Region

For promoter identification purposes, the sequence upstream of the start codon of the identified genes was defined as the respective promoter. To characterize these promoter regions, 5'RACE PCR analyses were performed using the primers listed in table 4.

TABLE 4

Primer sequences for 5'RACE PCR

| Feature name | Primer | Sequence | SEQ ID # |
|---|---|---|---|
| Glyma11g14950 | Loy1685 | CATCGCCGATCAACCGTTCTGTG | 102 |
| Glyma14g06680 | Loy1682 | GACTTAGCCCCGGCGACTCCCATA | 103 |
| Glyma02g47670 | Loy1649 | TGATCAAACGCTCTGTAAACTTTCTTCACA | 104 |
| Glyma14g02930 | Loy1665 | GACTGAACTGGGGTTGAAGGTGAACACT | 105 |
| Glyma17g27610 | Loy1672 | CATCTTCTGGTGCCGAGGCAGGGAT | 106 |

1.5 Isolation of the Promoter Region by PCR Amplification

The promoter regions of the respective genes were isolated via genomic PCR using the following sequence specific primers (table 5):

Promoters putatively conferring constitutive expression or expression in the epidermis amplified with these primer pairs are listed in table 6.

In addition 5'-deletions of the promoters are made by using different 5' primers in combination with the same 3' oligonucleotide primer. The resulting promoters are indicated by their respective length in base pairs (cp. table 6) and the corresponding primer pairs for PCR are listed in table 5.

Promoters are bioinformatically analyzed with MatInspector Professional 8.0.4, Release August 2010 (Genomatix Software GmbH; Munich, Germany) for transcription factor binding sites. Regions free of core motifs are permutated and the resulting nucleic acid sequences are synthesized. The principles for generating permutated promoters that retain their respective tissue specificities are described in EP10193800.9 and US61/419,895. The resulting sequences are indicated by the original identifier of the corresponding gene followed by "_perm" (cp. table 6).

TABLE 5

Primer sequences for PCR amplification of promoters putatively conferring constitutive expression or expression in the epidermis

| Feature name | Primer | Sequence | SEQ ID # |
|---|---|---|---|
| Glyma11g14950_1939bp | Loy1436 | TATATAGGTACCAAAGAGCCAAGTTGTTATTC | 107 |
|  | Loy1437 | TATATACCATGGTACTCACTCACACACAAAC | 108 |
| Glyma14g06680_1056bp | Loy1432 | TATATAGGTACCATTTCCAACTCCTGACTGAGA | 109 |
|  | Loy1433 | TATATACCATGGTCTTTCTCCTCGCCTGGGA | 110 |
| Glyma02g47670_1753bp | Loy1490 | TATATAGGTACCTCTCAATCAAGGCCTTTAT | 111 |
|  | Loy1491 | TATATACCATGGTTAATTAATTTCAATCTCTCCCTCTCTAT | 112 |
| Glyma14g02930_1688bp | Loy1492 | TATATAGGTACCCGGTTATTCTTAATCCTTTTCA | 113 |
|  | Loy1493 | TATATACCATGGTTAATTAAGCTGTGTGACCACTGATG | 114 |
| Glyma17g27610_1889bp | Loy1494 | TATATAGGTACCGATTCTAGATATTGAAGTTTGTGA | 115 |
|  | Loy1495 | TATATACCATGGTTAATTAATGTTGTGTTAACAAAGGGT | 116 |
| Glyma11g14950_500bp | Loy1436.500 | TATATAGGTACCCGCGCTTTACACGGAGTTAGTGAA | 117 |
|  | Loy1437 | TATATACCATGGTACTCACTCACACACAAAC | 108 |

TABLE 5-continued

Primer sequences for PCR amplification of promoters putatively conferring constitutive expression or expression in the epidermis

| Feature name | Primer | Sequence | SEQ ID # |
|---|---|---|---|
| Glyma11g14950_1000bp | Loy1436.1000 | TATATAGGTACCAAGAAAAAAAACATATCGGAGGAGGA | 118 |
| | Loy1437 | TATATACCATGGTACTCACTCACACACAAAC | 108 |
| Glyma11g14950_1500bp | Loy1436.1500 | TATATAGGTACCAATTTCAATTTCTCACCTTTTTAATTGT | 119 |
| | Loy1437 | TATATACCATGGTACTCACTCACACACAAAC | 108 |
| Glyma14g06680_500bp | Loy1432.500 | TATATAGGTACCGGAGAAAAGAAAAACTGTTGAC | 120 |
| | Loy1433 | TATATACCATGGTCTTTCTCCTCGCCTGGGA | 110 |
| Glyma14g06680_700bp | Loy1432.700 | TATATAGGTACCATTTATACCACATGTGGGAAGTATTG | 121 |
| | Loy1433 | TATATACCATGGTCTTTCTCCTCGCCTGGGA | 110 |
| Glyma14g06680_1000bp | Loy1432.1000 | TATATAGGTACCCATCTTTCACGCTACAAAACATTGGT | 122 |
| | Loy1433 | TATATACCATGGTCTTTCTCCTCGCCTGGGA | 110 |
| Glyma02g47670_500bp | Loy1490.500 | TATATAGGTACCCTGAAGATTACACCAGTAGTTAGT | 123 |
| | Loy1491 | TATATACCATGGTTAATTAATTTCAATCTCTCCCTCTCTAT | 112 |
| Glyma02g47670_1000bp | Loy1490.1000 | TATATAGGTACCTATGCCAGAATCAACAATGAAAC | 124 |
| | Loy1491 | TATATACCATGGTTAATTAATTTCAATCTCTCCCTCTCTAT | 112 |
| Glyma02g47670_1500bp | Loy1490.1500 | TATATAGGTACCAGCTAGGTAGCGGGTGGTGGTAGGA | 125 |
| | Loy1491 | TATATACCATGGTTAATTAATTTCAATCTCTCCCTCTCTAT | 112 |
| Glyma14g02930_500bp | Loy1492.500 | TATATAGGTACCCCACCGACCTTTTTTTATATAAAAAAAATC | 126 |
| | Loy1493 | TATATACCATGGTTAATTAAGCTGTGTGACCACTGATG | 114 |
| Glyma14g02930_1000bp | Loy1492.1000 | TATATAGGTACCTTAAATTACATGAATAACGAAATTAAG | 127 |
| | Loy1493 | TATATACCATGGTTAATTAAGCTGTGTGACCACTGATG | 114 |
| Glyma14g02930_1500bp | Loy1492.1500 | TATATAGGTACCAAACAAAATTATCCATCTCACA | 128 |
| | Loy1493 | TATATACCATGGTTAATTAAGCTGTGTGACCACTGATG | 114 |
| Glyma17g27610_500bp | Loy1494.500 | TATATAGGTACCAATAAACATATTAATCAACTATGAAAC | 129 |
| | Loy1495 | TATATACCATGGTTAATTAATGTTGTGTTAACAAAGGGT | 116 |
| Glyma17g27610_1000bp | Loy1494.1000 | TATATAGGTACCAAACTCATTCCACATGGACTGTGGCCT | 130 |
| | Loy1495 | TATATACCATGGTTAATTAATGTTGTGTTAACAAAGGGT | 116 |
| Glyma17g27610_1500bp | Loy1494.1500 | TATATAGGTACCTTGATTAACAAAAGTTTTATAAATAAAC | 131 |
| | Loy1495 | TATATACCATGGTTAATTAATGTTGTGTTAACAAAGGGT | 116 |

TABLE 6

Overview over G. max promoters conferring constitutive expression and expression in the epidermis

| Feature name | SEQ ID # |
|---|---|
| p-Glyma11g14950__1939bp | 1 |
| p-Glyma14g06680__1056bp | 2 |
| p-Glyma02g47670__1753bp | 3 |
| p-Glyma14g02930__1688bp | 4 |
| p-Glyma17g27610__1889bp | 5 |
| p-Glyma11g14950__1939bp_perm | 19 |
| p-Glyma11g14950__500bp | 20 |
| p-Glyma11g14950__1000bp | 21 |
| p-Glyma11g14950__1500bp | 22 |
| p-Glyma14g06680__1056bp_perm | 23 |
| p-Glyma14g06680__500bp | 24 |
| p-Glyma14g06680__700bp | 25 |
| p-Glyma14g06680__1000bp | 26 |
| p-Glyma02g47670__1753bp_perm | 27 |
| p-Glyma02g47670__500bp | 28 |
| p-Glyma02g47670__1000bp | 29 |
| p-Glyma02g47670__1500bp | 30 |
| p-Glyma14g02930__1688bp_perm | 31 |
| p-Glyma14g02930__500bp | 32 |
| p-Glyma14g02930__1000bp | 33 |
| p-Glyma14g02930__1500bp | 34 |
| p-Glyma17g27610__1889bp_perm | 35 |
| p-Glyma17g27610__500bp | 36 |
| p-Glyma17g27610__1000bp | 37 |
| p-Glyma17g27610__1500bp | 38 |

1.6 Cloning of Promoter Elements into the Context of a GUS Reporter Gene Cassette To facilitate sub-cloning, promoter elements were modified by the addition of KpnI+Acc65I restriction enzyme sites at their 5' end and PacI+NcoI sites at their 3' end.

Using the Multisite Gateway System (Invitrogen, Carlsbad, Calif., USA), the promoter::reporter-gene cassettes were assembled into binary constructs for plant transformation. The respective *Glycine max* promoters (with the prefix p- denoting promoter) were used in the reporter gene construct, and betaglucoronidase coding sequence (GUS) was utilized as reporter protein for subsequent histo-chemical analysis.

An ENTR/A vector containing the betaglucoronidase coding sequence followed by the t-nos nopalin synthase transcriptional terminator (Genbank V00087) was generated. *Glycine max* promoters were cloned using the restriction enzyme sites (see above) added by PCR amplification at either end. Positive pENTR/A clones underwent sequence analysis to ensure correctness.

The pENTR/B and pENTR/C did not contain any additional elements. By performing a site-specific recombination (LR-reaction), the created pENTR/A, pENTR/B and pENTR/C were combined with the pSUN destination vector (pSUN derivative) according to the manufacturers (Invitrogen, Carlsbad, Calif., USA) Multisite Gateway manual. The reactions yielded binary vectors LJK291, LJK296, LJK303, LJK304, LJK305 (cp. table7) with the respective *Glycine max* promoter, the GUS coding sequence c-GUS and the t-nos terminator, with promoter molecules having the prefix p-, coding sequences having the prefix c-, and terminator molecules having the prefix t-.

Table 7 shows an overview over reporter gene constructs with promoter elements putatively conferring constitutive expression or expression in the epidermis.

TABLE 7

Overview over G. max reporter gene constructs with promoters conferring constitutive expression or expression in the epidermis

| Feature name | SEQ ID # |
|---|---|
| LJK291 | |
| LJK296 | 256 |
| LJK303 | 257 |
| LJK304 | |
| LJK305 | |

1.7 Generation of Transgenic Soybean Plants (Amended Protocol According to WO2005/121345; Olhoft et al., 2007).

Soybean seed germination, propagation, *A. rhizogenes* and axillary meristem explant preparation, and inoculations were done as previously described (WO2005/121345; Olhoft et al., 2007) with the exception that the LJK291, LJK296, LJK303, LJK304, LJK305 (cp. example 1.6) each contained a mutated AHAS gene driven by the parsley ubiquitin promoter PcUbi4-2, mediating tolerance to imidazolinone herbicides for selection.

1.8 Promoter Evaluation in Transgenic Soybean

Expression patterns and levels driven by the constitutive promoters and promoters putatively conferring expression in the epidermis measured using GUS histo-chemical analysis following a protocol known in the art (Jefferson 1987). GUS expression was assayed in the following vegetative and reproductive tissue for the constitutive promoters at various developmental stages:
1) leaf surface
2) root
3) stem
4) stem section
5) meristem
6) petioles
7) flowers
8) bud
9) embryo
10) seedcoat
11) silique seed-pocket
12) silique end Expression in the epidermis was assayed in leaf surface views and sections based on visual assessment of the GUS staining. LJK291 and LJK296 showed constitutive expression in all analyzed tissues. LJK303, LJK304 and LJK305 showed strong expression in the lower leaf epidermis and parts of the spongy layer of mesophyll as well as some background expression in reproductive stages of the plant and can therefore be considered as epidermis preferential promoters. The permutated promoters and the 5' deleted versions of the promoters show the same expression patterns as the original promoters they are derived from.

The results are indicated in table 8.

TABLE 8

Expression profiles of constitutive promoters and promoters conferring expression in the epidermis

| Construct | Feature Name | Specificity | Events | leaf | upper epidermis | lower epidermis | spongy mesophyll | palisade mesophyll | root | stem |
|---|---|---|---|---|---|---|---|---|---|---|
| LJK291 | p-Glyma11g14950_1939bp | constitutive | 17 | ++ | n.d. | n.d. | n.d. | n.d. | ++ | +++ |
| LJK296 | p-Glyma14g06680_1056bp | constitutive | 15 | +++ | n.d. | n.d. | n.d. | n.d. | ++ | ++ |
| LJK303 | p-Glyma02g47670_1753bp | epidermis | 8 | ++ | + | +++ | +++ | + | n.d. | n.d. |
| LJK304 | P-Glyma14g02930_1688bp | epidermis | 4 | ++ | + | +++ | +++ | + | n.d. | n.d. |
| LJK305 | p-Glyma17g27610_1889bp[ | epidermis | 5 | + | + | ++ | ++ | + | n.d. | n.d. |

| Construct | Stem section | meristem | petioles | flower | bud | embryo | seedcoat | silique seed pocket | silique end | Induction yes/no |
|---|---|---|---|---|---|---|---|---|---|---|
| LJK291 | +++ | + | + | + | + | ++ | +++ | +++ | +++ | no |
| LJK296 | ++ | ++ | ++ | ++ | ++ | +++ | +++ | ++ | ++ | no |
| LJK303 | n.d. | n.d. | n.d. | n.d. | n.d. | + | + | + | + | no |
| LJK304 | n.d. | n.d. | n.d. | n.d. | n.d. | ++ | ++ | ++ | ++ | no |
| LJK305 | n.d. | n.d. | n.d. | n.d. | n.d. | + | + | + | + | no |

0 no GUS staining;
+ minimal GUS staining;
medium GUS staining;
+++ strong GUS staining;
n.d. no analysis Example 2

Identification and Validation of Pathogen-Inducible Promoters from Soybean 2.1 Identification of Pathogen-Inducible Transcripts by AFLP AFLP bands from table 1 were selected for pathogen-inducible expression in epidermis or both mesophyll and epidermis.

2.2 Identification of the Genes Corresponding to AFLP Bands

Expressed Sequence Tag (EST) sequences of AFLP bands were used as query for BLASTN searching against a soybean sequence database. The corresponding genes are listed in table 9

2.3 Identification of Pathogen-Inducible Transcripts by Microarray

In addition to identification of ESTs by AFLP, a microarray experiment was performed in triplicate for samples 3 and 5-8 from table 1, which identified the following genes: Glyma01g33070.2; Glyma01g42660.1 (cp. Table 9).

TABLE 9

Overview over corresponding genes for *G. max* promoters conferring pathogen- inducible expression

| Feature name | SEQ ID # |
|---|---|
| Glyma13g44640_gene | 230 |
| Glyma08g37270_gene | 232 |
| Glyma04g40860.1_gene | 234 |
| Glyma01g33070.2_gene | 236 |
| Glyma15g05820.1_gene | 238 |
| Glyma01g42660.1_gene | 240 |
| Glyma17g14320_gene | 242 |
| Glyma01g01510.1_gene | 244 |

2.4 Confirmation of Allele-Specific Expression Pattern Using Quantitative Reverse Transcriptase-Polymerase Chain Reaction (qRT-PCR)

In order to confirm the native expression patterns of soybean genes in an allele-specific manner from both AFLP and microarray approaches, quantitative reverse transcription PCR (qRT-PCR) was performed using total RNA isolated from the same materials as were used for the AFLP expression profiling and the microarray experiment (cp. table 1).

Primers for qRT-PCR were designed based on the sequences of the isolated EST fragments or on microarray data using the Vector NTI software package (Invitrogen, Carlsbad, Calif., USA). Primers were designed to distinguish individual alleles of the candidate gene in the tetraploid soybean genome. Primers for qRT-PCR are listed in table 10. The tubulin gene served as a control for normalization purposes (cp. table 3).

qRT-PCR was performed using QuantiTect Kit (Qiagen, Hilden, Germany) and SYBR Green qPCR Master Mix (Roche Diagnostics, Mannheim, Germany) in a Roche LightCycler (Roche Diagnostics, Mannheim, Germany). cDNA was synthesized using 800 ng of total RNA and 1 μl reverse transcriptase in a 20 μl volume. The cDNA was diluted with 60 μl of RNAse free water to a final volume of 80 μl. 4 μl of diluted cDNA were used in a 10 μl PCR reaction according to manufacturer's instruction. The thermocycling conditions were as follows: Denature at 95° C. for 2 minutes, and run 45 cycles at 95° C. for 10 seconds and 60° C. for 20 seconds and 72° C. for 20 seconds for amplification. After the final cycle of the amplification, the dissociation curve analysis was carried out to verify that the amplification occurred specifically and no primer dimer product was generated during the amplification process. The tubulin gene (primer sequences in table 2) was used as an endogenous reference gene to normalize the calculation using the Comparative Ct (Cycle of threshold) value method. The DeltaCt value was obtained by subtracting the Ct value of tubulin gene from the Ct value of the respective candidate gene, and the relative transcription quantity (expression level) of the candidate gene was expressed as $2^{-DeltaCt}$.

2.5 Identification of the Promoter Region

For promoter identification purposes, the sequence upstream of the start codon of the identified genes was defined as the respective promoters. To characterize these promoter regions, 5' RACE PCR analyses were performed using the primers listed in table 11.

TABLE 10

Primer sequences for qRT-PCR

| Feature name | Primer | Sequence | SEQ ID # |
|---|---|---|---|
| Glyma13g44640 | Loy1405 | GCCATGCCTCAGCTAACCGACAGATCA | 132 |
|  | Loy1407 | ACAGCCACTGCAGCAACCTGATACAAATGC | 133 |
| Glyma08g37270 | Loy1335 | GCTGGAGCTAGCGCTTATGCACGTCTC | 134 |
|  | Loy1337 | CAGCTGCAACCAATCCACTGATGTG | 135 |
| Glyma04g40860.1 | Loy1306 | AGTGGCTAGACCAGTTGAATTGCAACGA | 136 |
|  | Loy1307 | CATGCAAGCGAGGTGTTTACATTTTGCT | 137 |
| Glyma01g33070.2 | Loy1456 | AAATGGCTTTCGGAGTTTCCCTAGTGGCA | 138 |
|  | Loy1457 | GAACTGAAGCAAGAACAGCATTCCCCACAC | 139 |
| Glyma15g05820.1 | Loy1382 | TCACTATGCCCTCAAAACGGTGACG | 140 |
|  | Loy1383 | GCTTGATCAGATTGCAGAATTCCACGA | 141 |
| Glyma01g42660.1 | Loy1443 | CTCAGGCAGCGAACTTCAACATCACAAAT | 142 |
|  | Loy1444 | CCACGATTCGCCAGGGTTAAGCCTT | 143 |
| Glyma17g14320 | Loy1330 | AAAGAAGGTGGAATTGGAAGGGGC | 144 |
|  | Loy1331 | TTAACGTGGGTGATGGTGAGTGGC | 145 |
| Glyma01g01510.1 | Loy1373 | AACATTGTTTCAGGACATGCACACCG | 146 |
|  | Loy1375 | TGAAGTGGGGGTATTGATCAAGAGCCT | 147 |

TABLE 11

Primer sequences for 5'RACE PCR

| Feature name | Primer | Sequence | SEQ ID # |
|---|---|---|---|
| Glyma13g44640 | Loy1667 | CAGGAATAGGAAGACTCCAACAAGAAGAGC | 148 |
| Glyma08g37270 | Loy1657 | GGCATTGAAGAGAGGGCGCAGAGGCTTG | 149 |
| Glyma04g40860.1 | Loy1307 | CATGCAAGCGAGGTGTTTACATTTTGCT | 150 |
| Glyma01g33070.2 | Loy1765 | AAGCAAGAACAGCATTCCCCACAC | 151 |
| Glyma15g05820.1 | Loy1383 | GCTTGATCAGATTGCAGAATTCCACGA | 152 |
| Glyma01g42660.1 | Loy1663 | GCTTTTCGTGACGGCCATTGTAAATT | 153 |
| Glyma17g14320 | Loy1711 | CAACAAAAACTGCAGAAAGTCCATCC | 154 |
| Glyma01g01510.1 | Loy1766 | ATCCAATAAGCTGCAGCAACCATACCAC | 155 |

2.6 Isolation of the Promoter Region by PCR Amplification

The promoter regions of the respective genes were isolated via genomic PCR using the following sequence specific primers (table 12).

Promoters putatively conferring pathogen-inducible expression amplified with these primer pairs are listed in table 13.

In addition 5'-deletions of the promoters are made by using different 5' primers in combination with the same 3' oligonucleotide primer. The resulting promoters are indicated by their respective length in base pairs (cp. table 13) and the corresponding primer pairs for PCR are listed in table 12.

Promoters are bioinformatically analyzed with MatInspector professional 8.0.4, Release August 2010 (Genomatix Software GmbH; Munich, Germany) for transcription factor binding sites. Regions free of core motifs are permutated and the resulting nucleic acid sequences are synthesized. The principles for generating permutated promoters that retain their respective tissue specificities are described in EP10193800.9 and US61/419,895. The resulting sequences are indicated by the original identifier of the corresponding gene followed by "_perm" (cp. table 13).

TABLE 12

Primer sequences for PCR amplification of pathogen-inducible promoters

| Feature name | Primer | Sequence | SEQ ID # |
|---|---|---|---|
| Glyma13g44640_1047bp | Loy1700 | TATATAGGTACCGGGATGTTTATTTAAGGCATGGTCA | 156 |
|  | Loy1501 | TATATACCATGGTTAATTAACAAGGGAGTGGAA-TAACTT | 157 |
| Glyma08g37270_2043bp | Loy1712 | TATATAGGTACC AGCTCATTACCTCAAATTTCCCTAC | 158 |
|  | Loy1713 | TATATACCATGG TTCTCGCACACACAGAACAGAGA | 159 |
| Glyma04g40860.1_1917bp | Loy1527 | TATATAGGTACCTTTCTTAGATAAACATACGTACGTT | 160 |
|  | Loy1528 | TATATACCATGGTTAATTAATTCTAACAATACAA-AATCTGTATATG | 161 |
| Glyma01g33070.2_1921bp | Loy1525 | TATATAGGTACCAATTGACAAGTTGATTGTTGTA | 162 |
|  | Loy1526 | TATATACCATGGTTAATTAAGGAAATTAACTGAAC-CAATTACT | 163 |
| Glyma15g05820.1_1393bp | Loy1548 | TATATAGGTACCAAATTATAGGTGAAAAAATTC | 164 |
|  | Loy1549 | ATATATCCATGGTTTTGTGAGGAAATTAAAGG | 165 |
| Glyma01g42660.1_1948bp | Loy1518 | TATATAGGTACCTGAGAGAGATGCCAATTTTA-CAAGCC | 166 |
|  | Loy1519 | TATATACCATGGTGTAAATTAATTGCCGTTCGTTA-AAGA | 167 |
| Glyma17g14320_1607bp | Loy1779 | TATATAGGTACCTAAATAATTAATTTATTTCAAACACT | 168 |
|  | Loy1482 | TATATACCATGGTTGCGATATGAACGCAGAGA-GAGG | 169 |
| Glyma01g01510.1_2016bp | Loy1788 | TATATAGGTACCGTTGAAGATTCACCACTTCTC | 170 |
|  | Loy1544 | TATATACCATGGTTAAAGAATTGCAAAGAAGAAG-GAAG | 171 |
| Glyma13g44640_500bp | Loy1700.500 | TATATAGGTACCATAATGTAGCGTTGAATGTACT | 172 |
|  | Loy1501 | TATATACCATGGTTAATTAACAAGGGAGTGGAA-TAACTT | 157 |
| Glyma13g44640_700bp | Loy1700.700 | TATATAGGTACCAGTCACATACTGTTAACAATTATTC | 173 |
|  | Loy1501 | TATATACCATGGTTAATTAACAAGGGAGTGGAA-TAACTT | 157 |
| Glyma13g44640_1000bp | Loy1700.1000 | TATATAGGTACCTAATTAATCACAAAGTGAAGAAC | 174 |
|  | Loy1501 | TATATACCATGGTTAATTAACAAGGGAGTGGAA-TAACTT | 157 |
| Glyma08g37270_500bp | Loy1712.500 | TATATAGGTACCTTATGATTAGTATAAATCTATTG | 175 |
|  | Loy1713 | TATATACCATGGTTCTCGCACACACAGAACAGAGA | 159 |
| Glyma08g37270_1000bp | Loy1712.1000 | TATATAGGTACCTAGATTTTTAAATATTTATAATAA-AATAATAAG | 176 |
|  | Loy1713 | TATATACCATGGTTCTCGCACACACAGAACAGAGA | 159 |
| Glyma08g37270_1500bp | Loy1712.1500 | TATATAGGTACCTCATTAATTGAGTTATTTATATAA-AATG | 177 |
|  | Loy1713 | TATATACCATGGTTCTCGCACACACAGAACAGAGA | 159 |
| Glyma04g40860.1_500bp | Loy1527.500 | TATATAGGTACCTAATATAAGCGGAACTATACGGT | 178 |
|  | Loy1528 | TATATACCATGGTTAATTAATTCTAACAATACAA-AATCTGTATATG | 161 |
| Glyma04g40860.1_1000bp | Loy1527.1000 | TATATAGGTACCGTTGATAAATAATTTTTATGAATAA | 179 |
|  | Loy1528 | TATATACCATGGTTAATTAATTCTAACAATACAA-AATCTGTATATG | 161 |
| Glyma04g40860.1_1500bp | Loy1527.1500 | TATATAGGTACCGAAATATTTGATTCACAAGT | 180 |
|  | Loy1528 | TATATACCATGGTTAATTAATTCTAACAATACAAAATCTGTATATG | 161 |
| Glyma01g33070.2_500bp | Loy1525.500 | TATATAGGTACCATTGAATTCACTAATTTTATATTTTATAATTTG | 181 |
|  | Loy1526 | TATATACCATGGTTAATTAAGGAAATTAACTGAACCAATTACT | 163 |
| Glyma01g33070.2_1000bp | Loy1525.1000 | TATATAGGTACCCAACAGATTAAGATCTAGAATAAATAAAC | 182 |
|  | Loy1526 | TATATACCATGGTTAATTAAGGAAATTAACTGAACCAATTACT | 163 |
| Glyma01g33070.2_1500bp | Loy1525.1500 | TATATAGGTACCTACTTATGAATTAAGCTTAGTTCTTGCA | 183 |
|  | Loy1526 | TATATACCATGGTTAATTAAGGAAATTAACTGAACCAATTACT | 163 |
| Glyma15g05820.1_500bp | Loy1548.500 | TATATAGGTACCAATTTTTTTTTCAGTATTATTTCTATCT | 184 |
|  | Loy1549 | ATATATCCATGGTTTTGTGAGGAAATTAAAGG | 165 |

TABLE 12-continued

Primer sequences for PCR amplification of pathogen-inducible promoters

| Feature name | Primer | Sequence | SEQ ID # |
|---|---|---|---|
| Glyma15g05820.1_700bp | Loy1548.700 | TATATAGGTACCTCATCACAATCGAAAAATTCCATC | 185 |
| | Loy1549 | ATATATCCATGGTTTTGTGAGGAAATTAAAGG | 165 |
| Glyma15g05820.1_1000bp | Loy1548.1000 | TATATAGGTACCGCGCGCGCTCTCTTAGAACTTTTTTTG | 186 |
| | Loy1549 | ATATATCCATGGTTTTGTGAGGAAATTAAAGG | 165 |
| Glyma01g42660.1_500bp | Loy1518.500 | TATATAGGTACCCATTTTCAACATTCAGAGTGGGT | 187 |
| | Loy1519 | TATATACCATGGTGTAAATTAATTGCCGTTCGTTAAAGA | 167 |
| Glyma01g42660.1_1000bp | Loy1518.1000 | TATATAGGTACCTTTTTCACCCAATTAATTAGAGTATTTC | 188 |
| | Loy1519 | TATATACCATGGTGTAAATTAATTGCCGTTCGTTAAAGA | 167 |
| Glyma01g42660.1_1500bp | Loy1518.1500 | TATATAGGTACCGTTTTGCTATTGACTTTTGTTTTATTTCGT | 189 |
| | Loy1519 | TATATACCATGGTGTAAATTAATTGCCGTTCGTTAAAGA | 167 |
| Glyma17g14320_500bp | Loy1779.500 | TATATAGGTACCTTTTTTAATCTACTTTTTATTTGTTTAATC | 190 |
| | Loy1482 | TATATACCATGGTGTTGCGATATGAACGCAGAGAGAGG | 169 |
| Glyma17g14320_1000bp | Loy1779.1000 | TATATAGGTACCTTTAATTTGGAATAATTTTTTTCTTCTC | 191 |
| | Loy1482 | TATATACCATGGTGTTGCGATATGAACGCAGAGAGAGG | 169 |
| Glyma17g14320_1500bp | Loy1779.1500 | TATATAGGTACCTTAGAGGAAAAATTTTGTCATCCATAA | 192 |
| | Loy1482 | TATATACCATGGTGTTGCGATATGAACGCAGAGAGAGG | 169 |
| Glyma01g01510.1_500bp | Loy1788.500 | TATATAGGTACCACATGGCAACATTTTTTTTATCTCT | 193 |
| | Loy1544 | TATATACCATGGTTAAAGAATTGCAAAGAAGAAGGAAG | 171 |
| Glyma01g01510.1_1000bp | Loy1788.1000 | TATATAGGTACCTATATATATATATATAATAAACTATATCT | 194 |
| | Loy1544 | TATATACCATGGTTAAAGAATTGCAAAGAAGAAGGAAG | 171 |
| Glyma01g01510.1_1500bp | Loy1788.1500 | TATATAGGTACCTACCTGTTCACTAGCTAGTTACAAAAATATATC | 195 |
| | Loy1544 | TATATACCATGGTTAAAGAATTGCAAAGAAGAAGGAAG | 171 |

TABLE 13

Overview over G. max promoters conferring pathogen-inducible expression

| Feature name | SEQ ID # |
|---|---|
| p-Glyma13g44640_1047bp | 6 |
| p-Glyma08g37270_2043bp | 7 |
| p-Glyma04g40860.1_1917bp | 8 |
| p-Glyma01g33070.2_1921bp | 9 |
| pGlyma15g05820.1_1393bp | 10 |
| p-Glyma01g42660.1_1948bp | 11 |
| p-Glyma17g14320_1607bp | 12 |
| p-Glyma01g01510.1_2016bp | 13 |
| p-Glyma13g44640_1047bp_perm | 39 |
| p-Glyma13g44640_500bp | 40 |
| p-Glyma13g44640_700bp | 41 |
| p-Glyma13g44640_1000bp | 42 |
| p-Glyma08g37270_2043bp_perm | 43 |
| p-Glyma08g37270_500bp | 44 |
| p-Glyma08g37270_1000bp | 45 |
| p-Glyma08g37270_1500bp | 46 |
| p-Glyma04g40860.1_1917bp_perm | 47 |
| p-Glyma04g40860.1_500bp | 48 |
| p-Glyma04g40860.1_1000bp | 49 |
| p-Glyma04g40860.1_1500bp | 50 |
| p-Glyma01g33070.2_1921bp_perm | 51 |
| p-Glyma01g33070.2_500bp | 52 |
| p-Glyma01g33070.2_1000bp | 53 |
| p-Glyma01g33070.2_1500bp | 54 |
| p-Glyma15g05820.1_1393bp_perm | 55 |
| p-Glyma15g05820.1_500bp | 56 |
| p-Glyma15g05820.1_700bp | 57 |
| p-Glyma15g05820.1_1000bp | 58 |
| p-Glyma01g42660.1_1948bp_perm | 59 |
| p-Glyma01g42660.1_500bp | 60 |
| p-Glyma01g42660.1_1000bp | 61 |
| p-Glyma01g42660.1_1500bp | 62 |
| p-Glyma17g14320_1607bp_perm | 63 |
| p-Glyma17g14320_500bp | 64 |
| p-Glyma17g14320_1000bp | 65 |
| p-Glyma17g14320_1500bp | 66 |
| p-Glyma01g01510.1_2016bp_perm | 67 |
| p-Glyma01g01510.1_500bp | 68 |
| p-Glyma01g01510.1_1000bp | 69 |
| p-Glyma01g01510.1_1500bp | 70 |

2.7 Cloning of Promoter Elements into the Context of a GUS Reporter Gene Cassette To facilitate sub-cloning, promoter elements were modified by the addition of KpnI and Acc65I restriction enzyme sites at their 5' end and PacI and NcoI sites at their 3' end.

Using the Multisite Gateway System (Invitrogen, Carlsbad, Calif., USA), the promoter::reporter-gene cassettes were assembled into binary constructs for plant transformation. The respective *Glycine max* promoters (with the prefix p- denoting promoter) were used in the reporter gene construct, and beta-glucoronidase coding sequence (GUS) was utilized as reporter protein for subsequent histo-chemical analysis.

An ENTR/A vector containing the beta-glucoronidase coding sequence followed by the t-nos nopalin synthase transcriptional terminator (Genbank V00087) was generated. *Glycine max* promoters were cloned using the restriction enzyme sites (see above) added by PCR amplification at either end. Positive pENTR/A clones underwent sequence analysis to ensure correctness.

The pENTR/B and pENTR/C did not contain any additional elements. By performing a site-specific recombination (LR-reaction), the created pENTR/A, pENTR/B and pENTR/C were combined with the pSUN destination vector (pSUN derivative) according to the manufacturers (Invitrogen, Carlsbad, Calif., USA) Multisite Gateway manual. The reactions yielded binary vectors LJK306, LJK331, LJK334, LJK358, LJK360, LJK361, LJK363, LJK372 (cp. table 14) with the respective *Glycine max* promoter, the GUS coding sequence c-GUS and the t-nos terminator, with promoter molecules having the prefix p-, coding sequences having the prefix c-, and terminator molecules having the prefix t-.

Table 14 shows an overview over reporter gene constructs with promoter elements putatively conferring pathogen-inducible expression.

TABLE 14

Overview over G. max reporter gene constructs with
promoters conferring pathogen-inducible expression

| Feature name | SEQ ID # |
|---|---|
| LJK306 | 258 |
| LJK331 | |
| LJK334 | |
| LJK358 | |
| LJK360 | 259 |
| LJK361 | |
| LJK363 | |
| LJK372 | |

2.8 Generation of Transgenic Soybean Plants (Amended Protocol According to WO2005/121345; Olhoft et al., 2007).

Soybean seed germination, propagation, *A. rhizogenes* and axillary meristem explant preparation, and inoculations were done as previously described (WO2005/121345; Olhoft et al., 2007) with the exception that the constructs LJK306, LJK331, LJK334, LJK358, LJK360, LJK361, LJK363, LJK372 (cp. example 2.7) each contained a mutated AHAS gene driven by the parsley ubiquitin promoter PcUbi4-2, mediating tolerance to imidazolinone herbicides for selection.

2.9 Promoter Evaluation in Transgenic Soybean

Expression patterns and levels driven by the putatively pathogen-inducible promoters were measured using GUS histochemical analysis following a protocol known in the art (Jefferson 1987). Soybean transformation was conducted using an *Agrobacterium*-mediated transformation system.

The rust fungus is a wild isolate from Brazil. The plants were inoculated with *P. pachyrhizi*.

In order to obtain appropriate spore material for the inoculation, soy leaves which had been infected with rust 15-20 days ago, were taken 2-3 days before the inoculation and transferred to agar plates (1% agar in $H_2O$). The leaves were placed with their upper side onto the agar, which allowed the fungus to grow through the tissue and to produce very young spores. For the inoculation solution, the spores were knocked off the leaves and were added to a Tween-$H_2O$ solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays a spore density of $1-5\times10^5$ spores/ml was used. For microscopy, a density of $>5\times10^5$ spores/ml was used. The inoculated plants were placed for 24 hours in a darkened greenhouse chamber with an average of 22° C. and >90% of air humidity. The following cultivation was performed in a chamber with an average of 25° C. and 70% of air humidity for 48 hours.

GUS expression for pathogen-inducible promoters putatively conferring expression in the epidermis or in mesophyll and epidermis was assayed in leaf surface views and sections based on visual inspection. All promoters showed inducibility by soybean rust, either preferentially in the epidermis or in both epidermis and mesophyll. The permutated promoters and the 5' deleted versions of the promoters show the same expression patterns as the original promoters they are derived from.

The results are indicated in table 15.

TABLE 15

Expression profiles of pathogen-inducible promoters

| Construct | Feature name | Specificity | events | leaf | leaf section: upper epidermis | leaf section: lower epidermis |
|---|---|---|---|---|---|---|
| LJK306 | p-Glyma13g44640__1047bp | epidermis induced | 12 | ++ | + | ++ |
| LJK331 | p-Glyma08g37270__2043bp | mesophyll + epidermis induced | 12 | ++ | + | ++ |
| LJK334 | p-Glyma04g40860.1__1917bp | mesophyll + epidermis induced | 12 | +++ | ++ | ++ |
| LJK358 | p-Glyma01g33070.2__1921bp | mesophyll + epidermis induced | 17 | + | + | + |
| LJK360 | pGlyma15g05820.1__1393bp | mesophyll + epidermis induced | 16 | +++ | ++ | ++ |
| LJK361 | p-Glyma01g42660.1__1948bp | mesophyll + epidermis induced | 12 | + | 0 | + |
| LJK363 | p-Glyma17g14320__1607bp | mesophyll + epidermis induced | 12 | +++ | ++ | ++ |
| LJK372 | p-Glyma01g01510.1__2016bp | mesophyll + epidermis induced | 14 | ++ | 0 | + |

| Construct | leaf section: spongy mesophyll | leaf section: palisade mesophyll | embryo | seedcoat | silique seed pocket | silique end | Induction yes/no |
|---|---|---|---|---|---|---|---|
| LJK306 | ++ | + | + | + | + | + | y |
| LJK331 | ++ | ++ | 0 | 0 | 0 | 0 | y |
| LJK334 | ++ | ++ | 0 | 0 | 0 | 0 | y |
| LJK358 | + | + | 0 | 0 | 0 | 0 | y |
| LJK360 | +++ | +++ | + | + | + | + | y |
| LJK361 | + | + | 0 | 0 | 0 | 0 | y |

TABLE 15-continued

| Expression profiles of pathogen-inducible promoters | | | | | | | |
|---|---|---|---|---|---|---|---|
| LJK363 | ++ | ++ | 0 | 0 | 0 | 0 | y |
| LJK372 | ++ | ++ | 0 | 0 | 0 | 0 | y |

0 no GUS staining;
+ minimal GUS staining;
medium GUS staining;
+++ strong GUS staining;
n.d. no analysis Example 3

*A. thaliana* Promoters Putatively Conferring Expression in Green Tissue 3.1 Isolation of the Promoter Regions from of *A. thaliana* Putatively Conferring Expression in Green Tissue of Plants by PCR Amplification

*A. thaliana* promoter elements putatively conferring expression in green tissue of plants were amplified by PCR using the primers listed in table 21. Preferentially the cloned region encompassed 1-2 kb upstream of the transcriptional start site or up to the stop codon of the previous open-reading frame. The corresponding genes are listed in table 22. The corresponding promoter sequences are listed in table 23.

In addition 5'-deletions of the promoters are made by using different 5' primers in combination with the same 3' oligonucleotide primer. The resulting promoters are indicated by their respective length in base pairs (cp. table 23) and the corresponding primer pairs for PCR are listed in table 21.

Promoters are bioinformatically analyzed with MatInspector professional 8.0.4, Release August 2010 (Genomatix Software GmbH; Munich, Germany) for transcription factor binding sites. Regions free of core motifs are permutated and the resulting nucleic acid sequences are synthesized. The principles for generating permutated promoters that retain their respective tissue specificities are described in EP10193800.9 and US61/419,895. The resulting sequences are indicated by the original identifier of the corresponding gene followed by "_perm" (cp. table 23).

TABLE 21

Primer sequences for PCR amplification A. thaliana promoters putatively conferring expression in green tissue of plants

| Gene ID | Primer | Sequence | SEQ ID # |
|---|---|---|---|
| At1g30380_1970bp | Loy1116 | TATATACCCGGGTACCATGCAGAGGAT-CAAGAAGATTCTCC | 196 |
|  | Loy1117 | TATATACCATGGTTTCTTAGTTGATTCTA-CAAATCTTTTATTTTC | 197 |
| At1g49750_1922bp | Loy1124 | TATATACCCGGGTACCGTGAAAGCAGT-GAAGCCGTGA | 198 |
|  | Loy1125 | TATATACCATGGTGAGTTGATGA-GATTTTGTGGTGAGT | 199 |
| At3g62410_332bp | Loy1128 | TATATACCCGGGTACCGACATCTGTCTT-GACTTTTCCTTAAACAGTGTGTG | 200 |
|  | Loy1133 | TATATACCATGGCTTTGGATGGAGAAGG-TACACGGCAG | 201 |
| At1g61520_1970bp | Loy1120 | TATATACCCGGGTACCGACGAACT-CATGCTACTACTACAG | 202 |
|  | Loy1121 | TATATAACATGTT-GAGCTCTTTCTCTGTTCCT-CAACTCTTTTCT | 203 |
| At1g65490_1953bp | Loy1130 | TATATACCCGGGTACCGAAACGAAACT-GAACCGCCTCCTTT | 204 |
|  | Loy1131 | TATATAACATGTT-GAGCTCTTCGTTCTTCGTTGCGTTTTTGG TCATCG | 205 |
| At1g30380_500bp | Loy1116.500 | TATATACCCGGGTACCTGACTAAT-TAAGCTCGAAAGTGTTCTTCA | 206 |
|  | Loy1117 | TATATACCATGGTTTCTTAGTTGATTCTA-CAAATCTTTTATTTTC | 197 |
| At1g30380_1000bp | Loy1116.1000 | TATATACCCGGGTACCGGCTTTTGCGT-TAGGTTATATAACTCCA | 207 |
|  | Loy1117 | TATATACCATGGTTTCTTAGTTGATTCTA-CAAATCTTTTATTTTC | 197 |
| At1g30380_1500bp | Loy1116.1500 | TATATACCCGGGTACCTGTAGCAA-GAATTGATCGATATGCTTTG | 208 |
|  | Loy1117 | TATATACCATGGTTTCTTAGTTGATTCTA-CAAATCTTTTATTTTC | 197 |
| At1g49750_500bp | Loy1124.500 | TATATACCCGGGTACCGGACTCAATAAA-CAACTCAAAGATGA | 209 |
|  | Loy1125 | TATATACCATGGTGAGTTGATGA-GATTTTGTGGTGAGT | 199 |

TABLE 21-continued

Primer sequences for PCR amplification A. thaliana promoters putatively conferring expression in green tissue of plants

| Gene ID | Primer | Sequence | SEQ ID # |
|---|---|---|---|
| At1g49750_1000bp | Loy1124.1000 | TATATACCCGGGTACCTCACT-GATGTTCTCTAATGAACGTTC | 210 |
|  | Loy1125 | TATATACCATGGTGAGTTGATGA-GATTTTGTGGTGAGT | 199 |
| At1g49750_1500bp | Loy1124.1500 | TATATACCCGGGTACCAAGTGAAAATA-TAATATTCATACCTCTTG | 211 |
|  | Loy1125 | TATATACCATGGTGAGTTGATGA-GATTTTGTGGTGAGT | 199 |
| At3g62410_100bp | Loy1128.100 | TATATACCCGGGTACCACGCACACTTCA-TATATCTTG | 212 |
|  | Loy1133 | TATATACCATGGCTTTGGATGGAGAAGG-TACACGGCAG | 201 |
| At3g62410_200bp | Loy1128.200 | TATATACCCGGGTACCAAATTTTCAA-CATCGTACTGCTTCATAAAC | 213 |
|  | Loy1133 | TATATACCATGGCTTTGGATGGAGAAGG-TACACGGCAG | 201 |
| At1g61520_500bp | Loy1120.500 | TATATACCCGGGTACCGTTGAATTGTTA-TATCAAAATTTGA | 214 |
|  | Loy1121 | TATATAACATGTT-GAGCTCTTTCTCTGTTCCT-CAACTCTTTTCT | 203 |
| At1g61520_1000bp | Loy1120.1000 | TATATACCCGGGTACCTTTGGCTGAAT-CAGCTTCAGCAGA | 215 |
|  | Loy1121 | TATATAACATGTT-GAGCTCTTTCTCTGTTCCT-CAACTCTTTTCT | 203 |
| At1g61520_1500bp | Loy1120.1500 | TATATACCCGGGTAC-CAATGGTTCTGTTGCTCCTAATGTAGA | 216 |
|  | Loy1121 | TATATAACATGTT-GAGCTCTTTCTCTGTTCCT-CAACTCTTTTCT | 203 |
| At1g65490_500bp | Loy1130.500 | TATATACCCGGGTACCTTTTGTAAA-CAATTTTTGTGATATATAT | 217 |
|  | Loy1131 | TATATAACATGTT-GAGCTCTTCGTTCTTCGTTGCGTTTTTGGTCATCG | 205 |
| At1g65490_1000bp | Loy1130.1000 | TATATACCCGGGTACCAGAATTTTAAA-GACACACAAAGCA | 218 |
|  | Loy1131 | TATATAACATGTT-GAGCTCTTCGTTCTTCGTTGCGTTTTTGGTCATCG | 205 |
| At1g65490_1500bp | Loy1130.1500 | TATATACCCGGGTACCACCGCTTAA-TATCGTATGATTAG | 219 |
|  | Loy1131 | TATATAACATGTT-GAGCTCTTCGTTCTTCGTTGCGTTTTTGGTCATCG | 205 |

TABLE 22

Overview over corresponding genes for *A. thaliana* promoters conferring expression in green tissue of plants

| Feature name | SEQ ID # |
|---|---|
| At1g30380_gene | 246 |
| At1g49750_gene | 248 |
| At3g62410_gene | 250 |
| At1g61520_gene | 252 |
| At1g65490_gene | 254 |

TABLE 23

Overview over *A. thaliana* promoters conferring expression in green tissue of plants

| Feature name | SEQ ID # |
|---|---|
| p-mes-At1g30380__1970bp | 14 |
| p-mes-At1g49750__1922bp | 15 |
| p-mes-At3g62410__332bp | 16 |

TABLE 23-continued

Overview over *A. thaliana* promoters conferring expression in green tissue of plants

| Feature name | SEQ ID # |
|---|---|
| p-photo-At1g61520__1970bp | 17 |
| p-mes-At1g65490__1953bp | 18 |
| p-mes-At1g30380__1970bp__perm | 71 |
| p-mes-At1g30380__500bp | 72 |
| p-mes-At1g30380__1000bp | 73 |
| p-mes-At1g30380__1500bp | 74 |
| p-mes-At1g49750__1922bp__perm | 75 |
| p-mes-At1g49750__500bp | 76 |
| p-mes-At1g49750__1000bp | 77 |
| p-mes-At1g49750__1500bp | 78 |
| p-mes-At3g62410__332bp__perm | 79 |
| p-mes-At3g62410__100bp | 80 |
| p-mes-At3g62410__200bp | 81 |
| p-photo-At1g61520__1970bp__perm | 82 |
| p-photo-At1g61520__500bp | 83 |
| p-photo-At1g61520__1000bp | 84 |
| p-photo-At1g61520__1500bp | 85 |
| p-mes-At1g65490__1953bp__perm | 86 |

TABLE 23-continued

Overview over *A. thaliana* promoters conferring
expression in green tissue of plants

| Feature name | SEQ ID # |
|---|---|
| p-mes-At1g65490__500bp | 87 |
| p-mes-At1g65490__1000bp | 88 |
| p-mes-At1g65490__1500bp | 89 |

3.2 Cloning of Promoter Elements into the Context of a GFP Reporter Gene Cassette To facilitate sub-cloning the following restriction sites were added to the ends of the promoter element (table 24):

TABLE 24

Restriction enzyme sites for cloning *A. thaliana* promoters
putatively conferring expression in green tissue of plants

| Promoter | 5'end | 3'end |
|---|---|---|
| p-mes-At1g30380__1970bp | Kpnl | NcoI |
| p-mes-At1g49750__1922bp | Kpnl | NcoI |
| p-mes-At3g62410__332bp | Kpnl | NcoI |
| p-photo-At1g61520__1970bp | Kpnl | PciI |
| p-mes-At1g65490__1953bp | Kpnl | PciI |

Using the Multisite Gateway System (Invitrogen, Carlsbad, Calif., USA), the promoter::reporter-gene cassettes were assembled into binary constructs for plant transformation. The respective *Arabidopsis thaliana* promoters (with the prefix p- denoting promoter) were used in the reporter gene construct, and Green Fluorescent Protein coding sequence (c-AcGFP1; Clontech Laboratories Inc., Mountain View, Calif., USA) was utilized as reporter protein for subsequent fluorescence microscopic analysis.

An ENTR/A vector containing the Green Fluorescent protein coding sequence followed by the t-OCS *agrobacterium* terminator (Genbank DQ005456) was generated. *Arabidopsis thaliana* promoters were cloned using the restriction enzyme sites (see above) added by PCR amplification at either end. Positive pENTR/A clones underwent sequence analysis to ensure correctness.

The pENTR/B and pENTR/C did not contain any additional elements. By performing a site-specific recombination (LR-reaction), the created pENTR/A, pENTR/B and pENTR/C were combined with the pSUN destination vector (pSUN derivative) according to the manufacturers (Invitrogen, Carlsbad, Calif., USA) Multisite Gateway manual. The reactions yielded binary vectors LJK186, LJK189, LJK190, LJK192 and LJK193 (cp. table 25); with the respective *Arabidopsis thaliana* promoter, the Green Fluorescent Protein coding sequence c-AcGFP1 and the t-OCS terminator, with promoter molecules having the prefix p-, coding sequences having the prefix c-, and terminator molecules having the prefix t-.

TABLE 25

GFP reporter gene constructs for *A. thaliana* promoters
putatively conferring expression in green tissue of plants

| Vector | promoter element used | SEQ ID # |
|---|---|---|
| LJK186 | p-mes-At1g30380__1970bp | 260 |
| LJK189 | p-mes-At1g49750__1922bp | |
| LJK190 | p-mes-At3g62410__332bp | |
| LJK192 | p-photo-At1g61520__1970bp | |
| LJK193 | p-mes-At1g65490__1953bp | |

3.3 Test of the *A. thaliana* Promoters Putatively Conferring Expression in Green Tissue of Plants in Transgenic Soybean Expression patterns and levels driven by the promoters putatively conferring expression in green tissue of plants were measured using GFP analysis. Analysis was performed with the Leica DM5000B microscope and the DFC490 camera with the following settings: Saturation 1.01; Gain 1; Exposure 2.1s; GFP-filter: L5; Excitation 480/40 nm; Dichromatic mirror: 505 nm; Suppression filter: 527/30 nm.

The three promoter elements in vectors LJK 189, LJK 190 and LJK 192 showed medium to strong expression based on visual analysis exclusively in the mesophyll layer of leaves and can thus be rated mesophyll-specific. Promoter elements corresponding to LJK186 and LJK193 conferred preferential expression in the mesophyll layer of leaves as well as weak expression in the green tissue of the shoot and can thus be rated mesophyll-preferential. The permutated promoters and the 5' deleted versions of the promoters show the same expression patterns as the original promoters they are derived from.

The results are listed in table 26.

TABLE 26

Expression profiles of *A. thaliana* promoters conferring expression in the green tissue of plants

| | | | expression level | | | | | |
|---|---|---|---|---|---|---|---|---|
| construct | Putative specificity | promoter | Leaf mesophyll | Other leaf tissues | shoot (chlorophyll containing layer) | shoot (non-green) | root | flower |
| LJK186 | mesophyll | p-mes-At1g30380__1970bp | +++ | 0 | + | 0 | 0 | 0 |
| LJK189 | mesophyll | p-mes-At1g49750__1922bp | ++ | 0 | 0 | 0 | 0 | 0 |
| LJK190 | mesophyll | p-mes-At3g62410__332bp | ++ | 0 | 0 | 0 | 0 | 0 |
| LJK192 | mesophyll | p-photo-At1g61520__1970bp | +++ | 0 | 0 | 0 | 0 | 0 |
| LJK193 | mesophyll | p-mes-At1g65490__1953bp | +++ | 0 | + | 0 | 0 | 0 |

0 no expression;
+ minimal expression;
medium expression;
+++ strong expression;
n.d. no analysis

TABLE 27

Overview of Promoters of the Invention and corresponding homologs and fragments thereof

| Original promoter | | derivative promoters | |
|---|---|---|---|
| Seq ID NO | feature name | Seq ID NO | feature name |
| 1 | p-Glyma11g14950__1939bp | 19 | p-Glyma11g14950__1939bp__perm |
| | | 20 | p-Glyma11g14950__500bp |
| | | 21 | p-Glyma11g14950__1000bp |
| | | 22 | p-Glyma11g14950__1500bp |
| 2 | p-Glyma14g06680__1056bp | 23 | p-Glyma14g06680__1056bp__perm |
| | | 24 | p-Glyma14g06680__500bp |
| | | 25 | p-Glyma14g06680__700bp |
| | | 26 | p-Glyma14g06680__1000bp |
| 3 | p-Glyma02g47670__1753bp | 27 | p-Glyma02g47670__1753bp__perm |
| | | 28 | p-Glyma02g47670__500bp |
| | | 29 | p-Glyma02g47670__1000bp |
| | | 30 | p-Glyma02g47670__1500bp |
| 4 | p-Glyma14g02930__1688bp | 31 | p-Glyma14g02930__1688bp__perm |
| | | 32 | p-Glyma14g02930__500bp |
| | | 33 | p-Glyma14g02930__1000bp |
| | | 34 | p-Glyma14g02930__1500bp |
| 5 | p-Glyma17g27610__1889bp | 35 | p-Glyma17g27610__1889bp__perm |
| | | 36 | p-Glyma17g27610__500bp |
| | | 37 | p-Glyma17g27610__1000bp |
| | | 38 | p-Glyma17g27610__1500bp |
| 6 | p-Glyma13g44640__1047bp | 39 | p-Glyma13g44640__1047bp__perm |
| | | 40 | p-Glyma13g44640__500bp |
| | | 41 | p-Glyma13g44640__700bp |
| | | 42 | p-Glyma13g44640__1000bp |
| 7 | p-Glyma08g37270__2043bp | 43 | p-Glyma08g37270__2043bp__perm |
| | | 44 | p-Glyma08g37270__500bp |
| | | 45 | p-Glyma08g37270__1000bp |
| | | 46 | p-Glyma08g37270__1500bp |
| 8 | p-Glyma04g40860.1__1917bp | 47 | p-Glyma04g40860.1__1917bp__perm |
| | | 48 | p-Glyma04g40860.1__500bp |
| | | 49 | p-Glyma04g40860.1__1000bp |
| | | 50 | p-Glyma04g40860.1__1500bp |
| 9 | p-Glyma01g33070.2__1921bp | 51 | p-Glyma01g33070.2__1921bp__perm |
| | | 52 | p-Glyma01g33070.2__500bp |
| | | 53 | p-Glyma01g33070.2__1000bp |
| | | 54 | p-Glyma01g33070.2__1500bp |
| 10 | pGlyma15g05820.1__1393bp | 55 | p-Glyma15g05820.1__1393bp__perm |
| | | 56 | p-Glyma15g05820.1__500bp |
| | | 57 | p-Glyma15g05820.1__700bp |
| | | 58 | p-Glyma15g05820.1__1000bp |
| 11 | p-Glyma01g42660.1__1948bp | 59 | p-Glyma01g42660.1__1948bp__perm |
| | | 60 | p-Glyma01g42660.1__500bp |
| | | 61 | p-Glyma01g42660.1__1000bp |
| | | 62 | p-Glyma01g42660.1__1500bp |
| 12 | p-Glyma17g14320__1607bp | 63 | p-Glyma17g14320-1607bp__perm |
| | | 64 | p-Glyma17g14320__500bp |
| | | 65 | p-Glyma17g14320__1000bp |
| | | 66 | p-Glyma17g14320__1500bp |
| 13 | p-Glyma01g01510.1__2016bp | 67 | p-Glyma01g01510.1__2016bp__perm |
| | | 68 | p-Glyma01g01510.1__500bp |
| | | 69 | p-Glyma01g01510.1__1000bp |
| | | 70 | p-Glyma01g01510.1__1500bp |
| 14 | p-mes-At1g30380__1970bp | 71 | p-mes-At1g30380__1970bp__perm |
| | | 72 | p-mes-At1g30380__500bp |
| | | 73 | p-mes-At1g30380__1000bp |
| | | 74 | p-mes-At1g30380__1500bp |
| 15 | p-mes-At1g49750__1922bp | 75 | p-mes-At1g49750__1922bp__perm |
| | | 76 | p-mes-At1g49750__500bp |
| | | 77 | p-mes-At1g49750__1000bp |
| | | 78 | p-mes-At1g49750__1500bp |
| 16 | p-mes-At3g62410__332bp | 79 | p-mes-At3g62410__332bp__perm |
| | | 80 | p-mes-At3g62410__100bp |
| | | 81 | p-mes-At3g62410__200bp |
| 17 | p-photo-At1g61520__1970bp | 82 | p-photo-At1g61520__1970bp__perm |
| | | 83 | p-photo-At1g61520__500bp |
| | | 84 | p-photo-At1g61520__1000bp |
| | | 85 | p-photo-At1g61520__1500bp |
| 18 | p-mes-At1g65490__1953bp | 86 | p-mes-At1g65490__1953bp__perm |
| | | 87 | p-mes-At1g65490__500bp |
| | | 88 | p-mes-At1g65490__1000bp |
| | | 89 | p-mes-At1g65490__1500bp |

The invention claimed is:

1. An expression cassette for regulating expression in plants comprising
   a) at least one nucleic acid molecule capable of regulating expression in plants selected from the group consisting of:
      i) a nucleic acid molecule comprising a nucleic acid sequence selected from the group consisting of SEQ ID NOS: 3, 27, 28, 29 and 30,
      ii) a fragment of at least 1000 consecutive bases of a nucleic acid molecule comprising a nucleic acid sequence selected from the group consisting of SEQ ID NOS: 3, 27, 29 and 30,
      iii) a nucleic acid molecule with a sequence identity of at least 98% to a transcription-regulating nucleic acid molecule comprising a nucleic acid sequence selected from the group consisting of SEQ ID NOS: 3, 27, 28, 29 and 30, and
      iv) a nucleic acid molecule of at least 1000 consecutive bases with a sequence identity of at least 98% to a transcription-regulating nucleic acid molecule comprising a nucleic acid sequence selected from the group consisting of SEQ ID NOS: 3, 27, 29, and 30, and functionally linked thereto
   b) at least one nucleic acid molecule which is heterologous in relation to said nucleic acid molecule capable of regulating expression in plants.

2. A vector comprising the expression cassette of claim 1.

3. A transgenic host cell or non-human organism comprising at least one nucleic acid molecule capable of regulating expression in plants selected from the group consisting of:
   i) a nucleic acid molecule comprising a nucleic acid sequence selected from the group consisting of SEQ ID NOS: 3, 27, 28, 29 and 30,
   ii) a fragment of at least 1000 consecutive bases of a nucleic acid molecule comprising a nucleic acid sequence selected from the group consisting of SEQ ID NOS: 3, 27, 29 and 30,
   iii) a nucleic acid molecule with a sequence identity of at least 98% to a transcription-regulating nucleic acid molecule comprising a nucleic acid sequence selected from the group consisting of SEQ ID NOS: 3, 27, 28, 29 and 30, and
   iv) a nucleic acid molecule of at least 1000 consecutive bases with a sequence identity of at least 98% to a transcription-regulating nucleic acid molecule comprising a nucleic acid sequence selected from the group consisting of SEQ ID NOS: 3, 27, 29, and 30.

4. A transgenic plant or plant cell comprising at least one nucleic acid molecule capable of regulating expression in plants selected from the group consisting of:
   i) a nucleic acid molecule comprising a nucleic acid sequence selected from the group consisting of SEQ ID NOS: 3, 27, 28, 29 and 30,
   ii) a fragment of at least 1000 consecutive bases of a nucleic acid molecule comprising a nucleic acid sequence selected from the group consisting of SEQ ID NOS: 3, 27, 29 and 30,
   iii) a nucleic acid molecule with a sequence identity of at least 98% to a transcription-regulating nucleic acid molecule comprising a nucleic acid sequence selected from the group consisting of SEQ ID NOS: 3, 27, 28, 29 and 30, and
   iv) a nucleic acid molecule of at least 1000 consecutive bases with a sequence identity of at least 98% to a transcription-regulating nucleic acid molecule comprising a nucleic acid sequence selected from the group consisting of SEQ ID NOS: 3, 27, 29, and 30.

5. The transgenic plant or plant cell of claim 4, wherein said plant or plant cell is from a dicotyledonous plant.

6. A method for the production of an expression cassette comprising the steps of:
   a. providing a nucleic acid molecule capable of regulating expression in plants selected from the group consisting of:
      i) a nucleic acid molecule comprising a nucleic acid sequence selected from the group consisting of SEQ ID NOS: 3, 27, 28, 29 and 30,
      ii) a fragment of at least 1000 consecutive bases of a nucleic acid molecule comprising a nucleic acid sequence selected from the group consisting of SEQ ID NOS: 3, 27, 29 and 30,
      iii) a nucleic acid molecule with a sequence identity of at least 98% to a transcription-regulating nucleic acid molecule comprising a nucleic acid sequence selected from the group consisting of SEQ ID NOS: 3, 27, 28, 29 and 30, and
      iv) a nucleic acid molecule of at least 1000 consecutive bases with a sequence identity of at least 98% to a transcription-regulating nucleic acid molecule comprising a nucleic acid sequence selected from the group consisting of SEQ ID NOS: 3, 27, 29, and 30; and,
   b. functionally linking said nucleic acid molecule to a nucleic acid molecule heterologous to said nucleic acid molecule.

7. A method for the production of a transgenic plant comprising the steps of:
   a. providing the expression cassette of claim 1 ;
   b. transforming said expression cassette into a plant part or plant cell; and
   c. regenerating a plant from said transformed plant part or plant cell.

8. A transgenic host cell or non-human organism comprising the expression cassette of claim 1.

9. A transgenic plant or plant cell comprising the expression cassette of claim 1.

10. A method for the production of a transgenic plant comprising the steps of:
    a. providing the vector of claim 2;
    b. transforming said vector into a plant part or plant cell; and
    c. regenerating a plant from said transformed plant part of plant cell.

* * * * *

UNITED STATES PATENT AND TRADEMARK OFFICE
CERTIFICATE OF CORRECTION

PATENT NO. : 9,624,499 B2  
APPLICATION NO. : 14/005402  
DATED : April 18, 2017  
INVENTOR(S) : Josef Martin Kuhn et al.

Page 1 of 1

It is certified that error appears in the above-identified patent and that said Letters Patent is hereby corrected as shown below:

On the Title Page

At item (57), Line 1, "Isolated nucleic" should be -- Nucleic --.

At item (57), Line 2, "[cassettes," should be -- cassettes, --.

In the Claims

At Column 344, Line 57, "part of" should be -- part or --.

Signed and Sealed this  
Twenty-fourth Day of April, 2018

Andrei Iancu  
*Director of the United States Patent and Trademark Office*

SEQUENCE LISTING

<160> NUMBER OF SEQ ID NOS: 260

<210> SEQ ID NO 1
<211> LENGTH: 1945
<212> TYPE: DNA
<213> ORGANISM: Glycine max

<400> SEQUENCE: 1

| | | | | | |
|---|---|---|---|---|---|
| ccaaagagcc | aagttgttat | tccttctatg | tgttatttgt | tattctctca | acacctttgt | 60 |
| ggggctctct | ctctcccccc | gccctctcgt | ttctttaaac | cacataacac | actagatatg | 120 |
| ttttgcaatg | cactttgctt | atatgtgtaa | ttccatttaa | acaagttgca | aaaagagata | 180 |
| ttaccatata | ttttaagagt | gtgtttggat | ggaggaattt | aaaattctga | gaaatttta | 240 |
| attctaaaaa | ttttaaatac | ttcaattgaa | attcttttat | tttcaaaatt | ttgtgtttgg | 300 |
| ataaaaaaag | ttaaaattat | gagggtgaaa | aaaatgaat | gaaaaaaga | aaagatatga | 360 |
| ttggtgtgct | agttcctcta | tgccgagacc | caacaatcaa | tgttccagaa | tcttagacgg | 420 |
| tgtttcttga | taagaagaga | atttcaattt | ctcaccttt | taattgttta | aaattctgtt | 480 |
| ttaaaattcc | aaaattttaa | attcttcata | aaaaaacat | tcaaacaatg | aattatagat | 540 |
| tacagaaatt | caaattcttt | gataaagtat | ttttctcagt | taaaattctc | tatctaaaca | 600 |
| tactgtaaaa | atgtcaaaaa | ctccatcaga | tttgtaattt | catttaaaca | tgtaaaaatt | 660 |
| caagaaaatc | tttgtgaaat | tggagatgag | aaaaacacat | tagtttaaat | caagaaaaac | 720 |
| atgaaagaat | tagaaaaaat | aattaaaata | agaatttat | cttatttgt | gagaaaaaat | 780 |
| ttaagcaaat | caaatgtgag | aaaatgaaga | gaataaggta | aataagtatt | taaatttata | 840 |
| gtccttcata | aaaagttta | taatttatac | aagtgatatt | tattcagtat | tttctttaa | 900 |
| aatatttaat | tactattttt | ttatgttaaa | tatatttaa | agaaaaaaaa | catatcggag | 960 |
| gaggataaaa | aactgtaaaa | aaagaatttg | attagtaacg | agtaaattt | gaaaatatga | 1020 |
| actgatgatt | tttttagttg | cgtattttat | aagataagat | aagactatat | tatttttat | 1080 |
| ttagtatttt | tttatctttt | aaaagattaa | ataaaaatat | taattatca | ttgattttta | 1140 |
| aaatatcttg | aacatatatc | tgataagata | agagtagatt | attttttatt | tagtagtttt | 1200 |
| tacacttta | aaatattaaa | ttaaaatatt | gttattatta | ttatttttta | aggttaaatt | 1260 |
| taaagctact | atcttatata | ctcaagatat | aatttagaga | acgattgaat | tgaaaagaaa | 1320 |
| atcgtaaaag | taaagccag | ggtgattact | gatttactgc | aatgagtgaa | ttttgaaaag | 1380 |
| ataataaaat | catgcttttt | gaacgggcaa | gaaacacacc | aaaaataaaa | cttaactaac | 1440 |
| gcgctttaca | cggagttagt | gaaatccaat | tggccagtta | tctaaagcgc | acggacgacg | 1500 |
| tcattaattc | aaccaatggc | gcgggagaat | cacagataca | atctatccaa | taccaaaaaa | 1560 |
| aaaaaaagcg | accagttcac | gtcaacggtt | aaaaatcttt | agtttaagcg | cgtgccacgc | 1620 |
| cagcaccgtt | tcgtaatcgg | aaaattctcg | aatcacctag | agaacgttgg | agaaacccca | 1680 |
| cacaacactt | cgcttttcc | ccaagtccaa | ttccattagg | aacaaaaata | tctaccgtcc | 1740 |
| aaaattactg | atccaacggt | tcacagcgca | tgaaccgaac | cttccagaat | tcaaacacgt | 1800 |
| tctttaaagc | acaccccttc | ccacacattt | ctcctcaatt | cagttgaagg | aattgttgta | 1860 |
| acttttgat | tcctaaattc | tctaaaattc | gaaattctaa | tttcgttagg | ggaaagagat | 1920 |
| tgtttgtgtg | tgagtgagtg | ymagb | | | | 1945 |

<210> SEQ ID NO 2
<211> LENGTH: 1070

```
<212> TYPE: DNA
<213> ORGANISM: Glycine max

<400> SEQUENCE: 2
ccatttccaa ctcctgactg agaagtggat ttcatatcaa cattagcaat tagtagaata      60
ctatcatctt tcacgctaca aaacattggt actttggtag gtaaagattt gcaaacacga     120
ataagtaatt aagaaaggtt catacacatt caatgattct ggattcctac cttacgttat     180
ttgtttcgaa atacctagat gagagcatct tgttatttat tactacatat taattttccc     240
tgtgtacctt gtcgtagttt aaatttatta tttttcaat cataaataaa tataagaaat     300
atttttttct taatataatt ttatttata tttaaaaata aatcataatt tgaaagagct      360
acaaatttat accacatgtg ggaagtattg ttggtttctc caaccatact tattgagaat     420
aacttgaatt tatattcaac gtattaattg cttcacctt aacgtgccaa ataataata      480 ataaaaaact taaaactact gtattaatcg cgtgtggttg aatggaggca aattctattc    540
taaaaaagaa aagcattaac aaaaggagaa aagaaaaact gttgacacct gacagcagta    600
acagggaact gggaagtagc agtaggagta tttgcgtgtt ggtttccaac tctggaatcc    660
accgtgccaa actgcgaatg caggagaaat cgacacgtgt ccatttgcag gcgcgagttg    720
aacgtgacaa tgcaccaccg cccagcatcg aacgcagcca aggaccacgt cgaaaccaca    780
gtaatccacg ttccagtgct gcgcggaaca tggtcggtct ttctaggagt ggttggaatc    840
acgccagcta ggacaaaccc catcaatcat tggtcattat caaacaaaac atttcaaaaa    900
ttcaacatat tacgcctcgg gacccacctc ccactacacc tcaccctcac ttctattaac    960
tcgaacacat tcgggttata aatccgcaac cctccttctc actcactcac tcactcactc   1020
actcactcgc aagcaaaaag aaagaatccc aggcgaggag aaaggymagb              1070

<210> SEQ ID NO 3
<211> LENGTH: 1759
<212> TYPE: DNA
<213> ORGANISM: Glycine max

<400> SEQUENCE: 3
cctctcaatc aaggccttta tttgttctgc acaatttaaa ataaaataac aagaattttg     60
ttgctctaaa atctcattgc tccctatctt ggaacattgc gagtgcgaca acaaggcaac    120
cctaaagatg ataatgtgca cctcacttgt ggcgtcgaca actgtatggt gcgacgatag    180
agcggatgat gaagcagaag atggtgccaa ttaacatcaa cttcgatagg cacggaggac    240
accagcgggg tcgagctagg tagcgggtgg tggtaggaga aagggtcggt gagttgggct    300
tggaagggaa gggataggaa cgagtgaaca atgttttta ttttcttata aaatatatt      360 ctagtgcatt aattacaaga tattcatatc taacgtatca tatgtttctc acggtgggaa    420
atttgatgag ctttcccatc ctagaatcaa tcatcttttt atatgtagtt tgtgggatta    480
tggatgtagc tgtcttggaa aaacattaaa ctttaaacac accacgagaa actcgtaaga    540
cattcgttgg ggattacttg tgataacatg atccagaaac agaacaagag tttcaatgaa    600
tctaaatatt tcgaattgaa gcatttgact gttaaacatg tcattttagg ttgctatagt    660
tgtgggagat ataaggttaa tctaatggtt ggggaagaga gggggagggg gagacaaact    720
aatgaggcat atagcaacgc gcgccgggag gagtatgcca gaatcaacaa tgaaacgaca    780
tataatgact aataatcag attcaaacca ttttttttta taaatttttt gctaaaggct     840
actccaatag ttacagtacg cataggacga atggtatttg cgagcatatt atttgaaagt    900
```

```
atcatgaaaa atgtggtgtt gttgaaaggt ctacggtgca ttccattgac aaagtcaatt      960
actcgttcgt ggttaatttt gctgaaaaga taagctctat ggataaactc aactgagttg     1020
cttgtttatt tttacgtctt gcaaaacaaa agtattaaaa cgacatgata aactcacaag     1080
actacaatgt tgctctataa gaagaagaat ttcaatagaa acgtttcaga ttaaagcatt     1140
tgactagtag acatgtcgtc atcaaggtgt tgaatacatt gatgcaattt tcatgttaat     1200
tgaaggaaaa taataatgta actaaaccag ttttagaata attgaaagaa tcgctgaaga     1260
ttacaccagt agttagttgt tgagttattg tacactttgc atggggcgaa tggtatttat     1320
ttgcatgggg ttgttgaaga caacaatatt ggttggtggt tgagcactca gcacgggctt     1380
tgcctgaaac tttaatgttt ccccattctt cccgtgaacg ttcagaatcc agatccattg     1440
attctcatta cattacgatt tcgcgtcaaa agtagaaact aaaaacaaaa atagagaaaa     1500
ggagaacact tgccacctca tccaacagct gcttatttaa tctctacact tgctcgtagg     1560
gtctcaattc gaggtcgcag attagattcc caattctccg ttcgccatct gttaaggtaa     1620
gcttttcttc ttaaactatt gtactttcca gttcatgcat aatagtatca ggaaacaaaa     1680
aaaaaaagta taagataaga tcattgatgt gatgtgttgt gtagcgtagg agatagagag     1740
ggagagattg aaagymagb                                                  1759
```

<210> SEQ ID NO 4
<211> LENGTH: 1694
<212> TYPE: DNA
<213> ORGANISM: Glycine max

<400> SEQUENCE: 4

```
cggttattct taatccttt catgattgta tgtgagatgg agaataataa attaataatt       60
tgtgacaatt ttaaaatgta aactttagta atttgaaatt aaaaatcaaa ttatggaatc      120
taaagatcac cacaaattat cgatttacta ttctcacttt ggcgagtgtt gggtaatcaa      180
ccttccacaa acaaaattat ccatctcaca aaggatggtg agaatataac aaaaattaca      240
ctacaggaaa ataataata aacacaaaaa tttaatgtgg tacaatactt tttacttata      300
ttcacggaac aatctaaaaa gtatttcact ataaaaatat gattataaga ttataactca      360
cctcaaatag tgcatatcta gatatccgat tacctcactc aatggttaca agaaatgata      420
acactgtcac ataagatac ttttatctca acaaatgact tgttttagaa tctctcttct      480
cacactcttt attcatgtgt tgtgtttatc tactaattat cttctctatt tatagtggag      540
atgaccacca attataagct ttcttgaaag ttaaaacaaa ataatttttc aatgcatcca      600
ttcaactaag gttcatctag taaaatacaa tatttcactt tatatttaag ttacctaaac      660
cttagtgata aaatttgtaa gagaattatt aaattacatg aataacgaaa ttaaggtcat      720
gaaaatattg agttgagata taatcaatgt aaggaaaaac ataattagtc ttaacatata      780
agacaaatat taatttaatt tagaaaacaa aggaaaaaaa tgcataaaga agaaatatgt      840
ttgatatttt tttattccaa aagaatagga gaaatatatg acatatatct taaaaaatat      900
taaatagtga tgagaaaaaa ggaaatatga taactaatag aacaaaaagt ctaacaatct      960
ttcttaagga tttaagtgag attattttat agatatttta tactgaaaaa atataattca     1020
tcaaaatact ttttaaaaaa taattcatca aaatttatgt attttttat aatttataaa     1080
aaattctaac taaataccac caaattttat tattcttctt aaaaatcttt taagtcttac     1140
ttaaataaaa aaaacttatt tatactattt aaaaatttta atttaatacc accgaccttt     1200
ttttatataa aaaaaatctt ttaaaattat ttaaaatctt aatccaatgt aacctccatc     1260
```

| | |
|---|---|
| tcaccatttc ccaaatcaga ttccgagtca tcgatcctta aaaagtttac catatctttt | 1320 |
| ctatttttat gcttgatctt ttctaagtta agataacaac ctagtaaatt tttcggattc | 1380 |
| tgcagcagta acttcgattt gcactaaact aaacatctga ggatctcaga ggggcatcac | 1440 |
| attcacattg agccgaatca tcacaacgac attcttaaat cacataaaaa aaaatagtgc | 1500 |
| tcagtccgtg agagtttgta tcacggctct gacactgaca cattcgcacg ggatccctac | 1560 |
| tttcttctct tgttttgta ttctcccatc aattatttaa caacccatta aggttctcgt | 1620 |
| cagaaagttt agatttatc gttagttttt aaatattttt ttcatcgttt catcagtggt | 1680 |
| cacacagcgy magb | 1694 |

<210> SEQ ID NO 5
<211> LENGTH: 1895
<212> TYPE: DNA
<213> ORGANISM: Glycine max

<400> SEQUENCE: 5

| | |
|---|---|
| gattctagat attgaagttt gtgataggtt ttattctttt attacttaat actagtatat | 60 |
| tattatttt agttataaaa aattatagag agacaagagt tagattcaaa attgatgtta | 120 |
| ctaataatga taaaggacaa tacaaaattt ggagaaaaaa aataaattgg cgggctagcg | 180 |
| gtggcccgtg ggccagcttg aaacaagccg aactaggaaa agtaacccat tttgcttaac | 240 |
| gggacgggcc gggttggccc attaatggcg ggccaaaaac aggccggacc gacccatatt | 300 |
| gacaacccta ttaagaataa taacaatttg cggtaaatac acaaaaactg caccattaga | 360 |
| atgatgcctt ttgcatcagc attgttagtt tgattaacaa agttttata aataaacact | 420 |
| tttagattag tttctaatac aattgattga tgcaaaacaa gatgttgctg aacaagggcg | 480 |
| atgatcacca aaattaacaa ggatactatt tttacattaa ttatattgac aaccaatata | 540 |
| aaaatattta tttaagaact ttggtctatc aaacaaacca agataacaga aaggggatta | 600 |
| ttatagtgtt gataattgta gtttgaggat ttgattgaac ttttataaat aactaaagaa | 660 |
| tcaatcatat aattaagcct taaaaatata taattaacca aatcaaaata aacacatgac | 720 |
| tatcctaaaa aagttgaagc tcaggttttt tgtgttttca caataacttg gtctgcttag | 780 |
| tggattgaat agtggcagca attaacagac ccacgtctga gaaatcaacg gtggtgtttt | 840 |
| cactttctac ctcccgtgac tgtacccaac ttccgctctg ttactctgta aactcattcc | 900 |
| acatggactg tggccttcca gacatattac tatttaaatg tcaggtaaat cagcactaac | 960 |
| taaaaacaa acatgtgatt ttatttatc cgtaacatga tataaaaaat tttacaatac | 1020 |
| tcacatccat taatcatctg agtttgattt ttttataacc aaacatgtga tatgggtgtt | 1080 |
| acattagtct tcaagttctc ttagtgaaca aaaaaaccaa ttattaagat agatttgttt | 1140 |
| aaaagattaa attcttttat gttgacttgc aaattagcag tatgattact gtacattaag | 1200 |
| catactatat tggttatctt tcataaatat gcagttttt ttttcaatta atagaaatta | 1260 |
| tgactgaagt attttatttt tatttatacg attttattta agtttcattt ttctttttata | 1320 |
| tttaaagaga aagtaattta tagtctagac tattttcaa caacacatat ttaagtcttt | 1380 |
| taatttatga ataaacatat taatcaacta tgaaacatat gaggattaac ggcgaaggtg | 1440 |
| atggtcctaa accctccca ttaataattt gtcatattta aggctagaga tgaaagacaa | 1500 |
| cacaaccaat aaattaaaga agttcccttt caaaactgaa catcacaaaa gaaaatcaca | 1560 |
| acgtggaacg ttaatgaaac ggacaaccta aaccttttc tctgtccagc agcgttctcc | 1620 |

| tcctacaccc | tttattcttt | cttggctcga | aactgaaacc | tccaatacaa | ggcaatgaga | 1680 |
| acactcacga | gacaaagcaa | ggattctacc | ttttcttttg | tctagtattc | tagctcagct | 1740 |
| atatactatt | attaaaaaac | aaataacaaa | cacaatcatt | gtcttgatct | tgcccctcac | 1800 |
| aacattcagc | aaaaaaaaat | cttgccactc | acaactccca | catttctca | ccaaaataat | 1860 |
| ctcttatttc | acccttttgtt | aacacaacag | ymagb | | | 1895 |

<210> SEQ ID NO 6
<211> LENGTH: 1053
<212> TYPE: DNA
<213> ORGANISM: Glycine max

<400> SEQUENCE: 6

| gggatgttta | tttaaggcat | ggtcaagttg | acaagttgat | caaggactaa | ttaatcacaa | 60 |
| agtgaagaac | ataatcattc | gatggttttt | atgataaaga | gttcacgtga | catatgtgat | 120 |
| gctatcacac | gttccagcac | cttcaatatg | cattacatga | ctataattat | ggctaacttt | 180 |
| ctgttttatt | ttcctttagt | ttattgtatt | tctttgctgt | tttctccctt | tccttcggcc | 240 |
| atgggttttc | caggcaagct | gtattgtttc | gtgaaaatta | cagctgacat | tgcgacaatc | 300 |
| taatgttagc | taaatgctaa | tgcaatcact | attcatcaag | atggagtagt | cacatactgt | 360 |
| taacaattat | tctctgagta | tggtttaaac | ttttaataat | attatactag | tagcggcgcg | 420 |
| cagtacgtaa | taataaacgt | tccattctct | cttccaaatc | gagtaatccg | aatgtatata | 480 |
| tgcttgagaa | ttgagactac | taattaagta | aacacagaga | tacgaagatt | taattcccga | 540 |
| agtatatata | atgtagcgtt | gaatgtactt | tttataacaa | aaacatgggg | accctgaagg | 600 |
| agttagagga | caagtctatt | atttggaaaa | aaagaaaaa | agaggtaaat | aggtaaagag | 660 |
| aaggcttgga | ccattatgtt | ccaaaagttg | gctaaggcaa | agcgcaaagc | atcttagaaa | 720 |
| aatccttgca | ttaattttg | ttggtgttgc | ataaatggtg | atgacccaca | tgcaggttct | 780 |
| acatctcaca | aaccctgtgt | gtcttaataa | cttttgaatt | ctcctctctc | gcctttagat | 840 |
| aactgccacg | tgatttcagg | ttccatcctc | tcttcagcgt | tggttcatca | atcaccaaat | 900 |
| taaaaatgga | ttaaaaagtg | ctttctcggt | tttcctgaaa | gagaaccctt | tgtgactttg | 960 |
| tccatttctc | ctctgccaaa | aatcgtttca | aaattgaaca | agaaaagaaa | gaagcttctc | 1020 |
| ttgccaacaa | gttattccac | tcccttggym | agb | | | 1053 |

<210> SEQ ID NO 7
<211> LENGTH: 2049
<212> TYPE: DNA
<213> ORGANISM: Glycine max

<400> SEQUENCE: 7

| agctcattac | ctcaaatttc | cctaccccctt | atcatagatt | aatattgaaa | tttcaaaatt | 60 |
| tagcagtcag | taagttgaag | tctactaaat | tcaaattatt | atataaaaaa | aatactaacg | 120 |
| tcaacactga | gattatgaga | ttgttgtaaa | tatatttgga | catgttttat | ataaataaat | 180 |
| ttaaggctaa | aatacgtttt | ttttctcata | aaattgaaaa | taaacttttt | ttgttttaat | 240 |
| aaaattaaaa | tgtgacattt | tttcaacaag | agaaggttcc | gttgtatcta | aatccaaatc | 300 |
| ataactaatg | caaatgtaat | attttttaca | tcaattatgg | aaccttacct | tgaaagaaaa | 360 |
| aatgacaaat | tttaattta | tagaaatgaa | aaatgtaata | caaattaaaa | aaaaacataa | 420 |
| atttctaaaa | aaaattgtgg | aatatataaa | ttttttaattt | taagaaaacg | aaaaatatat | 480 |
| ttaaaattta | aatttaagta | aatttaacca | aaatagcaat | ataacactct | tagaattata | 540 |

```
atatcattaa ttgagttatt tatataaaat gtgtggatta ttataaattt caataacacg      600
agtcttttga taacttacat atatgcttga tgcaaaaact tcattcaatt ttacttcgtt      660
ttttcgtccg ctcaagttta taattctttg agaagccaga ctatagcttg ccttgtagtg      720
taatataaaa gggaaaaaaa aaaaaactat attacgcata aggatattgg gaaaattgat      780
aaccacagga acagggtata tatgatctta taatgtaaga agctatcctt actccacgta      840
tgacgaaact gttacttaga atcataatat catgaagaat ttaacacaac cattagtatt      900
ataaagaatt caaacaagag attcttgaat cttgtttagg aaagaacaac tatcaactat      960
ttatgtgttt ggtgaaaaat tgtaccatag acattttatt tatttattta tttgaagagg     1020
acattttatt gaaacacacg ttatagattt ttaaatattt ataataaaat aataagtttt     1080
tttattttat acgaaatttt tcattgaaaa atatacaaaa ttgaaactta cattatttta     1140
ggttgcataa ccatacatat gagaaaatgt taaagatttt tttgtgagaa aaggtatgta     1200
actaattttt cttaggttga tgttcagaag acattattat tattggaact aaaaaaacgt     1260
ttctcaaaat ctaacacact tatgtatgtt gtaatttagt attaaaaata ttaattaaaa     1320
tatcatttat aataatccta tttgtctcaa acaatattgc ctccaataaa atatatatgt     1380
agtctttata aaaaaaatta ttgtatttaa aaataaaaac ataattaata ttataataga     1440
actaaactaa taaaaatata ttttattaaa ataaatatata caaataaata ggtaataata     1500
tctattagaa atgttaagga caaaccattt ttcaacatat tatttatgat tagtataaat     1560
ctattgaaag ttataaaaaa aattgagctt tactttttaat ttttgtgtct cacttatgta     1620
attgaataaa tattgcataa attcagtttg atttttttta aaaaaaacat aatattaaca     1680
actcttgaca caattatagc gacttgtgtc tccagcaata tctaccatga taaacgaaca     1740
aaaaaaaaaa acttaatttt tttcctatga acgtatatag gaaaatttat acatgggaga     1800
aaaaatacgg cctgcctggc cgtatcctaa ttaagacgat acgttgaaaa ttattatttt     1860
atttaaaaaa aaaaaaaaaa aaaagaggaa ctaaaatctt aggatgggtc ccaccgcgtg     1920
gcgccatgcg aaaaaccgat agagagcact cgcaatggga ttgggataac gattaacgag     1980
cgacttcttc ttcaaaaaca cacaaacaca ctacactttg tctctgttct gtgtgtgcga     2040 gaagymagb                                                             2049
```

<210> SEQ ID NO 8
<211> LENGTH: 1923
<212> TYPE: DNA
<213> ORGANISM: Glycine max

<400> SEQUENCE: 8

```
tttcttagat aaacatacgt acgttgcttt ttaggaaaaa aaaatgaaac cacactgcac       60
agttatggaa cagaaatcgg ttacgggtca acttttgttt aagtggggtc caacatcttg      120
ggattttgcc aagaaagcta gtttgcagat caagaatttt aatagcagct acaagaaatt      180
taacatataa ttaagtaacg ggtgttgcta ggtgcaccga acattattgt tgatgtatcc      240
gacacttaat aaagacaaaa atactcccgt gtatttttaa acatgttttt gtgcacccag      300
ctcatttagg ttgatctgga taggttttag ttgatccgca gttaatatag ataattcaca      360
agtttctttc ggattaagtt gatccgcaag ggatttacgg atcaacttga tccgtaagaa      420
atatttgatt cacaagttaa tttttaagac ttacggatca agttggtcca caagttgatt      480
tttaagattt acggatcaag ttggtccata agtctcggat caatccgtaa accttaaaaa      540
```

```
tcaacttgtg ttaatccgta aagggagaaa aaaggaaggg ataattttgt tattttttaaa    600
gaatgttgtg tataccaaca ataatactgg atacacctaa caccactctt aaataaccag    660
tacaatcgtg tgaaaatgat agaattatat atatatataa aagacaaatc agtctttgca    720
acgactatag gctcttttcta aaattctgaa attaaattt gagtatgaaa tatatgttaa    780
atatttagag aaagattatt taatttacgt gtcataccta cctgactcga tagtgattta    840
aatcaaactc taaatccttg gatggagaat gactcattga aggtaatatt ttttttttca    900
attttatcat taacaaagtt gataaataat tttttatgaa taatataata aaaatgtaaa    960
taaatgttct tactaatgac ttataattac aaaattaatt atatttcatc caactatgaa   1020
aaagtgaaat atttttaagg tcataaattg aaatttattg ttaatttatt gagcttttca   1080
acttaataat ctatctctat tatataaaag aataggctag tgaaaaatct aaaatgaaca   1140
ttacatatta ttaacacttg atataaataa gaggaaaatg aaaattttga aaaaattact   1200
attgaaatga aaaaactaga agagaagaa gaacaataag agaaatttat gggatgagac   1260
gtacgtgtag gagtagtaat cgaccggtga gggaaggaga gtaaaagtaa agatgctcat   1320
ttttttagt aataaaaagg attcaacttt ttttattcac taaaaaataa tttgaaaaaa   1380
taatacagat gactttttat attttttta aattttttaa tataagcgga actatacggt   1440
gactgctagt tgtaataaaa gtacgcacaa cttttcaactc ttagttatac cattttagtc   1500
caacatgtga catctaacta gcttcacgaa aagtaattta tacatataca aacgagtgac   1560
gacgactttg ctttgactgg aacattcaac aatgtttggt ttaacattga tttagtctttt   1620
gcattttttcc ctcgtgttga ctcttcgcac ttttaaagct gtcgaattca atgagcacag   1680
ttgttactta tataaaacta ttaaatgtga gaaaagttg gtgtgatagg catgcatcca   1740
gcattagaca ataggactaa ttaaagaaga aatagtcagc gacgggatga tcacgtttct   1800
aagagatatc cactatcttc atctatctct ataaatacca atgcttagag tgataaactt   1860
ccattctcaa cttgcaatta gccacacata tcatatacag attttgtatt gttagaagym   1920
agb                                                                 1923
```

<210> SEQ ID NO 9
<211> LENGTH: 1927
<212> TYPE: DNA
<213> ORGANISM: Glycine max

<400> SEQUENCE: 9

```
aattgacaag ttgattgttg tatacgtgta agaatatgat atattagata aaagagtttt     60
ttcaaataat aaaaaaataa gaatttttt aaattgaata aaaggataaa ataaactttt    120
aaataaaata gtaaaataa aatttataat aagaaaaact agtaataagc taacttattt    180
ttcaaaaact tcttgttgat atataagcta cttgaagtaa cttttaaaat ataaactact    240
aaaaataact ttgtatatta acttataagt taataaaaaa aattataagt ttttgaaaag    300
tgttatcaaa catattatgc agcttagttc ttgcgaacaa ttccaatttt cttttgccct    360
ctactcgatc tgaagttggt tcatgctggg attttttccg aggtaaaata gaaatatttc    420
ttacttatga attaagctta gttccttgcat atatataccc tacactttc atttatttaa    480
ttttcatact ctagactttt cagaacatta ggttttcgca tagagcggtt attttatgtt    540
cctggttcag tgaccaataa gttatttttat tcatttaata tccatttatt tattttttatt    600
tctctgcaat cttcatttac tgtttaatta gtaaaattta ctgaaattga ttctctgttg    660
tttatgaata gcttaatcaa tgggataaat tcctaggttg ccaatgtttt ctgctttcct    720
```

| | | |
|---|---|---|
| tgcttgcttt gtgcaaactg tttgatgaaa catcctctcc aatgtgtcta accctgtgag | 780 |
| ttaaatgtgt tgcaaacaca tgattaaaat ccagccacga tcgaatccgt atatattaat | 840 |
| gaaataaata ataaaataat attaaaaaag ataacattgc aactttacaa cactaaaatc | 900 |
| taaaaataaa gcattacttt acaacagatt aagatctaga ataaataaac ttaggttaat | 960 |
| tgtttttttt aagaaagaa atcaaaacaa tatggtatca agtattttca ctgacccatc | 1020 |
| atgaaccaat atgttgtcga gttttactag ttttgaacaa ttttattttc ttaaaattga | 1080 |
| ttctgtaatt tatttcggac acaaaatcga ttcaccaatt ttttattatt atcatgaacc | 1140 |
| aatatgaccg ggtctatttt tccttttttt agaacgag tctaacttgg ttacttgaat | 1200 |
| gtgtggcttc agcccatttg attgcatacc gccaatttgg aaaatgaac aacacaataa | 1260 |
| gagtcgtgta tttgattgat atattcatct acctctattc atctacctga gcccttaatc | 1320 |
| cagtggacct acagtcacct acagtcagtt caggatgtac attctattcc ttcattttttt | 1380 |
| aaaattcatt aaatttataa ataaaatctt ataattatat aattgaattc actaattta | 1440 |
| tattttataa tttgtatcca ttaatttagg atcttaaata tgccactatt tcagtcatta | 1500 |
| tcttaattac cgagatttgt cgtaaatatg atacagaacc taaattcata tttaaaccttt | 1560 |
| cctataatta ggttttgaca ggagataaa ataatgtta aatattctag ttgattggca | 1620 |
| ggtatatatg tacagtcgag tttgaattct agattttctg aaaatatcta catacctgtt | 1680 |
| aaactcgagt attttacaaa aaccaagttg tactagctca catatcaacg gttttttctt | 1740 |
| cgtggcgact tcacgttctg ttgattagtc tttctgaccg ctgtattcaa ctacctgcaa | 1800 |
| taatttatta gttcccacag ctcacttatg atggagtata taaatttgta gatcaatcaa | 1860 |
| atcacatata actttgcaaa tcgatcaaat cacaatttag taattggttc agttaatttc | 1920 |
| cgymagb | 1927 |

<210> SEQ ID NO 10
<211> LENGTH: 1399
<212> TYPE: DNA
<213> ORGANISM: Glycine max

<400> SEQUENCE: 10

| | | |
|---|---|---|
| aaattatagg tgaaaaaatt ctactttcaa aattttaatg taaaagtatt ctcaaaggac | 60 |
| ccatttaatt aaagtatata tttaattttt taatcaaata tatattatgt ccatgttatt | 120 |
| ttaatttgtt ggatccactt ataatttta agaaacttaa aatattgtta ataaaatatg | 180 |
| cattttaat taattttaa atcattattt tataataaaa aatattatta tattccaaat | 240 |
| gcttatatca taaacatatt tttaacgtga caatattcat aactaattaa tcattttgtc | 300 |
| ttaggtttta cttttgagg ctacccactt taatccaact aatatgtatg agtcataatc | 360 |
| gaatcatatc gatcacttat agaaataaag ctagcgcgcg ctctcttaga acttttttg | 420 |
| tcttcacaat attcaaacca gcaatgttat ttaaagagaa agaaagccct tacctagcct | 480 |
| cttacgttaa tagaactgat cataattgat ttattttcaa attctgcatc taatttgaac | 540 |
| caaaagaaaa ttctatatct tgcgttcaaa caataaattc ggaaaattaa attttatgaa | 600 |
| acttaattcc taaaaagcat aatatttatg ataacgaata ttcatctta gttctgataa | 660 |
| actaaattaa aatattgata tataatttca acctcatcac aatcgaaaaa ttccatccac | 720 |
| agaaaaaaga tatattttt agaaaagaaa gtgcggtagg ccagacacat gactcacgtt | 780 |
| gagattcgtt cccaccccaaa aagagagata tctcaaatga agaaacatga aaatgaaaat | 840 |

| | |
|---|---:|
| gaagatgatg aaaataaaat aaaatatatg ctaatttcac gataaaaaaa aataattttt | 900 |
| tttttcagta ttatttctat cttttcttcc aaaagcacac ccttagttag taatttactc | 960 |
| aaggtggaga ctggagaagt tctttggtac ttttcgcggc agcatccaac ttcgtcgcct | 1020 |
| acgaacgtga caagccaagt gcaatagcat ttcttagaaa tatcccacca cttattgcaa | 1080 |
| gtggaagtgg ataatgaaaa agaaaacacc acccttttgac aaaatgcacc cattacgcgt | 1140 |
| aatcatttgc attatcactg catcccagta gacaaaagac gtgacccccag cttcatgcac | 1200 |
| ccttattata tacttgcaca agccgatttt gcttactagt tctccaaaag ttgaccaaac | 1260 |
| catccttata aattccttct ccacatcaca ttatattcat attcaacaca aatttaacta | 1320 |
| tctatttcgt ataacatttc atttcacttc acttagggtg gtgcatttgc aacccttttaa | 1380 |
| tttcctcaca aaagymagb | 1399 |

<210> SEQ ID NO 11
<211> LENGTH: 1954
<212> TYPE: DNA
<213> ORGANISM: Glycine max

<400> SEQUENCE: 11

| | |
|---|---:|
| tgagagagat gccaattttta caagccacaa tgcaaattaa ttttgttgt atattgtaaa | 60 |
| tcaatgcctt cttatctcaa cttgttatac aatgggccgt ttctgccaaa agtatttata | 120 |
| tatgtaaaaa acagaagtag gaggtgtgaa gatcaaacat gctgtggcaa taagataggc | 180 |
| ctagattgcc tccactacac atagcctatg ttttttttatt gtgggcctca atcatgaaac | 240 |
| ccaagcctct tacgccttct tttagcggtg gtactagtgg aggttctgtt tgtcttagag | 300 |
| gtgtctatag gaacaattgg acttttctaa tctcttgtat acacgcaagt aaataagccg | 360 |
| tgaaacttca agattcacca acccagaaga tcaggatcaa agaaatgttg aatatttaag | 420 |
| aataagattt ttcaagactt tcggccatgt tttgctattg acttttgttt tatttcgtac | 480 |
| ctgtattcag cattcttttt ccaaccttca gttctataaa aaaatccaaa tgtgactttt | 540 |
| gactttcaca tttatttttac cgcgtccaac ctgattagtt tattaattaa gaatgaaaat | 600 |
| gacatgttaa tatcatatct acaactacat ggagcaacat gagacttcct gtatgcatta | 660 |
| aaggcttgat ttgaccccaa atttgcttcg tgtttccaca attaaacttg cgagggtaca | 720 |
| ttctcagact attaattttc agattattac attaatgtag gaggattaaa ctcttaaaaa | 780 |
| gacagaactg acaagatatc actcgttctt attctaaata caattttttt aaaaaaatta | 840 |
| gttattaata acatctaact ttttcgtaaa aaaacattaa atttatcaat atttttttgta | 900 |
| tttttaagaa ttaactttaa aattattgag attttatttt tttgatattt tttcacccaa | 960 |
| ttaattagag tatttccagt taaatcagga cttttttgtct tctataataa gaggaaataa | 1020 |
| atgagagagg taactgtaac tagtaatttt ttcatatcct tacgagagag agagaaagag | 1080 |
| aaaaaaatag ttatcatatt tattatttat ttattgacca gaaaaattta tggagtaatt | 1140 |
| aaggacattt tatataaaat taaaaaatag acttatatat aaaaaaaact aataaaaaag | 1200 |
| tttttatcta tataaaaaaa aaagagagga agtgccgtta attacgttgt acatgtgatg | 1260 |
| cttattttac agatgttaga ggccaaactt cttgtgtaa atgatatacg cgtttttttg | 1320 |
| tgtagacttc ttaattttat gttatgttat aattatttta attatgtcgt acgtacgtag | 1380 |
| ataagctact tcttacgtgt tgaaattagt ttgccatcgg ctgctactat ttcacgtttg | 1440 |
| cgtatttcca ttttcaacat tcagagtggg ttgaaattat tgttcccata ttcattcatt | 1500 |
| gtaacgtcgg aggaaaagta aactttttttt taaaaaaaaa cttcttctct tcttaaatca | 1560 |

```
tcttttttag ttgggtgcaa tgcaaaatcg ttttttctttt cctttttcgc agtcgtagat    1620
gaatacaaga tccgagaccc ttatatagct agttaagtta cccagctttc cactatcaca    1680
cggctcgaac cacgtttcaa tatattaacg tgacttattt tgccaagcat ctatattttt    1740
ctacatgttc agttatttag atttcaaatt gcatgactag tcttcagtcc acaatttata    1800
tctgccacat ggcatcacca gatgaatttg tcaaaaacga accatgttgc ttccccaaca    1860
tatcaatgcc aaatcaaccc tataaaaata atatacacaa tctcacctgt taacattttt    1920
ttctttaacg aacggcaatt aatttacagy magb                                1954

<210> SEQ ID NO 12
<211> LENGTH: 1613
<212> TYPE: DNA
<213> ORGANISM: Glycine max

<400> SEQUENCE: 12
taaataatta atttatttca aacacttaat ttaaatttaa ttatacttgc taattaatta      60
aaaacactca atcatatatt attaaaaaaa atagttacat taaatactta gaggaaaaat     120
tttgtcatcc ataataatcc tattcaattt aaaacaaaaa atgttacacc agccgttaat     180
attttaaaac tctctcatct ttcatgactc accctaaaat atattttaa caatttatat      240 taaacattta tctaaaatga atttgaaaag tcaacaattt ttataaagga aaatcaacac     300
ttataataaa tgttttttc gtctcaaaat aagtatcaca tttgaaaaaa aaattatcct      360
aaaataagtg tctcatttga tttttttaa tgtaatatta ttttttttta ctactccctc      420
catcacaaaa taattgttat cttaggttat tttacacaaa taaaaagta aaaataaat       480 gaaatagagt aatgattgta taaaattaac cttatatcat tattaattta tttatagatt     540
tagttgttag ccattaatat tataagggat ataagccaaa aaggcaacta aactaaaata     600
aaattatttt aatttggaat aattttttc ttctcatacg acaattatat cgagacgaaa      660
agagtaatac acttaataaa tgttacttta attttttaat ataatattaa tactctctct     720
aaccataaat ataagacttt ttttaattaa tttgtaatct ttaagaaagt taattagtaa     780
cattaaactt gttaaaaatt taattatttt ttcaaaatta tccttaagct tattagaaat     840
cataatctct ctcttttcac ttaattgttt ttacacataa ttaaataatt tgtgttagtc     900
ttcttgtcca atccttataa gagaaataat gtatttatct tttagatata taacatttat     960
ggtaaaataa taaagatat ttgagtaaaa aagtaattaa tacaaaacac aattagaaaa     1020
tagtcttata aaaagaaaaa aaaaactgaa aaaaagagtt tttagggact gcaaaaatta    1080
ttaaggttaa ttttataaca ttattatttt tttaatctac tttttatttg tttaatctaa    1140 ataaatatatt ataacacgag acttatttta ggtggtaggg agtaatgttt aagatttgta   1200
tgagattgta aaaatcttc tacacagaaa cacaaccttc cagataatat gacacccacc     1260
cacaatcttc aactaatatc acccacacat atttattgca cacttcccat tagacaaggc    1320 tcccttttgtt tctatatata cttatgttaa ttgtgattgg tcccgagtct ggctgcctca    1380
caaaatagta gtattacagt acatcgttaa tttctcccag attcgctttg tcgtgtctcg    1440
agcatccttg atgtccaggg aaatccatat ttgtccttt ttctgcgtac tttcatcgaa     1500
ttattgcttg ttagctctat accaacttct tatatatccc atcctccaca tctacgcctg    1560
aatcatcgtc caactattag ttcctctctc tgcgttcata tcgcaacgym agb            1613

<210> SEQ ID NO 13
```

<211> LENGTH: 2022
<212> TYPE: DNA
<213> ORGANISM: Glycine max

<400> SEQUENCE: 13

```
gttgaagatt caccacttct cgatgaaagg atgaagatat ataaaattct acaagaaatt      60
aatttctgct aaaaaattcc cacccacaca gagcgactta aaagggtcat ctcaaacaca     120
aaaggaaaaa tcttcactct tcacgttgca agaattcgtc cgcagccaca tgaaaatcga     180
aaaggcaaac catctaaggg ataagtatca atctaactct caatactttt caagtcttca     240
attcgcattg ctgacttagt ttagtctatt cgtccctcct tctggataga ttttaggaaa     300
atgtgaggaa agaagttgat gaaaaataag tctcaagaaa ggaaacaaat taaaagtcaa     360
caaaccaaag cgaagcttta gaagaataaa gtatcgtgtt tgtagcaact agcaagtgga     420
tatttaaaag gacacttaga cacgacgctt atctagaaaa gttcaagcca gattaactaa     480
aggtttcact aaaaaaaatg gtgtagattt attttatacc tgttcactag ctagttacaa     540
aaatatatca tacataattt aattaactat acattaagtg gatgtaaaaa caatcttttt     600
ttaagggaag taatttacta gagacaacct aaagggtttt aatatctagt caagaacatt     660
aagtttgcga actacaatta atggtggtct actataaaat cttgttttca agcagtgatt     720
tttctattat tattattcat gactcattac taacttgacc cggtccaaaa ttaatttta      780
tgaattttgg gtttaaaaat gaggctttat ttagtttgag ggcgggttca ggtctttgag     840
tcgtcaatag gcctacttag tctagtgtca tattcttta aaatgtataa tttttttaaat     900
aattatatat taattataat atttcttgat ttgataagaa aaatatttta tataatataa     960
tattataatt acattgatgt tgttaattta tcttaatata tatatatata tatatatata    1020
tatatatata tataataaac tatatcttaa taataatttt atgcttcttc agttctataa    1080
tttttggtt atatctttag ttctataatt ttactatata taattattaa aattgatgta     1140
tatatcaaga aatcaaatta acccagcttt atttcaaata ttatcagatt gaggaatgct    1200
agtaagagat tctaacagta cacttgttta atattctagt gagagagcat gcacccacaa    1260
ttaatggaaa tctgaaatac aataaaaaaa tttattactt ttttaattta ttgtttttaa    1320
aataaatttg cactttaaaa attgagagca cgtacattag ttatttcttt cgtgctattg    1380
gtgtgatgca ttccttctta ctgaatagca gtactctaga ataaatcaga agcgttgtca    1440
ctctttcaat ccacttgcac aacttgtgtt agacgtatca ccattcacca atataatgca    1500
ccacgattgc accaacacat ggcaacattt ttttttatct ctttctattc atctcctttt    1560
atctcatcac tcttttatat ttcctttcta tctctcataa tccttaaaat tcgatttaat    1620
tagaaggaaa aaaaaaacat ctcatgcagg aagattttga aatcaaccca aaacaagtaa    1680
ctcactatat agtcatatat cggtgtgtac ctcttaatat ttgataggta tctcagtttg    1740
acttagttag gtggagtcta ttataatttt acactactag ttggctagtt gtggcaatgt    1800
ataagaattt tcaactgata agttcaataa ttctctgtat agcaaggttg gacgtgcaca    1860
acttgtgcta tgtccttact tttttaatta gtaaaaaaat attctcactt tggcttttaa    1920
aaaagaacac ttgcgtcaac gtctacgaaa tattctctat atatcttgtt tctttcttcc    1980
gttttcccga tcgggcttcc ttcttctttg caattcgyma gb                       2022
```

<210> SEQ ID NO 14
<211> LENGTH: 1976
<212> TYPE: DNA
<213> ORGANISM: Arabidopsis thaliana

<400> SEQUENCE: 14

```
tgcagaggat caagaagatt ctcccaattg ttgctaccgt gaagctcacg ccacattttg    60
gatatttttt cccttggaga cgcagctgga gtcatcagat cgccgcggtc aagaaaatcg   120
tcggctgagt attttggaag ctgaagtaga acgccagtg atttggtcga gtcattggag    180
attttgcaga tcctctgggc acttgagac aaatcttgtt cttcctttcg tgatttaatg    240
tggaagaggt gtttcttggt tgacaagaaa cccggaagat gtgacttgac ccggatcttg   300
atagatttcc atgcaagctt tagcttctgc ttcaatctcc agacccgttt agttcttctt   360
cttcttagct ttctcagtgg agttttgacc aatgcgttct ccatttctga gtttatcggt   420
cggataattt ttgaggtgat gatgatgatg atgataaagt tgtgatgtgt tgtagcaaga   480
attgatcgat atgctttgga atagatctct atgtgttata tatatgaagc aacatatgca   540
tatgttgctt ctgggaagat actcatatgc gttgacgaag aataaatgtt tgaccttgta   600
ctaaaacatt gttcggtacg gaagaatgat tattaattac cggtataata tacggtttag   660
gttttatatg cgagtagtga agtgaaggtt gctaataaaa atcagaattc cggttcaggt   720
aaaccatatc cagcaactct aattaaatct cctcttggaa aggttttgt tttaagtcaa     780
aacacaatct cattttgtca aaatgatttt agttggtcaa agtaataata atacgccatg   840
atgatagtta ttcttggcag cttaaggatt gaataattag ggctgctcta tatacaaaac   900
atatattaat gaaattaatt atgattattt gttaggaaaa tcaactctta caagagtcgt   960
ctactgtgtc ggcttttgcg ttaggttata taactccaac tttcctccta ataaacgggt  1020
ccacttttc taatgaaata tatattacta cttttggata agaacattta catgaaatcc   1080
aataaacacc cagaaataat tgttcttggc ttacaaataa agaaactcac atatctcatt  1140
atattttga ataaatggac gtagatgatt gacgtacatt tcagactaat atggtttgac   1200
ttaattgatt aattaaaagg tgaaaactaa tctttaattt tggtgtcact ctcgatcgat  1260
aaaaattcat tttttttgta ttagagtttt tgttaacaac ctaatacgaa caattgaact  1320
tgcatttaaa atacacttca tgcggtttat ttataagttg attatggata cgaatttaag  1380
cttttgttta atatatgaaa gataactgat tgatcaacta attcagatgg gataggtttg  1440
aaaaaattaa tcacaaaagg gtaaagaatt tgactaatta agctcgaaag tgttcttcac  1500
ggcaagttcg tctcttgaaa caactacgaa agtaccacta aacctatagt atacacgagc  1560
cttttccaat ttccacgagc actaaatgtt tcaaatgtaa tttgtgtttg gtttaaatca  1620
gaccgcttga agtccacacg atcatagtat tcaagttcca tgatttgtac taagatttaa  1680
tataagtata aatgggcctg catgaagccc aaaatgaaag gttttgaaag aaaatctgca  1740
ctgtgatgac gatgagacag tcttatccag agttgaaatc agccaataga cacttgacac  1800
ctcagcaaga ggtaacctaa acagaatcca tttctgtgat cgccaaagcc acacgatgat  1860
tcttgcctaa atcattttaa agactgtata gaggaaaaca aaactgcaaa acaaaaata   1920
aaaaaaacat cgcacaagaa aataaaagat ttgtagaatc aactaagaaa msatgb      1976
```

<210> SEQ ID NO 15
<211> LENGTH: 1928
<212> TYPE: DNA
<213> ORGANISM: Arabidopsis thaliana

<400> SEQUENCE: 15

```
gtgaaagcag tgaagccgtg accctatgag gttatgtcaa tgttgtgata atgttgtcta    60
```

```
ttttctttct ctataaagtg atagttatca ttagttgaag aatgctagga tgttatgtaa      120
ataagaaagt taagcaatgt tttcagtaaa tttcttttag cacaaattta ctatttttaa      180
gtgatgtcta atccaatttc tttccaagtt caattttctt tctctgccca tatctttaca      240
aaccattatt tttcggggtg aaactagttt tgagaacaag ttcgaacaaa tggttgaaac      300
ttgagttgct ttacggtata gtcaaatcat ttgaaaaaac catgttatta atttggaatt      360
ccgactttct agtcatacaa aaaaacaat aaatgaaata cgagaaagt agtgagtgag        420 aaaagtgaaa atataatatt catacctctt gtttcatata acgttctacc aatcctcttg      480
ttcctgcata ttaaaagtaa ctcatatcag aggagacatg ttgtatcaaa caacaagcaa      540
caacagataa acatttatct ttttttttag tttctttttt taaaaccaag ttgactatgt      600
tttagagcat cttcaatggt gagttttaa tattaattaa tcaaaaataa taatagaaaa       660
ggcaagagaa taagaatggt tcttatttta aagtatataa aatcttattt aaaatcccaa      720
ataccacata tcttagtata atgtcttaat atgatttgtt cattttatt tatcacttaa       780 aatttagtta aataacaaaa ttatatttaa ataaatattat aatattgata agagacactt    840
ggtgaatatt tcaccattag agatgctctt tcttgtttgt tgttacaaaa taatacaccc      900
atccccaact atccttgaaa aatcactgat gttctctaat gaacgttctc acaaaaaggt      960
aaatcatccg taaatggcca aaaactccac actgataatc attattgata aacttttgct     1020
ccgttcaatt ctcttttcta aatatgttat attatatatt agtatttatt tattaggagg     1080
ttttgtcggc aacaaaaaaa tagacaactc tcgtaaataa caaaaataag ttttcttatc     1140
aaatttagca cacaatcttc aaacttccaa aaataacatg aaattaatat taaaaagact     1200
aatataagca tttgattgat aattcacacg atttgtgatt taaaatcata attaattta      1260 tatatttaga taaaaataaa ttagttatta tgtaaaatta ctaatgctaa ttttggaaat     1320
ttgtgaagtt tgtgttataa ttgtccataa taaattttt catgttattt taaagtattt      1380
ctctataaaa agtaaaggtt gggccaggta aatgtactta ttggactcaa taaacaactc     1440
aaagatgatt aaattcatat attttactat gaaatatgtt ttactataaa aaacagctca     1500
aaatgctaca tttcattatt cctttctcca tttcattttt aaaattcata ctactcataa     1560
aagttcatag tatgactata agtttatgac tagtttaact ttcaactatc tagctttcat     1620
atgattccct agttcaaagt tatactactc ataaatttag atactcatac tatgaaattt     1680
ttatatagca aaaaaaaaat tacatctcag tttgatatca ataactaaac atacctatgt     1740
aaaaacttac atagtctact acccaaaata tcaataatta ttgtagctcc cactacccaa     1800
aagacaatgt ccattgactt cacaagcttc ttagtcttct ctatttctat gctctaaaat     1860
ctccttatat acatagtccc catacttatc ctcaaaactc accacaaaat ctcatcaact     1920 camsatgb                                                              1928
```

<210> SEQ ID NO 16
<211> LENGTH: 338
<212> TYPE: DNA
<213> ORGANISM: Arabidopsis thaliana

<400> SEQUENCE: 16

```
gacatctgtc ttgactttc cttaaacagt gtgtgatcat tttattatac ttaccagctt        60
attttttctc atcttttttg gataaaatac gcaacaggca cttgtatctt agaaaacggc      120
ttggatggct gcaaatttc aacatcgtac tgcttcataa acgatatcaa atacgtggaa       180
cttaattgtt ggttaataga ggataagaaa tggggttcac agaattaaat tcacgcacac      240
```

```
ttcatatatc ttgttccctc ccaattatct gaactatctt cttttatcaa aaactatatt    300
cacaggctgc cgtgtacctt ctccatccaa agmsatgb                             338
```

<210> SEQ ID NO 17
<211> LENGTH: 1995
<212> TYPE: DNA
<213> ORGANISM: Arabidopsis thaliana

<400> SEQUENCE: 17

```
gacgaactct gctactacta cagaaagcca aatgcaacca ctaattacag aggacgtacc     60
tgagaaacca agctttctt acttggagac aaaacttgct gaaacaagga ctgaagagaa    120
aaaatctttt ataagatgaa attctcccgt ataataagc agttataagc tatacacgag    180
tcacaacatc atcaatcaac aaaactcaga gccaaacttg ttcttcgaga ctaaatagag    240
actaatgcaa agttttttat caatgagcta tacacgagtc acaacatcat caatcattgt    300
atctcaaaac aaatcagata acacaatctg gatcctagct ttctgcatca aaaatacaaa    360
agacctataa acacaaaaac aattccactt tggatgcaat tgaacacgtc aaggaggcag    420
ctgaagtttg taactatgga tggtcaatct aagagggct aaagtgcaga tgctaaagtg    480
gcagcaccaa atggttctgt tgctcctaat gtagagacaa caaagcctct taagagcaaa    540
tcgaagactc aaaagcaaca caaagcaagc aaagcaacac aagccgtaaa ctaaagctaa    600
tcgaagaatc aaaagcaaca caaagcaaag taaagcaaac ccacaattaa acaatgtaac    660
catggtggat caaacccaag aacaagtgat tgcaacaagg atacaaagag aaacaacgag    720
agagacatgg agcgagagag aggaagcgag agagggagag agagagagag agagagagag    780
aaacacaaac ctactacact ccggcgatgg atccgacgag tctccagtga agaatcggcg    840
acggcgagat caccggcgaa gaatcagcat cattgacggc tatgaatctc aattttgagt    900
gttttgtgtc gaggagaggg tgaagaagag atgtggtttt tggatgtaat tccatatatt    960
agattagggt attattgaca ttttataatt ttggctgaat cagcttcagc agaatgaaca   1020
aatcaaactc agtcagattt tttttatttt ttggatgagt ttagaaaaaa acattcaact   1080
gaatcattca aatgatctat ttaaacatga aaaacaaaca acaattttca tcttcattga   1140
gatggttcat ccaaatggac aaacaaacag gaccttaata gaacaaccca aaaagaact    1200 cttacaaatt gattaataaa ataatttaat caaaagaat tatagatttt tattttaaaa   1260
actacaaata gtttaaaaaa aatataatat ttacaatttc catcacaaat tgtttcttaa   1320
tgcccaagga tgaaggatca catagttaat aagtaattaa gtactatttt attcatgtac   1380
tttctctttg ccctatccag agttgctaca agcctaaaac tcggttttac cacgattttt   1440
ctttggtgta tttgacagac tattaatggt ttgtttatct ctattatcag ttgaattgtt   1500
atatcaaaat ttgaactgat tgggtataaa agaaactga gaactgattc atgctaagga   1560
aaccttgttt aacaaatacc atggatgctt tttaaccgta tcagcctctc caatgttttc   1620
gtaaatcaat agttcaaaat ttttttctac cacacaagtg catctccatt ccaatttttca  1680 atctatataa atcatatgta ttttttgtat ccaatagtca tctttgtaaa gattttttgt   1740
tcgtgtgtgg cggataagca aaaacagaat aacataatct cttatccaac ttatattgcc   1800
acgtggacag atatagttgg tgaagcagat actaatctaa tctgagcaaa accagttggg   1860
ctatttgaaa gccacaagta cttggaacct ttgtttcttc taccctaaca tagcccttgc   1920
aaaccataac caaaccatca tcatcatcat ctcttggtga cagaagaaaa gagttgagga   1980
```
acagagaaah tatgb 1995

<210> SEQ ID NO 18
<211> LENGTH: 1959
<212> TYPE: DNA
<213> ORGANISM: Arabidopsis thaliana

<400> SEQUENCE: 18

| | | | | | |
|---|---|---|---|---|---|
| gaaacgaaac | tgaaccgcct | cctttcattt | ctcgttccag | ggcaaattta | tccattttg 60 |
| gctgaatggc | taaaatctgg | ttgggccagc | ccactttgtc | tttttgtgaa | agaaaaagtc 120 |
| agaaaggtgt | ccatggtgaa | aatttctttt | gtttcttcta | cttctttggc | tcttcatact 180 |
| ctatatctgt | ttttattctc | ttgtttctat | gttccgctat | agctcaagca | tgttgagtag 240 |
| cttgaagaaa | tcttcaagtc | ctgatatctt | taaactagga | aaggattatt | tattttagat 300 |
| atttgataat | agagtttagt | aaaaaatgat | atagttaaaa | aataaaaaa | aataaaaaaa 360 |
| taaaatgata | tagttaattt | tgtttgttaa | caaacatgca | acatgctgat | ttaaatctgg 420 |
| ataataagtt | aataacacat | tgataccaca | gttaccgctt | aatatcgtat | gattagtatt 480 |
| aaaaatcttc | tccagaattt | caacgttgtt | tttgctactc | acgcattgta | ccttaaatga 540 |
| tcttattcat | catttctaac | aaaacaattt | atgcattctt | cgccagtaga | agaacctagt 600 |
| agagtgctat | cggcaacaac | tccgtcttgt | tcatgcggat | gcaaaagaag | acgtccatgc 660 |
| ccacgtccac | gtccatgtcc | acctccacgt | ccacactatt | caagaaatta | tacagaccct 720 |
| tgaaaagaa | gaatgaagaa | gagaaaacaa | ggatcaatta | tgggattggt | acaatatagt 780 |
| tgagggtatt | gtctaatgta | gtacttttga | atatgcttat | agatttagac | atattaaaga 840 |
| ctattttctc | cttttaaatc | aatgaagaaa | atacttgagt | tcaatccttc | ttttgccttt 900 |
| gcataaccgt | ctctcatcca | caccaacaaa | acaaatccca | gaaccttctt | ttgcagaatt 960 |
| ttaaagacac | acaaagcaat | gaataagaac | acttggttta | caataacgat | cgaaactggt 1020 |
| ttacaataat | gaccgaatat | ggtttgcaaa | tatagatgaa | ttggaattta | attgattcga 1080 |
| tctatatcta | aaattaaatt | tcttgggttc | cctaaatact | atcctcttag | ggtttagatt 1140 |
| tctattatca | aaactctcgt | ttaatttgag | caaattggtt | aatcggagag | gttagggaaa 1200 |
| acaacgtttt | ctggtataaa | gagacgagag | aaacggtatt | gatggagtta | aaagtgatga 1260 |
| tgttgatgaa | atactgagtc | aacgttaata | aggcaagagc | cgactgtgag | aagcaaggtt 1320 |
| tcatggttgg | gaattttgtt | gcgcaacgga | gaagatgaag | tgaattttgt | tgcgcaacgg 1380 |
| atttccgcaa | gcttttcccg | agaaaacaaa | gatatcatct | acattctatt | tttgtgctgt 1440 |
| aacttttctg | aattttttgt | aaacaatttt | ttgtgatata | tatatatata | taaacaattt 1500 |
| tatatcatta | agtatggtac | tctttaatgt | ttttaacgga | acatgaccaa | aactgctagt 1560 |
| gaaagcattt | tgtcttaact | ttacaaaaga | agttatcttt | tttttaacac | aaactggttt 1620 |
| tcttcggtaa | ataaaaagac | taagtttgta | aatttattct | tagacaatta | tttactatta 1680 |
| ttgccgacta | atatgaaaat | gcaaagaagt | cgtatttggc | attatccaaa | agaagggaca 1740 |
| aaacacttat | ctcttaaaac | ttaaatttta | agccattcgt | ttaccaacaa | tgaatcttgt 1800 |
| ggctgatgta | gaaccgcgt | tcacttgtca | acatttagaa | ataatgttgg | ctttcaagaa 1860 |
| attaaataga | aacaaccaaa | atgtatgagg | ttgagcgtct | tctatatatt | tattacaaga 1920 |
| cttgcgatga | ccaaaaacgc | aacgaagaac | gaamsatgb | | 1959 |

<210> SEQ ID NO 19
<211> LENGTH: 1947

<212> TYPE: DNA
<213> ORGANISM: artificial
<220> FEATURE:
<223> OTHER INFORMATION: synthetic sequence

<400> SEQUENCE: 19

| | | | | | |
|---|---|---|---|---|---|
| ggtttctgcc | aagttgttat | tcctagatac | tgttatttgt | tattctcagt | tcacctttgt | 60 |
| ggggctctct | ctctccccgg | cgggagacgt | ttctttaaac | cacataacac | actagatatc | 120 |
| aaaacgttag | cactttgctt | atatgtgtaa | ttccatttaa | acaagttgca | aaaagagata | 180 |
| ttaccatata | ttttaagagt | gtgtttggat | ggaggaattt | aaaattctga | gaattttta | 240 |
| attctaaaaa | ttttaaatac | ttcaattgaa | attcttttat | tttcaaaatt | ttgtgtttgg | 300 |
| ataaaaaaag | ttaaaattat | gagggtgaaa | ttttatgaat | gaaaaaaaga | aaagatatga | 360 |
| ttggtgacga | tcaaggagat | acggctctgg | caacaatcaa | tgttccagaa | tcttagacgg | 420 |
| tgtttcttga | taagaagaga | attagttaaa | gagtggtttt | taattgttta | aaattctgtt | 480 |
| aattttaagg | aaaattttaa | attcttcata | aaaaaaacat | tcaaacaatg | aattatagat | 540 |
| tagtctttaa | gtttatcttt | gataaagtat | ttttctcagt | taaaattctc | tatctaaaca | 600 |
| tactgtaaaa | atgtcaaaaa | ctccatcaga | tttgtaattt | catttaaaca | tgtaaaaatt | 660 |
| caagaaaatc | tttgtgaaat | tggagatgag | ttttgtgta | atcattaaat | caagaaaaac | 720 |
| atgtttctta | atcttaaaat | aattaaaata | agaattttat | ctttatttgt | gagaaaaaat | 780 |
| ttaagcaaat | caaatgtgag | aaaatgaaga | gaataaggta | aataagtatt | taaatttata | 840 |
| gtccttcata | aaaagttta | taatttatac | aagtgatatt | tattcagata | aaagttttaa | 900 |
| aatatttaat | tactatttt | ttatgttaaa | tatattttaa | agaaaaattt | gtatacggag | 960 |
| gaggataaaa | aactgtaaaa | aaagaataac | taatcattgc | tcatttaaaa | ctttatatga | 1020 |
| actgatgatt | ttttagttg | cgtattttat | aagataagat | aagactatat | tatttttat | 1080 |
| ttagtatttt | tttatctttt | aaagattaa | ataaaaatat | taatttatca | ttgatttta | 1140 |
| aaatatcttg | ttgtattatc | tgataagata | agagtagatt | atttttatt | atcatcaaat | 1200 |
| tacactttta | aaatattaaa | ttaaaatatt | gttattatta | ttatttttta | aggttaaatt | 1260 |
| taaagctact | atcttatata | ctcttctata | ttaaatctct | tgctatgaat | tgaaaagaaa | 1320 |
| atcgtaaaag | taaagccag | gcactaatga | ctaaatgacc | aatgagtgaa | ttttgaaaag | 1380 |
| ataataaaat | catgcttttt | gaacgggcaa | gaaacacacc | aaaaataaaa | cttaactaac | 1440 |
| gcgctttaca | cggagttagt | gaaatccaat | tggccagtta | tctaaagcgc | acggacgacg | 1500 |
| tcattaattc | aaccaatggc | gcgggagaaa | gacagataca | atctatccaa | taccataaaa | 1560 |
| aaaaaaagcg | accagttcac | gtcaacggtt | aaaaatcttt | agtttaagcg | cgtgccacgc | 1620 |
| cagcaccgtt | tcgtaatcgg | aaaattctcg | aatcacctag | agaacgttgg | agaacccca | 1680 |
| ctgttgtctt | cgcttttttcc | ccaagtcctt | aaggtaatcc | aacaaaaata | tctaccgtcc | 1740 |
| aaaattactg | atccaacggt | tcactcgcgt | acttccgaac | cttccagaat | tcaaacacgt | 1800 |
| tctttaaagc | acacccgaag | ggtgtgtaaa | gaggagtatt | cagttgaacc | tattgttgta | 1860 |
| acttttttgat | aggataattc | tctaaaattc | gaaattctaa | taagcaatcc | ccttagagat | 1920 |
| tgtttgtgtc | actcactcag | ymagbrm | | | | 1947 |

<210> SEQ ID NO 20
<211> LENGTH: 506
<212> TYPE: DNA
<213> ORGANISM: Glycine max -continued

```
<400> SEQUENCE: 20
cgcgctttac acggagttag tgaaatccaa ttggccagtt atctaaagcg cacggacgac    60
gtcattaatt caaccaatgg cgcgggagaa tcacagatac aatctatcca ataccaaaaa   120
aaaaaaaagc gaccagttca cgtcaacggt taaaaatctt tagtttaagc gcgtgccacg   180
ccagcaccgt ttcgtaatcg gaaaattctc gaatcaccta gagaacgttg gagaaacccc   240
acacaacact tcgcttttc cccaagtcca attccattag gaacaaaaat atctaccgtc   300
caaaattact gatccaacgg ttcacagcgc atgaaccgaa ccttccagaa ttcaaacacg   360
ttctttaaag cacacccctt cccacacatt tctcctcaat tcagttgaag gaattgttgt   420 aacttttga ttcctaaatt ctctaaaatt cgaaattcta atttcgttag gggaaagaga   480
ttgtttgtgt gtgagtgagt gymagb                                         506

<210> SEQ ID NO 21
<211> LENGTH: 1006
<212> TYPE: DNA
<213> ORGANISM: Glycine max

<400> SEQUENCE: 21
aagaaaaaaa acatatcgga ggaggataaa aaactgtaaa aaagaatttt gattagtaac    60
gagtaaattt tgaaaatatg aactgatgat ttttttagtt gcgtatttta taagataaga   120
taagactata ttatttttta tttagtattt tttatctttt aaaagattaa ataaaaata   180 ttaatttatc attgattttt aaaatatctt gaacatatat ctgataagat aagagtagat   240
tattttttat ttagtagttt ttacactttt aaaatattaa attaaaatat tgttattatt   300 attattttt aaggttaaat ttaaagctac tatcttatat actcaagata taatttagag   360
aacgattgaa ttgaaaagaa aatcgtaaaa gtaaaagcca gggtgattac tgatttactg   420
caatgagtga attttgaaaa gataataaaa tcatgctttt tgaacgggca agaaacacac   480
caaaaataaa acttaactaa cgcgctttac acggagttag tgaaatccaa ttggccagtt   540
atctaaagcg cacggacgac gtcattaatt caaccaatgg cgcgggagaa tcacagatac   600
aatctatcca ataccaaaaa aaaaaaaagc gaccagttca cgtcaacggt taaaaatctt   660
tagtttaagc gcgtgccacg ccagcaccgt ttcgtaatcg gaaaattctc gaatcaccta   720
gagaacgttg gagaaacccc acacaacact tcgcttttc cccaagtcca attccattag   780
gaacaaaaat atctaccgtc caaaattact gatccaacgg ttcacagcgc atgaaccgaa   840
ccttccagaa ttcaaacacg ttctttaaag cacacccctt cccacacatt tctcctcaat   900
tcagttgaag gaattgttgt aacttttga ttcctaaatt ctctaaaatt cgaaattcta   960
atttcgttag gggaaagaga ttgtttgtgt gtgagtgagt gymagb                 1006

<210> SEQ ID NO 22
<211> LENGTH: 1506
<212> TYPE: DNA
<213> ORGANISM: Glycine max

<400> SEQUENCE: 22
aatttcaatt tctcaccttt ttaattgttt aaaattctgt tttaaaattc caaaatttta    60
aattcttcat aaaaaaaaca ttcaaacaat gaattataga ttacagaaat tcaaattctt   120
tgataaagta tttttctcag ttaaaattct ctatctaaac atactgtaaa aatgtcaaaa   180
actccatcag atttgtaatt tcatttaaac atgtaaaaat tcaagaaaat ctttgtgaaa   240
ttggagatga gaaaaacaca ttagtttaaa tcaagaaaaa catgaaagaa ttagaaaaaa   300
```

```
taattaaaat aagaatttta tctttatttg tgagaaaaaa tttaagcaaa tcaaatgtga    360
gaaaatgaag agaataaggt aaataagtat ttaaatttat agtccttcat aaaaagtttt    420
ataatttata caagtgatat ttattcagta ttttctttta aaatatttaa ttactatttt    480
tttatgttaa atatatttta aagaaaaaaa acatatcgga ggaggataaa aaactgtaaa    540
aaaagaattt gattagtaac gagtaaattt tgaaaatatg aactgatgat ttttttagtt    600
gcgtatttta taagataaga taagactata ttatttttta tttagtattt ttttatcttt    660
taaaagatta aataaaaata ttaatttatc attgattttt aaaatatctt gaacatatat    720
ctgataagat aagagtagat tatttttat ttagtagttt ttacactttt aaaatattaa    780
attaaaatat tgttattatt attatttttt aaggttaaat ttaaagctac tatcttatat    840
actcaagata taatttagag aacgattgaa ttgaaaagaa aatcgtaaaa gtaaaagcca    900
gggtgattac tgatttactg caatgagtga attttgaaaa gataataaaa tcatgctttt    960
tgaacgggca agaaacacac caaaaataaa acttaactaa cgcgctttac acggagttag   1020
tgaaatccaa ttggccagtt atctaaagcg cacggacgac gtcattaatt caaccaatgg   1080
cgcgggagaa tcacagatac aatctatcca ataccaaaaa aaaaaaaagc gaccagttca   1140
cgtcaacggt taaaaatctt tagtttaagc gcgtgccacg ccagcaccgt tcgtaatcg    1200 gaaaattctc gaatcaccta gagaacgttg gagaaacccc acacaacact tcgcttttc    1260 cccaagtcca attccattag gaacaaaaat atctaccgtc caaaattact gatccaacgg   1320
ttcacagcgc atgaaccgaa ccttccagaa ttcaaacacg ttctttaaag cacaccccctt   1380 cccacacatt tctcctcaat tcagttgaag gaattgttgt aacttttga ttcctaaatt    1440 ctctaaaatt cgaaattcta atttcgttag gggaagagaa ttgtttgtgt gtgagtgagt   1500 gymagb                                                               1506
```

<210> SEQ ID NO 23
<211> LENGTH: 1072
<212> TYPE: DNA
<213> ORGANISM: artificial
<220> FEATURE:
<223> OTHER INFORMATION: synthetic sequence

<400> SEQUENCE: 23

```
ggatttccaa ctcctgactc tcttcacgat ttcatatcaa catttcgtta atcatcaata     60
ctatcatctt tcacgctaca aaacattggt actttggtag gtaaagattt gcaaacacga    120 taagtaatt aagaaaggtt catacacatt caatgattct ggattcctac cttacgttat    180
ttgtttcgaa aatggatcta ctcagcatct tgttatttat tactacatat taattttggg    240
acacatgctt gtcgtagttt aaatttatta ttttagtta cataaataaa tataagaaat    300
atttttttct taatataatt ttatttata tttaaaaata aatcataatt tgaaagtgct    360
acaaatttat accacatgtg ggaagtaaac aaccaaagag gttggtatga atttgagaat    420
aacttgaatt tatattcaac gtattaattg cttcaccttt aacgtgccaa ataataata    480 ataaaaaaca atttactact gtattaatcg cgtgtggttg aatggaggca ataagataag    540
aaaaaaagaa aagcattaac aaatcctctt ttcttttct gttgacacct gacagcagta    600
acagggaact cccttcatcg tcatccagta tttgcgtgtt ggtttccaac tctggaatcc    660
aggcacggtt tgacgcttac gtcgagaaat cgacacgtgt ccatttgcag gcgcgagttg    720
aacgtgacaa tgcaccaccg cccagcatcg aacgcagcca aggaccacgt cgaaaccaca    780
```

```
gtaatccacg ttccagtgct gcgcggaaca tggtcggtct ttctaggagt ggttggaatc      840
acgccagcta ggacaaaccc catcaatcat tggtcattat caaacatttg taaagttttt      900
aagttgtata aacgcctcgg gacccacctc ggtgatgtgg agtgggagtg aagataattg      960
agcttgtgta aggggttata aatccgcaac cgaggaagag tgagtgagtg agtgagtctc     1020
actcactcgc aagcaaaatc tttcttaggg tccgctcctc tttcgymagb rm             1072

<210> SEQ ID NO 24
<211> LENGTH: 506
<212> TYPE: DNA
<213> ORGANISM: Glycine max

<400> SEQUENCE: 24
ggagaaaaga aaaactgttg acacctgaca gcagtaacag ggaactggga agtagcagta       60
ggagtatttg cgtgttggtt ccaactctg gaatccaccg tgccaaactg cgaatgcagg      120
agaaatcgac acgtgtccat ttgcaggcgc gagttgaacg tgacaatgca ccaccgccca      180
gcatcgaacg cagccaagga ccacgtcgaa accacagtaa tccacgttcc agtgctgcgc      240
ggaacatggt cggtctttct aggagtggtt ggaatcacgc cagctaggac aaaccccatc      300
aatcattggt cattatcaaa caaaacattt caaaaattca acatattacg cctcgggacc      360
cacctcccac tacacctcac cctcacttct attaactcga acacattcgg gttataaatc      420
cgcaaccctc cttctcactc actcactcac tcactcactc actcgcaagc aaaagaaag      480 aatcccaggc gaggagaaag gymagb                                          506

<210> SEQ ID NO 25
<211> LENGTH: 706
<212> TYPE: DNA
<213> ORGANISM: Glycine max

<400> SEQUENCE: 25
atttatacca catgtgggaa gtattgttgg tttctccaac catacttatt gagaataact       60
tgaatttata ttcaacgtat taattgcttc acctttaacg tgccaaaata ataataataa      120
aaaacttaaa actactgtat taatcgcgtg tggttgaatg gaggcaaatt ctattctaaa      180
aaagaaaagc attaacaaaa ggagaaaaga aaaactgttg acacctgaca gcagtaacag      240
ggaactggga agtagcagta ggagtatttg cgtgttggtt ccaactctg gaatccaccg      300 tgccaaactg cgaatgcagg agaaatcgac acgtgtccat ttgcaggcgc gagttgaacg      360
tgacaatgca ccaccgccca gcatcgaacg cagccaagga ccacgtcgaa accacagtaa      420
tccacgttcc agtgctgcgc ggaacatggt cggtctttct aggagtggtt ggaatcacgc      480
cagctaggac aaaccccatc aatcattggt cattatcaaa caaaacattt caaaaattca      540
acatattacg cctcgggacc cacctcccac tacacctcac cctcacttct attaactcga      600
acacattcgg gttataaatc cgcaaccctc cttctcactc actcactcac tcactcactc      660
actcgcaagc aaaagaaag aatcccaggc gaggagaaag gymagb                    706

<210> SEQ ID NO 26
<211> LENGTH: 1006
<212> TYPE: DNA
<213> ORGANISM: Glycine max

<400> SEQUENCE: 26
catctttcac gctacaaaac attggtactt tggtaggtaa agatttgcaa acacgaataa       60
gtaattaaga aaggttcata cacattcaat gattctggat tcctacctta cgttatttgt      120
```

-continued

```
ttcgaaatac ctagatgaga gcatcttgtt atttattact acatattaat tttccctgtg    180
taccttgtcg tagtttaaat ttattatttt ttcaatcata aataaatata agaaatattt    240
ttttcttaat ataattttat tttatattta aaaataaatc ataatttgaa agagctacaa    300
atttatacca catgtgggaa gtattgttgg tttctccaac catacttatt gagataaact    360
tgaatttata ttcaacgtat taattgcttc acctttaacg tgccaaaata ataataataa    420
aaaacttaaa actactgtat taatcgcgtg tggttgaatg gaggcaaatt ctattctaaa    480
aaagaaaagc attaacaaaa ggagaaaaga aaaactgttg cacctgaca gcagtaacag     540 ggaactggga gtagcagta ggagtatttg cgtgttggtt tccaactctg gaatccaccg     600
tgccaaactg cgaatgcagg agaaatcgac acgtgtccat ttgcaggcgc gagttgaacg    660
tgacaatgca ccaccgccca gcatcgaacg cagccaagga ccacgtcgaa accacagtaa    720
tccacgttcc agtgctgcgc ggaacatggt cggtctttct aggagtggtt ggaatcacgc    780
cagctaggac aaaccccatc aatcattggt cattatcaaa caaaacattt caaaaattca    840
acatattacg cctcgggacc cacctcccac tacacctcac cctcacttct attaactcga    900
acacattcgg gttataaatc cgcaaccctc cttctcactc actcactcac tcactcactc    960
actcgcaagc aaaaagaaag aatcccaggc gaggagaaag gymagb                   1006
```

<210> SEQ ID NO 27  
<211> LENGTH: 1761  
<212> TYPE: DNA  
<213> ORGANISM: artificial  
<220> FEATURE:  
<223> OTHER INFORMATION: synthetic sequence

<400> SEQUENCE: 27

```
ggagtcaatc aaggccttta tttgtagacg tgaatttaaa ataaaataac aagaattttg     60
ttgctctaaa atctcattgc tccctatctt ggaacattcg gagtgcgaca acaaggcaac    120
cctaaagatg ataatgtgca cgagtgaaca ccggtcgaca actgtatggt cgctgctatc    180
tgcggatgat gaagcagaag atcctgccaa ttaacatcaa caagctatcc gtgcctcctg    240
tggtcgcccc agctcgatcc atcgccctgg tggtaggaga aagggtcggt gagttgggct    300
tggaagggaa gggataggaa cctctgaaca atgttttta ttttcttata aaaatatatt     360
ctagtgcatt aattacaaga tattcatatc taacgtatca tatgtttctc acggtgggaa    420
ataactacag ctttcccatc ctagaatcaa tcatcttttt atatgtagtt tgtgggatta    480
tccatgtagc tgagaacctt ttacattaaa ctttaaacac accacgactt tgagcattct    540
gtaagcaacc cctaatcttg tgataacatg atccagaaac agaacaagag tttcaatgaa    600
tctaaatatt tcgaattgaa gcatttgact gttaaacatg tcattttagg ttgctatagt    660
tgtgggagat ataaggttaa tctaatggtt ccccttctct cccctgggg gagacaaact     720 aatgaggcat atagcaacgc gcgcgcccag gagtatgcca gaatcaacaa actaacgaca    780
tataatgact taataatcag tttcaaacca ttttttttta taaaatttt gcatttccga     840 tctccaatag ttacagtacg gtatcctgct taccattttg cgagcatatt atttgtaagt    900
atcatgaaaa atgtggtgtt gttgaaacca gatgccacgt aagcattgac aaagtcaatt    960
actgcttcgt ggttaatttt gctgaaaaga taagctctat ggataaactc aactgagttg   1020
cttgtttatt tttacgtgaa cgtaaacaaa agtattaaaa cgacatgata aactcacaag   1080
actacaatgt tgctctataa gaagaagaat ttcaatagaa acgtttcaga ttaaagcatt   1140
```

| | |
|---|---:|
| tgactagtag acatgtcgtc atcaaggtgt tgaatacaaa ctacgttatt tcatgttaat | 1200 |
| tgaaggaaaa taataatgta actaaaccag ttttagaata attgaaagaa tcgctcttct | 1260 |
| aatcaccagt agttagttgt tgagttattg tacactttgc atggggcgaa tggtatttat | 1320 |
| ttgcatgggg ttgttgaagt gttgtatatt ggttggtggt tctcgtgagt cgtgcccgtt | 1380 |
| tgcctgaaac tttaatgttt cgggattctt cccgtgaacc aagtcttacc agatccattg | 1440 |
| attctgtaat gtaatgcatt tcgcgtcaaa agtagtttgt aaaaacaaaa atagagaaaa | 1500 |
| ggagaacact tgccacctca tccaacagct gcttatttaa tctctacact tgctcgtagg | 1560 |
| gtctcataag ctccagcgag attagattcc caattctccg ttcgccatct gttaaggtaa | 1620 |
| gcttttcatc ttaaactatt gtactttcca gttcatgcat aatagtatca ggtttgttta | 1680 |
| aaaaaaagta taagataaga tcattgatgt gatgtgttgt gtagcgtagg agatagagag | 1740 |
| ggagagattg aaagymagbr m | 1761 |

<210> SEQ ID NO 28
<211> LENGTH: 506
<212> TYPE: DNA
<213> ORGANISM: Glycine max

<400> SEQUENCE: 28

| | |
|---|---:|
| ctgaagatta caccagtagt tagttgttga gttattgtac actttgcatg gggcgaatgg | 60 |
| tatttatttg catggggttg ttgaagacaa caatattggt tggtggttga gcactcagca | 120 |
| cgggctttgc ctgaaacttt aatgtttccc cattcttccc gtgaacgttc agaatccaga | 180 |
| tccattgatt ctcattacat tacgatttcg cgtcaaaagt agaaactaaa acaaaaata | 240 |
| gagaaaagga gaacacttgc cacctcatcc aacagctgct tatttaatct ctacacttgc | 300 |
| tcgtagggtc tcaattcgag gtcgcagatt agattcccaa ttctccgttc gccatctgtt | 360 |
| aaggtaagct tttcttctta aactattgta ctttccagtt catgcataat agtatcagga | 420 |
| aacaaaaaaa aaaagtataa gataagatca ttgatgtgat gtgttgtgta gcgtaggaga | 480 |
| tagagaggga gagattgaaa gymagb | 506 |

<210> SEQ ID NO 29
<211> LENGTH: 1006
<212> TYPE: DNA
<213> ORGANISM: Glycine max

<400> SEQUENCE: 29

| | |
|---|---:|
| tatgccagaa tcaacaatga aacgacatat aatgacttaa taatcagatt caaaccattt | 60 |
| tttttttataa aattttttgct aaaggctact ccaatagtta cagtacgcat aggacgaatg | 120 |
| gtatttgcga gcatattatt tgaaagtatc atgaaaaatg tggtgttgtt gaaaggtcta | 180 |
| cggtgcattc cattgacaaa gtcaattact cgttcgtggt taattttgct gaaaagataa | 240 |
| gctctatgga taaactcaac tgagttgctt gtttattttt acgtcttgca aaacaaaagt | 300 |
| attaaaacga catgataaac tcacaagact acaatgttgc tctataagaa gaagaatttc | 360 |
| aatagaaacg tttcagatta aagcatttga ctagtagaca tgtcgtcatc aaggtgttga | 420 |
| atacattgat gcaattttca tgttaattga aggaaaataa taatgtaact aaaccagttt | 480 |
| tagaataatt gaaagaatcg ctgaagatta caccagtagt tagttgttga gttattgtac | 540 |
| actttgcatg gggcgaatgg tatttatttg catggggttg ttgaagacaa caatattggt | 600 |
| tggtggttga gcactcagca cgggctttgc ctgaaacttt aatgtttccc cattcttccc | 660 |
| gtgaacgttc agaatccaga tccattgatt ctcattacat tacgatttcg cgtcaaaagt | 720 |

```
agaaactaaa aacaaaaata gagaaaagga gaacacttgc cacctcatcc aacagctgct        780
tatttaatct ctacacttgc tcgtagggtc tcaattcgag gtcgcagatt agattcccaa        840
ttctccgttc gccatctgtt aaggtaagct tttcttctta aactattgta ctttccagtt        900
catgcataat agtatcagga aacaaaaaaa aaaagtataa gataagatca ttgatgtgat        960
gtgttgtgta gcgtaggaga tagagaggga gagattgaaa gymagb                     1006
```

```
<210> SEQ ID NO 30
<211> LENGTH: 1506
<212> TYPE: DNA
<213> ORGANISM: Glycine max

<400> SEQUENCE: 30
agctaggtag cgggtggtgg taggagaaag ggtcggtgag ttgggcttgg aagggaaggg         60
ataggaacga gtgaacaatg ttttttattt tcttataaaa atatattcta gtgcattaat        120
tacaagatat tcatatctaa cgtatcatat gtttctcacg gtgggaaatt tgatgagctt        180
tcccatccta gaatcaatca tctttttata tgtagtttgt gggattatgg atgtagctgt        240
cttggaaaaa cattaaactt taaacacacc acgagaaact cgtaagcat tcgttgggga        300 ttacttgtga taacatgatc cagaaacaga acaagagttt caatgaatct aaatatttcg        360
aattgaagca tttgactgtt aaacatgtca ttttaggttg ctatagttgt gggagatata        420
aggttaatct aatggttggg gaagagaggg ggaggggag acaaactaat gaggcatata        480
gcaacgcgcg ccgggaggag tatgccagaa tcaacaatga aacgacatat aatgacttaa        540
taatcagatt caaaccattt ttttttataa aattttttgct aaaggctact ccaatagtta       600
cagtacgcat aggacgaatg gtatttgcga gcatatattt tgaaagtatc atgaaaaatg        660
tggtgttgtt gaaaggtcta cggtgcattc cattgacaaa gtcaattact cgttcgtggt        720
taattttgct gaaaagataa gctctatgga taaactcaac tgagttgctt gtttatttt         780 acgtcttgca aaacaaaagt attaaaacga catgataaac tcacaagact acaatgttgc        840
tctataagaa gaagaatttc aatagaaacg tttcagatta aagcatttga ctagtagaca        900
tgtcgtcatc aaggtgttga atacattgat gcaattttca tgttaattga aggaaaataa        960
taatgtaact aaaccagttt tagaataatt gaaagaatcg ctgaagatta caccagtagt       1020
tagttgttga gttattgtac actttgcatg gggcgaatgg tatttatttg catggggttg       1080
ttgaagacaa caatattggt tggtggttga gcactcagca cgggctttgc ctgaaacttt       1140
aatgtttccc cattcttccc gtgaacgttc agaatccaga tccattgatt ctcattacat       1200
tacgatttcg cgtcaaaagt agaaactaaa aacaaaaata gagaaaagga gaacacttgc       1260
cacctcatcc aacagctgct tatttaatct ctacacttgc tcgtagggtc tcaattcgag       1320
gtcgcagatt agattcccaa ttctccgttc gccatctgtt aaggtaagct tttcttctta       1380
aactattgta ctttccagtt catgcataat agtatcagga aacaaaaaaa aaaagtataa       1440
gataagatca ttgatgtgat gtgttgtgta gcgtaggaga tagagaggga gagattgaaa       1500 gymagb                                                                  1506
```

```
<210> SEQ ID NO 31
<211> LENGTH: 1696
<212> TYPE: DNA
<213> ORGANISM: artificial
<220> FEATURE:
<223> OTHER INFORMATION: synthetic sequence
```

<400> SEQUENCE: 31

```
gccaaattct taatccttt catgattgta tgtgagatgg agaataataa attaataatt        60
tgtgacaatt ttaaaatgta aactttagta atttgaaatt aaaaatcaaa ttatggaatc       120
taaagatcac gtgtttaata gcttttacta ttctcagttt ggcgagtgtt cccatatcaa       180
ccttccacaa acaaaattat ccatctcaca aaggatggtg agaatataac aaaaattagt       240
gatgtccttt tataataata aacacaaaaa tttaatgtgg tacaatactt tttacttata       300
ttcacggaac aatctaaaaa gtatttcact ataaaaatat gattataaga ttataactca       360
cctcaaatag tgcatatcta gatatggcta atggtcactc aatggttaca agaaatgata       420
acactgtcac ataatgatac ttttatctca acaaatgact tgttttagaa tctctcttct       480
cacactcttt attcatgtgt tgtgtttatc tactaattat cttctctatt tatagtggag       540
tactgcacca attataagct ttcttgaaag ttaaaacaaa ataatttttc aatgcatcca       600
ttcaactaag gttcatctag taaaattgtt tatttcactt tatatttaag ttacctaaac       660
gttagtgata aaatttgttt cagaattatt aaattacatg aataaccttt ataaggtcat       720
gaaatataac tcaacagata taatcaatgt aacctttaac ataattagag aatacatata       780
agacaaatat taatttaatt tagttttgtt tcctttaaaa tgcataaaga agaaatatgt       840
ttgatatttt tttaaaggtt ttcttaagga gaaatatatg acatatatct taataaaatat       900
taaatagtga tctcttttt cctaatatga taactaatag aacaaaaagt ctaacttaga       960
aagaaaagga tttaagtgag attattttat agatattta tactgttttt tatattaagt      1020
tcaaaatact ttttaaaaaa taattcatca aaataattgt atttttttat aatttataaa      1080
aaattctaac taaataccac caaattttat tattcttctt aaaaatcttt tatgtcttac      1140
ttaaataaaa aaaacttatt tatactattt aaaaatttta atttaatacc accgaccttt      1200
ttttatataa aaaaaatctt ttaaaattat ttaaaatctt aatccaatgt aacctccatg      1260
agtggatttc ccaaatcaga ttccgacagt tcgatcctta aaaagtttac catatctttt      1320
ctatttttat gcttgatctt ttcattgtta agataacaac ctagtttaa aaagcctaag      1380
acgtcgtcat tgaagctaaa cgtgatttga tttgtagtga ggatctcaga ggggcatcac      1440
attcacattg aggcgaatca tcacttgctg tatcttaaat cacataaaaa aaaatagtgc      1500
tcacaggcac tctcaaacat agtgccgaga ctgtgactca cattcgcacg ggatcggatg      1560
aaagaagaga acaaaaacat aagagggatc aattatttaa caacccatta aggttgagca      1620
gtcttagttt agattttatc gttagttttt aaatattttt ttcatcgtta gtagtcacca      1680
gtgtgtcggy magbrm                                                      1696
```

<210> SEQ ID NO 32
<211> LENGTH: 506
<212> TYPE: DNA
<213> ORGANISM: Glycine max

<400> SEQUENCE: 32

```
ccaccgacct ttttttatat aaaaaaaatc ttttaaaatt atttaaaatc ttaatccaat        60
gtaacctcca tctcaccatt tcccaaatca gattccgagt catcgatcct taaaaagttt       120
accatatctt ttctattttt atgcttgatc ttttctaagt taagataaca acctagtaaa       180
ttttcggat tctgcagcag taacttcgat ttgcactaaa ctaaacatct gaggatctca       240
gaggggcatc acattcacat tgagccgaat catcacaacg acattcttaa atcacataaa       300
aaaaaatagt gctcagtccg tgagagtttg tatcacggct ctgacactga cacattcgca       360
```

| | |
|---|---|
| cgggatccct actttcttct cttgttttg tattctccca tcaattattt aacaacccat | 420 |
| taaggttctc gtcagaaagt ttagatttta tcgttagttt ttaaatattt ttttcatcgt | 480 |
| ttcatcagtg gtcacacagc gymagb | 506 |

<210> SEQ ID NO 33
<211> LENGTH: 1006
<212> TYPE: DNA
<213> ORGANISM: Glycine max

<400> SEQUENCE: 33

| | |
|---|---|
| ttaaattaca tgaataacga aattaaggtc atgaaaatat tgagttgaga tataatcaat | 60 |
| gtaaggaaaa acataattag tcttaacata taagacaaat attaatttaa tttagaaaac | 120 |
| aaaggaaaaa aatgcataaa gaagaaatat gtttgatatt tttttattcc aaaagaatag | 180 |
| gagaaatata tgacatatat cttaaaaaat attaaatagt gatgagaaaa aaggaaatat | 240 |
| gataactaat agaacaaaaa gtctaacaat cttctttaag gatttaagtg agattatttt | 300 |
| atagatattt tatactgaaa aaatataatt catcaaaata cttttaaaa aataattcat | 360 |
| caaaatttat gtattttttt ataatttata aaaaattcta actaaatacc accaaatttt | 420 |
| attattcttc ttaaaaatct tttaagtctt acttaaataa aaaaaactta tttatactat | 480 |
| ttaaaaattt taatttaata ccaccgacct tttttatat aaaaaaaatc ttttaaaatt | 540 |
| atttaaaatc ttaatccaat gtaacctcca tctcaccatt tcccaaatca gattccgagt | 600 |
| catcgatcct taaaaagttt accatatctt ttctattttt atgcttgatc ttttctaagt | 660 |
| taagataaca acctagtaaa ttttcggat tctgcagcag taacttcgat ttgcactaaa | 720 |
| ctaaacatct gaggatctca gaggggcatc acattcacat tgagccgaat catcacaacg | 780 |
| acattcttaa atcacataaa aaaaaatagt gctcagtccg tgagagtttg tatcacggct | 840 |
| ctgacactga cacattcgca cgggatccct actttcttct cttgttttg tattctccca | 900 |
| tcaattattt aacaacccat taaggttctc gtcagaaagt ttagatttta tcgttagttt | 960 |
| ttaaatattt ttttcatcgt ttcatcagtg gtcacacagc gymagb | 1006 |

<210> SEQ ID NO 34
<211> LENGTH: 1506
<212> TYPE: DNA
<213> ORGANISM: Glycine max

<400> SEQUENCE: 34

| | |
|---|---|
| aaacaaaatt atccatctca caaggatgg tgagaatata acaaaaatta cactacagga | 60 |
| aaaataataa taaacacaaa aatttaatgt ggtacaatac ttttactta tattcacgga | 120 |
| acaatctaaa aagtatttca ctataaaaat atgattataa gattataact cacctcaaat | 180 |
| agtgcatatc tagatatccg attacctcac tcaatggtta caagaaatga taacactgtc | 240 |
| acataaagat acttttatct caacaaatga cttgttttag aatctctctt ctcacactct | 300 |
| ttattcatgt gttgtgttta tctactaatt atcttctcta tttatagtgg agatgaccac | 360 |
| caattataag ctttcttgaa agttaaaaca aaaataattt tcaatgcatc cattcaacta | 420 |
| aggttcatct agtaaaatac aatatttcac tttatattta agttacctaa accttagtga | 480 |
| taaaatttgt aagagaatta ttaaattaca tgaataacga aattaaggtc atgaaaatat | 540 |
| tgagttgaga tataatcaat gtaaggaaaa acataattag tcttaacata taagacaaat | 600 |
| attaatttaa tttagaaaac aaaggaaaaa aatgcataaa gaagaaatat gtttgatatt | 660 |

```
tttttattcc aaaagaatag gagaaatata tgacatatat cttaaaaaat attaaatagt      720
gatgagaaaa aaggaaatat gataactaat agaacaaaaa gtctaacaat ctttcttaag      780
gatttaagtg agattatttt atagatattt tatactgaaa aaatataatt catcaaaata      840 cttttttaaaa aataattcat caaaatttat gtattttttt ataatttata aaaaattcta     900
actaaatacc accaaatttt attattcttc ttaaaaatct tttaagtctt acttaaataa      960
aaaaaactta tttatactat ttaaaaattt taatttaata ccaccgacct ttttttatat     1020
aaaaaaaatc ttttaaaatt atttaaaatc ttaatccaat gtaacctcca tctcaccatt    1080
tcccaaatca gattccgagt catcgatcct taaaaagttt accatatctt ttctattttt    1140
atgcttgatc ttttctaagt taagataaca acctagtaaa ttttttcggat tctgcagcag   1200 taacttcgat ttgcactaaa ctaaacatct gaggatctca gagggcatc acattcacat    1260 tgagccgaat catcacaacg acattcttaa atcacataaa aaaaaatagt gctcagtccg    1320
tgagagtttg tatcacggct ctgacactga cacattcgca cgggatccct actttcttct    1380 cttgttttg tattctccca tcaattattt aacaacccat taaggttctc gtcagaaagt    1440
ttagatttta tcgttagttt ttaaatattt ttttcatcgt ttcatcagtg gtcacacagc    1500 gymagb                                                                1506

<210> SEQ ID NO 35
<211> LENGTH: 1897
<212> TYPE: DNA
<213> ORGANISM: artificial
<220> FEATURE:
<223> OTHER INFORMATION: synthetic sequence

<400> SEQUENCE: 35
cattctagat attgaagttt gtgataggtt ttattctttt attacttaat tgatctatat       60
tattattttt agttataaaa aattatagag agacaagagt tagattcttt attgatgtta      120
ctaataatga taaaggacaa tacaaaattt ggagaaaaaa aataaattgg cgggctaggc      180
caccgggcac ccggtcgaac taacaagccg aactaggaaa agtaacccat tttgcttaac      240
gggacgggcc gggttggccc attaatggcg ggccttttg tccccggacc gacccatatt      300
gacaacccta ttaagaataa taacaatttg cggtaaatac acaatttgac gaccattaga      360
atgatgcctt tcgtagtcc attgttagtt tgattaacaa agttttata aataaacact       420 tttagattag tttctaatac aattgattga tggttttgtt gatgttgctg aacttccgcg      480
atgatcacgt tttaattgta ggatactatt tttacattaa ttatattgac aaccaatata      540
aaaatattta tttaagaact ttccagatag tttgttacca agataacaga aaggggatta     600
ttatagtgaa ctattaacat caaactccta aacattgaac ttttataaat aactaaagaa    660
tcattcatat aattaagcct taaaaatata taattaacca aatctaaata aacacatgac     720
tatcctaaaa aagttgaacg agtccaaaaa acacaaagt gttattgaac cagacgaatc     780
acctaactta tcaccgtgca attaacagac ccacgtctga gaaatcaacg gtggtgtttt    840
cactttctac ctccgctgac tgtacccaac ttccgctctg ttactctgta ttgagtaagg    900
tgtacctgac accggaaggt ctcatattac tatttaaatg tcaggtaaat cagcactaac    960
taaaaaacaa acatgtgatt ttatttttatc cgtaacatga tataaaaaat tttacaatac   1020
tcacatccat taatcatctg agtttgattt ttttataacc aaacatgtga tatgggtgtt    1080
acattagtga agttcaagag aatcacttgt ttttaaccaa ttattaagat agatttgttt   1140
aaaagattaa attcttttat gttgacttgc aaatatcgag tatgattact gtacattaag   1200
```

```
catactatat tggttatctt tcataaatat gcagttttt ttttcaatta atagaaatta     1260
tgactcttca atttattt tatttatacg attttattta agtttcattt ttctttata      1320 tttaaagaga aagtaattta tagtctagac tatttttcaa caacacatat ttaagtcttt   1380
taatttatct tatttcatat taatcaacta tgaaacatat gaggattaac ggcgaagcac   1440
taccaggatt tgggaggcca ttaataattt gtcatattta aggctagact acaaagacaa   1500
cacaaccaat aaattaaaga agttcccttt caaaactgaa ctagtcaaaa gaaaatcaca   1560
acgtggaacg ttaatgaaac ggacaacgat ttggaaaaag agacaggtcg tcgcaagacc   1620
tcctacaccc tttattctta gaaccgacga aactgaaagc tccaatactt cgcaatgaga   1680
acactcacga gacaaagcat cctttctacc ttttcttttg tctagttaag atcgagtcga   1740
ttatactatt attaaaaaac aaataacaaa cacaatcatt gtcaactaga acggggagtg   1800
ttgtaagtcc aaaaaaaaat cttgggactc acaactccca catttctga ccaaaataat    1860 ctctataaac acctttgtt aacacatgtg ymagbrm                             1897

<210> SEQ ID NO 36
<211> LENGTH: 506
<212> TYPE: DNA
<213> ORGANISM: Glycine max

<400> SEQUENCE: 36
aataaacata ttaatcaact atgaaacata tgaggattaa cggcgaaggt gatggtccta     60
aaccctcccc attaataatt tgtcatattt aaggctagag atgaaagaca acacaaccaa   120
taaattaaag aagttccctt tcaaaactga acatcacaaa agaaaatcac aacgtggaac   180
gttaatgaaa cggacaacct aaaccttttt ctctgtccag cagcgttctc ctcctacacc   240
ctttattctt tcttggctcg aaactgaaac ctccaataca aggcaatgag aacactcacg   300
agacaaagca aggattctac ctttctttt gtctagtatt ctagctcagc tatatactat    360
tattaaaaaa caaataacaa acacaatcat tgtcttgatc ttgcccctca caacattcag   420
caaaaaaaaa tcttgccact cacaactccc acatttctc accaaaataa tctcttattt    480 cacccttgt taacacaaca gymagb                                         506

<210> SEQ ID NO 37
<211> LENGTH: 1006
<212> TYPE: DNA
<213> ORGANISM: Glycine max

<400> SEQUENCE: 37
aaactcattc cacatggact gtggccttcc agacatatta ctatttaaat gtcaggtaaa     60
tcagcactaa ctaaaaaaca aacatgtgat tttatttat ccgtaacatg atataaaaaa    120
ttttacaata ctcacatcca ttaatcatct gagtttgatt ttttataac caaacatgtg    180 atatgggtgt tacattagtc ttcaagttct cttagtgaac aaaaaaacca attattaaga   240
tagatttgtt taaaagatta aattcttta tgttgacttg caaattagca gtatgattac     300
tgtacattaa gcatactata ttggttatct tcataaaata tgcagttttt ttttcaatt    360 aatagaaatt atgactgaag tatttattt ttatttatac gattttattt aagtttcatt    420 tttctttat atttaaagag aaagtaattt atagtctaga ctattttca acaacacata    480 tttaagtctt ttaatttatg aataaacata ttaatcaact atgaaacata tgaggattaa   540
cggcgaaggt gatggtccta aaccctcccc attaataatt tgtcatattt aaggctagag   600
```

| | |
|---|---|
| atgaaagaca acacaaccaa taaattaaag aagttccctt tcaaaactga acatcacaaa | 660 |
| agaaaatcac aacgtggaac gttaatgaaa cggacaacct aaaccttttt ctctgtccag | 720 |
| cagcgttctc ctcctacacc ctttattctt tcttggctcg aaactgaaac ctccaataca | 780 |
| aggcaatgag aacactcacg agacaaagca aggattctac cttttctttt gtctagtatt | 840 |
| ctagctcagc tatatactat tattaaaaaa caaataacaa acacaatcat tgtcttgatc | 900 |
| ttgcccctca caacattcag caaaaaaaaa tcttgccact cacaactccc acattttctc | 960 |
| accaaaataa tctcttattt cacccttttgt taacacaaca gymagb | 1006 |

<210> SEQ ID NO 38
<211> LENGTH: 1506
<212> TYPE: DNA
<213> ORGANISM: Glycine max

<400> SEQUENCE: 38

| | |
|---|---|
| ttgattaaca aaagtttat aaataaacac ttttagatta gtttctaata caattgattg | 60 |
| atgcaaaaca agatgttgct gaacaagggc gatgatcacc aaaattaaca aggatactat | 120 |
| ttttacatta attatattga caccaatat aaaaatattt atttaagaac tttggtctat | 180 |
| caaacaaacc aagataacag aaaggggatt attatagtgt tgataattgt agtttgagga | 240 |
| tttgattgaa cttttataaa taactaaaga atcaatcata taattaagcc ttaaaaatat | 300 |
| ataattaacc aaatcaaaat aaacacatga ctatcctaaa aaagttgaag ctcaggtttt | 360 |
| ttgtgttttc acaataactt ggtctgctta gtggattgaa tagtggcagc aattaacaga | 420 |
| cccacgtctg agaaatcaac ggtggtgttt tcactttcta cctcccgtga ctgtacccaa | 480 |
| cttccgctct gttactctgt aaactcattc cacatggact gtggccttcc agacatatta | 540 |
| ctatttaaat gtcaggtaaa tcagcactaa ctaaaaaaca aacatgtgat tttatttat | 600 |
| ccgtaacatg atataaaaaa ttttacaata ctcacatcca ttaatcatct gagtttgatt | 660 |
| ttttataac caaacatgtg atatgggtgt tacattagtc ttcaagttct cttagtgaac | 720 |
| aaaaaaacca attattaaga tagatttgtt taaaagatta aattctttta tgttgacttg | 780 |
| caaattagca gtatgattac tgtacattaa gcatactata ttggttatct ttcataaata | 840 |
| tgcagttttt ttttttcaatt aatagaaatt atgactgaag tattttattt ttatttatac | 900 |
| gatttttatt aagtttcatt tttctttat atttaaagag aaagtaattt atagtctaga | 960 |
| ctatttttca acaacacata tttaagtctt ttaatttatg aataaacata ttaatcaact | 1020 |
| atgaaacata tgaggattaa cggcgaaggt gatggtccta aaccctcccc attaataatt | 1080 |
| tgtcatattt aaggctagag atgaaagaca acacaaccaa taaattaaag aagttccctt | 1140 |
| tcaaaactga acatcacaaa agaaaatcac aacgtggaac gttaatgaaa cggacaacct | 1200 |
| aaaccttttt ctctgtccag cagcgttctc ctcctacacc ctttattctt tcttggctcg | 1260 |
| aaactgaaac ctccaataca aggcaatgag aacactcacg agacaaagca aggattctac | 1320 |
| cttttctttt gtctagtatt ctagctcagc tatatactat tattaaaaaa caaataacaa | 1380 |
| acacaatcat tgtcttgatc ttgcccctca caacattcag caaaaaaaaa tcttgccact | 1440 |
| cacaactccc acattttctc accaaaataa tctcttattt cacccttttgt taacacaaca | 1500 |
| gymagb | 1506 |

<210> SEQ ID NO 39
<211> LENGTH: 1055
<212> TYPE: DNA
<213> ORGANISM: artificial

```
<220> FEATURE:
<223> OTHER INFORMATION: synthetic sequence

<400> SEQUENCE: 39
cccatgttta tttaaggcat ggtcaagttg acaagttgaa gttcgactaa ttaatcacaa        60
acacttcttc ataatcattc gatggttttt atgataaaga gttcacgtga catatgtgat      120
gctatcacac gttccagcag gttcaatatg cattacatga ctataattat ggcattgaaa      180
gacaaaaatt ttcctttagt ttattgtaaa tctttgctgt tttctccctt tggaagccgg      240
tacccaaaag gtccgttcga ctattgtttc gtgaaaatta cagcactgta acgctcaatc      300
taatgttagc taaatgctaa tcgttagtga taagtagttc tacctcatca cacatactgt      360
taacaattat tctgactcat accattaaac ttttaataat atttatgatg tagcggcgcg      420
cagtacgtaa taataaacgt tccattctct cttccaaatc gagtaatccg aatgtatata      480
tgcttgagaa ttgagactac taattaagta aacacagaga tacgaagatt taattcccga      540
agtatatata atgtagcgtt gaatgtactt tttataacaa aaacatcccc tggctgaagg      600
agttagagga caagtctatt atttggaaaa aaagaaaaa agaggtaaat aggtattctc      660
ttccgaacct ggtaaatgtt ccaaaagttg gctaagcgtt tcgcgtttcg tagaatcttt      720
ttaggttgca ttaattttg ttggtgttgc ataaatggtg atgacccaca tgcaggttct      780
acatctctgt ttggctgtgt gtcttaatat gaaaacttaa gaggagactc gcctttagat      840
aactgccacg tgatttcagg ttccatcctc tcttctcgca accaagtagt tagtccaaat      900
taaaaatgga ttaaaagtg cttagagcca aaggactttt cttcttggtt tgtgactttg      960
tccatttctg ctctgccaaa atcgtttca aaattcttgt tcttttcttt cttcgaagtc     1020
ttgccaacaa gttattcgtg agggaacgym agbrm                                1055

<210> SEQ ID NO 40
<211> LENGTH: 506
<212> TYPE: DNA
<213> ORGANISM: Glycine max

<400> SEQUENCE: 40
ataatgtagc gttgaatgta ctttttataa caaaaacatg gggaccctga aggagttaga       60
ggacaagtct attatttgga aaaaaagaa aaaagaggta ataggtaaa gagaaggctt       120
ggaccattat gttccaaaag ttggctaagg caaagcgcaa agcatcttag aaaaatcctt       180
gcattaattt ttgttggtgt tgcataaatg gtgatgaccc acatgcaggt tctacatctc       240
acaaccctg tgtgtcttaa taacttttga attctcctct ctcgccttta gataactgcc       300
acgtgatttc aggttccatc ctctcttcag cgttggttca tcaatcacca aattaaaaat       360
ggattaaaaa gtgctttctc ggttttcctg aagaagaac ctttgtgact tgtccattt       420
ctcctctgcc aaaaatcgtt tcaaaattga acaagaaaag aaagaagctt ctcttgccaa       480
caagttattc cactcccttg gymagb                                            506

<210> SEQ ID NO 41
<211> LENGTH: 706
<212> TYPE: DNA
<213> ORGANISM: Glycine max

<400> SEQUENCE: 41
agtcacatac tgttaacaat tattctctga gtatggttta aacttttaat aatattatac       60
tagtagcggc gcgcagtacg taataataaa cgttccattc tctcttccaa atcgagtaat      120
```

```
ccgaatgtat atatgcttga gaattgagac tactaattaa gtaaacacag agatacgaag      180
atttaattcc cgaagtatat ataatgtagc gttgaatgta cttttttataa caaaaacatg     240 gggaccctga aggagttaga ggacaagtct attatttgga aaaaaaagaa aaaagaggta      300
aataggtaaa gagaaggctt ggaccattat gttccaaaag ttggctaagg caaagcgcaa      360
agcatcttag aaaaatcctt gcattaattt ttgttggtgt tgcataaatg gtgatgaccc      420
acatgcaggt tctacatctc acaaaccctg tgtgtcttaa taacttttga attctcctct      480
ctcgccttta gataactgcc acgtgatttc aggttccatc ctctcttcag cgttggttca      540
tcaatcacca aattaaaaat ggattaaaaa gtgctttctc ggttttcctg aaagaagaac      600
ctttgtgact ttgtccattt ctcctctgcc aaaaatcgtt tcaaaattga acaagaaaag      660
aaagaagctt ctcttgccaa caagttattc cactcccttg gymagb                     706
```

<210> SEQ ID NO 42
<211> LENGTH: 1006
<212> TYPE: DNA
<213> ORGANISM: Glycine max

<400> SEQUENCE: 42

```
taattaatca caaagtgaag aacataatca ttcgatggtt tttatgataa agagttcacg      60
tgacatatgt gatgctatca cacgttccag cacttcaat atgcattaca tgactataat      120
tatggctaac tttctgtttt attttccttt agtttattgt atttctttgc tgttttctcc      180
ctttccttcg gccatgggtt ttccaggcaa gctgtattgt ttcgtgaaaa ttacagctga      240
cattgcgaca atctaatgtt agctaaatgc taatgcaatc actattcatc aagatggagt      300
agtcacatac tgttaacaat tattctctga gtatggttta aacttttaat aatattatac      360
tagtagcggc gcgcagtacg taataataaa cgttccattc tctcttccaa atcgagtaat      420
ccgaatgtat atatgcttga gaattgagac tactaattaa gtaaacacag agatacgaag      480
atttaattcc cgaagtatat ataatgtagc gttgaatgta cttttttataa caaaaacatg     540 gggaccctga aggagttaga ggacaagtct attatttgga aaaaaaagaa aaaagaggta      600
aataggtaaa gagaaggctt ggaccattat gttccaaaag ttggctaagg caaagcgcaa      660
agcatcttag aaaaatcctt gcattaattt ttgttggtgt tgcataaatg gtgatgaccc      720
acatgcaggt tctacatctc acaaaccctg tgtgtcttaa taacttttga attctcctct      780
ctcgccttta gataactgcc acgtgatttc aggttccatc ctctcttcag cgttggttca      840
tcaatcacca aattaaaaat ggattaaaaa gtgctttctc ggttttcctg aaagaagaac      900
ctttgtgact ttgtccattt ctcctctgcc aaaaatcgtt tcaaaattga acaagaaaag      960
aaagaagctt ctcttgccaa caagttattc cactcccttg gymagb                    1006
```

<210> SEQ ID NO 43
<211> LENGTH: 2051
<212> TYPE: DNA
<213> ORGANISM: artificial
<220> FEATURE:
<223> OTHER INFORMATION: synthetic sequence

<400> SEQUENCE: 43

```
tcgagtaatg gagtttaaag gctaccccctt atcatagatt aatattgaaa tttcaaaatt      60
tagcagtcag taagttgaag tctactaaat tcaaattatt atataaaaaa aatactaacg      120
tcaacactga gattatgaga ttgttgtaaa tatatttgga catgttttat ataaataaat      180
ttaaggctaa aatacgtttt ttttctcata aaattgaaaa taaacttttt ttgtttaaat      240
```

```
aaaattaaaa tgtgacattt tttcaacaac tctaggttcc gttgtatcta aatccaaatc    300
ataactaatg caaatgtaat ataaaaatgt agttaatacc ttggaatgga tgaaagaaaa    360
aatgacaaat tttaatttta tagaaatgaa aaatgtttat gtttaatttt aaaaacataa    420
atttctaaaa aaaattgtgg aatatataaa tttttaattt taagaaaacg aaaaatatat    480
ttaaaattta aatttaagta aatttaacca aaatagcaat atttgtgaga atcttaatta    540
atatcattaa ttgagttatt tatataaaat gtgtggatta ttataaattt caatatgacg    600
agtcttttga taacttacat atatcgaact acgttttga agtaagttaa atgaagcaa     660 aaaagcagcg ctcaagttta taattctttg agaagccaga gatatcgaac ggaacatcag    720
taatataaaa gggaaaataa aaaaactat aaatgcgtat tcctataagg gaaaattgat     780
aaccacagga acagggtata tatgatcttt attacattga agctatcctt actccacgta    840
tgacgaaact gttacttaga aagttaatat catgaagaat ttaacacaag gtatagtatt    900
ataaagaatt caaacaagag attcttgaat cttgtttagg aaagatgttg tatcaactat    960
ttatgtgttt ggtgaaaaat tgtaccatag acatttatt tatttattta tttgaagagg    1020
acattttatt gaaacacacg ttatagattt ttaaatattt ataataaaat aataagtttt    1080
tttattttat acgaaatttt tcattgaaat tatatgtttt ttgaaactta cattattttt    1140
ggttgcataa ccatacatat gagaaaatgt taaagatttt tttgtgagaa aaggtatgta    1200
actaattttt gaatccaact acaagtcttg acattattat tattggaact aaaaaaacgt    1260
ttctcaaaat ctaacacact tatgtatgtt catttttagt attaaaaata ttaattaaaa    1320
tatcatttat aataatccta tttgtctcaa acttataacg ctccaataaa atatatatgt    1380 agtcttttata aaaaaaatta ttgtatttaa aaataaaaac ataattaata tttattatca    1440
actaaactaa taaaaatata ttttattaaa ataaattata caaataaata ggtaataata    1500
tctattagaa atgttaagga caaaccaaaa aacaacatat tatttatgat tagtataaat    1560
ctattgaaag ttataaaaaa aattgagctt tactttaat ttttgtgtct cacttatgta     1620
attgaatttt tattgcataa attcagtttg attttttta aaaaaaacat aatattaaca     1680
actcttgaca gttaatatcg ctgttgtgtc tccagcaata tctaccatga taaacgaaca    1740
tttttttttt tgaattaaaa aaaggaatga acgtaattag gaaaatttat acatccctct    1800
tttttatgcc ggacggaggc cgtatcctaa ttaagacgat acgttgaaaa ttattatttt    1860
atttaaaaaa aataaaaaaa aaagaggaa ctaaaatctt accatgggtc ccaccgcgtg      1920
gcgccatggc ttttggcta tctctcgtga gcgttaggga ttgggataac gattaacgag    1980
cgacttcttc ttcaaaaaca cacaaacaca ctacactttg tctctgttct cacacacgct    2040
cttgymagbr m                                                       2051
```

<210> SEQ ID NO 44
<211> LENGTH: 506
<212> TYPE: DNA
<213> ORGANISM: Glycine max

<400> SEQUENCE: 44

```
ttatgattag tataaatcta ttgaaagtta taaaaaaat tgagctttac ttttaatttt      60
tgtgtctcac ttatgtaatt gaataaatat tgcataaatt cagtttgatt tttttaaaa    120 aaaacataat attaacaact cttgacacaa ttatagcgac ttgtgtctcc agcaatatct    180
accatgataa acgaacaaaa aaaaaaact taattttttt cctatgaacg tatataggaa    240
```

| | |
|---|---|
| aatttataca tgggagaaaa aatacggcct gcctggccgt atcctaatta agacgatacg | 300 |
| ttgaaaatta ttattttatt taaaaaaaaa aaaaaaaaaa agaggaacta aaatcttagg | 360 |
| atgggtccca ccgcgtggcg ccatgcgaaa aaccgataga gagcactcgc aatgggattg | 420 |
| ggataacgat taacgagcga cttcttcttc aaaaacacac aaacacacta cactttgtct | 480 |
| ctgttctgtg tgtgcgagaa gymagb | 506 |

<210> SEQ ID NO 45
<211> LENGTH: 1006
<212> TYPE: DNA
<213> ORGANISM: Glycine max

<400> SEQUENCE: 45

| | |
|---|---|
| tagatttttta aatatttata ataaaataat aagttttttt attttatacg aaattttca | 60 |
| ttgaaaaata tacaaaattg aaacttacat tattttaggt tgcataacca tacatatgag | 120 |
| aaaatgttaa agattttttt gtgagaaaag gtatgtaact aattttttctt aggttgatgt | 180 |
| tcagaagaca ttattattat tggaactaaa aaaacgtttc tcaaaatcta acacacttat | 240 |
| gtatgttgta atttagtatt aaaaatatta attaaaatat catttataat aatcctatttt | 300 |
| gtctcaaaca atattgcctc caataaaata tatatgtagt ctttataaaa aaaattattg | 360 |
| tatttaaaaa taaaaacata attaatatta taatagaact aaactaataa aaatatattt | 420 |
| tattaaaata aaatatacaa ataaataggt aataatatct attagaaatg ttaaggacaa | 480 |
| accattttttc aacatattat ttatgattag tataaatcta ttgaaagtta taaaaaaaat | 540 |
| tgagctttac ttttaattttt tgtgtctcac ttatgtaattt gaataaatat tgcataaatt | 600 |
| cagtttgatt ttttttaaaa aaacataat attaacaact cttgacacaa ttatagcgac | 660 |
| ttgtgtctcc agcaatatct accatgataa acgaacaaaa aaaaaaaact taatttttttt | 720 |
| cctatgaacg tatataggaa aatttataca tgggagaaaa aatacggcct gcctggccgt | 780 |
| atcctaatta agacgatacg ttgaaaatta ttattttatt taaaaaaaaa aaaaaaaaaa | 840 |
| agaggaacta aaatcttagg atgggtccca ccgcgtggcg ccatgcgaaa aaccgataga | 900 |
| gagcactcgc aatgggattg ggataacgat taacgagcga cttcttcttc aaaaacacac | 960 |
| aaacacacta cactttgtct ctgttctgtg tgtgcgagaa gymagb | 1006 |

<210> SEQ ID NO 46
<211> LENGTH: 1506
<212> TYPE: DNA
<213> ORGANISM: Glycine max

<400> SEQUENCE: 46

| | |
|---|---|
| tcattaattg agttatttat ataaaatgtg tggattatta taaatttcaa taacacgagt | 60 |
| cttttgataa cttacatata tgcttgatgc aaaaacttca ttcaatttta cttcgttttt | 120 |
| tcgtccgctc aagtttataa ttcttttgaga agccagacta tagcttgcct tgtagtgtaa | 180 |
| tataaaaggg aaaaaaaaaa aaactatatt acgcataagg atattgggaa aattgataac | 240 |
| cacaggaaca gggtatatat gatcttataa tgtaagaagc tatccttact ccacgtatga | 300 |
| cgaaactgtt acttagaatc ataatatcat gaagaattta acacaaccat tagtattata | 360 |
| aagaattcaa acaagagatt cttgaatctt gtttaggaaa gaacaactat caactattta | 420 |
| tgtgtttggt gaaaaattgt accatagaca tttttatttat ttatttatttt gaagaggaca | 480 |
| ttttattgaa acacacgtta tagattttta aatatttata ataaaataat aagttttttt | 540 |
| attttatacg aaattttttca ttgaaaaata tacaaaattg aaacttacat tattttaggt | 600 |

```
tgcataacca tacatatgag aaaatgttaa agattttttt gtgagaaaag gtatgtaact    660 aattttctt aggttgatgt tcagaagaca ttattattat tggaactaaa aaaacgtttc    720
tcaaaatcta acacacttat gtatgttgta atttagtatt aaaaatatta attaaaatat    780
catttataat aatcctattt gtctcaaaca atattgcctc caataaaata tatatgtagt    840
ctttataaaa aaaattattg tatttaaaaa taaaaacata attaatatta taatagaact    900
aaactaataa aaatatattt tattaaaata aaatatacaa ataaataggt aataatatct    960
attagaaatg ttaaggacaa accattttc aacatattat ttatgattag tataaatcta   1020
ttgaaagtta taaaaaaaat tgagctttac ttttaatttt tgtgtctcac ttatgtaatt   1080
gaataaatat tgcataaatt cagtttgatt ttttttaaaa aaaacataat attaacaact   1140
cttgacacaa ttatagcgac ttgtgtctcc agcaatatct accatgataa acgaacaaaa   1200
aaaaaaaact taatttttt cctatgaacg tatataggaa aatttataca tgggagaaaa   1260
aatacggcct gcctggccgt atcctaatta agacgatacg ttgaaaatta ttattttatt   1320
taaaaaaaaa aaaaaaaaaa agaggaacta aaatcttagg atgggtccca ccgcgtggcg   1380
ccatgcgaaa aaccgataga gagcactcgc aatgggattg ggataacgat taacgagcga   1440
cttcttcttc aaaaacacac aaacacacta cactttgtct ctgttctgtg tgtgcgagaa   1500 gymagb                                                              1506
```

<210> SEQ ID NO 47
<211> LENGTH: 1925
<212> TYPE: DNA
<213> ORGANISM: artificial
<220> FEATURE:
<223> OTHER INFORMATION: synthetic sequence

<400> SEQUENCE: 47

```
attcttagat aaacatacgt acgttgcttt ttaggaaaaa aaaatgaaac cacactgcac     60
agttatggaa gagaaatcgg ttacgggtca acttttgttt aagtggggtc caagtagaac    120
cctaaaacgg ttgaaagcta gtttgcagat caagaatttt aatagcagct acaagaaatt    180
taacatataa ttaagtaacg ggtgttggat ccacgtggca acattattgt actacatagg    240
ctcacttaat aaagacaaaa atactggcgt gtattttaa acatgttaaa cacgtggcag    300
ctcatttagg ttgatctgga taggtttatc aacttccgca gttaatatag ataattcaca    360
acaaagaaag ggattaagtt gtaggccaag ggatttacgg atcttgaact agcgtaagaa    420
atatttgatt cacaagttaa ttttatctg aatgcctagt tcaaggtcca caagttgatt    480
tttaagattt accctagttc aaccaggtat tcagagccta gttagggtaa accttaaaaa    540
tcatgatgtg ttaatcccaa aagggagaaa aaaggaaggg ataattttgt tattttaaa    600 gaatgaacac atatggttgt tattatgacc atacacctaa caccactctt aaataacctc    660
aacaatcgtg tgaaaatgat agaattatat atatatataa aagacaaatc agtctttgca    720
acgactatag gctctttcta aaattctgaa attaaatttt gagtatgaaa tatatgttaa    780
atatttagag aaagattatt taatttacgt gtcataccta cctgacagga tagtgattta    840
aatcaaactc taaatcgaac ctacgagaat gactcattga accattataa aaaaaattca    900
attttatcat taacaaacat gataaataat tttttatgaa taatataata aaaatgtaaa    960
taaatgttct tactaaactc ttataattac aaaattaatt atatttcatc caactatgaa   1020
aaagtgaaat atttttaagg tcataaattg aaatttattg ttaatttatt gagcttttca   1080
```

| | |
|---|---|
| acttaataat ctatgactat tatataaaag aatagggtag tgaaaaatct aaaatgaaca | 1140 |
| ttacatatta ttaacacttg atataaataa gaggaaaatg aaaattttga aaaaattact | 1200 |
| attgaaatga aaaactaga agagaagaa gaacaataag agaaatttat gggatgagac | 1260 |
| gtacgtgtag gagtcatta gctggccact cccttcctga gtaaaagtaa agatgctgta | 1320 |
| aaaaaaatct aataaaaagg attcaacttt ttaataagac taaaaaataa tttgaaaaaa | 1380 |
| ttttacagat gacttttat attttttta taattttaa tataagcgga actaatgcca | 1440 |
| ctgacgatct tgtaataaaa gtacgcagtt gaaagaactc ttagttatac caaaaatcag | 1500 |
| gttgtacaca catctaacta gcttcacgaa agtaattta tacataatgt ttgctcactg | 1560 |
| ctgcactttg ctttgactgg aacattcaac aatgtttggt ttaagtaact attagtcttt | 1620 |
| gcatttttcc ctcgtgttga ctcttcgcac ttttaaagct gtcgaattca atgagcacag | 1680 |
| ttgttactta tataaaacta ttaaatgtga gaaaagttg gtgtgatagg catgcatcca | 1740 |
| gcattagact tatcgactaa ttaaagaaga aatagtcagc gacgggatga tcacgtttct | 1800 |
| aagagatatc cactatctag tagattctct ataaatacca atgcttagag tgataaactt | 1860 |
| ccattctcat gaacgttaat cggtgtgtat agtataacag attttgtatt gaatcttgym | 1920 |
| agbrm | 1925 |

<210> SEQ ID NO 48
<211> LENGTH: 506
<212> TYPE: DNA
<213> ORGANISM: Glycine max

<400> SEQUENCE: 48

| | |
|---|---|
| taatataagc ggaactatac ggtgactgct agttgtaata aagtacgca caactttcaa | 60 |
| ctcttagtta taccatttta gtccaacatg tgacatctaa ctagcttcac gaaaagtaat | 120 |
| ttatacatat acaaacgagt gacgacgact ttgctttgac tggaacattc aacaatgttt | 180 |
| ggtttaacat tgatttagtc tttgcatttt tccctcgtgt tgactcttcg cacttttaaa | 240 |
| gctgtcgaat tcaatgagca cagttgttac ttatataaaa ctattaaatg tgagaaaaag | 300 |
| ttggtgtgat aggcatgcat ccagcattag acaataggac taattaaaga agaaatagtc | 360 |
| agcgacggga tgatcacgtt tctaagagat atccactatc ttcatctatc tctataaata | 420 |
| ccaatgctta gagtgataaa cttccattct caacttgcaa ttagccacac atatcatata | 480 |
| cagattttgt attgttagaa gymagb | 506 |

<210> SEQ ID NO 49
<211> LENGTH: 1006
<212> TYPE: DNA
<213> ORGANISM: Glycine max

<400> SEQUENCE: 49

| | |
|---|---|
| gttgataaat aattttttat gaataatata ataaaaatgt aaataaatgt tcttactaat | 60 |
| gacttataat tacaaaatta attatatttc atccaactat gaaaaagtga atatttttta | 120 |
| aggtcataaa ttgaaattta ttgttaattt attgagcttt tcaacttaat aatctatctc | 180 |
| tattatataa aagaataggc tagtgaaaaa tctaaaatga acattacata ttattaacac | 240 |
| ttgatataaa taagaggaaa atgaaaattt tgaaaaaatt actattgaaa tgaaaaaact | 300 |
| agaaagagaa gaagaacaat aagagaaatt tatgggatga gacgtacgtg taggagtagt | 360 |
| aatcgaccgg tgagggaagg agagtaaaag taaagatgct cattttttt agtaataaaa | 420 |
| aggattcaac ttttttatt cactaaaaaa taatttgaaa aataatacaa gatgactttt | 480 |

```
tatattttt   ttataatttt   taatataagc   ggaactatac   ggtgactgct   agttgtaata      540
aaagtacgca  caactttcaa   ctcttagtta   taccattta    gtccaacatg   tgacatctaa      600
ctagcttcac  gaaaagtaat   ttatacatat   acaaacgagt   gacgacgact   ttgctttgac      660
tggaacattc  aacaatgttt   ggtttaacat   tgatttagtc   tttgcatttt   tccctcgtgt      720
tgactcttcg  cactttaaa    gctgtcgaat   tcaatgagca   cagttgttac   ttatataaaa      780
ctattaaatg  tgagaaaaag   ttggtgtgat   aggcatgcat   ccagcattag   acaataggac      840
taattaaaga  agaaatagtc   agcgacggga   tgatcacgtt   tctaagagat   atccactatc      900
ttcatctatc  tctataaata   ccaatgctta   gagtgataaa   cttccattct   caacttgcaa      960
ttagccacac  atatcatata   cagattttgt   attgttagaa   gymagb                      1006

<210> SEQ ID NO 50
<211> LENGTH: 1506
<212> TYPE: DNA
<213> ORGANISM: Glycine max

<400> SEQUENCE: 50
gaaatatttg   attcacaagt   taatttttaa   gacttacgga   tcaagttggt   ccacaagttg       60
atttttaaga  tttacggatc    aagttggtcc   ataagtctcg   gatcaatccg   taaaccttaa      120
aaatcaactt  gtgttaatcc    gtaaagggag   aaaaaggaa    gggataattt   tgttattttt      180
aaagaatgtt  gtgtatacca    acaataatac   tggatacacc   taacaccact   cttaaataac      240
cagtacaatc  gtgtgaaaat    gatagaatta   tatatatata   taaagacaa    atcagtcttt      300 gcaacgacta  taggctcttt    ctaaaattct   gaaattaaat   tttgagtatg   aaatatatgt      360
taaatattta  gagaaagatt    atttaattta   cgtgtcatac   ctacctgact   cgatagtgat      420
ttaaatcaaa  ctctaaatcc    ttggatggag   aatgactcat   tgaaggtaat   attttttttt      480
tcaattttat  cattaacaaa    gttgataaat   aattttttat   gaataatata   ataaaaatgt      540
aaataaatgt  tcttactaat    gacttataat   tacaaaatta   attatatttc   atccaactat      600 gaaaagtga   aatattttta    aggtcataaa   ttgaaattta   ttgttaattt   attgagcttt      660
tcaacttaat  aatctatctc    tattatataa   agaataggc    tagtgaaaaa   tctaaaatga      720
acattacata  ttattaacac    ttgatataaa   taagaggaaa   atgaaaattt   tgaaaaaatt      780
actattgaaa  tgaaaaaact    agaaagagaa   gaagaacaat   aagagaaatt   tatgggatga      840
gacgtacgtg  taggagtagt    aatcgaccgg   tgagggaagg   agagtaaaag   taaagatgct      900 cattttttt   agtaataaaa    aggattcaac   ttttttatt    cactaaaaaa   taatttgaaa      960
aaataataca  gatgactttt    tatatttttt   ttataatttt   taatataagc   ggaactatac     1020
ggtgactgct  agttgtaata    aaagtacgca   caactttcaa   ctcttagtta   taccattta     1080 gtccaacatg  tgacatctaa    ctagcttcac   gaaaagtaat   ttatacatat   acaaacgagt     1140
gacgacgact  ttgctttgac    tggaacattc   aacaatgttt   ggtttaacat   tgatttagtc     1200
tttgcatttt  tccctcgtgt    tgactcttcg   cactttaaa    gctgtcgaat   tcaatgagca     1260
cagttgttac  ttatataaaa    ctattaaatg   tgagaaaaag   ttggtgtgat   aggcatgcat     1320
ccagcattag  acaataggac    taattaaaga   agaaatagtc   agcgacggga   tgatcacgtt     1380
tctaagagat  atccactatc    ttcatctatc   tctataaata   ccaatgctta   gagtgataaa     1440
cttccattct  caacttgcaa    ttagccacac   atatcatata   cagattttgt   attgttagaa     1500 gymagb                                                                          1506
```

<210> SEQ ID NO 51
<211> LENGTH: 1929
<212> TYPE: DNA
<213> ORGANISM: artificial
<220> FEATURE:
<223> OTHER INFORMATION: synthetic sequence

<400> SEQUENCE: 51

```
ttaactgttc aactatgttg tatacgtgta agaatatgat atattagata aaaagagttt      60
ttcaattaat aaaaaaaata gaatttttt aaattgaata aaaggataaa ataaactttt     120
atataaaata gtaaaataa aatttataat aagaaaaact agtaataagc taacttattt     180
ttgtttttga acttgttgat atataagcta cttgaagtaa cttttaaaat ataaactact     240
aaaaataact ttgtatatta acttataaca taataaaaaa ataatattgt ttttgaaaag     300
tgttatcaaa catattatgc aggaatcaag aacgcttgtt aaggttaaaa gaaaacggga     360
gatgagctag acttcaacca agtacgaccc taaaaaaggc tccataaata gaaatatttc     420
ttacttatga attaagctta gttcttgcat atatataccc tacactttc atttatttaa     480
ttttcatact ctagacttt cagaacatta ggttttcgca tagagcggtt attttatgtt     540
ggaccaagtc actccaataa gttattttat tcatttaata tccatttatt tatttttatt     600
tgagacgtat cttcatttac tgtttaatta gtaaaattta ctgaaatact aagagacaac     660
aaatacaata gcttaatcaa tgggataaat tcctagcatg ccaatgtttt cacgaaagga     720
acgaacgaaa cacgaaactg tttgatgaaa catcctctcc aatgtgtctt tgggagtgag     780
ttaaatgtgt tgcaaacaca tgattaaaat ccagccacga tcgaatccgt atatattaat     840
gattattata ataaaataat attaaaaaag ataacattgc aactttacaa cactaaaatc     900
taaaaataaa gcattacttt acaacagatt aagatctaga ataaataaac ttaggttaat     960
tgtttaaaaa ttcttttctt tagttttgtt ataccatagt tcataaaaca ctgacccatc    1020
atgaaccaat atcaacagct caaatgatc atttgaacaa ttttattttc ttaaaattga    1080
atctgtaatt tatttcggtg tgttttagct aacaccaatt ttttattatt atcatgaacc    1140
aatatctccg ggtctatttt tccttttttt agaacacgag tctaagaacc atacttgaat    1200
cacaccgttc agcccatttg taaccatacc gccaatttgg aaaaatgaac aacacaataa    1260
gagtcgtgta tttgattcta taattcatct acctctattc atctacctga gcccttaatc    1320
cagtggacct acagtcacct acagagtcaa gtcgatgtac attctattcc ttcatttttt    1380
aaaattcatt aaatttataa ataaaatctt ataattatat aattgaattc actaatttta    1440
tattttataa tttgtatcca ttaatttagg atcttaaata tgccactatt tcagtcatta    1500
tcttaattac cgagatttgt cgtaaatatg attgtcttgg atttaagata tttaaacctt    1560
cctataatta ggttttgaca ggagataaaa tataatcaat ttataagtag ttgattcgca    1620
ggtatatatg tacagtcgtc aaactattct agattttctg aaaatatcta catacctgtt    1680
aaactcctca taaatgtttt ttgcaagttg tactagctca catatcaacg gttttttctt    1740
cgtgcgctga agtggttctg ttgattagtc tttctgtggc gagtattcaa ctacctgcaa    1800
taattttatta gttcccacag ctcacaatac taggagtata taaatttgta gatcaatcaa    1860
atcacatata actttgcaaa tcgatcaaat cacaatttag taattggttg tcaattaaag    1920
ggymagbrm                                                            1929
```

<210> SEQ ID NO 52
<211> LENGTH: 506

<212> TYPE: DNA
<213> ORGANISM: Glycine max

<400> SEQUENCE: 52

```
attgaattca ctaatttat attttataat ttgtatccat taatttagga tcttaaatat      60
gccactattt cagtcattat cttaattacc gagatttgtc gtaaatatga tacagaacct    120
aaattcatat ttaaaccttc ctataattag gttttgacag gagataaaat ataatgttaa    180
atattctagt tgattggcag gtatatatgt acagtcgagt ttgaattcta gattttctga    240
aaatatctac atacctgtta aactcgagta ttttacaaaa accaagttgt actagctcac    300
atatcaacgg ttttttcttc gtggcgactt cacgttctgt tgattagtct ttctgaccgc    360
tgtattcaac tacctgcaat aatttattag ttcccacagc tcacttatga tggagtatat    420
aaatttgtag atcaatcaaa tcacatataa ctttgcaaat cgatcaaatc acaatttagt    480
aattggttca gttaatttcc gymagb                                         506
```

<210> SEQ ID NO 53
<211> LENGTH: 1006
<212> TYPE: DNA
<213> ORGANISM: Glycine max

<400> SEQUENCE: 53

```
caacagatta agatctagaa taaataaact taggttaatt gttttttta agaaaagaaa      60
tcaaaacaat atggtatcaa gtattttcac tgacccatca tgaaccaata tgttgtcgag    120
ttttactagt tttgaacaat tttatttct taaaattgat tctgtaattt atttcggaca    180
caaaatcgat tcaccaattt tttattatta tcatgaacca atatgaccgg gtctatttt    240
cctttttta gaacacgagt ctaacttggt tacttgaatg tgtggcttca gcccatttga    300
ttgcataccg ccaatttgga aaaatgaaca acacaataag agtcgtgtat ttgattgata    360
tattcatcta cctctattca tctacctgag ccctttaatcc agtggaccta cagtcaccta    420
cagtcagttc aggatgtaca ttctattcct tcatttttta aaattcatta aatttataaa    480
taaaatctta taattatata attgaattca ctaatttat attttataat ttgtatccat    540
taatttagga tcttaaatat gccactattt cagtcattat cttaattacc gagatttgtc    600
gtaaatatga tacagaacct aaattcatat ttaaaccttc ctataattag gttttgacag    660
gagataaaat ataatgttaa atattctagt tgattggcag gtatatatgt acagtcgagt    720
ttgaattcta gattttctga aaatatctac atacctgtta aactcgagta ttttacaaaa    780
accaagttgt actagctcac atatcaacgg ttttttcttc gtggcgactt cacgttctgt    840
tgattagtct ttctgaccgc tgtattcaac tacctgcaat aatttattag ttcccacagc    900
tcacttatga tggagtatat aaatttgtag atcaatcaaa tcacatataa ctttgcaaat    960
cgatcaaatc acaatttagt aattggttca gttaatttcc gymagb                  1006
```

<210> SEQ ID NO 54
<211> LENGTH: 1506
<212> TYPE: DNA
<213> ORGANISM: Glycine max

<400> SEQUENCE: 54

```
tacttatgaa ttaagcttag ttcttgcata tatataccct acactttca tttatttaat     60
tttcatactc tagactttc agaacattag gttttcgcat agagcggtta ttttatgttc    120
ctggttcagt gaccaataag ttatttatt catttaatat ccatttattt attttattt    180
```

```
ctctgcaatc ttcatttact gtttaattag taaaatttac tgaaattgat tctctgttgt      240
ttatgaatag cttaatcaat gggataaatt cctaggttgc caatgttttc tgctttcctt      300
gcttgctttg tgcaaactgt ttgatgaaac atcctctcca atgtgtctaa ccctgtgagt      360
taaatgtgtt gcaaacacat gattaaaatc cagccacgat cgaatccgta tatattaatg      420
aaataaataa taaaataata ttaaaaaaga taacattgca actttacaac actaaaatct      480
aaaaataaag cattacttta caacagatta agatctagaa taaataaact taggttaatt      540 gttttttta  agaaaagaaa tcaaaacaat atggtatcaa gtatttcac  tgacccatca      600 tgaaccaata tgttgtcgag ttttactagt tttgaacaat tttatttct  taaaattgat      660 tctgtaattt atttcggaca caaaatcgat tcaccaattt tttattatta tcatgaacca      720
atatgaccgg gtctattttt ccttttttta gaacacgagt ctaacttggt tacttgaatg      780
tgtggcttca gcccatttga ttgcataccg ccaatttgga aaaatgaaca acacaataag      840
agtcgtgtat ttgattgata tattcatcta cctctattca tctacctgag cccttaatcc      900
agtggaccta cagtcaccta cagtcagttc aggatgtaca ttctattcct tcatttttta      960
aaattcatta aatttataaa taaaatctta taattatata attgaattca ctaattttat     1020
attttataat ttgtatccat taatttagga tcttaaatat gccactattt cagtcattat     1080
cttaattacc gagatttgtc gtaaatatga tacagaacct aaattcatat ttaaaccttc     1140
ctataattag gttttgacag gagataaaat ataatgttaa atattctagt tgattggcag     1200
gtatatatgt acagtcgagt ttgaattcta gatttctga  aaatatctac atacctgtta     1260
aactcgagta ttttacaaaa accaagttgt actagctcac atatcaacgg ttttttcttc     1320
gtggcgactt cacgttctgt tgattagtct ttctgaccgc tgtattcaac tacctgcaat     1380
aatttattag ttcccacagc tcacttatga tggagtatat aaatttgtag atcaatcaaa     1440
tcacatataa ctttgcaaat cgatcaaatc acaatttagt aattggttca gttaatttcc     1500 gymagb                                                                 1506

<210> SEQ ID NO 55
<211> LENGTH: 1401
<212> TYPE: DNA
<213> ORGANISM: artificial
<220> FEATURE:
<223> OTHER INFORMATION: synthetic sequence

<400> SEQUENCE: 55
tttaatatcc acaaaaaatt ctactaagaa aattttaatg taaaagtatt gagtttggac       60
ccatttaatt aaagtatata tttaattttt taatcaaata tatattatgt ccatgttatt      120
ttaatttgtt ggatccactt ataattttta agaaacttaa aatattgtta ataaaatatg      180 cattttaat  taattttaa  atcattattt tataataaaa aatattatta tattccaaat      240
gcttatatca taaacatatt tttaacgtga caatattcat aactaattaa tcattttgtc      300
ttaggtttta cttttgagg  ctacccactt taatccaact aatatgtatg agtcataatc      360
cttagtatac gatcacttat agaaataaag ctagcgcgcg cagagaatca acttttttg      420 tcttcacaat taagtttggt ccaatgttat ttaaagagaa agaatcgggt tacctagcct      480
cttacgttaa tagaactgat cataattgat ttataaagtt taagagcatc taatttcttg      540
gttaagaaaa ttctatatct tgcgttcaaa caataaattc ggaaaattaa attttatgaa      600
acttaattcc taaaaagcat aatatttatg ataacgaata ttcatcttta gttctgataa      660
actaaattaa tatattgata tataatttca acctcatcac aatgcttaaa ttccatccac      720
```

```
agaaaaaaga tatatttttt agttttcttt cacgccatcg ccagacacat gactcacgtt      780
gagattcgtt cccacccaaa aagagagata tctcaaatga agaaacatga aaatgaaaat      840
gaagatgatg aaaataaaat aaaatatatg ctaatttcac gataaaaaaa aataaattta      900
aaaaacagta ttatttctat cttttcttcc aaaagcacac ccttagttag taatttactc      960
aaggacctct gacctcttca agaaaccatg ttttcgcggc agcatccaac ttcgtcgcct     1020
acgaacgtga caagccatca cgaatagcat ttcttagaaa tatcccacca cttattgcaa     1080
gtggaagtgg ataatgaaaa agaaaacacc acccttgac aaaatgcacc cattacgcgt      1140
aatcatttgc attatcactg catcccagta gacaaaagac gtgaccccag cttcatgcac     1200
ccttattata tacttcgtgt tcggcttttt gcttactagt tctccaaaag ttgaccaaac     1260
catccttata aattccttct ccacatcaca ttatattcat attcaacaca atttaacta     1320 tctatttcgt ataacttttc atttcacaag tgaatcccac cacgtaaacg ttgggaaatt     1380
aaaggagtgt tttgymagbr m                                               1401

<210> SEQ ID NO 56
<211> LENGTH: 506
<212> TYPE: DNA
<213> ORGANISM: Glycine max

<400> SEQUENCE: 56 aattttttt ttcagtatta tttctatctt ttcttccaaa agcacaccct tagttagtaa        60
tttactcaag gtggagactg gagaagttct tggtactttt cgcggcagc atccaacttc      120 gtcgcctacg aacgtgacaa gccaagtgca atagcatttc ttagaaatat cccaccactt     180
attgcaagtg gaagtggata atgaaaaga aaacaccacc ctttgacaaa atgcacccat      240
tacgcgtaat catttgcatt atcactgcat cccagtagac aaaagacgtg accccagctt     300
catgcaccct tattatatac ttgcacaagc cgatttgct tactagttct ccaaaagttg     360
accaaaccat cctattaaa tccttctcca catcacatta tattcatatt caacacaaat     420
ttaactatct atttcgtata catttcatt tcacttcact tagggtggtg catttgcaac     480
cctttaattt cctcacaaaa gymagb                                          506

<210> SEQ ID NO 57
<211> LENGTH: 706
<212> TYPE: DNA
<213> ORGANISM: Glycine max

<400> SEQUENCE: 57
tcatcacaat cgaaaaattc catccacaga aaaagatat attttttaga aaagaaagtg        60
cggtaggcca gacacatgac tcacgttgag attcgttccc acccaaaaag agagatatct      120
caaatgaaga aacatgaaaa tgaaaatgaa gatgatgaaa ataaaataaa atatatgcta      180
atttcacgat aaaaaaaat aatttttttt ttcagtatta tttctatctt ttcttccaaa      240
agcacaccct tagttagtaa tttactcaag gtggagactg gagaagttct tggtactttt     300 cgcggcagc atccaacttc gtcgcctacg aacgtgacaa gccaagtgca atagcatttc      360
ttagaaatat cccaccactt attgcaagtg gaagtggata atgaaaaga aaacaccacc      420 ctttgacaaa atgcacccat tacgcgtaat catttgcatt atcactgcat cccagtagac     480
aaaagacgtg accccagctt catgcaccct tattatatac ttgcacaagc cgatttgct     540 tactagttct ccaaaagttg accaaaccat cctattaaa tccttctcca catcacatta     600
```

| | |
|---|---|
| tattcatatt caacacaaat ttaactatct atttcgtata acatttcatt tcacttcact | 660 |
| tagggtggtg catttgcaac cctttaattt cctcacaaaa gymagb | 706 |

<210> SEQ ID NO 58
<211> LENGTH: 1006
<212> TYPE: DNA
<213> ORGANISM: Glycine max

<400> SEQUENCE: 58

| | |
|---|---|
| gcgcgcgctc tcttagaact ttttttgtct tcacaatatt caaaccagca atgttattta | 60 |
| aagagaaaga aagcccttac ctagcctctt acgttaatag aactgatcat aattgattta | 120 |
| ttttcaaatt ctgcatctaa tttgaaccaa agaaaattc tatatcttgc gttcaaacaa | 180 |
| taaattcgga aaattaaatt ttatgaaact taattcctaa aaagcataat atttatgata | 240 |
| acgaatattc atctttagtt ctgataaact aaattaaaat attgatatat aatttcaacc | 300 |
| tcatcacaat cgaaaaattc catccacaga aaaagatat attttttaga aaagaaagtg | 360 |
| cggtaggcca gacacatgac tcacgttgag attcgttccc acccaaaaag agagatatct | 420 |
| caaatgaaga aacatgaaaa tgaaaatgaa gatgatgaaa ataaaataaa atatatgcta | 480 |
| atttcacgat aaaaaaaaat aattttttt ttcagtatta tttctatctt tcttccaaa | 540 |
| agcacaccct tagttagtaa tttactcaag gtggagactg gagaagttct ttggtacttt | 600 |
| tcgcggcagc atccaacttc gtcgcctacg aacgtgacaa gccaagtgca atagcatttc | 660 |
| ttagaaatat cccaccactt attgcaagtg gaagtggata atgaaaaaga aaacaccacc | 720 |
| ctttgacaaa atgcacccat tacgcgtaat catttgcatt atcactgcat cccagtagac | 780 |
| aaaagacgtg accccagctt catgcacccct tattatatac ttgcacaagc cgattttgct | 840 |
| tactagttct ccaaaagttg accaaaccat ccttataaat tccttctcca catcacatta | 900 |
| tattcatatt caacacaaat ttaactatct atttcgtata acatttcatt tcacttcact | 960 |
| tagggtggtg catttgcaac cctttaattt cctcacaaaa gymagb | 1006 |

<210> SEQ ID NO 59
<211> LENGTH: 1956
<212> TYPE: DNA
<213> ORGANISM: artificial
<220> FEATURE:
<223> OTHER INFORMATION: synthetic sequence

<400> SEQUENCE: 59

| | |
|---|---|
| actctctcta cggttaaaat gttcggtgtt accaaattaa ttttttgttgt aataacattt | 60 |
| agtttgcctt cttatctcaa cttgttatac aatgggccgt ttctgccaaa agtatttata | 120 |
| tatgtaaaaa agtctagtag gaggtgtgaa ctagtttgta cgacaccgtt attctatccg | 180 |
| gatctttgcc tccactacac tatcggtatg ttttttttatt gtgggcctca atcatgaaac | 240 |
| ccaagcctca atgcggaaga aatagcggtg gtactagtgc tccaactgtt tgtcttagag | 300 |
| gtgtctaatc cttgttaacc tgaaaactaa tctcttgtat acacgcaagt aaataagccg | 360 |
| tgaaacttca agattcacca acccagatct agtccttcaa agaaatgttg aatatttaag | 420 |
| aataagattt ttcaagactt agccggtaca atgctattg acttttgtta tatttcgtac | 480 |
| ctgataagtc gtaagaaaaa ggttggaagt gttctataaa aaaatccaaa tgtgactttt | 540 |
| gactttcaca tttattttac cgcgtccaac ctgattagtt tattaattaa gaatgaaaat | 600 |
| gacatgttaa tatcatatct acaacatgat ggagcaacat gagacttcct gtatgcatta | 660 |
| aaggcttgat ttgaccccaa ataacgaagc acaaggtgt taatttgaac gctcccatgt | 720 |

```
aagagtctct attaattttc agattattac attaatgtac ctggattaaa ctcaattttt      780
ctcagaactg acatctatag tgagcaagtt attctaaata caattaaaaa ttaaaaatta      840
gttattaata acatctaact ttttcgtaaa aaacattaa atttatcaat aaaaaaagta       900
tttttaagaa ttaactttaa aattattgag atttattttt tttgatattt tttcacccaa      960
ttataatctc ataaaggtca atttagtcct cttttttgtct tcttattatt caggaaataa    1020
atgagagagg taactgtaac tagtaatttt ttcatatcct tacgagagag agagaaagag    1080
aaaaaaatag ttatcatatt tattatttat ttattgacca gaaaaattta tggagtaatt    1140
aaggacattt tatataaaat taaaaaatag acttatatat aaaaaaaact aataaaaaag    1200
tttttatcta tataaaaaaa aaagagagga agtgccgtta attacgttgt acatgtgatg    1260 cttatttttac agatgttaga ggggtttgaa tcttgtgtaa atgatatacg cgttttttttg   1320 tgatctgaag aattaaaata caatagttat aattattttta attatgtcgt acgtacgtag    1380
ataagctact tcttacgtgt tgaaattagt ttgccatgcc ctgctactat ttcacgtttg    1440
cgtatttcgt aaaagttgta acagagtggg ttgaaattat tgttcccata ttcattcatt    1500
gtaacgtcgg aggaaaagta aactttttt taaaaaaaaa gaagaagtct tcttaaatca    1560
tcttttttag tacccacgtt acgttttagc aaaagaaaa ggaaaaagcg tgtcgtagat    1620
gaatacaaga tccgagaccc ttatatagct agttaagtta ccctcgaaag cactatcaca    1680
cggctcgaac cacgttttcaa tatattaacg tgacttattt tgggttgcat ctatattaaa    1740
gatcatgttc agttatttag atttcaaatt gcatgactag tctagtgtcc acaatttata    1800
tctgccacat ggcatcacca gatgaatttg tcaaaaacgt tggttgttgc ttccccaaca    1860
tatcataccc aaatcaaccc tataaaaata atatacacaa tctcacctgt taacattttt    1920
ttctttaacg aacggcaatt aatttagtgy magbrm                               1956

<210> SEQ ID NO 60
<211> LENGTH: 506
<212> TYPE: DNA
<213> ORGANISM: Glycine max

<400> SEQUENCE: 60
cattttcaac attcagagtg ggttgaaatt attgttccca tattcattca ttgtaacgtc       60
ggaggaaaag taaactttttt tttaaaaaaa aacttcttct cttcttaaat catcttttttt    120 agttgggtgc aatgcaaaat cgttttttctt ttcctttttc gcagtcgtag atgaatacaa    180
gatccgagac ccttatatag ctagttaagt tacccagctt tccactatca cacggctcga    240
accacgtttc aatatattaa cgtgacttat tttgccaagc atctatattt ttctacatgt    300
tcagttattt agatttcaaa ttgcatgact agtcttcagt ccacaattta tatctgccac    360
atggcatcac cagatgaatt tgtcaaaaac gaaccatgtt gcttccccaa catatcaatg    420
ccaaatcaac cctataaaaa taatatacac aatctcacct gttaacattt ttttctttaa    480
cgaacggcaa ttaattttaca gymagb                                         506

<210> SEQ ID NO 61
<211> LENGTH: 1006
<212> TYPE: DNA
<213> ORGANISM: Glycine max

<400> SEQUENCE: 61
tttttcaccc aattaattag agtatttcca gttaaatcag gacttttttgt cttctataat     60
```

| | |
|---|---|
| aagaggaaat aaatgagaga ggtaactgta actagtaatt ttttcatatc cttacgagag | 120 |
| agagagaaag agaaaaaaat agttatcata tttattattt atttattgac cagaaaaatt | 180 |
| tatggagtaa ttaaggacat tttatataaa attaaaaaat agacttatat ataaaaaaaa | 240 |
| ctaataaaaa agtttttatc tatataaaaa aaaagagag gaagtgccgt taattacgtt | 300 |
| gtacatgtga tgcttatttt acagatgtta gaggccaaac tttcttgtgt aaatgatata | 360 |
| cgcgtttttt tgtgtagact tcttaatttt atgttatgtt ataattattt taattatgtc | 420 |
| gtacgtacgt agataagcta cttcttacgt gttgaaatta gtttgccatc ggctgctact | 480 |
| atttcacgtt tgcgtatttc cattttcaac attcagagtg ggttgaaatt attgttccca | 540 |
| tattcattca ttgtaacgtc ggaggaaaag taaactttt tttaaaaaaa aacttcttct | 600 |
| cttcttaaat catcttttt agttgggtgc aatgcaaaat cgttttttctt ttccttttc | 660 |
| gcagtcgtag atgaatacaa gatccgagac ccttatatag ctagttaagt tacccagctt | 720 |
| tccactatca cacggctcga accacgtttc aatatattaa cgtgacttat tttgccaagc | 780 |
| atctatattt ttctacatgt tcagttattt agatttcaaa ttgcatgact agtcttcagt | 840 |
| ccacaattta tatctgccac atggcatcac cagatgaatt tgtcaaaaac gaaccatgtt | 900 |
| gcttccccaa catatcaatg ccaaatcaac cctataaaaa taatatacac aatctcacct | 960 |
| gttaacattt ttttctttaa cgaacggcaa ttaatttaca gymagb | 1006 |

<210> SEQ ID NO 62
<211> LENGTH: 1506
<212> TYPE: DNA
<213> ORGANISM: Glycine max

<400> SEQUENCE: 62

| | |
|---|---|
| gttttgctat tgacttttgt tttatttcgt acctgtattc agcattcttt ttccaacctt | 60 |
| cagttctata aaaaaatcca aatgtgactt ttgactttca catttatttt accgcgtcca | 120 |
| acctgattag tttattaatt aagaatgaaa atgacatgtt aatatcatat ctacaactac | 180 |
| atggagcaac atgagacttc ctgtatgcat taaaggcttg atttgacccc aaatttgctt | 240 |
| cgtgtttcca caattaaact tgcgagggta cattctcaga ctattaattt tcagattatt | 300 |
| acattaatgt aggaggatta aactcttaaa aagacagaac tgacaagata tcactcgttc | 360 |
| ttattctaaa tacaattttt ttaaaaaaat tagttattaa taacatctaa cttttttcgta | 420 |
| aaaaaacatt aaatttatca atatttttg tattttaag aattaacttt aaaattattg | 480 |
| agatttatt tttttgatat ttttcaccc aattaattag agtatttcca gttaaatcag | 540 |
| gacttttgt cttctataat aagaggaaat aaatgagaga ggtaactgta actagtaatt | 600 |
| ttttcatatc cttacgagag agagagaaag agaaaaaaat agttatcata tttattattt | 660 |
| atttattgac cagaaaaatt tatggagtaa ttaaggacat tttatataaa attaaaaaat | 720 |
| agacttatat ataaaaaaaa ctaataaaaa agtttttatc tatataaaaa aaaagagag | 780 |
| gaagtgccgt taattacgtt gtacatgtga tgcttatttt acagatgtta gaggccaaac | 840 |
| tttcttgtgt aaatgatata cgcgtttttt tgtgtagact tcttaatttt atgttatgtt | 900 |
| ataattattt taattatgtc gtacgtacgt agataagcta cttcttacgt gttgaaatta | 960 |
| gtttgccatc ggctgctact atttcacgtt tgcgtatttc cattttcaac attcagagtg | 1020 |
| ggttgaaatt attgttccca tattcattca ttgtaacgtc ggaggaaaag taaactttt | 1080 |
| tttaaaaaaa aacttcttct cttcttaaat catcttttt agttgggtgc aatgcaaaat | 1140 |
| cgttttttctt ttccttttc gcagtcgtag atgaatacaa gatccgagac ccttatatag | 1200 |

```
ctagttaagt tacccagctt tccactatca cacggctcga accacgtttc aatatattaa    1260
cgtgacttat tttgccaagc atctatattt ttctacatgt tcagttattt agatttcaaa    1320
ttgcatgact agtcttcagt ccacaattta tatctgccac atggcatcac cagatgaatt    1380
tgtcaaaaac gaaccatgtt gcttccccaa catatcaatg ccaaatcaac cctataaaaa    1440
taatatacac aatctcacct gttaacattt ttttctttaa cgaacggcaa ttaatttaca    1500 gymagb                                                               1506

<210> SEQ ID NO 63
<211> LENGTH: 1615
<212> TYPE: DNA
<213> ORGANISM: artificial
<220> FEATURE:
<223> OTHER INFORMATION: synthetic sequence

<400> SEQUENCE: 63
taaataatta atttatttca aacacttaat ttaaatttaa ttatactacg aaattaatta      60
aaaacactca atcatatatt attaaaaaaa atagttacat taaatactta gtcctttaat     120
tttgtcatcc ataataatcc ttaagaattt aaaacaaaaa atgttacacc agccgttaat     180
attttaaaac tctctctagt ttcatgactc accctaaaat atattttta caatttatat      240 taaacatttta tctaaaatga atttgaaaag tcaacaattt ttataaagga aaatcaacac    300
ttataataaa tgttttttc gtgagtttta ttcatagtgt aaacttaaaa aaattatcct     360
aaaataagtg tctcatttga ttttttttaa tgtaatatta ttttttttta ctactccctc    420
catcacaaaa taattgttat cttaggttat tttacagtta taaaaaagta aaaaataaat    480
gaaatacagt aatgattgta taaaattaac cttatatcat tattaattta tttatagatt    540
tagttgttag ccattaatat tataagggat ataagccaaa aagcgttgat ttgatttta    600 aaattatttt aatttggaat aattttttc ttctcatacg acaatatata cgagacgaaa    660
agagtaattg acttaataaa tgttacttta atttttaat ataatattaa tactctctct    720
aaccataaat ataagacttt ttttaattaa tttgtaatct ttaagaaagt taattagtaa    780
cattaaactt gttaaaaatt taattatttt ttcaaaatta tccttaagct tattagaaat    840
cataatctct ctcttttcac ttaaaacaaa aatcacataa ttaaataatt tgtgttagtc    900
ttctacaggt taggaattaa gagaaataat gtatttatct tttagatata taacatttat    960
ggtaaaataa taaagatat ttgagtaaaa aagtaatatt atgttttgtg ttaatctttt    1020
atgtcttata aaagaaaaa aaaactgaa aaaagagtt taatccctga cgaaaaatta    1080
ttaaggttaa ttttataaca ttattatttt tttaatctac tttttatttg tttaatctaa   1140 ataaatatt ataacagctc tgaataaaat ccaccatccc tcattacaaa ttctaaacat    1200
actctttgta aaaaatcttc atgtgtcttt cacaaccttc cagataatat gacacccacc    1260
cacaatcttc aactaatatc acccacacat atttattgca cacttcccat tagacaaggc    1320
tccctttgtt tctatatata cttatgttaa ttgtgaaacc agggctcaga ccgacggaga    1380
caaaatagta gttaatgtca tgtagcaatt aaagagggag attcgctttg tcgtgtgagc    1440
tcgtaggaac tacaggtccg aaatccatat ttgtccttt aagacgcatg aaagtacgaa    1500
ttattgcaac aatcgagata accaacttct tatatatccc atcctccaca tctacgcctg    1560
aatcatcgtc caactattag ttcctctctc tgcgtagtat agcgttggym agbrm          1615

<210> SEQ ID NO 64
```

```
<211> LENGTH: 506
<212> TYPE: DNA
<213> ORGANISM: Glycine max

<400> SEQUENCE: 64
ttttttaatc tacttttat  ttgtttaatc taaataaaat attataacac gagacttatt      60
ttaggtggta gggagtaatg tttaagattt gtatgagatt gtaaaaaatc ttctacacag     120
aaacacaacc ttccagataa tatgacaccc acccacaatc ttcaactaat atcacccaca     180
catatttatt gcacacttcc cattagacaa ggctcccttt gtttctatat atacttatgt     240
taattgtgat tggtcccgag tctggctgcc tcacaaaata gtagtattac agtacatcgt     300
taatttctcc cagattcgct tgtcgtgtc  tcgagcatcc ttgatgtcca gggaaatcca     360
tatttgtcct tttttctgcg tactttcatc gaattattgc ttgttagctc tataccaact     420
tcttatatat cccatcctcc acatctacgc ctgaatcatc gtccaactat tagttcctct     480
ctctgcgttc atatcgcaac gymagb                                          506

<210> SEQ ID NO 65
<211> LENGTH: 1006
<212> TYPE: DNA
<213> ORGANISM: Glycine max

<400> SEQUENCE: 65
tttaatttgg aataattttt ttcttctcat acgacaatta tatcgagacg aaagagtaa      60 tacacttaat aaatgttact ttaatttttt aatataatat taatactctc tctaaccata    120
aatataagac ttttttttaat taatttgtaa tctttaagaa agttaattag taacattaaa    180
cttgttaaaa atttaattat tttttcaaaa ttatccttaa gcttattaga aatcataatc    240
tctctctttt cacttaattg tttttacaca taattaaata atttgtgtta gtcttcttgt    300
ccaatcctta taagagaaat aatgtattta tcttttagat atataacatt tatggtaaaa    360
taataaaaga tatttgagta aaaaagtaat taatacaaaa cacaattaga aaatagtctt    420
ataaaaagaa aaaaaaaact gaaaaaaaga gtttttaggg actgcaaaaa ttattaaggt    480
taattttata acattattat ttttttaatc tacttttat ttgtttaatc taaataaaat    540
attataacac gagacttatt ttaggtggta gggagtaatg tttaagattt gtatgagatt    600
gtaaaaaatc ttctacacag aaacacaacc ttccagataa tatgacaccc acccacaatc    660
ttcaactaat atcacccaca catatttatt gcacacttcc cattagacaa ggctcccttt    720
gtttctatat atacttatgt taattgtgat tggtcccgag tctggctgcc tcacaaaata    780
gtagtattac agtacatcgt taatttctcc cagattcgct tgtcgtgtc  tcgagcatcc    840 ttgatgtcca gggaaatcca tatttgtcct tttttctgcg tactttcatc gaattattgc    900
ttgttagctc tataccaact tcttatatat cccatcctcc acatctacgc ctgaatcatc    960
gtccaactat tagttcctct ctctgcgttc atatcgcaac gymagb                  1006

<210> SEQ ID NO 66
<211> LENGTH: 1506
<212> TYPE: DNA
<213> ORGANISM: Glycine max

<400> SEQUENCE: 66
ttagaggaaa aattttgtca tccataataa tcctattcaa tttaaaacaa aaatgttac       60 accagccgtt aatattttaa aactctctca tctttcatga ctcaccctaa aatatatttt    120
taacaattta tattaaacat ttatctaaaa tgaatttgaa aagtcaacaa tttttataaa    180
```

```
ggaaaatcaa cacttataat aaatgttttt ttcgtctcaa ataagtatc acatttgaaa    240 aaaaaattat cctaaaataa gtgtctcatt tgattttttt taatgtaata ttattttttt    300
ttactactcc ctccatcaca aaataattgt tatcttaggt tattttacac aaataaaaaa    360
gtaaaaaata aatgaaatag agtaatgatt gtataaaatt aaccttatat cattattaat    420
ttatttatag atttagttgt tagccattaa tattataagg gatataagcc aaaaaggcaa    480
ctaaactaaa ataaaattat tttaatttgg aataattttt ttcttctcat acgacaatta    540
tatcgagacg aaaagagtaa tacacttaat aaatgttact ttaattttt aatataatat     600 taatactctc tctaaccata aatataagac ttttttaat taatttgtaa tctttaagaa     660
agttaattag taacattaaa cttgttaaaa atttaattat tttttcaaaa ttatccttaa    720
gcttattaga aatcataatc tctctctttt cacttaattg tttttacaca taattaaata    780
atttgtgtta gtcttcttgt ccaatcctta taagagaaat aatgtattta tcttttagat    840 ataacatt tatggtaaaa taataaaaga tatttgagta aaaagtaat taatacaaaa       900 cacaattaga aaatagtctt ataaaagaa aaaaaaaact gaaaaaaaga gttttaggg     960 actgcaaaaa ttattaaggt taattttata acattattat ttttttaatc tacttttat   1020 ttgtttaatc taaataaaat attataacac gagacttatt ttaggtggta gggagtaatg  1080
tttaagattt gtatgagatt gtaaaaaatc ttctacacag aaacacaacc ttccagataa  1140 tatgcaccc acccacaatc ttcaactaat atcacccaca catattatt gcacacttcc    1200 cattagacaa ggctcccttt gtttctatat atacttatgt taattgtgat tggtcccgag   1260
tctggctgcc tcacaaaata gtagtattac agtacatcgt taatttctcc cagattcgct  1320
ttgtcgtgtc tcgagcatcc ttgatgtcca gggaaatcca tatttgtcct tttttctgcg  1380
tactttcatc gaattattgc ttgttagctc tataccaact tcttatatat cccatcctcc   1440
acatctacgc ctgaatcatc gtccaactat tagttcctct ctctgcgttc atatcgcaac  1500 gymagb                                                               1506
```

<210> SEQ ID NO 67
<211> LENGTH: 2024
<212> TYPE: DNA
<213> ORGANISM: artificial
<220> FEATURE:
<223> OTHER INFORMATION: synthetic sequence

<400> SEQUENCE: 67

```
caacttctaa gtggtgaaga ggatgaaagg atgaagatat ataaaattct acatgaaatt     60
aatttctgct aaaaaattcc ctgggtgtgt ctgcgactta aagggtcat ctcaaacaca     120 aaaggaaaaa tcttcactct tcacgttgca agaaaagcag gcgtcccaca tgaaaatcga    180
tttcgcaaac catctaaggg ataagtatca atctaactca caatacttt caagtctagt     240 taagcgtaac ctgacttagt ttagtctatt cgtccctcct tctggataga ttttaggaaa    300
atgtctcctt tcttgttgat gaaaaataag tctcaagaaa gctttgttat taaaagtcaa    360
caaacgttag cgaagcttta gaagaataaa gtatcgtgtt tgtagcaact agcaagtgga    420
tatttaaaag gacacttaga cacgacgctt atctagaaaa gttcaagcca gattaactaa    480
aggtttcact aaaaaaaatg gtgtagattt attttatacc tgttcactag ctagttacaa    540
aaatatatca tacataattt aattaactat acattaagtg gatgtaaaaa caatcttttt    600
ttaagggaag taatttacat ctctgaacct aaagggtttt aatatctagt caagaacatt    660
```

```
aagtttgcga actacaatta atggtggtct actataaaat cttgttttca agcagtgatt    720
tttctattat tattattcat gactcattac taacttgacc cggtccaaaa ttaattttta    780
tgaattttgg gtttaaaaat gaggctttat ttagtttgag ggcgggttca cctctttgag    840
tcgtcaatag gcgatgaatc tctagtgtca tattctttta aaatgtataa ttttttaaat    900
aattatatat taattataat atttctagat ttgataagaa aaatatttta tataatattt    960
aattataatt actaagatgt tgttaattta tcttaatata tatatatata tatatatata   1020
tatatatata tataataaac tatatcttaa taataatttt atgcttcttc agttctataa   1080
ttttttggtt atatctttag ttctataatt ttactatata taattattaa aattgatgta   1140
tatatcaaga aatcaaatta acccagcttt atttcaaata ttatcagaaa ctccttacga   1200
tcattgagat tctaacagta cacttgttta ataaagatct gagagagcat gcacccacaa   1260
ttaatggaaa tctgaattac aataaaaaaa tttattactt ttttaattta ttgtttttaa   1320
aataaatttg cactttaaaa attgagagca cgtacattag ttatttcttt cgtgctattg   1380
gtgactacgt aaggaagaat gacttatcgt catgagtaga ataaatcaga agccaacagt   1440
gagaaagtta ggtgaacgtg ttgaacacaa tctgcatagt ggtatcacca atataatgca   1500
cgtgctaacc accaacacat ggcaacattt ttttttatct ctttctattc atctccttt    1560 atctcatcac tcttttatat ttcgaaagat agagagataa tccttaaaat tcgatttaat   1620
tagaaggaaa aaaatttgta gagtacgtcg aagattttga aatcaaccca aaacaagtaa   1680
ctctgattat agtcatatat cggtgacatg gagaattata aactatccat tctcagtttg   1740
acttagttag gtggtcagat aatattaaaa tgtgatgaag ttggctagtt gtggcaatgt   1800
ataagaattt tcaactgata agttcaataa ttctctgtat agcaaggttg gacgtgcaca   1860
tgaacacgat acaggaaact ttttaatta gtaaaaaaat attctgtgtt tggcttttaa    1920
aaaagaacac ttgcgtcaac gtctacgaaa tattctctat atatcttgtt tctttcttcc   1980
gttttcccga tcgggcttcc ttcttctttc gttaaggyma gbrm                    2024

<210> SEQ ID NO 68
<211> LENGTH: 506
<212> TYPE: DNA
<213> ORGANISM: Glycine max

<400> SEQUENCE: 68
acatggcaac attttttttt atctctttct attcatctcc ttttatctca tcactctttt     60
atatttcctt tctatctctc ataatcctta aaattcgatt taattagaag gaaaaaaaaa    120
acatctcatg caggaagatt tgaaatcaa cccaaaacaa gtaactcact atatagtcat     180
atatcggtgt gtacctctta atatttgata ggtatctcag tttgacttag ttaggtggag    240
tctattataa ttttacacta ctagttggct agttgtggca atgtataaga attttcaact    300
gataagttca ataattctct gtatagcaag gttggacgtg cacaacttgt gctatgtcct    360
tactttttta attagtaaaa aaatattctc actttggctt taaaaaaga acacttgcgt     420 caacgtctac gaaatattct ctatatatct tgtttctttc ttccgttttc ccgatcgggc    480
ttccttcttc tttgcaattc gymagb                                         506

<210> SEQ ID NO 69
<211> LENGTH: 1006
<212> TYPE: DNA
<213> ORGANISM: Glycine max

<400> SEQUENCE: 69
```

```
tatatatata tatatataat aaactatatc ttaataataa ttttatgctt cttcagttct      60
ataatttttt ggttatatct ttagttctat aattttacta tatataatta ttaaaattga     120
tgtatatatc aagaaatcaa attaacccag ctttatttca aatattatca gattgaggaa     180
tgctagtaag agattctaac agtacacttg tttaatattc tagtgagaga gcatgcaccc     240
acaattaatg gaaatctgaa atacaataaa aaaatttatt acttttttaa tttattgttt     300
ttaaaataaa tttgcactt  aaaaattgag agcacgtaca ttagttattt ctttcgtgct     360
attggtgtga tgcattcctt cttactgaat agcagtactc tagaataaat cagaagcgtt     420
gtcactcttt caatccactt gcacaacttg tgttagacgt atcaccattc accaatataa     480
tgcaccacga ttgcaccaac acatggcaac attttttttt atctctttct attcatctcc     540
ttttatctca tcactctttt atatttcctt tctatctctc ataatcctta aaattcgatt     600
taattagaag gaaaaaaaaa acatctcatg caggaagatt ttgaaatcaa cccaaaacaa     660
gtaactcact atatagtcat atatcggtgt gtacctctta atatttgata ggtatctcag     720
tttgacttag ttaggtggag tctattataa ttttacacta ctagttggct agttgtggca     780
atgtataaga atttcaact  gataagttca ataattctct gtatagcaag gttggacgtg     840
cacaacttgt gctatgtcct tactttttta attagtaaaa aaatattctc actttggctt     900 ttaaaaaga  acacttgcgt caacgtctac gaaatattct ctatatatct tgtttctttc     960
ttccgttttc ccgatcgggc ttccttcttc tttgcaattc gymagb                  1006

<210> SEQ ID NO 70
<211> LENGTH: 1506
<212> TYPE: DNA
<213> ORGANISM: Glycine max

<400> SEQUENCE: 70
tacctgttca ctagctagtt acaaaaatat atcatacata atttaattaa ctatacatta      60
agtggatgta aaaacaatct tttttaagg  gaagtaattt actagagaca acctaaaggg     120
ttttaatatc tagtcaagaa cattaagttt gcgaactaca attaatggtg gtctactata     180
aaatcttgtt ttcaagcagt gattttctat ttattattat tcatgactca ttactaactt     240
gacccggtcc aaaattaatt tttatgaatt ttgggtttaa aaatgaggct ttatttagtt     300
tgagggcggg ttcaggtctt tgagtcgtca ataggcctac ttagtctagt gtcatattct     360
tttaaaatgt ataattttt  aaataattat atattaatta taatatttct tgatttgata     420
agaaaaatat tttatataat ataatattat aattacattg atgttgttaa tttatcttaa     480
tatatatata tatatatata tatatatata tatatataat aaactatatc ttaataataa     540
ttttatgctt cttcagttct ataatttttt ggttatatct ttagttctat aattttacta     600
tatataatta ttaaaattga tgtatatatc aagaaatcaa attaacccag ctttatttca     660
aatattatca gattgaggaa tgctagtaag agattctaac agtacacttg tttaatattc     720
tagtgagaga gcatgcaccc acaattaatg gaaatctgaa atacaataaa aaaatttatt     780
acttttttaa tttattgttt ttaaaataaa tttgcacttt aaaaattgag agcacgtaca     840
ttagttattt ctttcgtgct attggtgtga tgcattcctt cttactgaat agcagtactc     900
tagaataaat cagaagcgtt gtcactcttt caatccactt gcacaacttg tgttagacgt     960
atcaccattc accaatataa tgcaccacga ttgcaccaac acatggcaac attttttttt    1020
atctctttct attcatctcc ttttatctca tcactctttt atatttcctt tctatctctc    1080
```

```
ataatcctta aaattcgatt taattagaag gaaaaaaaaa acatctcatg caggaagatt    1140
ttgaaatcaa cccaaaacaa gtaactcact atatagtcat atatcggtgt gtacctctta    1200
atatttgata ggtatctcag tttgacttag ttaggtggag tctattataa ttttacacta    1260
ctagttggct agttgtggca atgtataaga attttcaact gataagttca ataattctct    1320
gtatagcaag gttggacgtg cacaacttgt gctatgtcct tactttttta attagtaaaa    1380
aaatattctc actttggctt ttaaaaaaga acacttgcgt caacgtctac gaaatattct    1440
ctatatatct tgtttctttc ttccgttttc ccgatcgggc ttccttcttc tttgcaattc    1500
gymagb                                                               1506
```

<210> SEQ ID NO 71
<211> LENGTH: 1978
<212> TYPE: DNA
<213> ORGANISM: artificial
<220> FEATURE:
<223> OTHER INFORMATION: synthetic sequence

<400> SEQUENCE: 71

```
acgtctggat caagaagatt ctcccaattg ttgctaccgt gaagctcacg ccacattttg      60
gatttttttt cccttggtct gcgtcgacct ctcatcagat cgccgcggtc aagaaaatcg     120
tcggctgaga taaaaccttg ctgaagtaga aacgccagtg atttggtgct ctcattggag     180
attttgcaga tcctctcccg gacttgagac aaatcttgtt cttcctttcg tgatttaatg     240
tggaagaggt gtttcttggt tgacaagaaa cggcgaagat gtgacttgac ccggatctag     300
atagatttcc atgcaagctt tagcttctgc ttcaatgagc agacccgttt agttcttctt     360
cttcttacga aagagtcacg agttttgacc aatgcgttct ccatttctga gtttatcggt     420
cggataattt tactggtgat gatgatgatg atgataaagt tgtgtacaca acatcgttct     480
taactagcta tacgaaacca atagatctct atgtgttata tatgaagc aacatatgca     540
tatgttgcta gacccttcta tgagtatacg caagacgaag aataaatgtt tgaccttgta     600
ctaaaacatt gttcggtacg gaagaatgat tattaattac cggatattat atgcgtttag     660
gttttatatg cctcatcact tcacttccaa cgtaataaaa atcagaattc cggttcaggt     720
aaaccatatc cagcaactct aattaaatct cctcttggat tggttttttgt tttaagtcaa     780
aacacaatct cattttgtca aaatgatttt agttggtcaa agtaataata atacgccatg     840
atgatagtta ttcttccgtc gaattcctat gaataattag ggctgctcta tatacaaaac     900
atatattaat gaaattaatt atgattattt gttaggaaaa tcaactctta caagtcagca     960
gaactgtgtc ggcttttgcg ttaggttata taactccaac ttaggaccta ataaacgggt    1020
ccacttttc taatgaaata tatattacta cttttggata agaacattta catgaaatcc    1080
aataaacacc cagaaataat tgtacttggc ttacaaataa agaaactcac atatctcatt    1140
atattttga ataaatggac gtagatgatt gacgtacatt tcagactaat atggtttgac    1200
ttaattgatt aattaaaagg tgaattctaa tctttaattt tggacagtga gacgatcgat    1260
aaaaattcat ttttttaacaa ttagagtttt tgttaacaac ctaattgctt gttaactact    1320
tgcatttaaa atacagttca tgcggtttat ttataagttg attatggata cgaatttaag    1380
cttttgaaat tatattgaaa gataactgat tgatcaacta attcagatgg ataggtttg    1440
aaaaaattaa tcacaaaagg gtaagaatt tgactaatta agctcgaaag tgttcttcac    1500
ggcaagttcg tctcttgaaa caactacgaa agtaccacta aacctatagt atacacgagc    1560
cttttcctta aaggacgagc actaaatgtt tcaaatgtaa tttcacaatg gtttaaatca    1620
```

```
gaccgcttga agtccacacg atcatagtat tcaagttcca tgatttgtac taagatttaa    1680
tataagtata aatgggcctg catgaagccc aaaatgaaac caaatgaaag aaaatctgca    1740
ctgtgatgac gatgagacag tcttatccag agttgaaatc agccaataga cacttgacac    1800
cagtcgttct ccattggatt tcagaatcca tttctgtgat cgccaaagcc acacgatgat    1860
tcttgcctaa atcattttaa agactgttat ctccttttgt tttgacgtta aacaaaaata    1920
aaaatttgta gcgtgttctt tttaaaagat ttgatcaatc aactatcttt msatgbrm      1978

<210> SEQ ID NO 72
<211> LENGTH: 506
<212> TYPE: DNA
<213> ORGANISM: Arabidopsis thaliana

<400> SEQUENCE: 72
tgactaatta agctcgaaag tgttcttcac ggcaagttcg tctcttgaaa caactacgaa      60
agtaccacta aacctatagt atacacgagc cttttccaat ttccacgagc actaaatgtt    120
tcaaatgtaa tttgtgtttg gtttaaatca gaccgcttga agtccacacg atcatagtat    180
tcaagttcca tgatttgtac taagatttaa tataagtata aatgggcctg catgaagccc    240
aaaatgaaag gttttgaaag aaaatctgca ctgtgatgac gatgagacag tcttatccag    300
agttgaaatc agccaataga cacttgacac ctcagcaaga ggtaacctaa acagaatcca    360
tttctgtgat cgccaaagcc acgatgat tcttgcctaa atcattttaa agactgtata     420
gaggaaaaca aaactgcaaa aacaaaaata aaaaaaacat cgcacaagaa ataaaagat    480 ttgtagaatc aactaagaaa msatgb                                         506

<210> SEQ ID NO 73
<211> LENGTH: 1006
<212> TYPE: DNA
<213> ORGANISM: Arabidopsis thaliana

<400> SEQUENCE: 73
ggcttttgcg ttaggttata taactccaac tttcctccta ataaacgggt ccactttttc      60
taatgaaata tatattacta cttttggata agaacattta catgaaatcc aataaacacc    120
cagaaataat tgttcttggc ttacaaataa agaaactcac atatctcatt atattttga     180 ataaatggac gtagatgatt gacgtacatt tcagactaat atggtttgac ttaattgatt    240
aattaaaagg tgaaaactaa tctttaattt tggtgtcact ctcgatcgat aaaaattcat    300 ttttttttgta ttagagtttt tgttaacaac ctaatacgaa caattgaact tgcatttaaa   360
atacacttca tgcggtttat ttataagttg attatggata cgaatttaag cttttgttta   420
atatatgaaa gataactgat tgatcaacta attcagatgg gataggtttg aaaaaattaa    480
tcacaaaagg gtaagaatt tgactaatta agctcgaaag tgttcttcac ggcaagttcg    540
tctcttgaaa caactacgaa agtaccacta aacctatagt atacacgagc cttttccaat   600
ttccacgagc actaaatgtt tcaaatgtaa tttgtgtttg gtttaaatca gaccgcttga    660
agtccacacg atcatagtat tcaagttcca tgatttgtac taagatttaa tataagtata   720
aatgggcctg catgaagccc aaaatgaaag gttttgaaag aaaatctgca ctgtgatgac    780
gatgagacag tcttatccag agttgaaatc agccaataga cacttgacac ctcagcaaga    840
ggtaacctaa acagaatcca tttctgtgat cgccaaagcc acgatgat tcttgcctaa    900 atcattttaa agactgtata gaggaaaaca aaactgcaaa aacaaaaata aaaaaaacat    960
```

```
cgcacaagaa aataaaagat ttgtagaatc aactaagaaa msatgb              1006

<210> SEQ ID NO 74
<211> LENGTH: 1506
<212> TYPE: DNA
<213> ORGANISM: Arabidopsis thaliana

<400> SEQUENCE: 74
tgtagcaaga attgatcgat atgctttgga atagatctct atgtgttata tatatgaagc    60
aacatatgca tatgttgctt ctgggaagat actcatatgc gttgacgaag aataaatgtt   120
tgaccttgta ctaaaacatt gttcggtacg gaagaatgat tattaattac cggtataata   180
tacggtttag gttttatatg cgagtagtga agtgaaggtt gctaataaaa atcagaattc   240
cggttcaggt aaaccatatc cagcaactct aattaaatct cctcttggaa aggttttgt    300 tttaagtcaa aacacaatct cattttgtca aaatgatttt agttggtcaa agtaataata   360
atacgccatg atgatagtta ttcttggcag cttaaggatt gaataattag ggctgctcta   420
tatacaaaac atatattaat gaaattaatt atgattattt gttaggaaaa tcaactctta   480
caagagtcgt ctactgtgtc ggcttttgcg ttaggttata taactccaac tttcctccta   540
ataaacgggt ccacttttc taatgaaata tatattacta cttttggata agaacattta    600
catgaaatcc aataaacacc cagaaataat tgttcttggc ttacaaataa agaaactcac   660
atatctcatt atatttttga ataaatggac gtagatgatt gacgtacatt tcagactaat   720
atggtttgac ttaattgatt aattaaaagg tgaaaactaa tctttaattt tggtgtcact   780
ctcgatcgat aaaaattcat tttttttgta ttagagtttt tgttaacaac ctaatacgaa   840
caattgaact tgcatttaaa atacacttca tgcggtttat ttataagttg attatggata   900
cgaatttaag ctttttgttta atatatgaaa gataactgat tgatcaacta attcagatgg   960 gataggttg aaaaaattaa tcacaaaagg gtaaagaatt tgactaatta agctcgaaag    1020
tgttcttcac ggcaagttcg tctcttgaaa caactacgaa agtaccacta aacctatagt   1080
atacacgagc cttttccaat ttccacgagc actaaatgtt tcaaatgtaa tttgtgtttg   1140 gtttaaaatca gaccgcttga agtccacacg atcatagtat tcaagttcca tgatttgtac  1200
taagatttaa tataagtata aatgggcctg catgaagccc aaaatgaaag gttttgaaag   1260
aaaatctgca ctgtgatgac gatgagacag tcttatccag agttgaaatc agccaataga   1320
cacttgacac ctcagcaaga ggtaacctaa acagaatcca tttctgtgat cgccaaagcc   1380
acacgatgat tcttgcctaa atcatttttaa agactgtata gaggaaaaca aaactgcaaa   1440
aacaaaaata aaaaaaacat cgcacaagaa aataaaagat ttgtagaatc aactaagaaa   1500 msatgb                                                             1506

<210> SEQ ID NO 75
<211> LENGTH: 1930
<212> TYPE: DNA
<213> ORGANISM: artificial
<220> FEATURE:
<223> OTHER INFORMATION: synthetic sequence

<400> SEQUENCE: 75
cactttcgtc acttcggcac tgggatactc caatacagtt agttgtgata atgttgtcat    60
aaatctttct ctataaagtg atagttatca ttagttgaag ttagctagga tgttatgtaa   120
ataagaaagt taagcaatgt tttcagtaaa tttcttaatc gtgtaattta ctattttaa    180 gtgatgtgat atccaatttg aaaggttcaa gttaaaagaa agtctgccca tatctttaca   240
```

```
aaccattatt tttcggggtg aaactagttt tgagttgttc ttcgaacaaa tggttgaaac      300
ttgagttgct ttacggtata gtcaaatcat ttgaaaaaac catgttatta atttggaatt      360
ccgactttct tcagtatgtt tttaaacaat aaatgaaata cgagaaaagt agtgagtgag      420
aaaagtgaaa taataatatt catacctgaa caatcatata acgttctacc ttaggagatg      480
ttcctgcata ttaaaagtaa ctcatatgag aggagacatg ttgtatcaaa caacaagcaa      540
caacagataa acatttatct tttaaaatc aaacttttt taaaaccaag ttgactatgt       600
tttagagcat cttcaatggt gagttttaa tattaattaa tcaaaaataa taatagaaaa      660
gcgttctctt attcttacgt tcttatttta aagtatataa aatcttattt aaaatcccaa      720
ataccacata tctttcatat tacagaatta tactaaacaa cattttatt ttagtgaaaa      780 aatttagtta aataacaaaa ttatatttaa ataatattat aatattgata agagacactt      840
ggtgaatatt tcaccattag agatgctctt tcttgtttgt tgttacaaaa taatactggg      900
atccccaact atccttgaaa aatcactgat gttctctaat gaacgttctc acaaaaaggt      960
aaatcatccg taaatggcca atttgaggtg tgagataatc attattcata aacttttgct     1020
ccgttcaatt ctcttttcta aatatgttat attatatatt agtatttatt tattaggtgg     1080
ttttgtcggc aacaaaaaaa tagacaactc tcgtaaataa caaaaataag ttttcttatc     1140
aaatttagca cacaatcttc aaacttccaa aaataacatg aaattaatat taaaaagact     1200
aatataagca tttgatacat aattcacacg atttgtgatt taaaatcata attaattta      1260 tatatttaga taaaaataaa ttagttatta tgtaaaatta ctaatgctaa ttttggaaat     1320
ttgtgaagtt tgtgttataa ttgtccataa taaatttttt catgttattt taaagtattt     1380
ctctataaaa agtaaaggtt gggccaggta aatgtactta ttggactcaa taaacaactc     1440
aaagatgatt aaattcatat attttactat gaaatatgtt ttactataaa aaacagctca     1500
aaatgctaca aaagtaataa ggaaagaggt tttcattttt aaaattcaat gaactcataa     1560
aagttcatag tatgactata tcaaatactg atcaaatact ttcaactatc tagcaaagta     1620
tactaaggga tcaagtttca atatgatgag tataatttag atacacatac tatgaaattt     1680
ttatatagca attttttta atgttctcag tttgaaatca ataactaaac ataggatact     1740
aaaaacttac atagtcatga acccaaaata tcaataatta ttgttcgagg gtgatgggtt     1800
ttctgttagt ccattgactt cacaacgaag aatctcttct ctatttctat gctctaaaat     1860
ctccttatat acatagtccc catacttatc ctcaaaactc accacaaaat ctcaagttga     1920 gtmsatgbrm                                                            1930
```

<210> SEQ ID NO 76  
<211> LENGTH: 506  
<212> TYPE: DNA  
<213> ORGANISM: Arabidopsis thaliana

<400> SEQUENCE: 76

```
ggactcaata aacaactcaa agatgattaa attcatatat tttactatga aatatgtttt       60
actataaaaa acagctcaaa atgctacatt tcattattcc tttctccatt tcattttaa      120 aattcatact actcataaaa gttcatagta tgactataag tttatgacta gtttaacttt      180
caactatcta gctttcatat gattccctag ttcaaagtta tactactcat aaatttagat      240
actcatacta tgaattttt atatagcaaa aaaaaaatta catctcagtt tgatatcaat      300
aactaaacat acctatgtaa aaacttacat agtctactac ccaaaatatc aataattatt      360
```

| | |
|---|---|
| gtagctccca ctacccaaaa gacaatgtcc attgacttca caagcttctt agtcttctct | 420 |
| atttctatgc tctaaaatct ccttatatac atagtcccca tacttatcct caaaactcac | 480 |
| cacaaaatct catcaactca msatgb | 506 |

<210> SEQ ID NO 77
<211> LENGTH: 1006
<212> TYPE: DNA
<213> ORGANISM: Arabidopsis thaliana

<400> SEQUENCE: 77

| | |
|---|---|
| tcactgatgt tctctaatga acgttctcac aaaaaggtaa atcatccgta aatggccaaa | 60 |
| aactccacac tgataatcat tattgataaa cttttgctcc gttcaattct cttttctaaa | 120 |
| tatgttatat tatatattag tatttattta ttaggaggtt ttgtcggcaa caaaaaaata | 180 |
| gacaactctc gtaaataaca aaaataagtt ttcttatcaa atttagcaca caatcttcaa | 240 |
| acttccaaaa ataacatgaa attaatatta aaaagactaa tataagcatt tgattgataa | 300 |
| ttcacacgat ttgtgattta aaatcataat taattttata tatttagata aaaataaatt | 360 |
| agttattatg taaaattact aatgctaatt ttggaaattt gtgaagtttg tgttataatt | 420 |
| gtccataata aattttttca tgttatttta aagtatttct ctataaaaag taaaggttgg | 480 |
| gccaggtaaa tgtacttatt ggactcaata acaactcaa agatgattaa attcatatat | 540 |
| tttactatga aatatgtttt actataaaaa acagctcaaa atgctacatt tcattattcc | 600 |
| tttctccatt tcattttttaa aattcatact actcataaaa gttcatagta tgactataag | 660 |
| tttatgacta gtttaacttt caactatcta gctttcatat gattccctag ttcaaagtta | 720 |
| tactactcat aaatttagat actcatacta tgaattttt atatagcaaa aaaaaaatta | 780 |
| catctcagtt tgatatcaat aactaaacat acctatgtaa aaacttacat agtctactac | 840 |
| ccaaaatatc aataattatt gtagctccca ctacccaaaa gacaatgtcc attgacttca | 900 |
| caagcttctt agtcttctct atttctatgc tctaaaatct ccttatatac atagtcccca | 960 |
| tacttatcct caaaactcac cacaaaatct catcaactca msatgb | 1006 |

<210> SEQ ID NO 78
<211> LENGTH: 1506
<212> TYPE: DNA
<213> ORGANISM: Arabidopsis thaliana

<400> SEQUENCE: 78

| | |
|---|---|
| aagtgaaaat ataatattca tacctcttgt ttcatataac gttctaccaa tcctcttgtt | 60 |
| cctgcatatt aaaagtaact catatcagag gagacatgtt gtatcaaaca acaagcaaca | 120 |
| acagataaac atttatcttt ttttttagtt tcttttttta aaaccaagtt gactatgttt | 180 |
| tagagcatct tcaatggtga gttttttaata ttaattaatc aaaaataata atagaaaagg | 240 |
| caagagaata agaatggttc ttattttaaa gtatataaaa tcttatttaa atcccaaat | 300 |
| accacatatc ttagtataat gtcttaatat gatttgttca tttttattta tcacttaaaa | 360 |
| tttagttaaa taacaaaatt atatttaaat aatattataa tattgataag agacacttgg | 420 |
| tgaatatttc accattagag atgctctttc tgtttgttg ttacaaaata atacacccat | 480 |
| ccccaactat ccttgaaaaa tcactgatgt tctctaatga acgttctcac aaaaaggtaa | 540 |
| atcatccgta aatggccaaa aactccacac tgataatcat tattgataaa cttttgctcc | 600 |
| gttcaattct cttttctaaa tatgttatat tatatattag tatttattta ttaggaggtt | 660 |
| ttgtcggcaa caaaaaaata gacaactctc gtaaataaca aaaataagtt ttcttatcaa | 720 |

```
atttagcaca caatcttcaa acttccaaaa ataacatgaa attaatatta aaaagactaa      780
tataagcatt tgattgataa ttcacacgat ttgtgattta aaatcataat taattttata      840
tatttagata aaaataaatt agttattatg taaaattact aatgctaatt ttggaaattt      900
gtgaagtttg tgttataatt gtccataata aattttttca tgttatttta aagtatttct      960
ctataaaaag taaaggttgg gccaggtaaa tgtacttatt ggactcaata aacaactcaa     1020
agatgattaa attcatatat tttactatga aatatgtttt actataaaaa acagctcaaa     1080
atgctacatt tcattattcc tttctccatt tcatttttaa aattcatact actcataaaa     1140
gttcatagta tgactataag tttatgacta gtttaacttt caactatcta gctttcatat     1200
gattccctag ttcaaagtta tactactcat aaatttagat actcatacta tgaaattttt     1260
atatagcaaa aaaaaaatta catctcagtt tgatatcaat aactaaacat acctatgtaa     1320
aaacttacat agtctactac ccaaaatatc ataattatt gtagctccca ctacccaaaa      1380
gacaatgtcc attgacttca caagcttctt agtcttctct atttctatgc tctaaaatct     1440
ccttatatac atagtcccca tacttatcct caaaactcac cacaaaatct catcaactca     1500 msatgb                                                                1506

<210> SEQ ID NO 79
<211> LENGTH: 340
<212> TYPE: DNA
<213> ORGANISM: artificial
<220> FEATURE:
<223> OTHER INFORMATION: synthetic sequence

<400> SEQUENCE: 79
ctgtagacag ttgactttc cttaaacagt gtgtgatcat ttttaatatg aatggtcgaa        60
taaaaaactc atctttttg gataaaatac gcaacaggct gaacatagat agaaaacggc       120
ttggtaccga cgtttaaaag ttgtagcatg acgaagtaaa acgatatcaa atacgtggaa      180
cttaattgtt ggttaataga ggataagaaa tggccaagtc agaattaaat tcacgcacac      240
aagtatatac ttgttccctc ccaaatatct gaactatctt cttttatcaa aagatataa       300 gtgtcgctgc cgtgtaccaa gaggtaggtt tcmsatgbrm                            340

<210> SEQ ID NO 80
<211> LENGTH: 106
<212> TYPE: DNA
<213> ORGANISM: Arabidopsis thaliana

<400> SEQUENCE: 80
acgcacactt catatatctt gttccctccc aattatctga actatcttct tttatcaaaa       60
actatattca caggctgccg tgtaccttct ccatccaaag msatgb                     106

<210> SEQ ID NO 81
<211> LENGTH: 206
<212> TYPE: DNA
<213> ORGANISM: Arabidopsis thaliana

<400> SEQUENCE: 81
aaattttcaa catcgtactg cttcataaac gatatcaaat acgtggaact taattgttgg       60
ttaatagagg ataagaaatg gggttcacag aattaaattc acgcacactt catatatctt      120
gttccctccc aattatctga actatcttct tttatcaaaa actatattca caggctgccg      180
tgtaccttct ccatccaaag msatgb                                           206
```

<210> SEQ ID NO 82
<211> LENGTH: 1997
<212> TYPE: DNA
<213> ORGANISM: artificial
<220> FEATURE:
<223> OTHER INFORMATION: synthetic sequence

<400> SEQUENCE: 82

| | | | | | |
|---|---|---|---|---|---|
| ctgcttgaga | cctactacta | cagaaagcca | aatgcaacca | ctaatttgtc | tcctgcatgg | 60 |
| actctttggt | ttcgaaagaa | tcttggagac | aaaacttgct | gaaacaagga | ctgaagagaa | 120 |
| aaaatctttt | ataagatgaa | attgacccgt | ataaataagc | agttataagc | atatgtgctg | 180 |
| tcacaacatc | atcaatcaac | aattgagtct | cggtaacttg | ttcttcgagt | gatttatctc | 240 |
| actaatgcaa | agtttttat | caatgacgat | atgtgctgtc | acaacatcat | caatcattgt | 300 |
| tagagtttac | aaatcagata | acacaatctg | ctaggatcga | agacgtagt | ttttatgttt | 360 |
| tgacctataa | acacaaaaac | ataaggtgaa | aggatgcaat | gaacacgtc | aaggaggctc | 420 |
| gacaagtttg | taactatgga | tggtcaatct | aaagacccga | tttcacgtct | acgatttcac | 480 |
| cgtcgtggtt | tacgttctgt | tgctggaaat | gtagagacaa | cattcggtct | aagagcaaa | 540 |
| tccaagactc | aaaagcaaca | caaacgttcg | ttagcaacac | aaggcgtaaa | ctaaagctaa | 600 |
| tcgaagaatc | aaaagcaaca | caaagcaaag | taaagcaaac | ggtgaattaa | acaatgtaac | 660 |
| catggtcctt | caaacccaag | aacaagtgat | tgcaacttcc | tatgtttctc | tttgaacgag | 720 |
| agagacatgg | agcgagagag | aggaagcgag | agagggagag | agagagagag | agagagagag | 780 |
| aaacacaaac | ctacttgtga | ggggcgatgg | atccgacgag | tgaggtcact | tctttcggcg | 840 |
| acggcgagat | caccggcgaa | gaatcagcaa | gtaactgccg | aatgaatctc | ttaattgagt | 900 |
| gttttgtcag | ctcctctcgg | tgaagaagag | atgtggtttt | tggatctaat | tccatatatt | 960 |
| agattagggt | attattgaca | ttttataatt | aaccgactta | gtcgaagtcg | tcttacttgt | 1020 |
| ttagtttgag | tctcagattt | ttttattt | tggatgagt | ttagaaaatt | tgattcaact | 1080 |
| gaatcattca | aatgatctat | ttaaacatga | aaaacaatgt | tgtattttca | tcttcattga | 1140 |
| gtaccaagta | ggtaatggac | aaacaatgtc | ctccttaata | gaacaaccca | aaaaacttga | 1200 |
| gaatgtttat | gattaataaa | ataatttaat | caaaaactat | tatagatttt | tattttaaaa | 1260 |
| actacaaata | gtttaaaata | aatataatat | ttacaatttc | catcacaaaa | actttcttaa | 1320 |
| tgcggttcct | tgaaggatca | catagttaat | aagtaattaa | gtactatttt | attcatgtac | 1380 |
| tttcagaatg | ccctatccag | agttgctaca | agcctaaatg | agccaaaatg | gtgctaaaaa | 1440 |
| gaaacctgta | tttgacagac | tattaatggt | ttgtttatct | ctaatatcag | ttgaatacaa | 1500 |
| tatagtttat | ttgaactgat | tgggtataaa | aagaaactga | gatgactaag | tacgattcct | 1560 |
| ttggaacaaa | ttgtttatgg | taggatgctt | tttaaccgta | tcagggactc | caatgttttc | 1620 |
| gtaaatcaat | agttcaaaaa | aaaaaagatg | gtgtgttcac | gtagaggtaa | ggttaaatca | 1680 |
| atctatataa | atcatatgta | ttttttgtat | ccaatagtca | tctttgtaaa | gatttttgt | 1740 |
| tcgtgtgtgg | cggataagca | aaaacagaat | aacataatct | cttatccaac | ttatattgcc | 1800 |
| acgtggacag | atatagttgg | tgaacgtcta | tgtaatctaa | tctctcgttt | tgcagttggg | 1860 |
| ctattacttt | cggtgttcat | gaaccttgct | ttgtttcttc | tacggattgt | atcgggaacg | 1920 |
| taaccataac | caaaccatca | tcatcatcat | ctcttggtga | cagaagaaaa | gagttgtcct | 1980 |
| tgtctcttth | tatgbrm | | | | | 1997 |

<210> SEQ ID NO 83
<211> LENGTH: 506
<212> TYPE: DNA
<213> ORGANISM: Arabidopsis thaliana

<400> SEQUENCE: 83

| | | | | | |
|---|---|---|---|---|---|
| gttgaattgt | tatatcaaaa | tttgaactga | ttgggtataa | aaagaaactg | agaactgatt | 60 |
| catgctaagg | aaaccttgtt | taacaaatac | catggatgct | ttttaaccgt | atcagcctct | 120 |
| ccaatgtttt | cgtaaatcaa | tagttcaaaa | ttttttttcta | ccacacaagt | gcatctccat | 180 |
| tccaattttc | aatctatata | aatcatatgt | attttttgta | tccaatagtc | atctttgtaa | 240 |
| agatttttg | ttcgtgtgtg | gcggataagc | aaaaacagaa | taacataatc | tcttatccaa | 300 |
| cttatattgc | cacgtggaca | gatatagttg | gtgaagcaga | tactaatcta | atctgagcaa | 360 |
| aaccagttgg | gctatttgaa | agccacaagt | acttggaacc | tttgtttctt | ctaccctaac | 420 |
| atagcccttg | caaaccataa | ccaaaccatc | atcatcatca | tctcttggtg | acagaagaaa | 480 |
| agagttgagg | aacagagaaa | htatgb | | | | 506 |

<210> SEQ ID NO 84
<211> LENGTH: 1006
<212> TYPE: DNA
<213> ORGANISM: Arabidopsis thaliana

<400> SEQUENCE: 84

| | | | | | |
|---|---|---|---|---|---|
| tttggctgaa | tcagcttcag | cagaatgaac | aaatcaaact | cagtcagatt | tttttattt | 60 |
| tttggatgag | tttagaaaaa | aacattcaac | tgaatcattc | aaatgatcta | tttaaacatg | 120 |
| aaaaacaaac | aacaattttc | atcttcattg | agatggttca | tccaaatgga | caaacaaaca | 180 |
| ggaccttaat | agaacaaccc | aaaaagaac | tcttacaaat | tgattaataa | ataatttaa | 240 |
| tcaaaagaa | ttatagattt | ttattttaaa | aactacaaat | agtttaaaaa | aatataata | 300 |
| tttacaattt | ccatcacaaa | ttgtttctta | atgcccaagg | atgaaggatc | acatagttaa | 360 |
| taagtaatta | agtactattt | tattcatgta | ctttctcttt | gccctatcca | gagttgctac | 420 |
| aagcctaaaa | ctcggtttta | ccacgatttt | tctttggtgt | atttgacaga | ctattaatgg | 480 |
| tttgtttatc | tctattatca | gttgaattgt | tatatcaaaa | tttgaactga | ttgggtataa | 540 |
| aaagaaactg | agaactgatt | catgctaagg | aaaccttgtt | taacaaatac | catggatgct | 600 |
| ttttaaccgt | atcagcctct | ccaatgtttt | cgtaaatcaa | tagttcaaaa | ttttttttcta | 660 |
| ccacacaagt | gcatctccat | tccaattttc | aatctatata | aatcatatgt | attttttgta | 720 |
| tccaatagtc | atctttgtaa | agatttttg | ttcgtgtgtg | gcggataagc | aaaaacagaa | 780 |
| taacataatc | tcttatccaa | cttatattgc | cacgtggaca | gatatagttg | gtgaagcaga | 840 |
| tactaatcta | atctgagcaa | aaccagttgg | gctatttgaa | agccacaagt | acttggaacc | 900 |
| tttgtttctt | ctaccctaac | atagcccttg | caaaccataa | ccaaaccatc | atcatcatca | 960 |
| tctcttggtg | acagaagaaa | agagttgagg | aacagagaaa | htatgb | | 1006 |

<210> SEQ ID NO 85
<211> LENGTH: 1506
<212> TYPE: DNA
<213> ORGANISM: Arabidopsis thaliana

<400> SEQUENCE: 85

| | | | | | |
|---|---|---|---|---|---|
| aatggttctg | ttgctcctaa | tgtagagaca | acaaagcctc | ttaagagcaa | atcgaagact | 60 |
| caaaagcaac | acaaagcaag | caaagcaaca | caagccgtaa | actaaagcta | atcgaagaat | 120 |

| | |
|---|---|
| caaaagcaac acaaagcaaa gtaaagcaaa cccacaatta aacaatgtaa ccatggtgga | 180 |
| tcaaacccaa gaacaagtga ttgcaacaag gatacaaaga gaaacaacga gagagacatg | 240 |
| gagcgagaga gaggaagcga gagagggaga gagagagaga gagagagaga gaaacacaaa | 300 |
| cctactacac tccggcgatg gatccgacga gtctccagtg aagaatcggc gacggcgaga | 360 |
| tcaccggcga agaatcagca tcattgacgg ctatgaatct caattttgag tgttttgtgt | 420 |
| cgaggagagg gtgaagaaga gatgtggttt ttggatgtaa ttccatatat tagattaggg | 480 |
| tattattgac attttataat tttggctgaa tcagcttcag cagaatgaac aaatcaaact | 540 |
| cagtcagatt tttttttattt tttggatgag tttagaaaaa acattcaac tgaatcattc | 600 |
| aaatgatcta tttaaacatg aaaaacaaac aacaattttc atcttcattg agatggttca | 660 |
| tccaaatgga caaacaaaca ggaccttaat agaacaaccc aaaaaagaac tcttacaaat | 720 |
| tgattaataa aataatttaa tcaaaaagaa ttatagattt ttattttaaa aactacaaat | 780 |
| agtttaaaaa aaatataata tttacaattt ccatcacaaa ttgtttctta atgcccaagg | 840 |
| atgaaggatc acatagttaa taagtaatta agtactattt tattcatgta ctttctcttt | 900 |
| gccctatcca gagttgctac aagcctaaaa ctcggtttta ccacgatttt tctttggtgt | 960 |
| atttgacaga ctattaatgg tttgtttatc tctattatca gttgaattgt tatatcaaaa | 1020 |
| tttgaactga ttgggtataa aaagaaactg agaactgatt catgctaagg aaaccttgtt | 1080 |
| taacaaatac catggatgct ttttaaccgt atcagcctct ccaatgtttt cgtaaatcaa | 1140 |
| tagttcaaaa ttttttttcta ccacacaagt gcatctccat tccaattttc aatctatata | 1200 |
| aatcatatgt attttttgta tccaatagtc atctttgtaa agattttttg ttcgtgtgtg | 1260 |
| gcggataagc aaaaacagaa taacataatc tcttatccaa cttatattgc cacgtggaca | 1320 |
| gatatagttg gtgaagcaga tactaatcta atctgagcaa aaccagttgg gctatttgaa | 1380 |
| agccacaagt acttggaacc tttgtttctt ctaccctaac atagcccttg caaaccataa | 1440 |
| ccaaaccatc atcatcatca tctcttggtg acagaagaaa agagttgagg aacagagaaa | 1500 |
| htatgb | 1506 |

<210> SEQ ID NO 86
<211> LENGTH: 1961
<212> TYPE: DNA
<213> ORGANISM: artificial
<220> FEATURE:
<223> OTHER INFORMATION: synthetic sequence

<400> SEQUENCE: 86

| | |
|---|---|
| ctttgctttc tgaaccgcct cctttcattt ctccaaggtc ggcaaattta tccattttg | 60 |
| gctgaatggc taaatctgg ttgggccagc gcactttgtc ttttacactt tcttttttcag | 120 |
| tctttccaca ggtaggtgaa aatttcttt gtttcttcta cttctttggc tcttcatact | 180 |
| ctatatctgt taaataagag aacaaagata caaggcgata tcgagttcgt acaagagtag | 240 |
| cttgaagaaa tcttcaagag gactatagaa atttgaagga aaggattatt tattttagat | 300 |
| atttgataat agagttatca taaaaatgat atagttaaaa aaataaaaaa aataaaaaaa | 360 |
| taaaatgata tagttaattt tgtttgttaa caaacatgca acatgctgat ttaaatctgg | 420 |
| ataataagtt aataacacat tgataccaca gttaccgctt atatacgtat gattagtatt | 480 |
| aaaaatcttc tccagaattt caacgttgtt tttgctactc acgcattgta ccttaaatga | 540 |
| tcttattcat catttctaac atttgttaaa tacgtaagaa gcggtcatct tcttggatca | 600 |
| tctcacgata gccgttgttg agggtcttgt tcatgcggat gcaaaagaag acgtccatgc | 660 |

```
ccacgtccac gtccatgtcc acctccacgt ccacactatt caagaaatta tacagtggga      720
acttaaagaa gaatgaagaa gagaaaacaa ggtagttaat accgattggt acaatatagt      780
actcccataa cagattacaa gtacttttga atatgcttat agatttagac atattaaaga      840
ctattttctc cttttaaatc aatgaagaaa atacttgagt tgttaggaag atttgccttt      900
gcataaccgt ctctcatcgt gtggttgttt tgtaatccca gaaccttctt atgcagaatt      960
ttaaagacac agtaagcaat gaataagaac acttggttta caataacgat cgaaactggt     1020
ttacaataat gaccgaatat ggtttgcaaa tatagatgaa ttggaattta attgattcga     1080
tctatatcta aaattaaatt tcttgccaag ggataatact atcctcttag ggtttagatt     1140
tctattatca aaactctcgt aattaaactc gaaattggtt aatcgctctc cttagggaaa     1200
acaacgtttt ctggtataaa gagacgagag aaacggtatt gatggagtta aaagtgatga     1260
tgttgatgaa atactgagtc aacgttttat tccgaagagc cgactgtgag aagcaaggtt     1320
tcatggttgg gaattttgtt gcgcaacgga gaagatgaag tgaattttgt tgcgcaacgg     1380
atttccgcaa gcttttcccg agaaaacaaa gatatcatct acattctatt tttgtgctgt     1440
aacttttctc ttaaaattgt aaacaatttt ttgtgatata tatatatata taaacaattt     1500
tatatcatta agtatggtac tctttaatgt ttttaacgga acatgaccaa aactgctagt     1560
gaaagcattt tgtcttaact ttacaaaaga agttatcttt ttaaattgtg tttgaccaaa     1620
tcttcggtaa ataaaaagac taagtttgta aatttattct tagacaatta tttactatta     1680
ttgccgacta atatgaaaat gcattcttca gcattttggc attatccaaa agaagggaca     1740
aaacacttat ctcttaaaac ttaaatttta agccattgca aaaccaacaa tgaatcttgt     1800
ggctgatcat ctaaccgcgt tcacttgtca acatttagaa ataatgttgc gtttcaaaga     1860
attaaataga aacttggttt ttgtatgagg ttgagcgtct tctatatatt tattacaact     1920
gaacgctact ggttttttgcg ttgcttcttg cttmsatgbr m                         1961

<210> SEQ ID NO 87
<211> LENGTH: 506
<212> TYPE: DNA
<213> ORGANISM: Arabidopsis thaliana

<400> SEQUENCE: 87
tttttgtaaa caattttttg tgatatatat atatatataa acaatttat atcattaagt        60 atggtactct ttaatgtttt taacggaaca tgaccaaaac tgctagtgaa agcattttgt      120
cttaacttta caaagaagt tatcttttt ttaacacaaa ctggttttct tcggtaaata       180 aaagactaa gtttgtaaat ttattcttag acaattattt actattattg ccgactaata      240
tgaaaatgca agaagtcgt atttggcatt atccaaaaga agggacaaaa cacttatctc      300
ttaaaactta aattttaagc cattcgttta ccaacaatga atcttgtggc tgatgtagaa      360
accgcgttca cttgtcaaca tttagaaata atgttggctt tcaaagaatt aaatagaaac      420
aaccaaaatg tatgaggttg agcgtcttct atatatttat tacaagactt gcgatgacca      480
aaaacgcaac gaagaacgaa msatgb                                           506

<210> SEQ ID NO 88
<211> LENGTH: 1006
<212> TYPE: DNA
<213> ORGANISM: Arabidopsis thaliana

<400> SEQUENCE: 88
```

-continued

| | |
|---|---|
| cagaatttta aagacacaca aagcaatgaa taagaacact tggtttacaa taacgatcga | 60 |
| aactggttta caataatgac cgaatatggt ttgcaaatat agatgaattg gaatttaatt | 120 |
| gattcgatct atatctaaaa ttaaatttct tgggttccct aaatactatc ctcttagggt | 180 |
| ttagatttct attatcaaaa ctctcgttta atttgagcaa attggttaat cggagaggtt | 240 |
| agggaaaaca acgttttctg gtataaagag acgagagaaa cggtattgat ggagttaaaa | 300 |
| gtgatgatgt tgatgaaata ctgagtcaac gttaataagg caagagccga ctgtgagaag | 360 |
| caaggtttca tggttgggaa ttttgttgcg caacggagaa gatgaagtga attttgttgc | 420 |
| gcaacggatt ccgcaagct tttcccgaga aaacaaagat atcatctaca ttctattttt | 480 |
| gtgctgtaac ttttctgaat tttttgtaaa caattttttg tgatatatat atatatataa | 540 |
| acaattttat atcattaagt atggtactct ttaatgtttt taacggaaca tgaccaaaac | 600 |
| tgctagtgaa agcattttgt cttaacttta caaagaagt tatcttttt ttaacacaaa | 660 |
| ctggttttct tcggtaaata aaagactaa gtttgtaaat ttattcttag acaattattt | 720 |
| actattattg ccgactaata tgaaaatgca agaagtcgt atttggcatt atccaaaaga | 780 |
| agggacaaaa cacttatctc ttaaaactta aattttaagc cattcgttta ccaacaatga | 840 |
| atcttgtggc tgatgtagaa accgcgttca cttgtcaaca tttagaaata atgttggctt | 900 |
| tcaaagaatt aaatagaaac aaccaaaatg tatgaggttg agcgtcttct atatattat | 960 |
| tacaagactt gcgatgacca aaacgcaac gaagaacgaa msatgb | 1006 |

<210> SEQ ID NO 89
<211> LENGTH: 1506
<212> TYPE: DNA
<213> ORGANISM: Arabidopsis thaliana

<400> SEQUENCE: 89

| | |
|---|---|
| accgcttaat atcgtatgat tagtattaaa aatcttctcc agaatttcaa cgttgttttt | 60 |
| gctactcacg cattgtacct taatgatct tattcatcat ttctaacaaa acaatttatg | 120 |
| cattcttcgc cagtagaaga acctagtaga gtgctatcgg caacaactcc gtcttgttca | 180 |
| tgcggatgca aaagaagacg tccatgccca cgtccacgtc catgtccacc tccacgtcca | 240 |
| cactattcaa gaaattatac agacccttga aaagaagaa tgaagaagag aaaacaagga | 300 |
| tcaattatgg gattggtaca atatagttga gggtattgtc taatgtagta cttttgaata | 360 |
| tgcttataga tttagacata ttaaagacta ttttctcctt ttaaatcaat gaagaaaata | 420 |
| cttgagttca atccttcttt tgcctttgca taaccgtctc tcatccacac caacaaaaca | 480 |
| aatcccagaa ccttcttttg cagaatttta aagacacaca aagcaatgaa taagaacact | 540 |
| tggtttacaa taacgatcga aactggttta caataatgac cgaatatggt ttgcaaatat | 600 |
| agatgaattg gaatttaatt gattcgatct atatctaaaa ttaaatttct tgggttccct | 660 |
| aaatactatc ctcttagggt ttagatttct attatcaaaa ctctcgttta atttgagcaa | 720 |
| attggttaat cggagaggtt agggaaaaca acgttttctg gtataaagag acgagagaaa | 780 |
| cggtattgat ggagttaaaa gtgatgatgt tgatgaaata ctgagtcaac gttaataagg | 840 |
| caagagccga ctgtgagaag caaggtttca tggttgggaa ttttgttgcg caacggagaa | 900 |
| gatgaagtga attttgttgc gcaacggatt ccgcaagct tttcccgaga aaacaaagat | 960 |
| atcatctaca ttctattttt gtgctgtaac ttttctgaat tttttgtaaa caattttttg | 1020 |
| tgatatatat atatatataa acaattttat atcattaagt atggtactct ttaatgtttt | 1080 |
| taacggaaca tgaccaaaac tgctagtgaa agcattttgt cttaacttta caaagaagt | 1140 |

```
tatcttttttt ttaacacaaa ctggttttct tcggtaaata aaagactaa gtttgtaaat       1200 ttattcttag acaattattt actattattg ccgactaata tgaaaatgca aagaagtcgt       1260
atttggcatt atccaaaaga agggacaaaa cacttatctc ttaaaactta aattttaagc       1320
cattcgttta ccaacaatga atcttgtggc tgatgtagaa accgcgttca cttgtcaaca       1380
tttagaaata atgttggctt tcaaagaatt aaatagaaac aaccaaaatg tatgaggttg       1440
agcgtcttct atatatttat tacaagactt gcgatgacca aaaacgcaac gaagaacgaa       1500 msatgb                                                                  1506
```

<210> SEQ ID NO 90
<211> LENGTH: 28
<212> TYPE: DNA
<213> ORGANISM: artificial
<220> FEATURE:
<223> OTHER INFORMATION: synthetic sequence

<400> SEQUENCE: 90

```
ccttcataga cctgaatcaa cacaccgy                                          28
```

<210> SEQ ID NO 91
<211> LENGTH: 27
<212> TYPE: DNA
<213> ORGANISM: artificial
<220> FEATURE:
<223> OTHER INFORMATION: synthetic sequence

<400> SEQUENCE: 91

```
ggaggagtca tgactgtgtt gattccy                                           27
```

<210> SEQ ID NO 92
<211> LENGTH: 18
<212> TYPE: DNA
<213> ORGANISM: artificial
<220> FEATURE:
<223> OTHER INFORMATION: synthetic sequence

<400> SEQUENCE: 92

```
cgccgggttt atgtgtcy                                                     18
```

<210> SEQ ID NO 93
<211> LENGTH: 21
<212> TYPE: DNA
<213> ORGANISM: artificial
<220> FEATURE:
<223> OTHER INFORMATION: synthetic sequence

<400> SEQUENCE: 93

```
ccggggctaa gtctaagtgt y                                                 21
```

<210> SEQ ID NO 94
<211> LENGTH: 30
<212> TYPE: DNA
<213> ORGANISM: artificial
<220> FEATURE:
<223> OTHER INFORMATION: synthetic sequence

<400> SEQUENCE: 94

```
cgtctgctac agcgtgtgga aggacgaggy                                        30
```

<210> SEQ ID NO 95
<211> LENGTH: 30
<212> TYPE: DNA

```
<213> ORGANISM: artificial
<220> FEATURE:
<223> OTHER INFORMATION: synthetic sequence

<400> SEQUENCE: 95
gagacgtggc ggtgcttctt gcggtaatcy                                    30

<210> SEQ ID NO 96
<211> LENGTH: 26
<212> TYPE: DNA
<213> ORGANISM: artificial
<220> FEATURE:
<223> OTHER INFORMATION: synthetic sequence

<400> SEQUENCE: 96
tggaatcaaa gacaggtaga ctggcy                                        26

<210> SEQ ID NO 97
<211> LENGTH: 27
<212> TYPE: DNA
<213> ORGANISM: artificial
<220> FEATURE:
<223> OTHER INFORMATION: synthetic sequence

<400> SEQUENCE: 97
ctgctttcag tgtaatggtt tccagay                                       27

<210> SEQ ID NO 98
<211> LENGTH: 31
<212> TYPE: DNA
<213> ORGANISM: artificial
<220> FEATURE:
<223> OTHER INFORMATION: synthetic sequence

<400> SEQUENCE: 98
ttgtctggtt tggaaagaag aaagttgtga y                                  31

<210> SEQ ID NO 99
<211> LENGTH: 29
<212> TYPE: DNA
<213> ORGANISM: artificial
<220> FEATURE:
<223> OTHER INFORMATION: synthetic sequence

<400> SEQUENCE: 99
cacacagagc acaaggaata gtggcaaty                                     29

<210> SEQ ID NO 100
<211> LENGTH: 22
<212> TYPE: DNA
<213> ORGANISM: artificial
<220> FEATURE:
<223> OTHER INFORMATION: synthetic sequence

<400> SEQUENCE: 100
tgggaatcca ctcaacgaag ty                                            22

<210> SEQ ID NO 101
<211> LENGTH: 21
<212> TYPE: DNA
<213> ORGANISM: artificial
<220> FEATURE:
<223> OTHER INFORMATION: synthetic sequence

<400> SEQUENCE: 101
cctgacagca tcagccatgt y                                             21
```

<210> SEQ ID NO 102
<211> LENGTH: 24
<212> TYPE: DNA
<213> ORGANISM: artificial
<220> FEATURE:
<223> OTHER INFORMATION: synthetic sequence

<400> SEQUENCE: 102
catcgccgat caaccgttct gtgy                                              24

<210> SEQ ID NO 103
<211> LENGTH: 25
<212> TYPE: DNA
<213> ORGANISM: artificial
<220> FEATURE:
<223> OTHER INFORMATION: synthetic sequence

<400> SEQUENCE: 103
gacttagccc cggcgactcc catay                                             25

<210> SEQ ID NO 104
<211> LENGTH: 31
<212> TYPE: DNA
<213> ORGANISM: artificial
<220> FEATURE:
<223> OTHER INFORMATION: synthetic sequence

<400> SEQUENCE: 104
tgatcaaacg ctctgtaaac tttcttcaca y                                      31

<210> SEQ ID NO 105
<211> LENGTH: 29
<212> TYPE: DNA
<213> ORGANISM: artificial
<220> FEATURE:
<223> OTHER INFORMATION: synthetic sequence

<400> SEQUENCE: 105
gactgaactg gggttgaagg tgaacacty                                         29

<210> SEQ ID NO 106
<211> LENGTH: 26
<212> TYPE: DNA
<213> ORGANISM: artificial
<220> FEATURE:
<223> OTHER INFORMATION: synthetic sequence

<400> SEQUENCE: 106
catcttctgg tgccgaggca gggaty                                            26

<210> SEQ ID NO 107
<211> LENGTH: 33
<212> TYPE: DNA
<213> ORGANISM: artificial
<220> FEATURE:
<223> OTHER INFORMATION: synthetic sequence

<400> SEQUENCE: 107
tatataggta ccaaagagcc aagttgttat tcy                                    33

<210> SEQ ID NO 108
<211> LENGTH: 32
<212> TYPE: DNA
<213> ORGANISM: artificial
<220> FEATURE:

```
<223> OTHER INFORMATION: synthetic sequence

<400> SEQUENCE: 108
tatataccat ggtactcact cacacacaaa cy                                    32

<210> SEQ ID NO 109
<211> LENGTH: 34
<212> TYPE: DNA
<213> ORGANISM: artificial
<220> FEATURE:
<223> OTHER INFORMATION: synthetic sequence

<400> SEQUENCE: 109
tatataggta ccatttccaa ctcctgactg agay                                  34

<210> SEQ ID NO 110
<211> LENGTH: 32
<212> TYPE: DNA
<213> ORGANISM: artificial
<220> FEATURE:
<223> OTHER INFORMATION: synthetic sequence

<400> SEQUENCE: 110
tatataccat ggtctttctc ctcgcctggg ay                                    32

<210> SEQ ID NO 111
<211> LENGTH: 32
<212> TYPE: DNA
<213> ORGANISM: artificial
<220> FEATURE:
<223> OTHER INFORMATION: synthetic sequence

<400> SEQUENCE: 111
tatataggta cctctcaatc aaggccttta ty                                    32

<210> SEQ ID NO 112
<211> LENGTH: 42
<212> TYPE: DNA
<213> ORGANISM: artificial
<220> FEATURE:
<223> OTHER INFORMATION: synthetic sequence

<400> SEQUENCE: 112
tatataccat ggttaattaa tttcaatctc tccctctcta ty                         42

<210> SEQ ID NO 113
<211> LENGTH: 35
<212> TYPE: DNA
<213> ORGANISM: artificial
<220> FEATURE:
<223> OTHER INFORMATION: synthetic sequence

<400> SEQUENCE: 113
tatataggta cccggttatt cttaatcctt ttcay                                 35

<210> SEQ ID NO 114
<211> LENGTH: 39
<212> TYPE: DNA
<213> ORGANISM: artificial
<220> FEATURE:
<223> OTHER INFORMATION: synthetic sequence

<400> SEQUENCE: 114
tatataccat ggttaattaa gctgtgtgac cactgatgy                             39
```

```
<210> SEQ ID NO 115
<211> LENGTH: 37
<212> TYPE: DNA
<213> ORGANISM: artificial
<220> FEATURE:
<223> OTHER INFORMATION: synthetic sequence

<400> SEQUENCE: 115
tatataggta ccgattctag atattgaagt ttgtgay                              37

<210> SEQ ID NO 116
<211> LENGTH: 40
<212> TYPE: DNA
<213> ORGANISM: artificial
<220> FEATURE:
<223> OTHER INFORMATION: synthetic sequence

<400> SEQUENCE: 116
tatataccat ggttaattaa tgttgtgtta acaaagggty                           40

<210> SEQ ID NO 117
<211> LENGTH: 37
<212> TYPE: DNA
<213> ORGANISM: artificial
<220> FEATURE:
<223> OTHER INFORMATION: synthetic sequence

<400> SEQUENCE: 117
tatataggta cccgcgcttt acacggagtt agtgaay                              37

<210> SEQ ID NO 118
<211> LENGTH: 39
<212> TYPE: DNA
<213> ORGANISM: artificial
<220> FEATURE:
<223> OTHER INFORMATION: synthetic sequence

<400> SEQUENCE: 118
tatataggta ccaagaaaaa aaacatatcg gaggaggay                            39

<210> SEQ ID NO 119
<211> LENGTH: 41
<212> TYPE: DNA
<213> ORGANISM: artificial
<220> FEATURE:
<223> OTHER INFORMATION: synthetic sequence

<400> SEQUENCE: 119
tatataggta ccaatttcaa tttctcacct ttttaattgt y                         41

<210> SEQ ID NO 120
<211> LENGTH: 35
<212> TYPE: DNA
<213> ORGANISM: artificial
<220> FEATURE:
<223> OTHER INFORMATION: synthetic sequence

<400> SEQUENCE: 120
tatataggta ccggagaaaa gaaaaactgt tgacy                                35

<210> SEQ ID NO 121
<211> LENGTH: 39
<212> TYPE: DNA
<213> ORGANISM: artificial
<220> FEATURE:
<223> OTHER INFORMATION: synthetic sequence
```

<400> SEQUENCE: 121
tatataggta ccatttatac cacatgtggg aagtattgy            39

<210> SEQ ID NO 122
<211> LENGTH: 39
<212> TYPE: DNA
<213> ORGANISM: artificial
<220> FEATURE:
<223> OTHER INFORMATION: synthetic sequence

<400> SEQUENCE: 122
tatataggta cccatctttc acgctacaaa acattggty            39

<210> SEQ ID NO 123
<211> LENGTH: 37
<212> TYPE: DNA
<213> ORGANISM: artificial
<220> FEATURE:
<223> OTHER INFORMATION: synthetic sequence

<400> SEQUENCE: 123
tatataggta ccctgaagat tacaccagta gttagty               37

<210> SEQ ID NO 124
<211> LENGTH: 36
<212> TYPE: DNA
<213> ORGANISM: artificial
<220> FEATURE:
<223> OTHER INFORMATION: synthetic sequence

<400> SEQUENCE: 124
tatataggta cctatgccag aatcaacaat gaaacy                36

<210> SEQ ID NO 125
<211> LENGTH: 38
<212> TYPE: DNA
<213> ORGANISM: artificial
<220> FEATURE:
<223> OTHER INFORMATION: synthetic sequence

<400> SEQUENCE: 125
tatataggta ccagctaggt agcgggtggt ggtaggay              38

<210> SEQ ID NO 126
<211> LENGTH: 43
<212> TYPE: DNA
<213> ORGANISM: artificial
<220> FEATURE:
<223> OTHER INFORMATION: synthetic sequence

<400> SEQUENCE: 126
tatataggta ccccaccgac cttttttat ataaaaaaaa tcy         43

<210> SEQ ID NO 127
<211> LENGTH: 40
<212> TYPE: DNA
<213> ORGANISM: artificial
<220> FEATURE:
<223> OTHER INFORMATION: synthetic sequence

<400> SEQUENCE: 127
tatataggta ccttaaatta catgaataac gaaattaagy            40

<210> SEQ ID NO 128
<211> LENGTH: 35

```
<212> TYPE: DNA
<213> ORGANISM: artificial
<220> FEATURE:
<223> OTHER INFORMATION: synthetic sequence

<400> SEQUENCE: 128
tatataggta ccaaacaaaa ttatccatct cacay                              35

<210> SEQ ID NO 129
<211> LENGTH: 40
<212> TYPE: DNA
<213> ORGANISM: artificial
<220> FEATURE:
<223> OTHER INFORMATION: synthetic sequence

<400> SEQUENCE: 129
tatataggta ccaataaaca tattaatcaa ctatgaaacy                         40

<210> SEQ ID NO 130
<211> LENGTH: 40
<212> TYPE: DNA
<213> ORGANISM: artificial
<220> FEATURE:
<223> OTHER INFORMATION: synthetic sequence

<400> SEQUENCE: 130
tatataggta ccaaactcat tccacatgga ctgtggccty                         40

<210> SEQ ID NO 131
<211> LENGTH: 41
<212> TYPE: DNA
<213> ORGANISM: artificial
<220> FEATURE:
<223> OTHER INFORMATION: synthetic sequence

<400> SEQUENCE: 131
tatataggta ccttgattaa caaaagttttt ataaataaac y                      41

<210> SEQ ID NO 132
<211> LENGTH: 28
<212> TYPE: DNA
<213> ORGANISM: artificial
<220> FEATURE:
<223> OTHER INFORMATION: synthetic sequence

<400> SEQUENCE: 132
gccatgcctc agctaaccga cagatcay                                      28

<210> SEQ ID NO 133
<211> LENGTH: 31
<212> TYPE: DNA
<213> ORGANISM: artificial
<220> FEATURE:
<223> OTHER INFORMATION: synthetic sequence

<400> SEQUENCE: 133
acagccactg cagcaacctg atacaaatgc y                                  31

<210> SEQ ID NO 134
<211> LENGTH: 28
<212> TYPE: DNA
<213> ORGANISM: artificial
<220> FEATURE:
<223> OTHER INFORMATION: synthetic sequence

<400> SEQUENCE: 134
```

```
gctggagcta gcgcttatgc acgtctcy                                        28
```

```
<210> SEQ ID NO 135
<211> LENGTH: 26
<212> TYPE: DNA
<213> ORGANISM: artificial
<220> FEATURE:
<223> OTHER INFORMATION: synthetic sequence

<400> SEQUENCE: 135
cagctgcaac caatccactg atgtgy                                          26
```

```
<210> SEQ ID NO 136
<211> LENGTH: 29
<212> TYPE: DNA
<213> ORGANISM: artificial
<220> FEATURE:
<223> OTHER INFORMATION: synthetic sequence

<400> SEQUENCE: 136
agtggctaga ccagttgaat tgcaacgay                                       29
```

```
<210> SEQ ID NO 137
<211> LENGTH: 29
<212> TYPE: DNA
<213> ORGANISM: artificial
<220> FEATURE:
<223> OTHER INFORMATION: synthetic sequence

<400> SEQUENCE: 137
catgcaagcg aggtgtttac attttgcty                                       29
```

```
<210> SEQ ID NO 138
<211> LENGTH: 30
<212> TYPE: DNA
<213> ORGANISM: artificial
<220> FEATURE:
<223> OTHER INFORMATION: synthetic sequence

<400> SEQUENCE: 138
aaatggcttt cggagtttcc ctagtggcay                                      30
```

```
<210> SEQ ID NO 139
<211> LENGTH: 31
<212> TYPE: DNA
<213> ORGANISM: artificial
<220> FEATURE:
<223> OTHER INFORMATION: synthetic sequence

<400> SEQUENCE: 139
gaactgaagc aagaacagca ttccccacac y                                    31
```

```
<210> SEQ ID NO 140
<211> LENGTH: 26
<212> TYPE: DNA
<213> ORGANISM: artificial
<220> FEATURE:
<223> OTHER INFORMATION: synthetic sequence

<400> SEQUENCE: 140
tcactatgcc ctcaaaacgg tgacgy                                          26
```

```
<210> SEQ ID NO 141
<211> LENGTH: 28
<212> TYPE: DNA
<213> ORGANISM: artificial
```

```
<220> FEATURE:
<223> OTHER INFORMATION: synthetic sequence

<400> SEQUENCE: 141
gcttgatcag attgcagaat tccacgay                                28

<210> SEQ ID NO 142
<211> LENGTH: 30
<212> TYPE: DNA
<213> ORGANISM: artificial
<220> FEATURE:
<223> OTHER INFORMATION: synthetic sequence

<400> SEQUENCE: 142
ctcaggcagc gaacttcaac atcacaaaty                              30

<210> SEQ ID NO 143
<211> LENGTH: 26
<212> TYPE: DNA
<213> ORGANISM: artificial
<220> FEATURE:
<223> OTHER INFORMATION: synthetic sequence

<400> SEQUENCE: 143
ccacgattcg ccagggttaa gcctty                                  26

<210> SEQ ID NO 144
<211> LENGTH: 25
<212> TYPE: DNA
<213> ORGANISM: artificial
<220> FEATURE:
<223> OTHER INFORMATION: synthetic sequence

<400> SEQUENCE: 144
aaagaaggtg gaattggaag gggcy                                   25

<210> SEQ ID NO 145
<211> LENGTH: 25
<212> TYPE: DNA
<213> ORGANISM: artificial
<220> FEATURE:
<223> OTHER INFORMATION: synthetic sequence

<400> SEQUENCE: 145
ttaacgtggg tgatggtgag tggcy                                   25

<210> SEQ ID NO 146
<211> LENGTH: 27
<212> TYPE: DNA
<213> ORGANISM: artificial
<220> FEATURE:
<223> OTHER INFORMATION: synthetic sequence

<400> SEQUENCE: 146
aacattgttt caggacatgc acaccgy                                 27

<210> SEQ ID NO 147
<211> LENGTH: 28
<212> TYPE: DNA
<213> ORGANISM: artificial
<220> FEATURE:
<223> OTHER INFORMATION: synthetic sequence

<400> SEQUENCE: 147
tgaagtgggg gtattgatca agagccty                                28
```

<210> SEQ ID NO 148
<211> LENGTH: 31
<212> TYPE: DNA
<213> ORGANISM: artificial
<220> FEATURE:
<223> OTHER INFORMATION: synthetic sequence

<400> SEQUENCE: 148
caggaatagg aagactccaa caagaagagc y                              31

<210> SEQ ID NO 149
<211> LENGTH: 29
<212> TYPE: DNA
<213> ORGANISM: artificial
<220> FEATURE:
<223> OTHER INFORMATION: synthetic sequence

<400> SEQUENCE: 149
ggcattgaag agagggcgca gaggcttgy                                 29

<210> SEQ ID NO 150
<211> LENGTH: 29
<212> TYPE: DNA
<213> ORGANISM: artificial
<220> FEATURE:
<223> OTHER INFORMATION: synthetic sequence

<400> SEQUENCE: 150
catgcaagcg aggtgtttac attttgcty                                 29

<210> SEQ ID NO 151
<211> LENGTH: 25
<212> TYPE: DNA
<213> ORGANISM: artificial
<220> FEATURE:
<223> OTHER INFORMATION: synthetic sequence

<400> SEQUENCE: 151
aagcaagaac agcattcccc acacy                                     25

<210> SEQ ID NO 152
<211> LENGTH: 28
<212> TYPE: DNA
<213> ORGANISM: artificial
<220> FEATURE:
<223> OTHER INFORMATION: synthetic sequence

<400> SEQUENCE: 152
gcttgatcag attgcagaat tccacgay                                  28

<210> SEQ ID NO 153
<211> LENGTH: 27
<212> TYPE: DNA
<213> ORGANISM: artificial
<220> FEATURE:
<223> OTHER INFORMATION: synthetic sequence

<400> SEQUENCE: 153
gcttttcgtg acggccattg taaatty                                   27

<210> SEQ ID NO 154
<211> LENGTH: 27
<212> TYPE: DNA
<213> ORGANISM: artificial
<220> FEATURE:
<223> OTHER INFORMATION: synthetic sequence

```
<400> SEQUENCE: 154
caacaaaaac tgcagaaagt ccatccy                                          27

<210> SEQ ID NO 155
<211> LENGTH: 29
<212> TYPE: DNA
<213> ORGANISM: artificial
<220> FEATURE:
<223> OTHER INFORMATION: synthetic sequence

<400> SEQUENCE: 155
atccaataag ctgcagcaac cataccacy                                        29

<210> SEQ ID NO 156
<211> LENGTH: 38
<212> TYPE: DNA
<213> ORGANISM: artificial
<220> FEATURE:
<223> OTHER INFORMATION: synthetic sequence

<400> SEQUENCE: 156
tatataggta ccgggatgtt tatttaaggc atggtcay                              38

<210> SEQ ID NO 157
<211> LENGTH: 40
<212> TYPE: DNA
<213> ORGANISM: artificial
<220> FEATURE:
<223> OTHER INFORMATION: synthetic sequence

<400> SEQUENCE: 157
tatataccat ggttaattaa caagggagtg gaataactty                            40

<210> SEQ ID NO 158
<211> LENGTH: 38
<212> TYPE: DNA
<213> ORGANISM: artificial
<220> FEATURE:
<223> OTHER INFORMATION: synthetic sequence

<400> SEQUENCE: 158
tatataggta ccagctcatt acctcaaatt tccctacy                              38

<210> SEQ ID NO 159
<211> LENGTH: 36
<212> TYPE: DNA
<213> ORGANISM: artificial
<220> FEATURE:
<223> OTHER INFORMATION: synthetic sequence

<400> SEQUENCE: 159
tatataccat ggttctcgca cacacagaac agagay                                36

<210> SEQ ID NO 160
<211> LENGTH: 38
<212> TYPE: DNA
<213> ORGANISM: artificial
<220> FEATURE:
<223> OTHER INFORMATION: synthetic sequence

<400> SEQUENCE: 160
tatataggta cctttcttag ataaacatac gtacgtty                              38

<210> SEQ ID NO 161
```

```
<211> LENGTH: 47
<212> TYPE: DNA
<213> ORGANISM: artificial
<220> FEATURE:
<223> OTHER INFORMATION: synthetic sequence

<400> SEQUENCE: 161
tatataccat ggttaattaa ttctaacaat acaaaatctg tatatgy          47

<210> SEQ ID NO 162
<211> LENGTH: 35
<212> TYPE: DNA
<213> ORGANISM: artificial
<220> FEATURE:
<223> OTHER INFORMATION: synthetic sequence

<400> SEQUENCE: 162 tataggta ccaattgaca agttgattgt tgtay                         35

<210> SEQ ID NO 163
<211> LENGTH: 44
<212> TYPE: DNA
<213> ORGANISM: artificial
<220> FEATURE:
<223> OTHER INFORMATION: synthetic sequence

<400> SEQUENCE: 163
tatataccat ggttaattaa ggaaattaac tgaaccaatt acty             44

<210> SEQ ID NO 164
<211> LENGTH: 34
<212> TYPE: DNA
<213> ORGANISM: artificial
<220> FEATURE:
<223> OTHER INFORMATION: synthetic sequence

<400> SEQUENCE: 164 tataggta ccaaattata ggtgaaaaaa ttcy                          34

<210> SEQ ID NO 165
<211> LENGTH: 33
<212> TYPE: DNA
<213> ORGANISM: artificial
<220> FEATURE:
<223> OTHER INFORMATION: synthetic sequence

<400> SEQUENCE: 165
atatatccat ggttttgtga ggaaattaaa ggy                         33

<210> SEQ ID NO 166
<211> LENGTH: 39
<212> TYPE: DNA
<213> ORGANISM: artificial
<220> FEATURE:
<223> OTHER INFORMATION: synthetic sequence

<400> SEQUENCE: 166 tataggta cctgagagag atgccaattt tacaagccy                     39

<210> SEQ ID NO 167
<211> LENGTH: 40
<212> TYPE: DNA
<213> ORGANISM: artificial
<220> FEATURE:
<223> OTHER INFORMATION: synthetic sequence

<400> SEQUENCE: 167
``` tataccat ggtgtaaatt aattgccgtt cgttaaagay                    40

<210> SEQ ID NO 168
<211> LENGTH: 39
<212> TYPE: DNA
<213> ORGANISM: artificial
<220> FEATURE:
<223> OTHER INFORMATION: synthetic sequence

<400> SEQUENCE: 168
tatataggta cctaaataat taatttattt caaacacty                    39

<210> SEQ ID NO 169
<211> LENGTH: 39
<212> TYPE: DNA
<213> ORGANISM: artificial
<220> FEATURE:
<223> OTHER INFORMATION: synthetic sequence

<400> SEQUENCE: 169
tatataccat ggtgttgcga tatgaacgca gagagaggy                    39

<210> SEQ ID NO 170
<211> LENGTH: 34
<212> TYPE: DNA
<213> ORGANISM: artificial
<220> FEATURE:
<223> OTHER INFORMATION: synthetic sequence

<400> SEQUENCE: 170
tatataggta ccgttgaaga ttcaccactt ctcy                         34

<210> SEQ ID NO 171
<211> LENGTH: 39
<212> TYPE: DNA
<213> ORGANISM: artificial
<220> FEATURE:
<223> OTHER INFORMATION: synthetic sequence

<400> SEQUENCE: 171
tatataccat ggttaaagaa ttgcaaagaa gaaggaagy                    39

<210> SEQ ID NO 172
<211> LENGTH: 35
<212> TYPE: DNA
<213> ORGANISM: artificial
<220> FEATURE:
<223> OTHER INFORMATION: synthetic sequence

<400> SEQUENCE: 172
tatataggta ccataatgta gcgttgaatg tacty                        35

<210> SEQ ID NO 173
<211> LENGTH: 38
<212> TYPE: DNA
<213> ORGANISM: artificial
<220> FEATURE:
<223> OTHER INFORMATION: synthetic sequence

<400> SEQUENCE: 173
tatataggta ccagtcacat actgttaaca attattcy                     38

<210> SEQ ID NO 174
<211> LENGTH: 36
<212> TYPE: DNA

<213> ORGANISM: artificial
<220> FEATURE:
<223> OTHER INFORMATION: synthetic sequence

<400> SEQUENCE: 174
tatataggta cctaattaat cacaaagtga agaacy                          36

<210> SEQ ID NO 175
<211> LENGTH: 36
<212> TYPE: DNA
<213> ORGANISM: artificial
<220> FEATURE:
<223> OTHER INFORMATION: synthetic sequence

<400> SEQUENCE: 175
tatataggta ccttatgatt agtataaatc tattgy                          36

<210> SEQ ID NO 176
<211> LENGTH: 46
<212> TYPE: DNA
<213> ORGANISM: artificial
<220> FEATURE:
<223> OTHER INFORMATION: synthetic sequence

<400> SEQUENCE: 176
tatataggta ccagatttt taaatattta taataaaata ataagy                46

<210> SEQ ID NO 177
<211> LENGTH: 41
<212> TYPE: DNA
<213> ORGANISM: artificial
<220> FEATURE:
<223> OTHER INFORMATION: synthetic sequence

<400> SEQUENCE: 177
tatataggta cctcattaat tgagttattt atataaaatg y                    41

<210> SEQ ID NO 178
<211> LENGTH: 36
<212> TYPE: DNA
<213> ORGANISM: artificial
<220> FEATURE:
<223> OTHER INFORMATION: synthetic sequence

<400> SEQUENCE: 178
tatataggta cctaatataa gcggaactat acggty                          36

<210> SEQ ID NO 179
<211> LENGTH: 39
<212> TYPE: DNA
<213> ORGANISM: artificial
<220> FEATURE:
<223> OTHER INFORMATION: synthetic sequence

<400> SEQUENCE: 179
tatataggta ccgttgataa ataattttt atgaataay                        39

<210> SEQ ID NO 180
<211> LENGTH: 33
<212> TYPE: DNA
<213> ORGANISM: artificial
<220> FEATURE:
<223> OTHER INFORMATION: synthetic sequence

<400> SEQUENCE: 180
tatataggta ccgaaatatt tgattcacaa gty                             33

<210> SEQ ID NO 181
<211> LENGTH: 46
<212> TYPE: DNA
<213> ORGANISM: artificial
<220> FEATURE:
<223> OTHER INFORMATION: synthetic sequence

<400> SEQUENCE: 181
tatataggta ccattgaatt cactaatttt atattttata atttgy                    46

<210> SEQ ID NO 182
<211> LENGTH: 42
<212> TYPE: DNA
<213> ORGANISM: artificial
<220> FEATURE:
<223> OTHER INFORMATION: synthetic sequence

<400> SEQUENCE: 182
tatataggta cccaacagat taagatctag aataaataaa cy                        42

<210> SEQ ID NO 183
<211> LENGTH: 41
<212> TYPE: DNA
<213> ORGANISM: artificial
<220> FEATURE:
<223> OTHER INFORMATION: synthetic sequence

<400> SEQUENCE: 183
tatataggta cctacttatg aattaagctt agttcttgca y                         41

<210> SEQ ID NO 184
<211> LENGTH: 42
<212> TYPE: DNA
<213> ORGANISM: artificial
<220> FEATURE:
<223> OTHER INFORMATION: synthetic sequence

<400> SEQUENCE: 184
tatataggta ccaatttttt ttttcagtat tatttctatc ty                        42

<210> SEQ ID NO 185
<211> LENGTH: 37
<212> TYPE: DNA
<213> ORGANISM: artificial
<220> FEATURE:
<223> OTHER INFORMATION: synthetic sequence

<400> SEQUENCE: 185
tatataggta cctcatcaca atcgaaaaat tccatcy                              37

<210> SEQ ID NO 186
<211> LENGTH: 40
<212> TYPE: DNA
<213> ORGANISM: artificial
<220> FEATURE:
<223> OTHER INFORMATION: synthetic sequence

<400> SEQUENCE: 186
tatataggta ccgcgcgcgc tctcttagaa cttttttgy                            40

<210> SEQ ID NO 187
<211> LENGTH: 36
<212> TYPE: DNA
<213> ORGANISM: artificial
<220> FEATURE:

-continued

<223> OTHER INFORMATION: synthetic sequence

<400> SEQUENCE: 187
tatataggta cccatttca acattcagag tgggty                36

<210> SEQ ID NO 188
<211> LENGTH: 41
<212> TYPE: DNA
<213> ORGANISM: artificial
<220> FEATURE:
<223> OTHER INFORMATION: synthetic sequence

<400> SEQUENCE: 188
tatataggta ccttttcac ccaattaatt agagtatttc y           41

<210> SEQ ID NO 189
<211> LENGTH: 43
<212> TYPE: DNA
<213> ORGANISM: artificial
<220> FEATURE:
<223> OTHER INFORMATION: synthetic sequence

<400> SEQUENCE: 189
tatataggta ccgttttgct attgactttt gttttatttc gty        43

<210> SEQ ID NO 190
<211> LENGTH: 43
<212> TYPE: DNA
<213> ORGANISM: artificial
<220> FEATURE:
<223> OTHER INFORMATION: synthetic sequence

<400> SEQUENCE: 190
tatataggta cctttttaa tctactttt atttgtttaa tcy          43

<210> SEQ ID NO 191
<211> LENGTH: 41
<212> TYPE: DNA
<213> ORGANISM: artificial
<220> FEATURE:
<223> OTHER INFORMATION: synthetic sequence

<400> SEQUENCE: 191
tatataggta cctttaattt ggaataattt ttttcttctc y          41

<210> SEQ ID NO 192
<211> LENGTH: 40
<212> TYPE: DNA
<213> ORGANISM: artificial
<220> FEATURE:
<223> OTHER INFORMATION: synthetic sequence

<400> SEQUENCE: 192
tatataggta ccttagagga aaatttgt catccataay              40

<210> SEQ ID NO 193
<211> LENGTH: 39
<212> TYPE: DNA
<213> ORGANISM: artificial
<220> FEATURE:
<223> OTHER INFORMATION: synthetic sequence

<400> SEQUENCE: 193
tatataggta ccacatggca acatttttt ttatctcty              39

```
<210> SEQ ID NO 194
<211> LENGTH: 44
<212> TYPE: DNA
<213> ORGANISM: artificial
<220> FEATURE:
<223> OTHER INFORMATION: synthetic sequence

<400> SEQUENCE: 194
tatataggta cctatatata tatatatata ataaactata tcty          44

<210> SEQ ID NO 195
<211> LENGTH: 46
<212> TYPE: DNA
<213> ORGANISM: artificial
<220> FEATURE:
<223> OTHER INFORMATION: synthetic sequence

<400> SEQUENCE: 195
tatataggta cctacctgtt cactagctag ttacaaaaat atatcy        46

<210> SEQ ID NO 196
<211> LENGTH: 42
<212> TYPE: DNA
<213> ORGANISM: artificial
<220> FEATURE:
<223> OTHER INFORMATION: synthetic sequence

<400> SEQUENCE: 196
tatatacccg ggtaccatgc agaggatcaa gaagattctc cy            42

<210> SEQ ID NO 197
<211> LENGTH: 46
<212> TYPE: DNA
<213> ORGANISM: artificial
<220> FEATURE:
<223> OTHER INFORMATION: synthetic sequence

<400> SEQUENCE: 197
tatataccat ggtttcttag ttgattctac aaatcttttta ttttcy       46

<210> SEQ ID NO 198
<211> LENGTH: 38
<212> TYPE: DNA
<213> ORGANISM: artificial
<220> FEATURE:
<223> OTHER INFORMATION: synthetic sequence

<400> SEQUENCE: 198
tatatacccg ggtaccgtga aagcagtgaa gccgtgay                 38

<210> SEQ ID NO 199
<211> LENGTH: 39
<212> TYPE: DNA
<213> ORGANISM: artificial
<220> FEATURE:
<223> OTHER INFORMATION: synthetic sequence

<400> SEQUENCE: 199
tatataccat ggtgagttga tgagattttg tggtgagty                39

<210> SEQ ID NO 200
<211> LENGTH: 52
<212> TYPE: DNA
<213> ORGANISM: artificial
<220> FEATURE:
<223> OTHER INFORMATION: synthetic sequence
```

<400> SEQUENCE: 200
tatatacccg ggtaccgaca tctgtcttga cttttcctta aacagtgtgt gy        52

<210> SEQ ID NO 201
<211> LENGTH: 39
<212> TYPE: DNA
<213> ORGANISM: artificial
<220> FEATURE:
<223> OTHER INFORMATION: synthetic sequence

<400> SEQUENCE: 201
tatataccat ggctttggat ggagaaggta cacggcagy                        39

<210> SEQ ID NO 202
<211> LENGTH: 41
<212> TYPE: DNA
<213> ORGANISM: artificial
<220> FEATURE:
<223> OTHER INFORMATION: synthetic sequence

<400> SEQUENCE: 202
tatatacccg ggtaccgacg aactcatgct actactacag y                     41

<210> SEQ ID NO 203
<211> LENGTH: 45
<212> TYPE: DNA
<213> ORGANISM: artificial
<220> FEATURE:
<223> OTHER INFORMATION: synthetic sequence

<400> SEQUENCE: 203 tataacat gttgagctct ttctctgttc ctcaactctt ttcty                   45

<210> SEQ ID NO 204
<211> LENGTH: 42
<212> TYPE: DNA
<213> ORGANISM: artificial
<220> FEATURE:
<223> OTHER INFORMATION: synthetic sequence

<400> SEQUENCE: 204
tatatacccg ggtaccgaaa cgaaactgaa ccgcctcctt ty                    42

<210> SEQ ID NO 205
<211> LENGTH: 49
<212> TYPE: DNA
<213> ORGANISM: artificial
<220> FEATURE:
<223> OTHER INFORMATION: synthetic sequence

<400> SEQUENCE: 205
tatataacat gttgagctct tcgttcttcg ttgcgttttt ggtcatcgy             49

<210> SEQ ID NO 206
<211> LENGTH: 46
<212> TYPE: DNA
<213> ORGANISM: artificial
<220> FEATURE:
<223> OTHER INFORMATION: synthetic sequence

<400> SEQUENCE: 206
tatatacccg ggtacctgac taattaagct cgaaagtgtt cttcay                46

<210> SEQ ID NO 207
<211> LENGTH: 45

<212> TYPE: DNA
<213> ORGANISM: artificial
<220> FEATURE:
<223> OTHER INFORMATION: synthetic sequence

<400> SEQUENCE: 207
tatatacccg ggtaccggct tttgcgttag gttatataac tccay          45

<210> SEQ ID NO 208
<211> LENGTH: 45
<212> TYPE: DNA
<213> ORGANISM: artificial
<220> FEATURE:
<223> OTHER INFORMATION: synthetic sequence

<400> SEQUENCE: 208
tatatacccg ggtacctgta gcaagaattg atcgatatgc tttgy          45

<210> SEQ ID NO 209
<211> LENGTH: 43
<212> TYPE: DNA
<213> ORGANISM: artificial
<220> FEATURE:
<223> OTHER INFORMATION: synthetic sequence

<400> SEQUENCE: 209
tatatacccg ggtaccggac tcaataaaca actcaaagat gay            43

<210> SEQ ID NO 210
<211> LENGTH: 43
<212> TYPE: DNA
<213> ORGANISM: artificial
<220> FEATURE:
<223> OTHER INFORMATION: synthetic sequence

<400> SEQUENCE: 210
tatatacccg ggtacctcac tgatgttctc taatgaacgt tcy            43

<210> SEQ ID NO 211
<211> LENGTH: 46
<212> TYPE: DNA
<213> ORGANISM: artificial
<220> FEATURE:
<223> OTHER INFORMATION: synthetic sequence

<400> SEQUENCE: 211
tatatacccg ggtaccaagt gaaaatataa tattcatacc tcttgy         46

<210> SEQ ID NO 212
<211> LENGTH: 38
<212> TYPE: DNA
<213> ORGANISM: artificial
<220> FEATURE:
<223> OTHER INFORMATION: synthetic sequence

<400> SEQUENCE: 212
tatatacccg ggtaccacgc acacttcata tatcttgy                  38

<210> SEQ ID NO 213
<211> LENGTH: 47
<212> TYPE: DNA
<213> ORGANISM: artificial
<220> FEATURE:
<223> OTHER INFORMATION: synthetic sequence

<400> SEQUENCE: 213

```
tatatacccg ggtaccaaat tttcaacatc gtactgcttc ataaacy            47
```

<210> SEQ ID NO 214
<211> LENGTH: 42
<212> TYPE: DNA
<213> ORGANISM: artificial
<220> FEATURE:
<223> OTHER INFORMATION: synthetic sequence

<400> SEQUENCE: 214

```
tatatacccg ggtaccgttg aattgttata tcaaaatttg ay                 42
```

<210> SEQ ID NO 215
<211> LENGTH: 41
<212> TYPE: DNA
<213> ORGANISM: artificial
<220> FEATURE:
<223> OTHER INFORMATION: synthetic sequence

<400> SEQUENCE: 215

```
tatatacccg ggtacctttg gctgaatcag cttcagcaga y                  41
```

<210> SEQ ID NO 216
<211> LENGTH: 43
<212> TYPE: DNA
<213> ORGANISM: artificial
<220> FEATURE:
<223> OTHER INFORMATION: synthetic sequence

<400> SEQUENCE: 216

```
tatatacccg ggtaccaatg gttctgttgc tcctaatgta gay                43
```

<210> SEQ ID NO 217
<211> LENGTH: 47
<212> TYPE: DNA
<213> ORGANISM: artificial
<220> FEATURE:
<223> OTHER INFORMATION: synthetic sequence

<400> SEQUENCE: 217

```
tatatacccg ggtacctttt tgtaaacaat tttttgtgat atataty            47
```

<210> SEQ ID NO 218
<211> LENGTH: 42
<212> TYPE: DNA
<213> ORGANISM: artificial
<220> FEATURE:
<223> OTHER INFORMATION: synthetic sequence

<400> SEQUENCE: 218

```
tatatacccg ggtacccaga attttaaaga cacacaaagc ay                 42
```

<210> SEQ ID NO 219
<211> LENGTH: 40
<212> TYPE: DNA
<213> ORGANISM: artificial
<220> FEATURE:
<223> OTHER INFORMATION: synthetic sequence

<400> SEQUENCE: 219

```
tatatacccg ggtaccaccg cttaatatcg tatgattagy                    40
```

<210> SEQ ID NO 220
<211> LENGTH: 1957
<212> TYPE: DNA
<213> ORGANISM: Glycine max
<220> FEATURE:
<221> NAME/KEY: misc_feature
<222> LOCATION: (1957)..(1957)
<223> OTHER INFORMATION: n is a, c, g, or t

<400> SEQUENCE: 220

```
atggctggaa aaggcgaggg tcctgctatc ggaatcgatt tgggaacgac gtactcttgc      60
gtcggcgtgt ggcaacacga tcgtgttgaa atcatagcca acgatcaggg taacagaact     120
accccatcct acgtggcttt caccgacaca gaacggttga tcggcgatgc ggcgaagaac     180
caggtcgcta tgaacccaac caacaccgtt tttgatgcta agcgtttgat tggaaggcgt     240
ttttccgatg catcagtaca aggtgacatg aaattgtggc cgttcaaggt gattcctggc     300
cctgctgaga aacctatgat tgtggtgaac tacaagggg aggagaaaca gttttccgcg      360
gaagagatat cctccatggt tcttatgaag atgaaggaga ttgcggaggc gtatctaggt     420
tccaccataa agaatgcggt tgtcactgtg cctgcttact caacgactc acaacgtcaa      480
gccaccaagg acgctggtgt catttctggg ctcaacgtga tgcgaattat caacgagcct     540
accgcggctg ccattgctta tgggctcgac aaaaaggcca ctagctctgg ggagaagaat     600
gttctcattt ttgatctcgg tggtgggact tttgatgtct ctcttctcac catcgaggag     660
ggtattttcg aggtgaaggc cactgctggt gatactcact gggaggtga agattttgat     720
aacagaatgg tgaaccattt tgttcaggaa ttcaagagga gaacaagaa ggatattagt      780
ggaaatgcca gagctctgag gaggttgaga acagcatgtg agcgggcaaa gaggactctc     840
tcttccactg ctcaaaccac catagagatt gattccttgt acgagggtat tgacttctac     900
acaaccatta cccgtgcccg ttttgaagag ctaaacatgg atttattcag gaagtgcatg     960
gagcccgtgg agaagtgttt gcgggatgcc aagatggata gagtaccgt ccatgatgtt     1020
gttcttgttg gtggttctac taggattccc aaggttcaac agttgttgca ggacttcttc     1080
aacggaaagg aactttgcaa gagtattaac ccagatgaag ctgttgctta tggtgctgca     1140
gtgcaggctg cgattctcag tggcgagggt aatgagaaag tgcaggatct tcttttgttg     1200
gatgttactc ctctatccac tggtttggag actgcaggag gagtcatgac tgtgttgatt     1260
cccagaaaca caaccattcc caccaagaag gagcaggtgt tctcaaccta ctctgacaac     1320
cagcccggtg tgttgattca ggtctatgaa ggtgaacgaa cgaggactcg tgacaacaat     1380
ttgcttggca aatttgagtt atctggaatt cctcctgctc ccagaggtgt tcctcagatc     1440
actgtttgct tcgacattga tgccaacggt atattgaacg tgtctgcgga ggacaaaacc     1500
actggacaga gaacaagat tacaattacc aacgacaagg gcaggctttc taaggaggag     1560
attgagaaga tggtgcagga agctgagaaa tacaagtctg aggacgagga gcataagaag     1620
aaagtggagg ccaaaaatgc attggaaaat tatgcctata acatgaggaa cacaatcaag     1680
gatgacaaga ttgcttccaa actgtcttct gatgataaga gaaaattga agatgcgatt     1740
gagcaggcta tccaatggct agatggaaac caacttgctg aggctgacga atttgaggat     1800
aagatgaagg agttggagag catttgtaat cccatcatag caaagatgta ccagggtgct     1860
ggtggtgatg cgggtggagc catggatgag gatggtcctg cagctggcag tggaagcggt     1920
gctggacccca aaattgagga agtcgattaa gymaggn                             1957
```

<210> SEQ ID NO 221
<211> LENGTH: 1839
<212> TYPE: PRT
<213> ORGANISM: Glycine max

```
<400> SEQUENCE: 221

Met Glu Thr Ala Leu Ala Gly Leu Tyr Leu Tyr Ser Gly Leu Tyr Gly
1               5                   10                  15

Leu Gly Leu Tyr Pro Arg Ala Leu Ala Ile Leu Glu Gly Leu Tyr Ile
            20                  25                  30

Leu Glu Ala Ser Pro Leu Glu Gly Leu Tyr Thr His Arg Thr His Arg
        35                  40                  45

Thr Tyr Arg Ser Glu Arg Cys Tyr Ser Val Ala Leu Gly Leu Tyr Val
    50                  55                  60

Ala Leu Thr Arg Pro Gly Leu Asn His Ile Ser Ala Ser Pro Ala Arg
65                  70                  75                  80

Gly Val Ala Leu Gly Leu Ile Leu Glu Ile Leu Glu Ala Leu Ala Ala
                85                  90                  95

Ser Asn Ala Ser Pro Gly Leu Asn Gly Leu Tyr Ala Ser Asn Ala Arg
            100                 105                 110

Gly Thr His Arg Thr His Arg Pro Arg Ser Glu Arg Thr Tyr Arg Val
        115                 120                 125

Ala Leu Ala Leu Ala Pro His Glu Thr His Arg Ala Ser Pro Thr His
        130                 135                 140

Arg Gly Leu Ala Arg Gly Leu Glu Ile Leu Glu Gly Leu Tyr Ala Ser
145                 150                 155                 160

Pro Ala Leu Ala Ala Leu Ala Leu Tyr Ser Ala Ser Asn Gly Leu Asn
                165                 170                 175

Val Ala Leu Ala Leu Ala Met Glu Thr Ala Ser Asn Pro Arg Thr His
            180                 185                 190

Arg Ala Ser Asn Thr His Arg Val Ala Leu Pro His Glu Ala Ser Pro
        195                 200                 205

Ala Leu Ala Leu Tyr Ser Ala Arg Gly Leu Glu Ile Leu Glu Gly Leu
        210                 215                 220

Tyr Ala Arg Gly Ala Arg Gly Pro His Glu Ser Glu Arg Ala Ser Pro
225                 230                 235                 240

Ala Leu Ala Ser Glu Arg Val Ala Leu Gly Leu Asn Gly Leu Tyr Ala
                245                 250                 255

Ser Pro Met Glu Thr Leu Tyr Ser Leu Glu Thr Arg Pro Pro Arg Pro
            260                 265                 270

His Glu Leu Tyr Ser Val Ala Leu Ile Leu Glu Pro Arg Gly Leu Tyr
        275                 280                 285

Pro Arg Ala Leu Ala Gly Leu Leu Tyr Ser Pro Arg Met Glu Thr Ile
        290                 295                 300

Leu Glu Val Ala Leu Val Ala Leu Ala Ser Asn Thr Tyr Arg Leu Tyr
305                 310                 315                 320

Ser Gly Leu Tyr Gly Leu Gly Leu Leu Tyr Ser Gly Leu Asn Pro His
                325                 330                 335

Glu Ser Glu Arg Ala Leu Ala Gly Leu Gly Leu Ile Leu Glu Ser Glu
            340                 345                 350

Arg Ser Glu Arg Met Glu Thr Val Ala Leu Leu Glu Met Glu Thr Leu
        355                 360                 365

Tyr Ser Met Glu Thr Leu Tyr Ser Gly Leu Ile Leu Glu Ala Leu Ala
        370                 375                 380

Gly Leu Ala Leu Ala Thr Tyr Arg Leu Glu Gly Leu Tyr Ser Glu Arg
385                 390                 395                 400

Thr His Arg Ile Leu Glu Leu Tyr Ser Ala Ser Asn Ala Leu Ala Val
                405                 410                 415
```

```
Ala Leu Val Ala Leu Thr His Arg Val Ala Leu Pro Arg Ala Leu Ala
            420                 425                 430

Thr Tyr Arg Pro His Glu Ala Ser Asn Ala Ser Pro Ser Glu Arg Gly
        435                 440                 445

Leu Asn Ala Arg Gly Gly Leu Asn Ala Leu Ala Thr His Arg Leu Tyr
    450                 455                 460

Ser Ala Ser Pro Ala Leu Ala Gly Leu Tyr Val Ala Leu Ile Leu Glu
465                 470                 475                 480

Ser Glu Arg Gly Leu Tyr Leu Glu Ala Ser Asn Val Ala Leu Met Glu
                485                 490                 495

Thr Ala Arg Gly Ile Leu Glu Ile Leu Glu Ala Ser Asn Gly Leu Pro
            500                 505                 510

Arg Thr His Arg Ala Leu Ala Ala Leu Ala Ala Leu Ala Ile Leu Glu
            515                 520                 525

Ala Leu Ala Thr Tyr Arg Gly Leu Tyr Leu Glu Ala Ser Pro Leu Tyr
        530                 535                 540

Ser Leu Tyr Ser Ala Leu Ala Thr His Arg Ser Glu Arg Ser Glu Arg
545                 550                 555                 560

Gly Leu Tyr Gly Leu Leu Tyr Ser Ala Ser Asn Val Ala Leu Leu Glu
                565                 570                 575

Ile Leu Glu Pro His Glu Ala Ser Pro Leu Glu Gly Leu Tyr Gly Leu
            580                 585                 590

Tyr Gly Leu Tyr Thr His Arg Pro His Glu Ala Ser Pro Val Ala Leu
        595                 600                 605

Ser Glu Arg Leu Glu Leu Glu Thr His Arg Ile Leu Glu Gly Leu Gly
    610                 615                 620

Leu Gly Leu Tyr Ile Leu Glu Pro His Glu Gly Leu Val Ala Leu Leu
625                 630                 635                 640

Tyr Ser Ala Leu Ala Thr His Arg Ala Leu Ala Gly Leu Tyr Ala Ser
                645                 650                 655

Pro Thr His Arg His Ile Ser Leu Glu Gly Leu Tyr Gly Leu Tyr Gly
            660                 665                 670

Leu Ala Ser Pro Pro His Glu Ala Ser Pro Ala Ser Asn Ala Arg Gly
        675                 680                 685

Met Glu Thr Val Ala Leu Ala Ser Asn His Ile Ser Pro His Glu Val
    690                 695                 700

Ala Leu Gly Leu Asn Gly Leu Pro His Glu Leu Tyr Ser Ala Arg Gly
705                 710                 715                 720

Leu Tyr Ser Ala Ser Asn Leu Tyr Ser Leu Tyr Ser Ala Ser Pro Ile
                725                 730                 735

Leu Glu Ser Glu Arg Gly Leu Tyr Ala Ser Asn Ala Leu Ala Ala Arg
            740                 745                 750

Gly Ala Leu Ala Leu Glu Ala Arg Gly Ala Arg Gly Leu Glu Ala Arg
        755                 760                 765

Gly Thr His Arg Ala Leu Ala Cys Tyr Ser Gly Leu Ala Arg Gly Ala
    770                 775                 780

Leu Ala Leu Tyr Ser Ala Arg Gly Thr His Arg Leu Glu Ser Glu Arg
785                 790                 795                 800

Ser Glu Arg Thr His Arg Ala Leu Ala Gly Leu Asn Thr His Arg Thr
                805                 810                 815

His Arg Ile Leu Glu Gly Leu Ile Leu Glu Ala Ser Pro Ser Glu Arg
            820                 825                 830
```

-continued

Leu Glu Thr Tyr Arg Gly Leu Gly Leu Tyr Ile Leu Glu Ala Ser Pro
                835                 840                 845

Pro His Glu Thr Tyr Arg Thr His Arg Thr His Arg Ile Leu Glu Thr
    850                 855                 860

His Arg Ala Arg Gly Ala Leu Ala Ala Arg Gly Pro His Glu Gly Leu
865                 870                 875                 880

Gly Leu Leu Glu Ala Ser Asn Met Glu Thr Ala Ser Pro Leu Glu Pro
                885                 890                 895

His Glu Ala Arg Gly Leu Tyr Ser Cys Tyr Ser Met Glu Thr Gly Leu
                900                 905                 910

Pro Arg Val Ala Leu Gly Leu Leu Tyr Ser Cys Tyr Ser Leu Glu Ala
            915                 920                 925

Arg Gly Ala Ser Pro Ala Leu Ala Leu Tyr Ser Met Glu Thr Ala Ser
        930                 935                 940

Pro Leu Tyr Ser Ser Glu Arg Thr His Arg Val Ala Leu His Ile Ser
945                 950                 955                 960

Ala Ser Pro Val Ala Leu Val Ala Leu Leu Glu Val Ala Leu Gly Leu
                965                 970                 975

Tyr Gly Leu Tyr Ser Glu Arg Thr His Arg Ala Arg Gly Ile Leu Glu
            980                 985                 990

Pro Arg Leu Tyr Ser Val Ala Leu Gly Leu Asn Gly Leu Asn Leu Glu
        995                 1000                1005

Leu Glu Gly Leu Asn Ala Ser Pro Pro His Glu Pro His Glu Ala
    1010                1015                1020

Ser Asn Gly Leu Tyr Leu Tyr Ser Gly Leu Leu Glu Cys Tyr Ser
    1025                1030                1035

Leu Tyr Ser Ser Glu Arg Ile Leu Glu Ala Ser Asn Pro Arg Ala
    1040                1045                1050

Ser Pro Gly Leu Ala Leu Ala Val Ala Leu Ala Leu Ala Thr Tyr
    1055                1060                1065

Arg Gly Leu Tyr Ala Leu Ala Ala Leu Ala Val Ala Leu Gly Leu
    1070                1075                1080

Asn Ala Leu Ala Ala Leu Ala Ile Leu Glu Leu Glu Ser Glu Arg
    1085                1090                1095

Gly Leu Tyr Gly Leu Gly Leu Tyr Ala Ser Asn Gly Leu Leu Tyr
    1100                1105                1110

Ser Val Ala Leu Gly Leu Asn Ala Ser Pro Leu Glu Leu Glu Leu
    1115                1120                1125

Glu Leu Glu Ala Ser Pro Val Ala Leu Thr His Arg Pro Arg Leu
    1130                1135                1140

Glu Ser Glu Arg Thr His Arg Gly Leu Tyr Leu Glu Gly Leu Thr
    1145                1150                1155

His Arg Ala Leu Ala Gly Leu Tyr Gly Leu Tyr Val Ala Leu Met
    1160                1165                1170

Glu Thr Thr His Arg Val Ala Leu Leu Glu Ile Leu Glu Pro Arg
    1175                1180                1185

Ala Arg Gly Ala Ser Asn Thr His Arg Thr His Arg Ile Leu Glu
    1190                1195                1200

Pro Arg Thr His Arg Leu Tyr Ser Leu Tyr Ser Gly Leu Gly Leu
    1205                1210                1215

Asn Val Ala Leu Pro His Glu Ser Glu Arg Thr His Arg Thr Tyr
    1220                1225                1230

Arg Ser Glu Arg Ala Ser Pro Ala Ser Asn Gly Leu Asn Pro Arg

-continued

```
            1235                1240                1245

Gly Leu Tyr Val Ala Leu Leu Glu Ile Leu Gly Leu Asn Val
        1250                1255                1260

Ala Leu Thr Tyr Arg Gly Leu Gly Leu Tyr Gly Leu Ala Arg Gly
        1265                1270                1275

Thr His Arg Ala Arg Gly Thr His Arg Ala Arg Gly Ala Ser Pro
        1280                1285                1290

Ala Ser Asn Ala Ser Asn Leu Glu Leu Glu Gly Leu Tyr Leu Tyr
        1295                1300                1305

Ser Pro His Glu Gly Leu Leu Glu Ser Glu Arg Gly Leu Tyr Ile
        1310                1315                1320

Leu Glu Pro Arg Pro Arg Ala Leu Ala Pro Arg Ala Arg Gly Gly
        1325                1330                1335

Leu Tyr Val Ala Leu Pro Arg Gly Leu Asn Ile Leu Glu Thr His
        1340                1345                1350

Arg Val Ala Leu Cys Tyr Ser Pro His Glu Ala Ser Pro Ile Leu
        1355                1360                1365

Glu Ala Ser Pro Ala Leu Ala Ser Asn Gly Leu Tyr Ile Leu
        1370                1375                1380

Glu Leu Glu Ala Ser Asn Val Ala Leu Ser Glu Arg Ala Leu Ala
        1385                1390                1395

Gly Leu Ala Ser Pro Leu Tyr Ser Thr His Arg Thr His Arg Gly
        1400                1405                1410

Leu Tyr Gly Leu Asn Leu Tyr Ser Ala Ser Asn Leu Tyr Ser Ile
        1415                1420                1425

Leu Glu Thr His Arg Ile Leu Glu Thr His Arg Ala Ser Asn Ala
        1430                1435                1440

Ser Pro Leu Tyr Ser Gly Leu Tyr Ala Arg Gly Leu Glu Ser Glu
        1445                1450                1455

Arg Leu Tyr Ser Gly Leu Gly Leu Ile Leu Glu Gly Leu Leu Tyr
        1460                1465                1470

Ser Met Glu Thr Val Ala Leu Gly Leu Asn Gly Leu Ala Leu Ala
        1475                1480                1485

Gly Leu Leu Tyr Ser Thr Tyr Arg Leu Tyr Ser Ser Glu Arg Gly
        1490                1495                1500

Leu Ala Ser Pro Gly Leu Gly Leu His Ile Ser Leu Tyr Ser Leu
        1505                1510                1515

Tyr Ser Leu Tyr Ser Val Ala Leu Gly Leu Ala Leu Ala Leu Tyr
        1520                1525                1530

Ser Ala Ser Asn Ala Leu Ala Leu Glu Gly Leu Ala Ser Asn Thr
        1535                1540                1545

Tyr Arg Ala Leu Ala Thr Tyr Arg Ala Ser Asn Met Glu Thr Ala
        1550                1555                1560

Arg Gly Ala Ser Asn Thr His Arg Ile Leu Glu Leu Tyr Ser Ala
        1565                1570                1575

Ser Pro Ala Ser Pro Leu Tyr Ser Ile Leu Glu Ala Leu Ala Ser
        1580                1585                1590

Glu Arg Leu Tyr Ser Leu Glu Ser Glu Arg Ser Glu Arg Ala Ser
        1595                1600                1605

Pro Ala Ser Pro Leu Tyr Leu Tyr Ser Leu Tyr Ser Ile Leu
        1610                1615                1620

Glu Gly Leu Ala Ser Pro Ala Leu Ala Ile Leu Glu Gly Leu Gly
        1625                1630                1635
```

| Leu | Asn | Ala | Leu | Ala | Ile | Leu | Glu | Gly | Leu | Asn | Thr | Arg | Pro | Leu |
|---|---|---|---|---|---|---|---|---|---|---|---|---|---|---|
| 1640 | | | | 1645 | | | | | 1650 | | | | | |

| Glu | Ala | Ser | Pro | Gly | Leu | Tyr | Ala | Ser | Asn | Gly | Leu | Asn | Leu | Glu |
|---|---|---|---|---|---|---|---|---|---|---|---|---|---|---|
| 1655 | | | | | 1660 | | | | | 1665 | | | | |

| Ala | Leu | Ala | Gly | Leu | Ala | Leu | Ala | Ala | Ser | Pro | Gly | Leu | Pro | His |
|---|---|---|---|---|---|---|---|---|---|---|---|---|---|---|
| 1670 | | | | | 1675 | | | | | 1680 | | | | |

| Glu | Gly | Leu | Ala | Ser | Pro | Leu | Tyr | Ser | Met | Glu | Thr | Leu | Tyr | Ser |
|---|---|---|---|---|---|---|---|---|---|---|---|---|---|---|
| 1685 | | | | | 1690 | | | | | 1695 | | | | |

| Gly | Leu | Leu | Glu | Gly | Leu | Ser | Glu | Arg | Ile | Leu | Glu | Cys | Tyr | Ser |
|---|---|---|---|---|---|---|---|---|---|---|---|---|---|---|
| 1700 | | | | | 1705 | | | | | 1710 | | | | |

| Ala | Ser | Asn | Pro | Arg | Ile | Leu | Glu | Ile | Leu | Glu | Ala | Leu | Ala | Leu |
|---|---|---|---|---|---|---|---|---|---|---|---|---|---|---|
| 1715 | | | | | 1720 | | | | | 1725 | | | | |

| Tyr | Ser | Met | Glu | Thr | Thr | Tyr | Arg | Gly | Leu | Asn | Gly | Leu | Tyr | Ala |
|---|---|---|---|---|---|---|---|---|---|---|---|---|---|---|
| 1730 | | | | | 1735 | | | | | 1740 | | | | |

| Leu | Ala | Gly | Leu | Tyr | Gly | Leu | Tyr | Ala | Ser | Pro | Ala | Leu | Ala | Gly |
|---|---|---|---|---|---|---|---|---|---|---|---|---|---|---|
| 1745 | | | | | 1750 | | | | | 1755 | | | | |

| Leu | Tyr | Gly | Leu | Tyr | Ala | Leu | Ala | Met | Glu | Thr | Ala | Ser | Pro | Gly |
|---|---|---|---|---|---|---|---|---|---|---|---|---|---|---|
| 1760 | | | | | 1765 | | | | | 1770 | | | | |

| Leu | Ala | Ser | Pro | Gly | Leu | Tyr | Pro | Arg | Ala | Leu | Ala | Ala | Leu | Ala |
|---|---|---|---|---|---|---|---|---|---|---|---|---|---|---|
| 1775 | | | | | 1780 | | | | | 1785 | | | | |

| Gly | Leu | Tyr | Ser | Glu | Arg | Gly | Leu | Tyr | Ser | Glu | Arg | Gly | Leu | Tyr |
|---|---|---|---|---|---|---|---|---|---|---|---|---|---|---|
| 1790 | | | | | 1795 | | | | | 1800 | | | | |

| Ala | Leu | Ala | Gly | Leu | Tyr | Pro | Arg | Leu | Tyr | Ser | Ile | Leu | Glu | Gly |
|---|---|---|---|---|---|---|---|---|---|---|---|---|---|---|
| 1805 | | | | | 1810 | | | | | 1815 | | | | |

| Leu | Gly | Leu | Val | Ala | Leu | Ala | Ser | Pro | Gly | Leu | Tyr | Met | Ala | Gly |
|---|---|---|---|---|---|---|---|---|---|---|---|---|---|---|
| 1820 | | | | | 1825 | | | | | 1830 | | | | |

| Pro | Arg | Thr | Glu | Ile | Asn |
|---|---|---|---|---|---|
| 1835 | | | | | |

<210> SEQ ID NO 222
<211> LENGTH: 877
<212> TYPE: DNA
<213> ORGANISM: Glycine max
<220> FEATURE:
<221> NAME/KEY: misc_feature
<222> LOCATION: (877)..(877)
<223> OTHER INFORMATION: n is a, c, g, or t

<400> SEQUENCE: 222

```
atggagggga aggagcagga tgtgtcgttg ggagcgaaca agttccccga gagacagcca      60
attgggacgg cggcgcagag ccaagacgac ggcaaggact accaggagcc ggcgccggcg     120
ccgctggttg acccgacgga gtttacgtca tggtcgtttt acagagcagg gatagcagag     180
tttgtggcca cttttctgtt tctctacatc actgtcttaa ccgttatggg agtcgccggg     240
gctaagtcta agtgtagtac cgttgggatt caaggaatcg cttgggcctt cggtggcatg     300
atcttcgccc tcgtttactg caccgctggc atctcagggg acacataaa cccggcggtg     360
acatttgggc tgtttttggc gaggaagttg tcgttgccca gggcgatttt ctacatcgtg     420
atgcaatgct gggtgctat ttgtggcgct ggcgtggtga agggtttcga ggggaaaaca     480
aaatacggtc cgttgaatgg tggtgccaac tttgttgccc ctggttacac caagggtgat     540
ggtcttggtg ctgagattgt tggcactttc atccttgttt acaccgtttt ctccgccacc     600
gatgccaaac gtagcgccag agactcccac gtcccatttt ggcacccctt gccaattggg     660
ttcgctgtgt tcttggttca cttggcaacc atccccatca ccggaactgg tatcaaccct     720
```

```
gctcgtagtc ttggtgctgc tatcatcttc aacaaggacc ttggttggga tgaacactgg      780
atcttctggg tgggaccatt catcggtgca gctcttgcag cactctacca ccaggtcgta      840
atcagggcca ttcccttcaa gtccaagtga gymaggn                               877
```

<210> SEQ ID NO 223
<211> LENGTH: 301
<212> TYPE: PRT
<213> ORGANISM: Glycine max

<400> SEQUENCE: 223

```
Met Glu Gly Lys Glu Gln Asp Val Ser Leu Gly Ala Asn Lys Phe Pro
1               5                   10                  15

Glu Arg Gln Pro Ile Gly Thr Ala Ala Gln Ser Gln Asp Asp Gly Lys
            20                  25                  30

Asp Tyr Gln Glu Pro Ala Pro Ala Pro Leu Val Asp Pro Thr Glu Phe
        35                  40                  45

Thr Ser Trp Ser Phe Tyr Arg Ala Gly Ile Ala Glu Phe Val Ala Thr
    50                  55                  60

Phe Leu Phe Leu Tyr Ile Thr Val Leu Thr Val Met Gly Val Ala Gly
65                  70                  75                  80

Ala Lys Ser Lys Cys Ser Thr Val Gly Ile Gln Gly Ile Ala Trp Ala
                85                  90                  95

Phe Gly Gly Met Ile Phe Ala Leu Val Tyr Cys Thr Ala Gly Ile Ser
            100                 105                 110

Gly Gly His Ile Asn Pro Ala Val Thr Phe Gly Leu Phe Leu Ala Arg
        115                 120                 125

Lys Leu Ser Leu Pro Arg Ala Ile Phe Tyr Ile Val Met Gln Cys Leu
    130                 135                 140

Gly Ala Ile Cys Gly Ala Gly Val Val Lys Gly Phe Glu Gly Lys Thr
145                 150                 155                 160

Lys Tyr Gly Ala Leu Asn Gly Gly Ala Asn Phe Val Ala Pro Gly Tyr
                165                 170                 175

Thr Lys Gly Asp Gly Leu Gly Ala Glu Ile Val Gly Thr Phe Ile Leu
            180                 185                 190

Val Tyr Thr Val Phe Ser Ala Thr Asp Ala Lys Arg Ser Ala Arg Asp
        195                 200                 205

Ser His Val Pro Ile Leu Ala Pro Leu Pro Ile Gly Phe Ala Val Phe
    210                 215                 220

Leu Val His Leu Ala Thr Ile Pro Ile Thr Gly Thr Gly Ile Asn Pro
225                 230                 235                 240

Ala Arg Ser Leu Gly Ala Ala Ile Ile Phe Asn Lys Asp Leu Gly Trp
                245                 250                 255

Asp Glu His Trp Ile Phe Trp Val Gly Pro Phe Ile Gly Ala Ala Leu
            260                 265                 270

Ala Ala Leu Tyr His Gln Val Val Ile Arg Ala Ile Pro Phe Lys Ser
        275                 280                 285

Lys Gly Leu Tyr Met Ala Gly Pro Arg Thr Glu Ile Asn
    290                 295                 300
```

<210> SEQ ID NO 224
<211> LENGTH: 901
<212> TYPE: DNA
<213> ORGANISM: Glycine max
<220> FEATURE:
<221> NAME/KEY: misc_feature
<222> LOCATION: (901)..(901)

<223> OTHER INFORMATION: n is a, c, g, or t

<400> SEQUENCE: 224

```
atgcctgcag agaagtccaa cagtttcgat aacgaagtgg aagcgttcgt tgaggttgat      60
ccaacaggga ggttcgggcg ttacagcgat cttcttggtt gcggtgctgt gaagaaagtt     120
tacagagcgt ttgatcaaga ggaaggaatc gaggtggcgt ggaatcaggt tcggctgagg     180
aacttcagcg aagaccctgt tctcatcaat cgccttcact ctgaggtgga tttgctcaga     240
accctcagca acaagtacat catcgtctgc tacagcgtgt ggaaggacga ggaacgccac     300
aatatcaatt tcatcactga agtctgcacc tccgggaacc tcagggatta ccgcaagaag     360
caccgccacg tctccattaa ggcattcaag aaatggtcca acaggtcct tgagggattg      420
gagtatcttc atacgcatga cccctgcatc attcacaggg acctcaattg cagcaacatc     480
tttgttaacg gcaacattgg ccaggtgaaa attggtgatc ttggattggc tgcaatagtg     540
ggacggaacc atgcagcaca ttcaattta gggacaccag agtacatggc accggagctg      600
tatgaagaag attacactga gatggtggac atatactctt ttggaatgtg tttgcttgaa     660
atggtgacaa cagaaatacc ctacagtgaa tgtgacagtg tggccaagat atacaagaag    720
gtcacgatgg gaatcaagcc tgaggccttg agcaaagtca cagatcctga ggtgaaggaa     780
ttcattgaga agtgcatagc acagccaagg gcaagacctt cagccacaga tctccttaag    840
gatccttttct tttatgaact caacaatgat gaagaatcaa cgccaatcaa ttgagymagg   900
n                                                                    901
```

<210> SEQ ID NO 225
<211> LENGTH: 309
<212> TYPE: PRT
<213> ORGANISM: Glycine max

<400> SEQUENCE: 225

```
Met Pro Ala Glu Lys Ser Asn Ser Phe Asp Asn Glu Val Glu Ala Phe
1               5                   10                  15

Val Glu Val Asp Pro Thr Gly Arg Phe Gly Arg Tyr Ser Asp Leu Leu
                20                  25                  30

Gly Cys Gly Ala Val Lys Lys Val Tyr Arg Ala Phe Asp Gln Glu Glu
            35                  40                  45

Gly Ile Glu Val Ala Trp Asn Gln Val Arg Leu Arg Asn Phe Ser Glu
        50                  55                  60

Asp Pro Val Leu Ile Asn Arg Leu His Ser Glu Val Asp Leu Leu Arg
65                  70                  75                  80

Thr Leu Ser Asn Lys Tyr Ile Ile Val Cys Tyr Ser Val Trp Lys Asp
                85                  90                  95

Glu Glu Arg His Asn Ile Asn Phe Ile Thr Glu Val Cys Thr Ser Gly
            100                 105                 110

Asn Leu Arg Asp Tyr Arg Lys Lys His Arg His Val Ser Ile Lys Ala
        115                 120                 125

Phe Lys Lys Trp Ser Lys Gln Val Leu Glu Gly Leu Glu Tyr Leu His
    130                 135                 140

Thr His Asp Pro Cys Ile Ile His Arg Asp Leu Asn Cys Ser Asn Ile
145                 150                 155                 160

Phe Val Asn Gly Asn Ile Gly Gln Val Lys Ile Gly Asp Leu Gly Leu
                165                 170                 175

Ala Ala Ile Val Gly Arg Asn His Ala Ala His Ser Ile Leu Gly Thr
            180                 185                 190
```

```
Pro Glu Tyr Met Ala Pro Glu Leu Tyr Glu Glu Asp Tyr Thr Glu Met
        195                 200                 205

Val Asp Ile Tyr Ser Phe Gly Met Cys Leu Leu Glu Met Val Thr Thr
210                 215                 220

Glu Ile Pro Tyr Ser Glu Cys Asp Ser Val Ala Lys Ile Tyr Lys Lys
225                 230                 235                 240

Val Thr Met Gly Ile Lys Pro Glu Ala Leu Ser Lys Val Thr Asp Pro
            245                 250                 255

Glu Val Lys Glu Phe Ile Glu Lys Cys Ile Ala Gln Pro Arg Ala Arg
            260                 265                 270

Pro Ser Ala Thr Asp Leu Leu Lys Asp Pro Phe Phe Tyr Glu Leu Asn
        275                 280                 285

Asn Asp Glu Glu Ser Thr Pro Ile Asn Gly Leu Tyr Met Ala Gly Pro
    290                 295                 300

Arg Thr Glu Ile Asn
305
```

<210> SEQ ID NO 226
<211> LENGTH: 1110
<212> TYPE: DNA
<213> ORGANISM: Glycine max
<220> FEATURE:
<221> NAME/KEY: misc_feature
<222> LOCATION: (1110)..(1110)
<223> OTHER INFORMATION: n is a, c, g, or t

<400> SEQUENCE: 226

```
atgatttgca ccgtgaaaca acccgtcata tcgatcagag gttctgatct tttcctgcgt      60
aaaaagtgtt caccttcaac cccagttcag tcatgttccc ttgtttcacc ttcttcaaag    120
gaaaaaaact ctctaagatc attggtgtca gtgcaaaagc cactgcacct ttctcgtgtt    180
gcttatgagg ctgatagatc aaaggttgga ggggctgggg ctccatcaga ggctgctaag    240
aaggtgaaga ttgggatata ctttgcaaca tggtgggcac tgaatgtggt gttcaacatt    300
tataacaaga aggtgctgaa tgcattccca taccccttggc ttacctcaac tctctccctt    360
gcatgtggct ctctcataat gttgttctgt tgggccacca agatagttga gcctcctaag    420
actgatcttc agttctggaa gaatttgttc cctgttgctg ttctacatac aataggacat    480
gtagcggcaa ctgttagcat gtcaaaagtt gccgtatcat tcacccatat cattaagagt    540
gctgagcctg ctttcagtgt aatggtttcc agactactgg gcgaggattt cccggtgcca    600
gtctacctgt ctttgattcc aattatcgg ggatgtgctc ttgcagctgt gactgagctc    660
aatttcaata tgattggttt tatggggggct atgatatcga atttggcatt cgtactccgt    720
aatatctatt cgaaaaaggg catgaaggga aaggatatta gtggaatgaa ttactatggt    780
tgtttatcta tgttgtccct tgtaattctc acaccatttg cgattgctgt ggagggacca    840
cagatgtggg cagctggatg gcaaacagca ctctctcaaa ttggaccca aattatatgg    900
tgggtggcag ctcagagcat atttatcat ctttacaatc aagtgtcata catgtctctg    960
gatgagatct ctcccttaac atttagcatt ggaaacacca tgaaacgtat atctgttata   1020
gtttcttcaa tcattatctt ccacacacca gttcagccta ttaatgctct aggagctgct   1080
attgccatct tcggaacctt cttgymaggn                                    1110
```

<210> SEQ ID NO 227
<211> LENGTH: 379
<212> TYPE: PRT

<213> ORGANISM: Glycine max

<400> SEQUENCE: 227

```
Met Ile Cys Thr Val Lys Gln Pro Val Ile Ser Ile Arg Gly Ser Asp
1               5                   10                  15

Leu Phe Leu Arg Lys Lys Cys Ser Pro Ser Thr Pro Val Gln Ser Cys
            20                  25                  30

Ser Leu Val Ser Pro Ser Ser Lys Glu Lys Asn Ser Leu Arg Ser Leu
        35                  40                  45

Val Ser Val Gln Lys Pro Leu His Leu Ser Arg Val Ala Tyr Glu Ala
    50                  55                  60

Asp Arg Ser Lys Val Gly Gly Ala Gly Ala Pro Ser Glu Ala Ala Lys
65                  70                  75                  80

Lys Val Lys Ile Gly Ile Tyr Phe Ala Thr Trp Trp Ala Leu Asn Val
                85                  90                  95

Val Phe Asn Ile Tyr Asn Lys Lys Val Leu Asn Ala Phe Pro Tyr Pro
            100                 105                 110

Trp Leu Thr Ser Thr Leu Ser Leu Ala Cys Gly Ser Leu Ile Met Leu
        115                 120                 125

Phe Cys Trp Ala Thr Lys Ile Val Glu Pro Pro Lys Thr Asp Leu Gln
    130                 135                 140

Phe Trp Lys Asn Leu Phe Pro Val Ala Val Leu His Thr Ile Gly His
145                 150                 155                 160

Val Ala Ala Thr Val Ser Met Ser Lys Val Ala Val Ser Phe Thr His
                165                 170                 175

Ile Ile Lys Ser Ala Glu Pro Ala Phe Ser Val Met Val Ser Arg Leu
            180                 185                 190

Leu Gly Glu Asp Phe Pro Val Pro Val Tyr Leu Ser Leu Ile Pro Ile
        195                 200                 205

Ile Gly Gly Cys Ala Leu Ala Ala Val Thr Glu Leu Asn Phe Asn Met
    210                 215                 220

Ile Gly Phe Met Gly Ala Met Ile Ser Asn Leu Ala Phe Val Leu Arg
225                 230                 235                 240

Asn Ile Tyr Ser Lys Lys Gly Met Lys Gly Lys Asp Ile Ser Gly Met
                245                 250                 255

Asn Tyr Tyr Gly Cys Leu Ser Met Leu Ser Leu Val Ile Leu Thr Pro
            260                 265                 270

Phe Ala Ile Ala Val Glu Gly Pro Gln Met Trp Ala Ala Gly Trp Gln
        275                 280                 285

Thr Ala Leu Ser Gln Ile Gly Pro Gln Ile Ile Trp Trp Val Ala Ala
    290                 295                 300

Gln Ser Ile Phe Tyr His Leu Tyr Asn Gln Val Ser Tyr Met Ser Leu
305                 310                 315                 320

Asp Glu Ile Ser Pro Leu Thr Phe Ser Ile Gly Asn Thr Met Lys Arg
                325                 330                 335

Ile Ser Val Ile Val Ser Ser Ile Ile Phe His Thr Pro Val Gln
            340                 345                 350

Pro Ile Asn Ala Leu Gly Ala Ala Ile Ala Phe Gly Thr Phe Gly
        355                 360                 365

Leu Tyr Met Ala Gly Pro Arg Thr Glu Ile Asn
    370                 375
```

<210> SEQ ID NO 228
<211> LENGTH: 1269

<212> TYPE: DNA
<213> ORGANISM: Glycine max
<220> FEATURE:
<221> NAME/KEY: misc_feature
<222> LOCATION: (1269)..(1269)
<223> OTHER INFORMATION: n is a, c, g, or t

<400> SEQUENCE: 228

```
ccaccccatc agcaccaacc caataataat agtgttccat tgttcctaca gccatcatat      60
gcgagatcaa agtcggtgat cttcgatgaa ctgcgaaact ttcgcatcag cctcaggtgg     120
tgtgcccttg accactcttc atgcgcagga aaatcattt cctacgcgac tttcatattc      180
ttcaccatca ttgttcctct tctcgcgtcc atcttcgtcg aaatccctgc ctcggcacca     240
gaagatgacc ccatctcctt caacaagctt gttcaactgc aaaatctgg tctcgccatt      300
attgccttt tcactctctc cggtttcttc aaaaggtatg gccttaggca gcttctgttc      360
ctagatgctt tgcaagaaga caccacctat gttcgacgtg ctacacacg ggagcttgag      420
aaggctttca gatacttgac atgcataatc ttaccttgtt tatttgtgga acttgcccac     480
aaaatcatat tcttttcagc agttaaattt tcagccccac acatcagccc tgggttgcca     540
ctgaactcaa ttgtgtttgt attggtgttg ctgtcttggc tgtacagaac tggggtattc     600
ctgttggtgt gtgtgctttt taggctcact tgtgagcttc aaaagctgag gtttgaaggg     660
gtgcacaagc tgtttgaagg gtgtgggtct gaggcaggtg tgatattcaa agagcatgtg     720
aggatcagaa ggcagttgtg ggatacaagt cataggtata ggttcttcat aattgggtgt     780
gtggttacaa tcactattag tcagctaggt gctttgctgc tggttttggc ttccaagtct     840
gataagacct tcttcaattc cggggacctt gtgatttgtt cagctgtgca gttaagtggc     900
ttctttttgt gtattttagg agcaacaaga atcacacaca gagcacaagg aatagtggca     960
attgccacaa gatggcacat gcttgtgact gaagcatctt ctgaatcaaa gcaatgcaaa    1020
gctcgagtgt cagaaggact tgctagtgac agtgattctg atgattcctc caacatacat    1080
gtgtcagtga tcccatcaca actttcttct ttccaaacca gacaaacttt agtgacgtat    1140
ttacaacaca atcaaagggg aataacggtg tatgggtatt cacttgatcg acgatttctt    1200
cacactctgt ttgccttcga gttttctctc gtgctttgga ttttgagtag ggtggttgtc    1260
ttgymaggn                                                            1269
```

<210> SEQ ID NO 229
<211> LENGTH: 433
<212> TYPE: PRT
<213> ORGANISM: Glycine max
<220> FEATURE:
<221> NAME/KEY: misc_feature
<222> LOCATION: (421)..(421)
<223> OTHER INFORMATION: Xaa can be any naturally occurring amino acid

<400> SEQUENCE: 229

```
Pro Pro His Gln His Gln Pro Asn Asn Ser Val Pro Leu Phe Leu
1               5                  10                  15

Gln Pro Ser Tyr Ala Arg Ser Lys Ser Val Ile Phe Asp Glu Leu Arg
            20                  25                  30

Asn Phe Arg Ile Ser Leu Arg Trp Cys Ala Leu Asp His Ser Ser Cys
        35                  40                  45

Ala Gly Lys Ile Ile Ser Tyr Ala Thr Phe Ile Phe Phe Thr Ile Ile
    50                  55                  60

Val Pro Leu Leu Ala Ser Ile Phe Val Glu Ile Pro Ala Ser Ala Pro
65                  70                  75                  80
```

-continued

Glu Asp Asp Pro Ile Ser Phe Asn Lys Leu Val Gln Leu Pro Lys Ser
            85                  90                  95

Gly Leu Ala Ile Ile Ala Phe Phe Thr Leu Ser Gly Phe Phe Lys Arg
        100                 105                 110

Tyr Gly Leu Arg Gln Leu Leu Phe Leu Asp Ala Leu Gln Glu Asp Thr
        115                 120                 125

Thr Tyr Val Arg Arg Gly Tyr Thr Arg Glu Leu Glu Lys Ala Phe Arg
130                 135                 140

Tyr Leu Thr Cys Ile Ile Leu Pro Cys Leu Phe Val Glu Leu Ala His
145                 150                 155                 160

Lys Ile Ile Phe Phe Ser Ala Val Lys Phe Ser Ala Pro His Ile Ser
                165                 170                 175

Pro Gly Leu Pro Leu Asn Ser Ile Val Phe Val Leu Val Leu Leu Ser
            180                 185                 190

Trp Leu Tyr Arg Thr Gly Val Phe Leu Leu Val Cys Val Leu Phe Arg
        195                 200                 205

Leu Thr Cys Glu Leu Gln Lys Leu Arg Phe Glu Gly Val His Lys Leu
    210                 215                 220

Phe Glu Gly Cys Gly Ser Glu Ala Gly Val Ile Phe Lys Glu His Val
225                 230                 235                 240

Arg Ile Arg Arg Gln Leu Trp Asp Thr Ser His Arg Tyr Arg Phe Phe
                245                 250                 255

Ile Ile Gly Cys Val Val Thr Ile Thr Ile Ser Gln Leu Gly Ala Leu
            260                 265                 270

Leu Leu Val Leu Ala Ser Lys Ser Asp Lys Thr Phe Phe Asn Ser Gly
        275                 280                 285

Asp Leu Val Ile Cys Ser Ala Val Gln Leu Ser Gly Phe Phe Leu Cys
    290                 295                 300

Ile Leu Gly Ala Thr Arg Ile Thr His Arg Ala Gln Gly Ile Val Ala
305                 310                 315                 320

Ile Ala Thr Arg Trp His Met Leu Val Thr Glu Ala Ser Ser Glu Ser
                325                 330                 335

Lys Gln Cys Lys Ala Arg Val Ser Glu Gly Leu Ala Ser Asp Ser Asp
            340                 345                 350

Ser Asp Asp Ser Ser Asn Ile His Val Ser Val Ile Pro Ser Gln Leu
        355                 360                 365

Ser Ser Phe Gln Thr Arg Gln Thr Leu Val Thr Tyr Leu Gln His Asn
370                 375                 380

Gln Arg Gly Ile Thr Val Tyr Gly Tyr Ser Leu Asp Arg Arg Phe Leu
385                 390                 395                 400

His Thr Leu Phe Ala Phe Glu Phe Ser Leu Val Leu Trp Ile Leu Ser
                405                 410                 415

Arg Val Val Val Xaa Gly Leu Tyr Met Ala Gly Pro Arg Thr Glu Ile
            420                 425                 430

Asn

<210> SEQ ID NO 230
<211> LENGTH: 1246
<212> TYPE: DNA
<213> ORGANISM: Glycine max
<220> FEATURE:
<221> NAME/KEY: misc_feature
<222> LOCATION: (1246)..(1246)
<223> OTHER INFORMATION: n is a, c, g, or t

<400> SEQUENCE: 230

```
atgaatcttc ttgttctctt cctgcctgtt tgggtgctaa gcatttcttt ttcctcacca      60
attcttcatg ctgcttcctc catttctctt tctcaaaatg cacaagctga atctccagga     120
attcaggagg ttagaacagt gcaccaccag aatttgaata agagaattct aatcgcacta     180
gttgcttgtt ctgctcttct tgttggagtc ttcctattcc tgttatatgt ctggttcggt     240
cgacataaaa acttaagatg ctccaaaagt aaaagccaag aaaccatcga ggctgcaaaa     300
ggggaaacca taagctcggt taatgctaaa cttaactact ctaagatggc agataaaaag     360
agttcagttg ctattttga ctatcagctg ttagaggctg caacaaacag ctttaacaca      420
agtaatatta tgggagagag tggttctaga attgtttaca gagctcattt tgatgaacat     480
ttccaggcag ctgttaagaa agcagatagt gacgctgata gagaatttga gaatgaagtg     540
agttggttga gcaagataca gcatcagaat atcataaaaa ttatgggtta ttgcattcat     600
ggtgaatcga ggtttcttgt ttatgaattg atggagaatg gatctctgga aactcaatta     660
catgggccta atcggggtgc atctttaact tggcctctaa ggttaagaat tgctgttgat     720
gttgccagag cactagaata tctccacgag cacaacaatc ctcctgtggt tcatagagac     780
ctaaaatcgt ctaatgtttt tctggattct aactttaatg ccaagttatc agattttgga     840
tttgctatgg ttttgggaat gcaacacaag aacatgaaga tattttcagg taaactaact     900
gataagagcg atgtctatgc ttttggggtt gtccttctag agctcctaac cggaaaaaaa     960
cccatggaaa acatgacctc gaaccaatat caatcccttg tatcatgggc catgcctcag    1020
ctaaccgaca gatcaaagct tccaagtatt ctggatcctg ttatcagaga cacaatggat    1080
ttgaagcatt tgtatcaggt tgctgcagtg gctgtactct gtgtgcaatc agaaccaagt    1140
tataggccac taataactga tgtgttgcac tctcttatcc ctttggtacc agttgagctt    1200
ggagggtcac taagagttac agaaccaatc agctcatagg ymaggn                   1246
```

<210> SEQ ID NO 231
<211> LENGTH: 424
<212> TYPE: PRT
<213> ORGANISM: Glycine max

<400> SEQUENCE: 231

```
Met Asn Leu Leu Val Leu Phe Leu Pro Val Trp Val Leu Ser Ile Ser
1               5                   10                  15

Phe Ser Ser Pro Ile Leu His Ala Ala Ser Ser Ile Ser Leu Ser Gln
            20                  25                  30

Asn Ala Gln Ala Glu Ser Pro Gly Ile Gln Glu Val Arg Thr Val His
        35                  40                  45

His Gln Asn Leu Asn Lys Arg Ile Leu Ile Ala Leu Val Ala Cys Ser
    50                  55                  60

Ala Leu Leu Val Gly Val Phe Leu Phe Leu Leu Tyr Val Trp Phe Gly
65                  70                  75                  80

Arg His Lys Asn Leu Arg Cys Ser Lys Ser Lys Ser Gln Glu Thr Ile
                85                  90                  95

Glu Ala Ala Lys Gly Glu Thr Ile Ser Ser Val Asn Ala Lys Leu Asn
            100                 105                 110

Tyr Ser Lys Met Ala Asp Lys Lys Ser Ser Val Ala Ile Phe Asp Tyr
        115                 120                 125

Gln Leu Leu Glu Ala Ala Thr Asn Ser Phe Asn Thr Ser Asn Ile Met
    130                 135                 140
```

```
Gly Glu Ser Gly Ser Arg Ile Val Tyr Arg Ala His Phe Asp Glu His
145                 150                 155                 160

Phe Gln Ala Ala Val Lys Lys Ala Asp Ser Asp Ala Asp Arg Glu Phe
                165                 170                 175

Glu Asn Glu Val Ser Trp Leu Ser Lys Ile Gln His Gln Asn Ile Ile
            180                 185                 190

Lys Ile Met Gly Tyr Cys Ile His Gly Glu Ser Arg Phe Leu Val Tyr
        195                 200                 205

Glu Leu Met Glu Asn Gly Ser Leu Glu Thr Gln Leu His Gly Pro Asn
    210                 215                 220

Arg Gly Ser Ser Leu Thr Trp Pro Leu Arg Leu Arg Ile Ala Val Asp
225                 230                 235                 240

Val Ala Arg Ala Leu Glu Tyr Leu His Glu His Asn Asn Pro Pro Val
                245                 250                 255

Val His Arg Asp Leu Lys Ser Ser Asn Val Phe Leu Asp Ser Asn Phe
            260                 265                 270

Asn Ala Lys Leu Ser Asp Phe Gly Phe Ala Met Val Leu Gly Met Gln
        275                 280                 285

His Lys Asn Met Lys Ile Phe Ser Gly Lys Leu Thr Asp Lys Ser Asp
    290                 295                 300

Val Tyr Ala Phe Gly Val Val Leu Leu Glu Leu Leu Thr Gly Lys Lys
305                 310                 315                 320

Pro Met Glu Asn Met Thr Ser Asn Gln Tyr Gln Ser Leu Val Ser Trp
                325                 330                 335

Ala Met Pro Gln Leu Thr Asp Arg Ser Lys Leu Pro Ser Ile Leu Asp
            340                 345                 350

Pro Val Ile Arg Asp Thr Met Asp Leu Lys His Leu Tyr Gln Val Ala
        355                 360                 365

Ala Val Ala Val Leu Cys Val Gln Ser Glu Pro Ser Tyr Arg Pro Leu
    370                 375                 380

Ile Thr Asp Val Leu His Ser Leu Ile Pro Leu Val Pro Val Glu Leu
385                 390                 395                 400

Gly Gly Ser Leu Arg Val Thr Glu Pro Ile Ser Ser Gly Leu Tyr Met
                405                 410                 415

Ala Gly Pro Arg Thr Glu Ile Asn
            420

<210> SEQ ID NO 232
<211> LENGTH: 1564
<212> TYPE: DNA
<213> ORGANISM: Glycine max
<220> FEATURE:
<221> NAME/KEY: misc_feature
<222> LOCATION: (1564)..(1564)
<223> OTHER INFORMATION: n is a, c, g, or t

<400> SEQUENCE: 232
atggcgatgg caatggcgct tcgcaggctt tcatcttcaa ttgacaagcc tctgcgccct      60
ctcttcaatg ccggttccct ctactacaag tcgtctttgc ctgatgaagc tgtttacgac     120
aaggagcgac ccggagttac atggccgaag cagttgaatg ctccacttga ggtcgtggat     180
cctgagattg ctgatattat tgagcttgag aaagctaggc aatggaaggg gctagaattg     240
ataccgtcag agaatttcac ctctgtgtct gtgatgcaag cggttggatc ggttatgacc     300
aacaaataca gtgaggggta ccctggtgca agatattatg gtggaaatga gtatattgac     360
atggctgaaa cactgtgcca aaagcgtgcc ctagaagctt ttagattgga tcccgctaaa     420
```

```
tggggagtga acgtgcagcc tctgtcaggg tctcctgcaa atttccacgt tacactgca    480 ttgcttaaac ctcatgaaag aatcatggca cttgatcttc ctcatggtgg ccatctttct    540
cacggatatc agactgatac caaaaagata tctgcagtct cgatattttt tgagacaatg    600
ccatatcgat tgaatgaaag tacaggatac atcgactatg accagatgga gaaatctgct    660
acactcttca ggccaaaatt aattgttgct ggagctagcg cttatgcacg tctctatgat    720
tatgaacgtg tacgcaaggt ttgcgataaa cagaaagcta tactattggc agatatggca    780
cacatcagtg gattggttgc agctggtgtc atcccatcac cttttgatta tgctgatgta    840
gttactacca caactcacaa gtcacttcga ggaccacgtg gagctatgat attctacaga    900 aaggggtta agaaattaa caaacaagga aagaggtat tgtatgacta cgaagacaaa    960
atcaaccaag ctgttttccc tggactgcaa ggtggccctc acaaccacac tattactggt    1020
ttagctgttg cgttgaagca ggccactact cccgaatata gagcatatca gagcaagtt    1080 ctcagcaaca gctttaaatt tgcacaggct ctgagtgaga aagctatga gcttgtctct    1140 ggtggaaccg agaatcacct ggttttggtg aatctgaaga ataagggtat tgatggctcc    1200
agagttgaga aggtgttgga agcagttcat attgcagcta ataaaaacac tgttcctgga    1260
gatgtgtctg ccatggttcc tggtggcatc aggatgggaa cccctgctct tacttctaga    1320
ggatttgttg aggaggattt tgtcaaggta gcagagtttt ttgatgcagc agtgaagata    1380
gctgtgaaga ttaagggaga gagcaaagga acaaagctga aggacttctt ggccacaatt    1440
gagtcatctt ctacctttca atcggagata gcaaagctcc gccttgatgt tgaggagtat    1500
gcaaaacaat ttccaaccat tggttttgat aaagcaacca tgaagcacaa gaattgagym    1560 aggn                                                                  1564
```

<210> SEQ ID NO 233
<211> LENGTH: 530
<212> TYPE: PRT
<213> ORGANISM: Glycine max

<400> SEQUENCE: 233

```
Met Ala Met Ala Met Ala Leu Arg Arg Leu Ser Ser Ile Asp Lys
1               5                   10                  15

Pro Leu Arg Pro Leu Phe Asn Ala Gly Ser Leu Tyr Tyr Lys Ser Ser
            20                  25                  30

Leu Pro Asp Glu Ala Val Tyr Asp Lys Glu Arg Pro Gly Val Thr Trp
        35                  40                  45

Pro Lys Gln Leu Asn Ala Pro Leu Glu Val Val Asp Pro Glu Ile Ala
    50                  55                  60

Asp Ile Ile Glu Leu Glu Lys Ala Arg Gln Trp Lys Gly Leu Glu Leu
65                  70                  75                  80

Ile Pro Ser Glu Asn Phe Thr Ser Val Ser Val Met Gln Ala Val Gly
                85                  90                  95

Ser Val Met Thr Asn Lys Tyr Ser Glu Gly Tyr Pro Gly Ala Arg Tyr
            100                 105                 110

Tyr Gly Gly Asn Glu Tyr Ile Asp Met Ala Glu Thr Leu Cys Gln Lys
        115                 120                 125

Arg Ala Leu Glu Ala Phe Arg Leu Asp Pro Ala Lys Trp Gly Val Asn
    130                 135                 140

Val Gln Pro Leu Ser Gly Ser Pro Ala Asn Phe His Val Tyr Thr Ala
145                 150                 155                 160
```

```
Leu Leu Lys Pro His Glu Arg Ile Met Ala Leu Asp Leu Pro His Gly
            165                 170                 175

Gly His Leu Ser His Gly Tyr Gln Thr Asp Thr Lys Lys Ile Ser Ala
        180                 185                 190

Val Ser Ile Phe Phe Glu Thr Met Pro Tyr Arg Leu Asn Glu Ser Thr
        195                 200                 205

Gly Tyr Ile Asp Tyr Asp Gln Met Glu Lys Ser Ala Thr Leu Phe Arg
        210                 215                 220

Pro Lys Leu Ile Val Ala Gly Ala Ser Ala Tyr Ala Arg Leu Tyr Asp
225                 230                 235                 240

Tyr Glu Arg Val Arg Lys Val Cys Asp Lys Gln Lys Ala Ile Leu Leu
            245                 250                 255

Ala Asp Met Ala His Ile Ser Gly Leu Val Ala Ala Gly Val Ile Pro
            260                 265                 270

Ser Pro Phe Asp Tyr Ala Asp Val Val Thr Thr Thr His Lys Ser
        275                 280                 285

Leu Arg Gly Pro Arg Gly Ala Met Ile Phe Tyr Arg Lys Gly Val Lys
        290                 295                 300

Glu Ile Asn Lys Gln Gly Lys Glu Val Leu Tyr Asp Tyr Glu Asp Lys
305                 310                 315                 320

Ile Asn Gln Ala Val Phe Pro Gly Leu Gln Gly Gly Pro His Asn His
            325                 330                 335

Thr Ile Thr Gly Leu Ala Val Ala Leu Lys Gln Ala Thr Thr Pro Glu
            340                 345                 350

Tyr Arg Ala Tyr Gln Glu Gln Val Leu Ser Asn Ser Phe Lys Phe Ala
        355                 360                 365

Gln Ala Leu Ser Glu Arg Ser Tyr Glu Leu Val Ser Gly Gly Thr Glu
        370                 375                 380

Asn His Leu Val Leu Val Asn Leu Lys Asn Lys Gly Ile Asp Gly Ser
385                 390                 395                 400

Arg Val Glu Lys Val Leu Glu Ala Val His Ile Ala Ala Asn Lys Asn
            405                 410                 415

Thr Val Pro Gly Asp Val Ser Ala Met Val Pro Gly Gly Ile Arg Met
            420                 425                 430

Gly Thr Pro Ala Leu Thr Ser Arg Gly Phe Val Glu Glu Asp Phe Val
        435                 440                 445

Lys Val Ala Glu Phe Phe Asp Ala Ala Val Lys Ile Ala Val Lys Ile
        450                 455                 460

Lys Gly Glu Ser Lys Gly Thr Lys Leu Lys Asp Phe Leu Ala Thr Ile
465                 470                 475                 480

Glu Ser Ser Ser Thr Phe Gln Ser Glu Ile Ala Lys Leu Arg Leu Asp
            485                 490                 495

Val Glu Glu Tyr Ala Lys Gln Phe Pro Thr Ile Gly Phe Asp Lys Ala
        500                 505                 510

Thr Met Lys His Lys Asn Gly Leu Tyr Met Ala Gly Pro Arg Thr Glu
        515                 520                 525

Ile Asn
    530

<210> SEQ ID NO 234
<211> LENGTH: 208
<212> TYPE: DNA
<213> ORGANISM: Glycine max
<220> FEATURE:
<221> NAME/KEY: misc_feature
```

<222> LOCATION: (208)..(208)
<223> OTHER INFORMATION: n is a, c, g, or t

<400> SEQUENCE: 234

```
atggccctcc tcctcttccg tgcctccaaa ttgatgtcat ttgctgctct tttagcaata    60
cttttactgc ttatgtcctc cacaatggga agtgctgctc agcctagttt taagctcgtg   120
cgaaagcttc tccaaactaa atacccgcct gcttatcctg gatatcctgg tggtggagga   180
tatagcccaa aaacaccatg agymaggn                                      208
```

<210> SEQ ID NO 235
<211> LENGTH: 78
<212> TYPE: PRT
<213> ORGANISM: Glycine max

<400> SEQUENCE: 235

Met Ala Leu Leu Leu Phe Arg Ala Ser Lys Leu Met Ser Phe Ala Ala
1               5                   10                  15

Leu Leu Ala Ile Leu Leu Leu Met Ser Ser Thr Met Gly Ser Ala
            20                  25                  30

Ala Gln Pro Ser Phe Lys Leu Val Arg Lys Leu Leu Gln Thr Lys Tyr
        35                  40                  45

Pro Pro Ala Tyr Pro Gly Tyr Pro Gly Gly Gly Tyr Ser Pro Lys
    50                  55                  60

Thr Pro Gly Leu Tyr Met Ala Gly Pro Arg Thr Glu Ile Asn
65                  70                  75

<210> SEQ ID NO 236
<211> LENGTH: 1186
<212> TYPE: DNA
<213> ORGANISM: Glycine max
<220> FEATURE:
<221> NAME/KEY: misc_feature
<222> LOCATION: (1186)..(1186)
<223> OTHER INFORMATION: n is a, c, g, or t

<400> SEQUENCE: 236

```
atggattcgg ggcttgctat atcttctcct aaaccttatt cagtgatcac aactggttct    60
tatgcatcaa aagcttcgca gcacacaaaa aaaactcaaa taaatataaa tttgaagcgg   120
gtacaacaat taagtttggg ccatcgttac aaatgcattg aaggagggtt tgcatatcaa   180
gaatgcaata gaaagtatgt tgtgcaagca gtccctgaat catcttttga ttctgaacct   240
catacttcca atcctcaaat cattttgcac tctgtcaaag atttcttagc tactttatgc   300
acactttcct atccatatgc aatgattggc ttagcattat gtgcactttc ttcgtctctc   360
cttgcagtgg aaaaactatc agacatatct ctatcatttt tgttggtgt gttacaagct   420
gcggtacctc aattgttttt cgcaatttat agtaatgctc taaatcaagt gtctgacctt   480
gaaatagata agataaacaa accacatctt ccattggcat ccgggcaatt atcccttaaa   540
actgttgtca tcattgctgc gtcattttta actttgagtt tttggcttag ctggatagta   600
ggttcatggc ctttgatttg aatcttgta ttgattactt caatatggac cgcttattca   660
gtcaatgtac ccttcttgag atggaagaaa aacccaatac tcgcggcaat gtgcatggtt   720
tcatcttggg catttgtatt gccaattaca ttttttcttc acatgcagac ttttgtgttg   780
aagaggccaa ttgtctttcc aagatcactt attttggcta ttgtaatcat gaacttcttc   840
tttgtgggta tggcattggc aaaggatata cctgatgttg aaggagataa aatatatggc   900
attgatactt ttgcaatacg tataggtcaa aaacaagtat tttggatttg tattttcctt   960
```

```
tttgaaatgg ctttcggagt tccctagtg gcaggagcaa catcttctag ccttttggtc    1020
aaaatcatca cgggtgtggg gaatgctgtt cttgcttcag ttctctggtt ccaagccaat    1080
tctatagatt tgagcagcaa aacttctggt ggatcctttt atatgttgat ctggaagcta    1140
atgtacgcat catacttcct cgtggcttta attagataag ymaggn                  1186
```

<210> SEQ ID NO 237
<211> LENGTH: 404
<212> TYPE: PRT
<213> ORGANISM: Glycine max

<400> SEQUENCE: 237

```
Met Asp Ser Gly Leu Ala Ile Ser Ser Pro Lys Pro Tyr Ser Val Ile
1               5                   10                  15

Thr Thr Gly Ser Tyr Ala Ser Lys Ala Ser Gln His Thr Lys Lys Thr
            20                  25                  30

Gln Ile Lys Tyr Asn Leu Lys Arg Val Gln Gln Leu Ser Leu Gly His
        35                  40                  45

Arg Tyr Lys Cys Ile Glu Gly Gly Phe Ala Tyr Gln Glu Cys Asn Arg
    50                  55                  60

Lys Tyr Val Val Gln Ala Val Pro Glu Ser Ser Phe Asp Ser Glu Pro
65                  70                  75                  80

His Thr Ser Asn Pro Gln Ile Ile Leu His Ser Val Lys Asp Phe Leu
                85                  90                  95

Ala Thr Leu Cys Thr Leu Ser Tyr Pro Tyr Ala Met Ile Gly Leu Ala
            100                 105                 110

Leu Cys Ala Leu Ser Ser Ser Leu Leu Ala Val Glu Lys Leu Ser Asp
        115                 120                 125

Ile Ser Leu Ser Phe Phe Val Gly Val Leu Gln Ala Ala Val Pro Gln
    130                 135                 140

Leu Phe Phe Ala Ile Tyr Ser Asn Ala Leu Asn Gln Val Ser Asp Leu
145                 150                 155                 160

Glu Ile Asp Lys Ile Asn Lys Pro His Leu Pro Leu Ala Ser Gly Gln
                165                 170                 175

Leu Ser Leu Lys Thr Val Val Ile Ile Ala Ala Ser Phe Leu Thr Leu
            180                 185                 190

Ser Phe Trp Leu Ser Trp Ile Val Gly Ser Trp Pro Leu Ile Trp Asn
        195                 200                 205

Leu Val Leu Ile Thr Ser Ile Trp Thr Ala Tyr Ser Val Asn Val Pro
    210                 215                 220

Phe Leu Arg Trp Lys Lys Asn Pro Ile Leu Ala Ala Met Cys Met Val
225                 230                 235                 240

Ser Ser Trp Ala Phe Val Leu Pro Ile Thr Phe Phe Leu His Met Gln
                245                 250                 255

Thr Phe Val Leu Lys Arg Pro Ile Val Phe Pro Arg Ser Leu Ile Leu
            260                 265                 270

Ala Ile Val Ile Met Asn Phe Phe Val Gly Met Ala Leu Ala Lys
        275                 280                 285

Asp Ile Pro Asp Val Glu Gly Asp Lys Ile Tyr Gly Ile Asp Thr Phe
    290                 295                 300

Ala Ile Arg Ile Gly Gln Lys Gln Val Phe Trp Ile Cys Ile Phe Leu
305                 310                 315                 320

Phe Glu Met Ala Phe Gly Val Ser Leu Val Ala Gly Ala Thr Ser Ser
                325                 330                 335
```

```
Ser Leu Leu Val Lys Ile Ile Thr Gly Val Gly Asn Ala Val Leu Ala
            340                 345                 350

Ser Val Leu Trp Phe Gln Ala Asn Ser Ile Asp Leu Ser Ser Lys Thr
        355                 360                 365

Ser Gly Gly Ser Phe Tyr Met Leu Ile Trp Lys Leu Met Tyr Ala Ser
    370                 375                 380

Tyr Phe Leu Val Ala Leu Ile Arg Gly Leu Tyr Met Ala Gly Pro Arg
385                 390                 395                 400

Thr Glu Ile Asn
```

<210> SEQ ID NO 238
<211> LENGTH: 985
<212> TYPE: DNA
<213> ORGANISM: Glycine max
<220> FEATURE:
<221> NAME/KEY: misc_feature
<222> LOCATION: (985)..(985)
<223> OTHER INFORMATION: n is a, c, g, or t

<400> SEQUENCE: 238

| | | | | |
|---|---|---|---|---|
| atggaggaac | gtagtttgta | ctcactagtg | tttcttgtgc | ttgctttggc | tattgtgaac | 60 |
| aaagtgcatg | ggcaagggac | gcgtgtaggg | ttctattcga | gtacatgccc | acgcgctgag | 120 |
| tccattgtta | agtccacagt | tacaacccat | gttaattctg | atagtacttt | ggctgctggg | 180 |
| ttgcttcgga | tgcacttcca | tgattgcttt | gtgcaaggtt | gtgacgcttc | tgttctcatt | 240 |
| gccggttctg | gcactgagag | aacagcattt | gcaaaccttg | gtttacgagg | atttgaggtt | 300 |
| attgatgatg | caaagaaaca | gctcgaggct | gcatgccccg | gtgttgtgtc | ttgcgctgat | 360 |
| atccttgctc | ttgctgctcg | tgattccgtt | gttctgagtg | gtggactgag | ttatcaagtg | 420 |
| cttactggac | gcagagatgg | acgcatatca | caggcttccg | acgtgagtaa | cttgcctgct | 480 |
| cctttttgact | ctgttgatgt | tcagaaacaa | aagttcacag | caaagggcct | caacactcaa | 540 |
| gacctcgtca | cccttgttgg | tgcacatacc | attggtacta | cagcttgcca | gttcttcagt | 600 |
| aacagattgt | acaacttcac | cgcgaatggt | cctgaccctt | ccatcgaccc | ttcatttctt | 660 |
| tcccaactac | aatcactatg | ccctcaaaac | ggtgacggtt | caaaacgagt | agcgctagat | 720 |
| acgggtagtc | aaaccaaatt | tgatttatct | tactatagta | atttgaggaa | ttctcgtgga | 780 |
| attctgcaat | ctgatcaagc | actatggagt | gatgcttcca | caaagacaac | tgttcagagg | 840 |
| tacttgggct | taataagagg | gttacttgga | ttaacattca | acgtggaatt | tgggaagtct | 900 |
| atggtgaaaa | tgggcaacat | tgagttgaaa | accggtaccg | atggtgaaat | tcgcaagata | 960 |
| tgttctgcca | tcaactaggy | maggn | | | | 985 |

<210> SEQ ID NO 239
<211> LENGTH: 337
<212> TYPE: PRT
<213> ORGANISM: Glycine max

<400> SEQUENCE: 239

```
Met Glu Glu Arg Ser Leu Tyr Ser Leu Val Phe Leu Val Leu Ala Leu
1               5                   10                  15

Ala Ile Val Asn Lys Val His Gly Gln Gly Thr Arg Val Gly Phe Tyr
            20                  25                  30

Ser Ser Thr Cys Pro Arg Ala Glu Ser Ile Val Lys Ser Thr Val Thr
        35                  40                  45

Thr His Val Asn Ser Asp Ser Thr Leu Ala Ala Gly Leu Leu Arg Met
```

```
                50                  55                  60
His Phe His Asp Cys Phe Val Gln Gly Cys Asp Ala Ser Val Leu Ile
 65                  70                  75                  80

Ala Gly Ser Gly Thr Glu Arg Thr Ala Phe Ala Asn Leu Gly Leu Arg
                 85                  90                  95

Gly Phe Glu Val Ile Asp Asp Ala Lys Lys Gln Leu Glu Ala Ala Cys
                100                 105                 110

Pro Gly Val Val Ser Cys Ala Asp Ile Leu Ala Leu Ala Ala Arg Asp
            115                 120                 125

Ser Val Val Leu Ser Gly Leu Ser Tyr Gln Val Leu Thr Gly Arg
            130                 135                 140

Arg Asp Gly Arg Ile Ser Gln Ala Ser Asp Val Ser Asn Leu Pro Ala
145                 150                 155                 160

Pro Phe Asp Ser Val Asp Val Gln Lys Gln Lys Phe Thr Ala Lys Gly
                165                 170                 175

Leu Asn Thr Gln Asp Leu Val Thr Leu Val Gly Ala His Thr Ile Gly
                180                 185                 190

Thr Thr Ala Cys Gln Phe Phe Ser Asn Arg Leu Tyr Asn Phe Thr Ala
                195                 200                 205

Asn Gly Pro Asp Pro Ser Ile Asp Pro Ser Phe Leu Ser Gln Leu Gln
210                 215                 220

Ser Leu Cys Pro Gln Asn Gly Asp Gly Ser Lys Arg Val Ala Leu Asp
225                 230                 235                 240

Thr Gly Ser Gln Thr Lys Phe Asp Leu Ser Tyr Tyr Ser Asn Leu Arg
                245                 250                 255

Asn Ser Arg Gly Ile Leu Gln Ser Asp Gln Ala Leu Trp Ser Asp Ala
                260                 265                 270

Ser Thr Lys Thr Thr Val Gln Arg Tyr Leu Gly Leu Ile Arg Gly Leu
                275                 280                 285

Leu Gly Leu Thr Phe Asn Val Glu Phe Gly Lys Ser Met Val Lys Met
            290                 295                 300

Gly Asn Ile Glu Leu Lys Thr Gly Thr Asp Gly Glu Ile Arg Lys Ile
305                 310                 315                 320

Cys Ser Ala Ile Asn Gly Leu Tyr Met Ala Gly Pro Arg Thr Glu Ile
                325                 330                 335

Asn

<210> SEQ ID NO 240
<211> LENGTH: 679
<212> TYPE: DNA
<213> ORGANISM: Glycine max
<220> FEATURE:
<221> NAME/KEY: misc_feature
<222> LOCATION: (679)..(679)
<223> OTHER INFORMATION: n is a, c, g, or t

<400> SEQUENCE: 240
atggccgtca cgaaaagcct ctcaatcttc ctcttcatcg caatgagctg cgtcgccgca      60
gctcaggcag cgaacttcaa catcacaaat aactgcacct acacggtgtg ggccgctgcc     120
gtgcccggcg gcggcgcaag gcttaaccct ggcgaatcgt ggaacatcag cgtgacgaac     180
ggcacaacaa gaggacgcat ctggggtcga caaaactgca ccttcgacaa cgcgggacgc     240
gggaagtgcc tcaccggcga ctgcgagggt gttctggagt gcaacaaaac aggtacaccc     300
ccgaacacgg tcgttgattt cgcgttgaac cagtataaca acctcgactt ctacgacatc     360
```

```
tccctcgtcg acggtttcaa cgttccccta cagctgaccc cgacctacaa ctgcagttcc      420
gttaaatgcg ccgccgacat catcggagag tgccccactc agctccaggt tcctggcggc      480
tgcaacaacc cctgcacggt tttcaatacg actcagtact gttgtagcac cggagctgct      540
gggtgcggtc ccacagatta ttccaagttc ttcaaggaga ggtgccctga tgcctacagt      600
taccctatgg acgatgcaac cagcatgttc acttgcatgg gatccgatta tagggttgtg      660
ttttgccctt aagymaggn                                                    679
```

<210> SEQ ID NO 241
<211> LENGTH: 235
<212> TYPE: PRT
<213> ORGANISM: Glycine max

<400> SEQUENCE: 241

```
Met Ala Val Thr Lys Ser Leu Ser Ile Phe Leu Phe Ile Ala Met Ser
1               5                   10                  15

Cys Val Ala Ala Gln Ala Ala Asn Phe Asn Ile Thr Asn Asn Cys
            20                  25                  30

Thr Tyr Thr Val Trp Ala Ala Ala Val Pro Gly Gly Gly Ala Arg Leu
        35                  40                  45

Asn Pro Gly Glu Ser Trp Asn Ile Ser Val Thr Asn Gly Thr Thr Arg
    50                  55                  60

Gly Arg Ile Trp Gly Arg Thr Asn Cys Thr Phe Asp Asn Ala Gly
65                  70                  75                  80

Gly Lys Cys Leu Thr Gly Asp Cys Glu Gly Val Leu Glu Cys Asn Lys
                85                  90                  95

Thr Gly Thr Pro Pro Asn Thr Val Val Asp Phe Ala Leu Asn Gln Tyr
            100                 105                 110

Asn Asn Leu Asp Phe Tyr Asp Ile Ser Leu Val Asp Gly Phe Asn Val
        115                 120                 125

Pro Leu Gln Leu Thr Pro Thr Tyr Asn Cys Ser Ser Val Lys Cys Ala
    130                 135                 140

Ala Asp Ile Ile Gly Glu Cys Pro Thr Gln Leu Gln Val Pro Gly Gly
145                 150                 155                 160

Cys Asn Asn Pro Cys Thr Val Phe Asn Thr Thr Gln Tyr Cys Cys Ser
                165                 170                 175

Thr Gly Ala Ala Gly Cys Gly Pro Thr Asp Tyr Ser Lys Phe Phe Lys
            180                 185                 190

Glu Arg Cys Pro Asp Ala Tyr Ser Tyr Pro Met Asp Asp Ala Thr Ser
        195                 200                 205

Met Phe Thr Cys Met Gly Ser Asp Tyr Arg Val Val Phe Cys Pro Gly
    210                 215                 220

Leu Tyr Met Ala Gly Pro Arg Thr Glu Ile Asn
225                 230                 235
```

<210> SEQ ID NO 242
<211> LENGTH: 1543
<212> TYPE: DNA
<213> ORGANISM: Glycine max
<220> FEATURE:
<221> NAME/KEY: misc_feature
<222> LOCATION: (1543)..(1543)
<223> OTHER INFORMATION: n is a, c, g, or t

<400> SEQUENCE: 242

```
atgcttccct tttcaactct ctttcaaacc ccgttaacca ccgagtattg gtacaaccac      60
```

```
cccacaacaa cacttctagc gttcttgctc atctcccttg ttacttgcta tgcatggctc    120
aagcccaagg cccaaaggct tccaccgggc ccatcgggcc tccctttctt cgggaacctc    180
ctatccttgg acccagacct ccacacttac ttcgccgtcc tgcccagat ccacggtcca     240
atcttcaagc tccagctcgg gagcaaactc tgcatcgtgc tgacttcgcc gcccatggct    300
cgcgcggtgc tcaaagagaa cgacaccgtt ttcgcaaacc gtgacgtccc tgccgcgggc    360
cgggccgcga gctacggcgg atccgacata gtgtggaccc catacgggcc cgagtggcgg    420
atgctgcgga aggtgtgcgt ggctaagatg ctgagccacg ccacgctgga tacggtgtac    480
gatctgcgcc gcgaggaggt gcgcaaaacg gtgtcgtatt tgcacgaccg agtggggagt    540
gcggttttt tgacggtgat aaatgtgata acgaacatgc tgtggggagg ggtggtggaa     600
ggggcggaga gagagagcat ggggggcggag ttcaggagc ttgtggcgga gatgacgcag    660
ctttttggga agccgaacgt gtcggatttt tttcccgggt tggcccggtt cgatttgcaa    720
ggtgtggaga acagatgaa cgcgctggtg ccacggttcg atgggatatt tgaacggatg     780
attggtgaaa gaagaaggt ggaattgaa ggggcagaaa ggatggactt tctgcagttt      840
ttgttgaagt tgaaggagga aggcggtgat gccaagacgc cactcaccat cacccacgtt    900
aaggcactcc ttatggacat ggttgtcggt ggaactgaca catcttccaa cacaattgag    960
tttgcaatgg cagaaatgat gcacaatcca gagataatga agagagtcca agaggagttg   1020
gaagttgtag tagggaaaga taacacggta gaagagtctc acattcataa gttatcctac   1080
ttgcaagctg tgatgaaaga aactctaaga ttacaccctg tgcttccact tctagtacct   1140
cattgtccta gcgaaaccac tattgtggga ggttacacaa tcccaaaggg gtctcgggtg   1200
tttgtgaatg tgtgggctat tcatagagac ccttcaattt ggaagaaatc actcgaattt   1260
gatcctacaa gattcttaga tgcaaaattg gatttcagtg gcaatgactt caactatttc   1320
ccctttggat ctggaagaag aatttgtgca ggaatagcaa tggctgagaa gacggttttg   1380
cattttcttg ccacactcgt acacttattt gattggacag tacccaagg agaaaagtta    1440
gaggtatcag agaaatttgg aattgttctc aaaaagaaaa tacctttggt tgctatcccc   1500
accccacggt tatccaaccc agatctttat caataggyma ggn                     1543
```

<210> SEQ ID NO 243
<211> LENGTH: 523
<212> TYPE: PRT
<213> ORGANISM: Glycine max

<400> SEQUENCE: 243

Met Leu Pro Phe Ser Thr Leu Phe Gln Thr Pro Leu Thr Thr Glu Tyr
 1               5                   10                  15

Trp Tyr Asn His Pro Thr Thr Thr Leu Leu Ala Phe Leu Leu Ile Ser
            20                  25                  30

Leu Val Thr Cys Tyr Ala Trp Leu Lys Pro Lys Ala Gln Arg Leu Pro
        35                  40                  45

Pro Gly Pro Ser Gly Leu Pro Phe Phe Gly Asn Leu Leu Ser Leu Asp
    50                  55                  60

Pro Asp Leu His Thr Tyr Phe Ala Val Leu Ala Gln Ile His Gly Pro
65                  70                  75                  80

Ile Phe Lys Leu Gln Leu Gly Ser Lys Leu Cys Ile Val Leu Thr Ser
                85                  90                  95

Pro Pro Met Ala Arg Ala Val Leu Lys Glu Asn Asp Thr Val Phe Ala
            100                 105                 110

```
Asn Arg Asp Val Pro Ala Ala Gly Arg Ala Ala Ser Tyr Gly Gly Ser
        115                 120                 125

Asp Ile Val Trp Thr Pro Tyr Gly Pro Glu Trp Arg Met Leu Arg Lys
130                 135                 140

Val Cys Val Ala Lys Met Leu Ser His Ala Thr Leu Asp Thr Val Tyr
145                 150                 155                 160

Asp Leu Arg Arg Glu Glu Val Arg Lys Thr Val Ser Tyr Leu His Asp
                165                 170                 175

Arg Val Gly Ser Ala Val Phe Leu Thr Val Ile Asn Val Ile Thr Asn
            180                 185                 190

Met Leu Trp Gly Gly Val Glu Gly Ala Glu Arg Glu Ser Met Gly
        195                 200                 205

Ala Glu Phe Arg Glu Leu Val Ala Glu Met Thr Gln Leu Leu Gly Lys
    210                 215                 220

Pro Asn Val Ser Asp Phe Phe Pro Gly Leu Ala Arg Phe Asp Leu Gln
225                 230                 235                 240

Gly Val Glu Lys Gln Met Asn Ala Leu Val Pro Arg Phe Asp Gly Ile
                245                 250                 255

Phe Glu Arg Met Ile Gly Glu Arg Lys Lys Val Glu Leu Glu Gly Ala
            260                 265                 270

Glu Arg Met Asp Phe Leu Gln Phe Leu Leu Lys Leu Lys Glu Glu Gly
        275                 280                 285

Gly Asp Ala Lys Thr Pro Leu Thr Ile Thr His Val Lys Ala Leu Leu
    290                 295                 300

Met Asp Met Val Val Gly Gly Thr Asp Thr Ser Ser Asn Thr Ile Glu
305                 310                 315                 320

Phe Ala Met Ala Glu Met Met His Asn Pro Glu Ile Met Lys Arg Val
                325                 330                 335

Gln Glu Glu Leu Glu Val Val Gly Lys Asp Asn Thr Val Glu Glu
            340                 345                 350

Ser His Ile His Lys Leu Ser Tyr Leu Gln Ala Val Met Lys Glu Thr
        355                 360                 365

Leu Arg Leu His Pro Val Leu Pro Leu Leu Val Pro His Cys Pro Ser
    370                 375                 380

Glu Thr Thr Ile Val Gly Gly Tyr Thr Ile Pro Lys Gly Ser Arg Val
385                 390                 395                 400

Phe Val Asn Val Trp Ala Ile His Arg Asp Pro Ser Ile Trp Lys Lys
                405                 410                 415

Ser Leu Glu Phe Asp Pro Thr Arg Phe Leu Asp Ala Lys Leu Asp Phe
            420                 425                 430

Ser Gly Asn Asp Phe Asn Tyr Phe Pro Phe Gly Ser Gly Arg Arg Ile
        435                 440                 445

Cys Ala Gly Ile Ala Met Ala Glu Lys Thr Val Leu His Phe Leu Ala
    450                 455                 460

Thr Leu Val His Leu Phe Asp Trp Thr Val Pro Gln Gly Glu Lys Leu
465                 470                 475                 480

Glu Val Ser Glu Lys Phe Gly Ile Val Leu Lys Lys Ile Pro Leu
                485                 490                 495

Val Ala Ile Pro Thr Pro Arg Leu Ser Asn Pro Asp Leu Tyr Gln Gly
            500                 505                 510

Leu Tyr Met Ala Gly Pro Arg Thr Glu Ile Asn
        515                 520
```

<210> SEQ ID NO 244
<211> LENGTH: 1486
<212> TYPE: DNA
<213> ORGANISM: Glycine max
<220> FEATURE:
<221> NAME/KEY: misc_feature
<222> LOCATION: (1486)..(1486)
<223> OTHER INFORMATION: n is a, c, g, or t

<400> SEQUENCE: 244

```
atggaggtga agaatgaaaa gaaagccccg agtgttgaaa ggaggcatat tgaggcgccc      60
aaaaatttga tggaggtagt gtccatatta acggaagcca taaagtcgct cggttacaag     120
gagaaatggc acatcctcaa cttgcccata gccattgctt ccgctgtgtt ggacatgggt     180
aagaaaacag ttgcaagaga atgcggtgaa agaagtgatt gtgtacagct gaaggccccc     240
gaagtcataa aggagttata tgagataaag aaattgttga cacggacctt gcttttcagc     300
agaaaacggt tcatgggtt cttatttgct gctggattcg acaaggagga tgtcctccta     360
agaaagagaa cagctcggat tctaaggcca gttttcacag ttatacgtga tatagaatca     420
aaaagtgtgt tggtgtttat tcggggaact cgtagcctaa acgacacgct aacagctgca     480
ctctgtgctc ccgtctcctt cgagcatagg aggaacaaca acattgtttc aggacatgca     540
caccgtggta tggttgctgc agcttattgg attctagact actgcactcc tgtactaaaa     600
aaggctcttg atcaataccc ccacttcaaa atcaagatcg ttgggcactc gcttggtggt     660
gctgcctgta tgacattgga gttagccgaa tttgggaagc cctttatcat ttccattatc     720
aatggttatg acatagtgcc tacattgtca gtttcttctg ttcatgattt catttctgag     780
ggtcgcgatc ggagcaatga tcaaaacatc ctaaccgcag ttagatctca cataccaatc     840
gcaaaagcca ttgcaggaca tgcaataacc cgctgcacag aggttgtgaa gaaacataaa     900
cacggaactc gctcattgct tccctggcac atacgtgaga atattgactc atcgccaagc     960
tcaaaatcag ataacatagc tgaagcttat ggatcatctg agacaaattt tgaatctctc    1020
ttgactgaag agcacttaat catggagtct atgtcagatg atgacgaata taattcttct    1080
agtgaaggat ctgacggtga tgactccgat ggcgacgaag acgaattgtc gaataaagtg    1140
gggaagctta aactgggaaa agaagtagcc acaaacaaaa acatagctga agaagagagt    1200
gattgtccaa tcacaacatc aagtagacgt cgtctttatc ctcccggaag gatcatgcat    1260
attattccta ttgcacattc gtctgaaaat cctaattcaa accacaatgg ttgtgatgag    1320
aaacatgttt ccctatatga aacgcctaga gagctctatg gaaagctcag actttcaaga    1380
aggatgatac ttgatcataa gtcaaacaag tatctgaagg tgttacaaca attaatcaat    1440
caactagaga aagagagctt caaatatcat ggaggatgag ymaggn                   1486
```

<210> SEQ ID NO 245
<211> LENGTH: 504
<212> TYPE: PRT
<213> ORGANISM: Glycine max

<400> SEQUENCE: 245

```
Met Glu Val Lys Asn Glu Lys Lys Ala Pro Ser Val Glu Arg Arg His
1               5                   10                  15

Ile Glu Ala Pro Lys Asn Leu Met Glu Val Val Ser Ile Leu Thr Glu
            20                  25                  30

Ala Ile Lys Ser Leu Gly Tyr Lys Glu Lys Trp His Ile Leu Asn Leu
        35                  40                  45

Pro Ile Ala Ile Ala Ser Ala Val Leu Asp Met Gly Lys Lys Thr Val
```

```
                    50                  55                  60
Ala Arg Glu Cys Gly Glu Arg Ser Asp Cys Val Gln Leu Lys Ala Pro
 65                  70                  75                  80

Glu Val Ile Lys Glu Leu Tyr Glu Ile Lys Lys Leu Leu Thr Arg Thr
                 85                  90                  95

Leu Leu Phe Ser Arg Lys Arg Phe His Gly Phe Leu Phe Ala Ala Gly
                100                 105                 110

Phe Asp Lys Glu Asp Val Leu Leu Arg Lys Arg Thr Ala Arg Ile Leu
            115                 120                 125

Arg Pro Val Phe Thr Val Ile Arg Asp Ile Glu Ser Lys Ser Val Leu
        130                 135                 140

Val Phe Ile Arg Gly Thr Arg Ser Leu Asn Asp Thr Leu Thr Ala Ala
145                 150                 155                 160

Leu Cys Ala Pro Val Ser Phe Glu His Arg Arg Asn Asn Asn Ile Val
                165                 170                 175

Ser Gly His Ala His Arg Gly Met Val Ala Ala Tyr Trp Ile Leu
                180                 185                 190

Asp Tyr Cys Thr Pro Val Leu Lys Lys Ala Leu Asp Gln Tyr Pro His
            195                 200                 205

Phe Lys Ile Lys Ile Val Gly His Ser Leu Gly Gly Ala Ala Cys Met
        210                 215                 220

Thr Leu Glu Leu Ala Glu Phe Gly Lys Pro Phe Ile Ile Ser Ile Ile
225                 230                 235                 240

Asn Gly Tyr Asp Ile Val Pro Thr Leu Ser Val Ser Ser Val His Asp
                245                 250                 255

Phe Ile Ser Glu Gly Arg Asp Arg Ser Asn Asp Gln Asn Ile Leu Thr
            260                 265                 270

Ala Val Arg Ser His Ile Pro Ile Ala Lys Ala Ile Ala Gly His Ala
        275                 280                 285

Ile Thr Arg Cys Thr Glu Val Val Lys Lys His Lys His Gly Thr Arg
        290                 295                 300

Ser Leu Leu Pro Trp His Ile Arg Glu Asn Ile Asp Ser Ser Pro Ser
305                 310                 315                 320

Ser Lys Ser Asp Asn Ile Ala Glu Ala Tyr Gly Ser Ser Glu Thr Asn
                325                 330                 335

Phe Glu Ser Leu Leu Thr Glu Glu His Leu Ile Met Glu Ser Met Ser
            340                 345                 350

Asp Asp Asp Glu Tyr Asn Ser Ser Glu Gly Ser Asp Gly Asp Asp
        355                 360                 365

Ser Asp Gly Asp Glu Asp Glu Leu Ser Asn Lys Val Gly Lys Leu Lys
        370                 375                 380

Leu Gly Lys Glu Val Ala Thr Asn Lys Asn Ile Ala Glu Glu Ser
385                 390                 395                 400

Asp Cys Pro Ile Thr Thr Ser Ser Arg Arg Arg Leu Tyr Pro Pro Gly
                405                 410                 415

Arg Ile Met His Ile Ile Pro Ile Ala His Ser Ser Glu Asn Pro Asn
            420                 425                 430

Ser Asn His Asn Gly Cys Asp Glu Lys His Val Ser Leu Tyr Glu Thr
        435                 440                 445

Pro Arg Glu Leu Tyr Gly Lys Leu Arg Leu Ser Arg Arg Met Ile Leu
        450                 455                 460

Asp His Lys Ser Asn Lys Tyr Leu Lys Val Leu Gln Gln Leu Ile Asn
465                 470                 475                 480
```

-continued

Gln Leu Glu Lys Glu Ser Phe Lys Tyr His Gly Gly Leu Tyr Met
                485                 490                 495

Ala Gly Pro Arg Thr Glu Ile Asn
            500

<210> SEQ ID NO 246
<211> LENGTH: 398
<212> TYPE: DNA
<213> ORGANISM: Arabidopsis thaliana
<220> FEATURE:
<221> NAME/KEY: misc_feature
<222> LOCATION: (398)..(398)
<223> OTHER INFORMATION: n is a, c, g, or t

<400> SEQUENCE: 246
atggctagca ctatgatgac tacattgcct cagttcaatg gtcttcgagc caccaaaatc      60
tctgcagctc ctgtacaagg cctggcaagt gttcagccca tgagacgcaa gggaaatgga     120
gctttgggtg caaagtgtga cttcatcggt tcatcaacaa atctgataat ggtaacgtcg     180
acgaccctga tgttgttcgc ggggagattc ggacttgcgc catcagccaa taggaaggcg     240
acagctggac ttaggttgga ggcacgtgac tcaggtctac aaacgggtga cccggccggg     300
ttcacgcttg cggacacttt ggcttgtggc accgttggtc atatcatcgg tgtaggagtt     360
gtccttggcc ttaaaaacat tggtgctatt gaatggn                              398

<210> SEQ ID NO 247
<211> LENGTH: 139
<212> TYPE: PRT
<213> ORGANISM: Arabidopsis thaliana

<400> SEQUENCE: 247

Met Ala Ser Thr Met Met Thr Thr Leu Pro Gln Phe Asn Gly Leu Arg
1               5                   10                  15

Ala Thr Lys Ile Ser Ala Ala Pro Val Gln Gly Leu Ala Ser Val Gln
            20                  25                  30

Pro Met Arg Arg Lys Gly Asn Gly Ala Leu Gly Ala Lys Cys Asp Phe
        35                  40                  45

Ile Gly Ser Ser Thr Asn Leu Ile Met Val Thr Ser Thr Thr Leu Met
    50                  55                  60

Leu Phe Ala Gly Arg Phe Gly Leu Ala Pro Ser Ala Asn Arg Lys Ala
65                  70                  75                  80

Thr Ala Gly Leu Arg Leu Glu Ala Arg Asp Ser Gly Leu Gln Thr Gly
                85                  90                  95

Asp Pro Ala Gly Phe Thr Leu Ala Asp Thr Leu Ala Cys Gly Thr Val
            100                 105                 110

Gly His Ile Ile Gly Val Gly Val Val Leu Gly Leu Lys Asn Ile Gly
        115                 120                 125

Ala Ile Ala Thr Gly Pro Arg Thr Glu Ile Asn
    130                 135

<210> SEQ ID NO 248
<211> LENGTH: 1490
<212> TYPE: DNA
<213> ORGANISM: Arabidopsis thaliana
<220> FEATURE:
<221> NAME/KEY: misc_feature
<222> LOCATION: (1490)..(1490)
<223> OTHER INFORMATION: n is a, c, g, or t

<400> SEQUENCE: 248

```
atggcttcaa ttctctcaat tcttcttctc attctttcac tttcaaatct ccacttcact      60
tcaaccaccg gaaacaacca cattaacgac agaaaatcct tagaaatcat tatcggtggt     120
ggtaacgaca caatcctcc accgtcacct tcaccggaac cagaaccaga acctgcagat      180
tgccctcctc cccctcctcc tcctccatgc cctcctccac cttctccccc tccatgccct    240
cctccaccct ctcctcctcc aagccctcct cctccacagc ttccacctcc tccacagctt    300
ccgccgcctg caccgcctaa accccagcca tcgccgccaa cacctgatct accgtttgcg    360
agctcattat aaagaaagt ctatccagtt ctccaaagat ttaaggatct agtcgcagat     420
gataaactta agtcttggga aggccccgac atttgcaaca atacctcgg actcaaatgc     480
gccattttcc cgaaaacaaa gcatctcgca ctcgcgagcg tccagtttaa tgggttaaac    540
ttgagaggca agataggcaa gatcctcaag ttagataact tcctcgacaa gttagaagaa    600
gtcaccatct tccacgcaaa ctccaacggt ttcacaggct ctgtgcctga tttcagcaat    660
ttgaaattct tatacgagct cgatctaagc aacaacaaac tcacaggaga tttcccaact    720
agtgtcttga aggaaacaa tctcacgttt cttgatctca ggttcaattc tttctcaggc    780
tctgttcctc ctcaggtctt taatctcgac ctcgacgtct tgttcatcaa caacaacaat    840
cttgttcaga agcttccact caatcttgga tccatcactg ctctttacct caccttcgcc    900
aacaacaggt tcacgggtcc aattcccgaa agcataggca acatcaagta cctacaagaa    960
gtccttttcc tgaataacaa gttaaccgga tgcttaccgt accaaatcgg aaacctaacc   1020
cgagccactg ttttcgatgt tgggttcaac caattaaccg gtccaatacc gtactctttc   1080
ggttgcttag aaacgatgga acaactcaat ttagccggaa acaagttcta tggaaccata   1140
ccggagattg tatgcgagat tgcttgtctc caaaacgttt ctctctcgaa taattacttc   1200
actcaggttg gtccgaaatg tagaaaactc atcaagagaa aaattatgga cgttagtatg   1260
aattgtatac ttgatcttcc aaaccagaaa acgccatcgg agtgtgctaa gttcttcatg   1320
cggaaacaga cttgtcctaa ttccaagtct ttgtttactg tcccttgtga taagaatcca   1380
aaccggggta aaccggatca agaacgattg gaggaggaaa aagctcaagt ttctcatccg   1440
gtaacttaca acacacttaa cccggaccgg cttcggaatc tataaatggn              1490
```

<210> SEQ ID NO 249
<211> LENGTH: 503
<212> TYPE: PRT
<213> ORGANISM: Arabidopsis thaliana

<400> SEQUENCE: 249

```
Met Ala Ser Ile Leu Ser Ile Leu Leu Ile Leu Ser Leu Ser Asn
1               5                   10                  15

Leu His Phe Thr Ser Thr Thr Gly Asn Asn His Ile Asn Asp Arg Lys
                20                  25                  30

Ser Leu Glu Ile Ile Ile Gly Gly Gly Asn Asp Asn Pro Pro
        35                  40                  45

Ser Pro Ser Pro Glu Pro Glu Pro Glu Pro Ala Asp Cys Pro Pro Pro
    50                  55                  60

Pro Pro Pro Pro Pro Cys Pro Pro Pro Ser Pro Pro Cys Pro
65                  70                  75                  80

Pro Pro Pro Ser Pro Pro Pro Ser Pro Pro Pro Gln Leu Pro Pro
                85                  90                  95

Pro Pro Gln Leu Pro Pro Pro Ala Pro Pro Lys Pro Gln Pro Ser Pro
                100                 105                 110
```

Pro Thr Pro Asp Leu Pro Phe Ala Ser Ser Leu Leu Lys Lys Val Tyr
            115                 120                 125

Pro Val Leu Gln Arg Phe Lys Asp Leu Val Ala Asp Lys Leu Lys
        130                 135                 140

Ser Trp Glu Gly Pro Asp Ile Cys Asn Lys Tyr Leu Gly Leu Lys Cys
145                 150                 155                 160

Ala Ile Phe Pro Lys Thr Lys His Leu Ala Leu Ala Ser Val Gln Phe
                165                 170                 175

Asn Gly Leu Asn Leu Arg Gly Lys Ile Gly Lys Ile Leu Lys Leu Asp
            180                 185                 190

Asn Phe Leu Asp Lys Leu Glu Glu Val Thr Ile Phe His Ala Asn Ser
        195                 200                 205

Asn Gly Phe Thr Gly Ser Val Pro Asp Phe Ser Asn Leu Lys Phe Leu
        210                 215                 220

Tyr Glu Leu Asp Leu Ser Asn Asn Lys Leu Thr Gly Asp Phe Pro Thr
225                 230                 235                 240

Ser Val Leu Lys Gly Asn Asn Leu Thr Phe Leu Asp Leu Arg Phe Asn
                245                 250                 255

Ser Phe Ser Gly Ser Val Pro Pro Gln Val Phe Asn Leu Asp Leu Asp
            260                 265                 270

Val Leu Phe Ile Asn Asn Asn Leu Val Gln Lys Leu Pro Leu Asn
        275                 280                 285

Leu Gly Ser Ile Thr Ala Leu Tyr Leu Thr Phe Ala Asn Asn Arg Phe
        290                 295                 300

Thr Gly Pro Ile Pro Glu Ser Ile Gly Asn Ile Lys Tyr Leu Gln Glu
305                 310                 315                 320

Val Leu Phe Leu Asn Asn Lys Leu Thr Gly Cys Leu Pro Tyr Gln Ile
                325                 330                 335

Gly Asn Leu Thr Arg Ala Thr Val Phe Asp Val Gly Phe Asn Gln Leu
            340                 345                 350

Thr Gly Pro Ile Pro Tyr Ser Phe Gly Cys Leu Glu Thr Met Glu Gln
        355                 360                 365

Leu Asn Leu Ala Gly Asn Lys Phe Tyr Gly Thr Ile Pro Glu Ile Val
        370                 375                 380

Cys Glu Ile Ala Cys Leu Gln Asn Val Ser Leu Ser Asn Asn Tyr Phe
385                 390                 395                 400

Thr Gln Val Gly Pro Lys Cys Arg Lys Leu Ile Lys Arg Lys Ile Met
                405                 410                 415

Asp Val Ser Met Asn Cys Ile Leu Asp Leu Pro Asn Gln Lys Thr Pro
            420                 425                 430

Ser Glu Cys Ala Lys Phe Phe Met Arg Lys Gln Thr Cys Pro Asn Ser
        435                 440                 445

Lys Ser Leu Phe Thr Val Pro Cys Asp Lys Asn Pro Asn Arg Gly Lys
450                 455                 460

Pro Asp Gln Glu Arg Leu Glu Glu Lys Ala Gln Val Ser His Pro
465                 470                 475                 480

Val Thr Tyr Asn Thr Leu Asn Pro Asp Arg Leu Arg Asn Leu Ala Thr
                485                 490                 495

Gly Pro Arg Thr Glu Ile Asn
            500

<210> SEQ ID NO 250
<211> LENGTH: 401

<212> TYPE: DNA
<213> ORGANISM: Arabidopsis thaliana
<220> FEATURE:
<221> NAME/KEY: misc_feature
<222> LOCATION: (401)..(401)
<223> OTHER INFORMATION: n is a, c, g, or t

<400> SEQUENCE: 250

```
atggcaacta tagctactgg tcttaacatt gcaacccagc gtgtcttcgt caccagcgag    60
aatcggccag tttgtctcgc cggtccggtc catttgaaca attcgtggaa tcttgggtca   120
agaacaacta accggatgat gaaacttcag ccgattaaag cagcaccgga aggagggata   180
tcggacgtag tggagaaaag cattaaggaa gctcaggaga cttgtgcggg cgatcctgtg   240
agtggagagt gtgtagctgc gtgggacgag gttgaagaac ttagcgcagc agctagccat   300
gctagagaca gaagaaggc tgatggttcg gaccctttgg aggaatactg caaagacaat   360
cctgagacca acgagtgccg tacttacgac aactgaatgg n                       401
```

<210> SEQ ID NO 251
<211> LENGTH: 140
<212> TYPE: PRT
<213> ORGANISM: Arabidopsis thaliana

<400> SEQUENCE: 251

```
Met Ala Thr Ile Ala Thr Gly Leu Asn Ile Ala Thr Gln Arg Val Phe
  1               5                  10                  15

Val Thr Ser Glu Asn Arg Pro Val Cys Leu Ala Gly Pro Val His Leu
             20                  25                  30

Asn Asn Ser Trp Asn Leu Gly Ser Arg Thr Thr Asn Arg Met Met Lys
         35                  40                  45

Leu Gln Pro Ile Lys Ala Ala Pro Glu Gly Gly Ile Ser Asp Val Val
     50                  55                  60

Glu Lys Ser Ile Lys Glu Ala Gln Glu Thr Cys Ala Gly Asp Pro Val
 65                  70                  75                  80

Ser Gly Glu Cys Val Ala Ala Trp Asp Glu Val Glu Glu Leu Ser Ala
                 85                  90                  95

Ala Ala Ser His Ala Arg Asp Lys Lys Lys Ala Asp Gly Ser Asp Pro
            100                 105                 110

Leu Glu Glu Tyr Cys Lys Asp Asn Pro Glu Thr Asn Glu Cys Arg Thr
        115                 120                 125

Tyr Asp Asn Ala Thr Gly Pro Arg Thr Glu Ile Asn
    130                 135                 140
```

<210> SEQ ID NO 252
<211> LENGTH: 827
<212> TYPE: DNA
<213> ORGANISM: Arabidopsis thaliana
<220> FEATURE:
<221> NAME/KEY: misc_feature
<222> LOCATION: (827)..(827)
<223> OTHER INFORMATION: n is a, c, g, or t

<400> SEQUENCE: 252

```
atggcagcac aagcacttgt gtcttcttca cttacctcct ctgttcagac agctagacag    60
atatttggct caaaccagt tgcgtctgcc tcacagaaga agagttcctt tgttgttaaa   120
gctgctgcaa ctccacctgt caagcaagga gccaacagac cattgtggtt tgcttcatcg   180
cagagtctct cttacttgga tggcagctta cctggtgact atggattcga ccctcttggt   240
ctttcagacc cagaaggtac tggaggattc attgagccaa gatggctagc atacggagag   300
```

```
atcatcaacg gacggttcgc catgttgggt gcagctggag ctattgctcc tgagatttta      360
ggaaaggctg gtctgattcc agcagagact gctcttcctt ggttccaaac cggtgtgatt      420
ccaccagcag ggacatacac ttactgggca gacaattaca cactctttgt tctcgagatg      480
gctctgatgg gattcgctga gcaccggagg ttacaggact ggtacaaccc aggatctatg      540
ggaaaacagt acttcttggg gttagagaag ggtttggccg gttcaggtaa cccggcttac      600
cccggtggac ctttcttcaa ccctcttggg tttgggaaag atgagaagtc actgaaggag      660
ttgaaactca aggaggtcaa gaacggtaga ctggctatgc tcgccatcct cggttacttt      720
atccaaggac tagtgaccgg tgtgggacct tatcagaacc tgcttgatca cttggctgat      780
cccgtcaaca acaacgtctt gaccagcctc aagttccact gaatggn                   827
```

<210> SEQ ID NO 253
<211> LENGTH: 282
<212> TYPE: PRT
<213> ORGANISM: Arabidopsis thaliana

<400> SEQUENCE: 253

```
Met Ala Ala Gln Ala Leu Val Ser Ser Leu Thr Ser Ser Val Gln
1               5                   10                  15

Thr Ala Arg Gln Ile Phe Gly Ser Lys Pro Val Ala Ser Ala Ser Gln
            20                  25                  30

Lys Lys Ser Ser Phe Val Val Lys Ala Ala Thr Pro Val Lys
        35                  40                  45

Gln Gly Ala Asn Arg Pro Leu Trp Phe Ala Ser Ser Gln Ser Leu Ser
    50                  55                  60

Tyr Leu Asp Gly Ser Leu Pro Gly Asp Tyr Gly Phe Asp Pro Leu Gly
65                  70                  75                  80

Leu Ser Asp Pro Glu Gly Thr Gly Gly Phe Ile Glu Pro Arg Trp Leu
                85                  90                  95

Ala Tyr Gly Glu Ile Ile Asn Gly Arg Phe Ala Met Leu Gly Ala Ala
            100                 105                 110

Gly Ala Ile Ala Pro Glu Ile Leu Gly Lys Ala Gly Leu Ile Pro Ala
        115                 120                 125

Glu Thr Ala Leu Pro Trp Phe Gln Thr Gly Val Ile Pro Pro Ala Gly
    130                 135                 140

Thr Tyr Thr Tyr Trp Ala Asp Asn Tyr Thr Leu Phe Val Leu Glu Met
145                 150                 155                 160

Ala Leu Met Gly Phe Ala Glu His Arg Arg Leu Gln Asp Trp Tyr Asn
                165                 170                 175

Pro Gly Ser Met Gly Lys Gln Tyr Phe Leu Gly Leu Glu Lys Gly Leu
            180                 185                 190

Ala Gly Ser Gly Asn Pro Ala Tyr Pro Gly Gly Pro Phe Phe Asn Pro
        195                 200                 205

Leu Gly Phe Gly Lys Asp Glu Lys Ser Leu Lys Glu Leu Lys Leu Lys
    210                 215                 220

Glu Val Lys Asn Gly Arg Leu Ala Met Leu Ala Ile Leu Gly Tyr Phe
225                 230                 235                 240

Ile Gln Gly Leu Val Thr Gly Val Gly Pro Tyr Gln Asn Leu Leu Asp
                245                 250                 255

His Leu Ala Asp Pro Val Asn Asn Val Leu Thr Ser Leu Lys Phe
            260                 265                 270

His Ala Thr Gly Pro Arg Thr Glu Ile Asn
```

<210> SEQ ID NO 254
<211> LENGTH: 272
<212> TYPE: DNA
<213> ORGANISM: Arabidopsis thaliana
<220> FEATURE:
<221> NAME/KEY: misc_feature
<222> LOCATION: (272)..(272)
<223> OTHER INFORMATION: n is a, c, g, or t

<400> SEQUENCE: 254

```
atgggttcaa agtcaccaaa tattgtcgca cttgtgttac cactacttct tatactttac     60
actctttcct ctcaagttga agtcgtggaa tctacagggc gcaaacttgc gttttgggga    120
aatcctatcg tgtggactcc acactcaaat tcatgtggag gttctccagc atcagtattt    180
gcttcttcca agtggacgac aggccgacca tgcagacgta gtcgtcctcc aggaactaat    240
attcctgttt ctgatcaatc tccatagatg gn                                   272
```

<210> SEQ ID NO 255
<211> LENGTH: 97
<212> TYPE: PRT
<213> ORGANISM: Arabidopsis thaliana

<400> SEQUENCE: 255

Met Gly Ser Lys Ser Pro Asn Ile Val Ala Leu Val Leu Pro Leu Leu
1               5                   10                  15

Leu Ile Leu Tyr Thr Leu Ser Ser Gln Val Glu Val Glu Ser Thr
            20                  25                  30

Gly Arg Lys Leu Ala Phe Trp Gly Asn Pro Ile Val Trp Thr Pro His
        35                  40                  45

Ser Asn Ser Cys Gly Gly Ser Pro Ala Ser Val Phe Ala Ser Ser Lys
    50                  55                  60

Trp Thr Thr Gly Arg Pro Cys Arg Arg Ser Arg Pro Pro Gly Thr Asn
65                  70                  75                  80

Ile Pro Val Ser Asp Gln Ser Pro Ala Thr Gly Pro Arg Thr Glu Ile
                85                  90                  95

Asn

<210> SEQ ID NO 256
<211> LENGTH: 12992
<212> TYPE: DNA
<213> ORGANISM: artificial
<220> FEATURE:
<223> OTHER INFORMATION: vector sequence

<400> SEQUENCE: 256

```
gtgattttgt gccgagctgc cggtcgggga gctgttggct ggctggtggc aggatatatt     60
gtggtgtaaa caaattgacg cttagacaac ttaataacac attgcggacg tctttaatgt    120
actgaattta gttactgatc actgattaag tctagatatt gttttgtttt cacataaatg    180
tcgttttgga ttattcatgt aatattttaa actaaagtac aatttttgac tactttagtt    240
tactagttaa gcttttattt ttttgactaa ccattgaatg atgaagagat caacgcatca    300
tatttacaac ttacatagtc ttttggaagt gtaaattgct aatactacct aaaatatatc    360
tataattaac taatattttt tcgtcaatta taatagatca attaaaaggc tatcaaaagg    420
aaaaaaatga atccacatc ctgccatcat aacctcatgc tggaaaaaga atgaaaaaa     480
tataaaaaat ttcttttgtt tattaaattt acaactttaa tactagtttc ttttctattt    540
```

-continued

```
tttaaaagct tttgtcactt acttaaaaaa aaaaaacttt ttgaaatatt cctacttcca    600
atgtctgatt agtgcttctg gatttccttt ttggatcatg tgaatcctaa atcagaaaaa    660
ttcatataat acccaattca gtatattttc atacttcaat ttacaagagt tctctatgtt    720
tttagcttct ttcttttaag ccaaatgttt taagcatctt ttatacatta aaataattta    780
gtgttgagtt gagattttt ttttttttt ttggatttac ttgttcaaaa tctgaaaaaa    840
tgtttacaga aggttaaaat gaaccaaaag gcatatcaag ctagattttg aattacccta    900
tttcatcgta tacacaaaac tgataatgtg gacacagttg attttacttc tcgatgacat    960
cgtagtttta tttaatttgg aaaccacggc ccatatgagc acatttcaat taaaaaccaa   1020
tggtaagagc attttccatg caagattcga gagatattaa cccagtgact gttaaaacag   1080
cttagaaccc taataacgaa tttcaattac tcaatttacc attcgcattt cgcaataacc   1140
aaactgagcc agtcacaagg agtaaaccga accggattat ttatttataa aatgaaagaa   1200
aggaaaccaa acaacaacag cagtagtagt ctgacgtaaa ccaaaaagca ggcagatcaa   1260
caactaaaag aaactcaaat taccaaaaca aacaggaaat tgcaaactaa gttttttttac   1320
catatgcata caaagaccat aaaaggttct gataatcacc ggtttcatct ctcagtattt   1380
aatccggcca tctccttccg ttatgacatc gttgaaagtg ccaccattcg ggatcatcgg   1440
caacacatgt tcttggtgcg gacaaatcac atccaacagg taaggtcctg gtgtatccag   1500
cattgtctga atagcttctc ggagatctgc tttctttgtc accctcgccg ctggaatccc   1560
gcaagctgct gcaaacagca acatgttcgg gaatatctcg tcctcctgag ccggatcccc   1620
gagaaatgtg tgagctcggt tagctttgta gaaccgatct tcccattgca taaccatgcc   1680
aagatgctgg ttgtttaata aaagtacctt cactggaaga ttctctacac gaatagtggc   1740
tagctcttgc acattcatta taaagcttcc atctccgtca atatccacaa ctatcgcatc   1800
agggttagca acagacgctc caatcgcagc aggaagtcca atcccatag ctccaaggcc   1860
tcctgatgat agccactgcc ttggtttctt gtaattgtag aactgcgccg cccacatttg   1920
atgttgcccg acaccagtac ttattatggc ttttccatca gtcaactcat caaggacctt   1980
aatcgcatac tgtggaggaa tagcttcccc aaacgtctta aagctcaacg gaaacttctg   2040
tttctgtacg ttcaactcat tcctccaaac tccaaaatca agcttaagct cctccgctcg   2100
gttctcaaga accttattca tcccttgcaa agccagctta acatcaccac acacagacac   2160
atgaggagtc ttattcttcc caatctcagc cgagtcaata tcaatatgaa caatcttagc   2220
cctactagca aaagcctcaa gcttacccgt gacacgatca tcaaaccttta ccccaaacgc   2280
caacaacaaa tcactatgct ccacagcgta atttgcatac acagtcccat gcattccaag   2340
catatgtaac gacaactcat catcacaagg ataagatccc agccccatca acgtactcgc   2400
aacagggatc cccgtaagct caacaaacct acccaattca tcgctagaat tcaaacaacc   2460
accaccaaca tacaacacag gcttcttaga ctcagaaatc aacctaacaa tctgctccaa   2520
atgagaatct tccggaggtt taggcatcct agacatataa ccaggtaatc tcatagcctg   2580
ttcccaatta ggaatcgcaa gctgttgttg aatatcttta ggaacatcaa ccaaaacagg   2640
tccaggtcta ccagaagtag ctaaaaagaa agcttcctca ataatcctag ggatatcttc   2700
aacatccatc acaagatagt tatgcttcgt aatcgaacgc gttacctcaa caatcggagt   2760
ctcttgaaac gcatctgtac caatcatacg acgagggact tgtcctgtga ttgctacaag   2820
aggaacacta tctaacaacg catcggctaa tccgctaacg agatttgtag ctccgggacc   2880
```

```
tgaagtggct atacagatac ctggtttacc tgaggatcga gcgtatcctt ctgctgcgaa    2940
tacacctcct tgttcgtgac gaggaaggac gttacggatt gaggaagagc gggttaaggc    3000
ttggtgaatc tccattgatg tacctccagg gtaagcgaat acggtttcta cgccttgacg    3060
ttctaaagct tcgacgagga tatcagcgcc tttgcgggt  tgatctggag cgaatcggga    3120
gatgaatgtt tcgggtttgg taggtttggt tggagaggga gtggttgtga cattggtggt    3180
tgtgttgagc acggcggaga tggaggaggg agagctggat ttgataccgc ggcggcggga    3240
ggaggaggat gatttgttgg ggtttaggga gaatgggagg gagaatctgg agattggtaa    3300
tggtgatttg gaggaggaag gagatggttt ggtggagaag gagatcgaag aagatgttgt    3360
tgttgttgtt gttgccgccg ccatggttca gctgcacata cataacatat caagatcaga    3420
acacacatat acacacacaa atacaatcaa gtcaacaact ccaaaaagtc cagatctaca    3480
tatatacata cgtaaataac aaaatcatgt aaataatcac aatcatgtaa tccagatcta    3540
tgcacatata tatatacaca attaataaaa aaatgatat  aacagatcta tatctatgta    3600
tgtaacaaca caatcagatg agagaagtga tgttttcaga tctgtataca tacaaacaca    3660
aacagatgaa caattgatac gtagatccat atgtatacgt acaattagct acacgattaa    3720
atgaaaaaaa tcaacgattt cggattggta cacacaaacg caacaatatg aagaaattca    3780
tatctgatta gatataaaca taaccacgtg tagatacaca gtcaaatcaa caaatttata    3840
gcttctaaac ggatgagatg aacaagataa agatattcac ataaggcata cataagataa    3900
gcagattaac aaactagcaa taatacatac ctaattaaaa caaggaataa cagagagaga    3960
gagagagaga gagatttacc ttgaaaatga agaggagaag agaggatttc ttaaaattgg    4020
gggtagagaa agaaagatga tgaattgtga gaaggagag  atagaagggg gggttgtata    4080
tataggctgt agaagattat ttttgtgtt  gaggcggtga aggaagaggg gatctgacta    4140
tgacacgttt gcggttacgt atttcgatag gagtctttca acgcttaacg ccgttactct    4200
atatgaccgt ttgggccgta acggggccgt ttgttaacgc tgatgttgat tcttttcttt    4260
ctttctttct tccttttta  aagaagcaat tgtacaatcg ttgctagctg tcaaacggat    4320
aattcggata cggatatgcc tatattcata tccgtaattt ttggattcga attgactgcg    4380
atcgccaatt gacgcgtact agtgtacaag cttgcggccg cgaattcggt acatccggcc    4440
agtgaattat caactatgta taataaagtt gccatgatta cgccaagctt gcatgcccat    4500
atgctcgagg cggccgcaga tatcagatct ggtcgaccta gaggatcccc gggtacccca    4560
ctttgtacaa gaaagctggg tccatgatta cgccaagctt gcatgcccat atgctcgagg    4620
cggccgcaga tatcagatct ggtcgaccta gaggatcccc gggtaccagc ctgctttttt    4680
gtacaaactt gccatgatta cgccaagctt gaattcccga tctagtaaca tagatgacac    4740
cgcgcgcgat aatttatcct agtttgcgcg ctatattttg ttttctatcg cgtattaaat    4800
gtataattgc gggactctaa tcataaaaac ccatctcata aataacgtca tgcattacat    4860
gttaattatt acatgcttaa cgtaattcaa cagaaattat atgataatca tcgcaagacc    4920
ggcaacagga ttcaatctta agaaacttta ttgccaaatg tttgaacgat cggggaaatt    4980
cgagcccata tgctcgaggc ggccttactc ggtagcaatt cccgaggctg tagccgacga    5040
tggtgcgcca ggagagttgt tgattcattg tttgcctccc tgctgcggtt tttcaccgaa    5100
gttcatgcca gtccagcgtt tttgcagcag aaaagccgcc gacttcggtt tgcggtcgcg    5160
agtgaagatc ccttttcttgt taccgccaac gcgcaatatg ccttgcgagg tcgcaaaatc    5220
ggcgaaattc catacctgtt caccgacgac ggcgctgacg cgatcaaaga cgcggtgata    5280
```

```
catatccagc catgcacact gatactcttc actccacatg tcggtgtaca ttgagtgcag   5340
cccggctaac gtatccacgc cgtattcggt gatgataatc ggctgatgca gtttctcctg   5400
ccaggccaga agttctttttt ccagtacctt ctctgccgtt tccaaatcgc cgctttggac   5460
ataccatccg taataacggt tcaggcacag cacatcaaag agatcgctga tggtatcggt   5520
gtgagcgtcg cagaacatta cattgacgca ggtgatcgga cgcgtcgggt cgagtttacg   5580
cgttgcttcc gccagtggcg cgaaatattc ccgtgcacct tgcggacggg tatccggttc   5640
gttggcaata ctccacatca ccacgcttgg gtggttttttg tcacgcgcta tcagctcttt   5700
aatcgcctgt aagtgcgctt gctgagtttc cccgttgact gcctcttcgc tgtacagttc   5760
tttcggcttg ttgcccgctt cgaaaccaat gcctaaagag aggttaaagc cgacagcagc   5820
agtttcatca atcaccacga tgccatgttc atctgcccag tcgagcatct cttcagcgta   5880
agggtaatgc gaggtacggt aggagttggc cccaatccag tccattaatg cgtggtcgtg   5940
caccatcagc acgttatcga atcctttgcc acgcaagtcc gcatcttcat gacgaccaaa   6000
gccagtaaag tagaacggtt tgtggttaat caggaactgt tcgcccttca ctgccactga   6060
ccggatgccg acgcgaagcg ggtagatatc acactctgtc tggcttttgg ctgtgacgca   6120
cagttcatag agataaccttt cacccggttg ccagaggtgc ggattcacca cttgcaaagt   6180
cccgctagtg ccttgtccag ttgcaaccac ctgttgatcc gcatcacgca gttcaacgct   6240
gacatcacca ttggccacca cctgccagtc aacagacgcg tggttacagt cttgcgcgac   6300
atgcgtcacc acggtgatat cgtccaccca ggtgttcggc gtggtgtaga gcattacgct   6360
gcgatggatt ccggcatagt taaagaaatc atggaagtaa gactgctttt tcttgccgtt   6420
ttcgtcggta atcaccattc ccggcgggat agtctgccag ttcagttcgt tgttcacaca   6480
aacggtgata cctgcacatc aacaaatttt ggtcatatat tagaaaagtt ataaattaaa   6540
atatacacac ttataaacta cagaaaagca attgctatat actacattct ttttattttga   6600
aaaaaatatt tgaaatatta tattactact aattaatgat aattattata tatatatcaa   6660
aggtagaagc agaaacttac gtacacttttt cccggcaata acatacggcg tgacatcggc   6720
ttcaaatggc gtatagccgc cctgatgctc catcacttcc tgattattga cccacacttt   6780
gccgtaatga gtgaccgcat cgaaacgcag cacgatacgc tggcctgccc aacctttcgg   6840
tataaagact tcgcgctgat accagacgtt gcccgcataa ttacgaatat ctgcatcggc   6900
gaactgatcg ttaaaactgc ctggcacagc aattgcccgg cttcttgta acgcgctttc   6960
ccaccaacgc tgaccaattc cacagttttc gcgatccaga ctgaatgccc acaggccgtc   7020
gagttttttg atttcacggg ttggggtttc tacaggacgt accatggtct ttctcctcgc   7080
ctgggattct ttcttttttgc ttgcgagtga gtgagtgagt gagtgagtga gtgagaagga   7140
gggttgcgga tttataaccc gaatgtgttc gagttaatag aagtgagggt gaggtgtagt   7200
gggaggtggg tcccgaggcg taatatgttg aattttttgaa atgttttgtt tgataatgac   7260
caatgattga tggggtttgt cctagctggc gtgattccaa ccactcctag aaagaccgac   7320
catgttccgc gcagcactgg aacgtggatt actgtggttt cgacgtggtc cttggctgcg   7380
ttcgatgctg ggcggtggtg cattgtcacg ttcaactcgc gcctgcaaat ggacacgtgt   7440
cgatttctcc tgcattcgca gtttggcacg gtggattcca gagttggaaa ccaacacgca   7500
aatactccta ctgctacttc ccagttccct gttactgctg tcaggtgtca acagttttttc   7560
ttttctcctt ttgttaatgc ttttcttttt tagaatagaa tttgcctcca ttcaaccaca   7620
```

```
cgcgattaat acagtagttt taagttttt attattatta ttttggcacg ttaaaggtga    7680
agcaattaat acgttgaata taaattcaag ttattctcaa taagtatggt tggagaaacc   7740
aacaatactt cccacatgtg gtataaattt gtagctcttt caaattatga tttattttta   7800
aatataaaat aaaattatat taagaaaaaa atatttctta tatttattta tgattgaaaa   7860
aataataaat ttaaactacg acaaggtaca cagggaaaat taatatgtag taataaataa   7920
caagatgctc tcatctaggt atttcgaaac aaataacgta aggtaggaat ccagaatcat   7980
tgaatgtgta tgaacctttc ttaattactt attcgtgttt gcaaatcttt acctaccaaa   8040
gtaccaatgt tttgtagcgt gaaagatgat agtattctac taattgctaa tgttgatatg   8100
aaatccactt ctcagtcagg agttggaaat ggtacccaac ttttctatac aaagttgata   8160
gcttggcgta atcgatgtac cgatatcaat ttaaattggc cggccgagct ccctgcaggg   8220
ggcccggcgc gcctctagat taattaaagg ccttagttac taatcagtga tcagattgtc   8280
gtttcccgcc ttcagtttaa actatcagtg tttgacagga tatattggcg ggtaaaccta   8340
agagaaaaga gcgtttatta gaataatcgg atatttaaaa gggcgtgaaa aggtttatcc   8400
gttcgtccat ttgtatgtca atatccatga taagtcgcgc tgtatgtgtt tgtttgaata   8460
ttcatggaac gcagtggcgg ttttcatggc ttgttatgac tgttttttg gggtacagtc    8520 tatgcctcgg gcatccaagc agcaagcgcg ttacgccgtg ggtcgatgtt tgatgttatg   8580
gagcagcaac gatgttacgc agcagggcag tcgccctaaa acaaagttaa acatcatggg   8640
tgaagcggtc atcgccgagg tgtccaccca gctgtcggaa gtcgtgggtg tcatcgagcg   8700
ccacctcgaa ccgaccctcc tcgccgtgca tctgtatggt agcgccgttg acggcggcct   8760
taagccccat tcggacatcg acctgcttgt caccgttacc gtccgtctcg acgagaccac   8820
gcgccgcgcg cttatcaacg accttctgga acgtccgcc tcccccggcg agagcgaaat    8880
cctgcgcgcg gttgaggtga cgattgtggt gcacgatgac atcatcccct ggcgctatcc   8940
ggccaaacgc gaactccagt tcggcgaatg gcagcgtaat gatattctgg cgggtatctt   9000
tgaaccggcc accatcgaca ttgatctggc gatcctgctc accaaggccc gggagcatag   9060
cgtggccctc gtcggccccg cggccgagga acttttcgac ccggtgccgg aacaggatct   9120
gttcgaagca ctgaacgaga cgctgaccct gtggaactcc ccgccggatt gggcgggcga   9180
tgagcgcaat gtggtcctta cgctgagccg gatttggtac tcggcggtta ccggcaagat   9240
cgcgccgaag gatgtcgccg ccgactgggc gatggagcgc cttccggcgc aataccagcc   9300
cgtgatcctc gaagcgcgcc aagcctatct gggccaagaa gaagaccgtc tcgcgtcccg   9360
ggccgaccag ctcgaagaat tgtccactca tgtcaagggc gagatcacga aggtcgttgg   9420
caaataatgt ctagctagaa attcgttcaa gccgacgccg cttcgcggcg ggcttaact   9480 caagcgttag atgcactaag cacataattg ctcacagcca aactatcgat gagttgaagg   9540
accccgtaga aaagatcaaa ggatcttctt gagatccttt ttttctgcgc gtaatctgct   9600
gcttgcaaac aaaaaaacca ccgctaccag cggtggtttg tttgccggat caagagctac   9660
caactctttt tccgaaggta actggcttca gcagagcgca gataccaaat actgtccttc   9720
tagtgtagcc gtagttaggc caccacttca agaactctgt agcaccgcct acatacctcg   9780
ctctgctaat cctgttacca gtggctgctg ccagtggcga taagtcgtgt cttaccgggt   9840
tggactcaag acgatagtta ccggataagg cgcagcggtc gggctgaacg gggggttcgt   9900
gcacacagcc cagcttggag cgaacgacct acaccgaact gagatacccta cagcgtgagc    9960 tatgagaaag cgccacgctt cccgaaggga gaaaggcgga caggtatccg gtaagcggca  10020
```

```
gggtcggaac aggagagcgc acgagggagc ttccaggggg aaacgcctgg tatctttata   10080
gtcctgtcgg gtttcgccac ctctgacttg agcgtcgatt tttgtgatgc tcgtcagggg   10140
ggcggagcct atggaaaaac gccagcaacg cggcctttt  acggttcctg gccttttgct   10200
ggccttttgc tcacatgttc tttcctgcgt tatcccctga ttctgtggat aaccgtatta   10260
ccgcctttga gtgagctgat accgctcgcc gcagccgaac gaccgagcgc agcgagtcag   10320
tgagcgagga agcggaagag cgcctgatgc ggtattttct ccttacgcat ctgtgcggta   10380
tttcacaccg cataggccgc gataggccga cgcgaagcgg cggggcgtag ggagcgcagc   10440
gaccgaaggg taggcgcttt ttgcagctct tcggctgtgc gctggccaga cagttatgca   10500
caggccaggc gggttttaag agttttaata agttttaaag agtttaggc  ggaaaaatcg   10560 cctttttct  cttttatatc agtcacttac atgtgtgacc ggttcccaat gtacggcttt   10620
gggttcccaa tgtacgggtt ccggttccca atgtacggct ttgggttccc aatgtacgtg   10680
ctatccacag gaaagagacc ttttcgacct ttttcccctg ctagggcaat ttgccctagc   10740
atctgctccg tacattagga accggcggat gcttcgccct cgatcaggtt gcggtagcgc   10800
atgactagga tcgggccagc ctgccccgcc tcctccttca aatcgtactc cggcaggtca   10860
tttgacccga tcagcttgcg cacggtgaaa cagaacttct tgaactctcc ggcgctgcca   10920
ctgcgttcgt agatcgtctt gaacaaccat ctggcttctg ccttgcctgc ggcgcggcgt   10980
gccaggcggt agagaaaacg gccgatgccg gggtcgatca aaagtaatc  ggggtgaacc   11040 gtcagcacgt ccgggttctt gccttctgtg atctcgcggt acatccaatc agcaagctcg   11100
atctcgatgt actccggccg cccggtttcg ctctttacga tcttgtagcg gctaatcaag   11160
gcttcaccct cggataccgt caccaggcgg ccgttcttgg ccttcttggt acgctgcatg   11220
gcaacgtgcg tggtgtttaa ccgaatgcag gttttctacca ggtcgtcttt ctgctttccg   11280
ccatcggctc gccggcagaa cttgagtacg tccgcaacgt gtggacggaa cacgcggccg   11340
ggcttgtctc ccttcccttc ccggtatcgg ttcatggatt cggttagatg ggaaaccgcc   11400
atcagtacca ggtcgtaatc ccacacactg gccatgccgg cggggcctgc ggaaacctct   11460
acgtgcccgt ctggaagctc gtagcggatc acctcgccag ctcgtcggtc acgcttcgac   11520
agacggaaaa cggccacgtc catgatgctg cgactatcgc gggtgcccac gtcatagagc   11580
atcggaacga aaaatctgg  ttgctcgtcg cccttgggcg gcttcctaat cgacggcgca   11640
ccggctgccg gcggttgccg ggattctttg cggattcgat cagcggcccc ttgccacgat   11700
tcaccggggc gtgcttctgc ctcgatgcgt tgccgctggg cggcctgcgc ggccttcaac   11760
ttctccacca ggtcatcacc cagcgccgcg ccgatttgta ccgggccgga tggtttgcga   11820
ccgctcacgc cgattcctcg ggcttggggg ttccagtgcc attgcagggc cggcagacaa   11880
cccagccgct tacgcctggc caaccgcccg ttcctccaca catgggcat  tccacggcgt   11940 cggtgcctgg ttgttcttga ttttccatgc cgcctccttt agccgctaaa attcatctac   12000
tcatttattc atttgctcat ttactctggt agctgcgcga tgtattcaga tagcagctcg   12060
gtaatggtct tgccttggcg taccgcgtac atcttcagct tggtgtgatc ctccgccggc   12120
aactgaaagt tgacccgctt catggctggc gtgtctgcca ggctggccaa cgttgcagcc   12180
ttgctgctgc gtgcgctcgg acggccggca cttagcgtgt tgtgcttttt gctcatttc    12240 tctttacctc attaactcaa atgagttttg atttaatttc agcggccagc gcctggacct   12300
cgcgggcagc gtcgccctcg ggttctgatt caagaacggt tgtgccggcg gcggcagtgc   12360
```

```
ctgggtagct cacgcgctgc gtgatacggg actcaagaat gggcagctcg tacccggcca    12420
gcgcctcggc aacctcaccg ccgatgcgcg tgcctttgat cgcccgcgac acgacaaagg    12480
ccgcttgtag ccttccatcc gtgacctcaa tgcgctgctt aaccagctcc accaggtcgg    12540
cggtggccca aatgtcgtaa gggcttggct gcaccggaat cagcacgaag tcggctgcct    12600
tgatcgcgga cacagccaag tccgccgcct ggggcgctcc gtcgatcact acgaagtcgc    12660
gccggccgat ggccttcacg tcgcggtcaa tcgtcgggcg gtcgatgccg acaacggtta    12720
gcggttgatc ttcccgcacg gccgcccaat cgcgggcact gccctgggga tcggaatcga    12780
ctaacagaac atcggccccg gcgagttgca gggcgcgggc tagatgggtt gcatggtcg    12840
tcttgcctga cccgcctttc tggttaagta cagcgataac cttcatgcgt tccccttgcg    12900
tatttgttta tttactcatc gcatcatata cgcagcgacc gcatgacgca agctgtttta    12960
ctcaaataca catcacctttt ttagatgatc ak                                 12992
```

<210> SEQ ID NO 257
<211> LENGTH: 13688
<212> TYPE: DNA
<213> ORGANISM: artificial
<220> FEATURE:
<223> OTHER INFORMATION: vector sequence

<400> SEQUENCE: 257

```
gtgattttgt gccgagctgc cggtcgggga gctgttggct ggctggtggc aggatatatt      60
gtggtgtaaa caaattgacg cttagacaac ttaataacac attgcggacg tctttaatgt     120
actgaattta gttactgatc actgattaag tctagatatt gttttttgttt cacataaatg     180
tcgttttgga ttattcatgt aatattttaa actaaagtac aattttttgac tactttagtt     240
tactagttaa gcttttattt ttttgactaa ccattgaatg atgaagagat caacgcatca     300
tatttacaac ttacatagtc ttttggaagt gtaaattgct aatactacct aaaatatatc     360
tataattaac taatatttt tcgtcaatta taatagatca attaaaaggc tatcaaaagg      420
aaaaaaatga atccacatc ctgccatcat aacctcatgc tggaaaaaga atgaaaaaa       480
tataaaaaat ttcttttgtt tattaaattt acaactttaa tactagtttc ttttctattt     540
tttaaaagct tttgtcactt acttaaaaaa aaaaactttt ttgaaatatt cctacttcca     600
atgtctgatt agtgcttctg gatttccttt tggatcatg tgaatcctaa atcagaaaaa      660
ttcatataat acccaattca gtatatttc atacttcaat ttacaagagt tctctatgtt     720
tttagcttct ttcttttaag ccaaatgttt taagcatctt ttatacatta aaataattta     780
gtgttgagtt gagatttttt tttttttttt ttggatttac ttgttcaaaa tctgaaaaaa     840
tgtttacaga aggttaaaat gaaccaaaag gcatatcaag ctagattttg aattacccta     900
tttcatcgta tacacaaaac tgataatgtg gacacagttg attttacttc tcgatgacat     960
cgtagtttta tttaatttgg aaaccacggc ccatatgagc acatttcaat taaaaaccaa    1020
tggtaagagc atttcccatg caagattcga gagatattaa cccagtgact gttaaaacag    1080
cttagaaccc taataacgaa tttcaattac tcaatttacc attcgcattt cgcaataacc    1140
aaactgagcc agtcacaagg agtaaaccga accggattat ttattatataa aatgaaagaa    1200
aggaaaccaa acaacaacag cagtagtagt ctgacgtaaa ccaaaaagca ggcagatcaa    1260
caactaaaag aaactcaaat taccaaaaca aacaggaaat tgcaaactaa gtttttttac    1320
catatgcata caaagaccat aaaaggttct gataatcacc ggtttcatct ctcagtattt    1380
aatccggcca tctccttccg ttatgacatc gttgaaagtg ccaccattcg ggatcatcgg    1440
```

```
caacacatgt tcttggtgcg acaaatcac atccaacagg taaggtcctg gtgtatccag    1500
cattgtctga atagcttctc ggagatctgc tttctttgtc accctcgccg ctggaatccc    1560
gcaagctgct gcaaacagca acatgttcgg gaatatctcg tcctcctgag ccggatcccc    1620
gagaaatgtg tgagctcggt tagctttgta gaaccgatct tcccattgca taaccatgcc    1680
aagatgctgg ttgtttaata aaagtacctt cactggaaga ttctctacac gaatagtggc    1740
tagctcttgc acattcatta taaagcttcc atctccgtca atatccacaa ctatcgcatc    1800
agggttagca acagacgctc caatcgcagc aggaagtcca atcccatag ctccaaggcc    1860 tcctgatgat agccactgcc ttggtttctt gtaattgtag aactgcgccg cccacatttg    1920
atgttgcccg acaccagtac ttattatggc ttttccatca gtcaactcat caaggacctt    1980
aatcgcatac tgtggaggaa tagcttcccc aaacgtctta aagctcaacg gaaacttctg    2040
tttctgtacg ttcaactcat tcctccaaac tccaaaatca agcttaagct cctccgctcg    2100
gttctcaaga accttattca tcccttgcaa agccagctta acatcaccac acacagacac    2160
atgaggagtc ttattcttcc caatctcagc cgagtcaata tcaatatgaa caatcttagc    2220
cctactagca aaagcctcaa gcttacccgt gacacgatca tcaaaccta ccccaaacgc    2280 caacaacaaa tcactatgct ccacagcgta atttgcatac acagtcccat gcattccaag    2340
catatgtaac gacaactcat catcacaagg ataagatccc agccccatca acgtactcgc    2400
aacagggatc cccgtaagct caacaaacct acccaattca tcgctagaat caaacaacc    2460 accaccaaca tacaacacag gcttcttaga ctcagaaatc aacctaacaa tctgctccaa    2520
atgagaatct tccggaggtt taggcatcct agacatataa ccaggtaatc tcatagcctg    2580
ttcccaatta ggaatcgcaa gctgttgttg aatatcttta ggaacatcaa ccaaaacagg    2640
tccaggtcta ccagaagtag ctaaaaagaa agcttcctca ataatcctag ggatatcttc    2700
aacatccatc acaagatagt tatgcttcgt aatcgaacgc gttacctcaa caatcggagt    2760
ctcttgaaac gcatctgtac caatcatacg acgagggact tgtcctgtga ttgctacaag    2820
aggaacacta tctaacaacg catcggctaa tccgctaacg agatttgtag ctccgggacc    2880
tgaagtggct atacagatac ctggtttacc tgaggatcga gcgtatcctt ctgctgcgaa    2940
tacacctcct tgttcgtgac gaggaaggac gttacggatt gaggaagagc gggttaaggc    3000
ttggtgaatc tccattgatg tacctccagg gtaagcgaat acggtttcta cgccttgacg    3060
ttctaaagct tcgacgagga tatcagcgcc tttgcggggt tgatctggag cgaatcggga    3120
gatgaatgtt tcgggtttgg taggtttggt tggagaggga gtggttgtga cattggtggt    3180
tgtgttgagc acggcggaga tggaggaggg agagctggat ttgataccgc ggcggcggga    3240
ggaggaggat gatttgttgg ggtttaggga gaatgggagg gagaatctgg agattggtaa    3300
tggtgatttg gaggaggaag gagatggttt ggtggagaag gagatcgaag aagatgttgt    3360
tgttgttgtt gttgccgccg ccatggttca gctgcacata cataacatat caagatcaga    3420
acacacatat acacacacaa atacaatcaa gtcaacaact ccaaaaagtc cagatctaca    3480
tatatacata cgtaaataac aaaatcatgt aaataatcac aatcatgtaa tccagatcta    3540
tgcacatata tatatacaca attaataaaa aaaatgatat aacagatcta tatctatgta    3600
tgtaacaaca caatcagatg agagaagtga tgttttcaga tctgtataca tacaaacaca    3660
aacagatgaa caattgatac gtagatccat atgtatacgt acaattagct acacgattaa    3720
atgaaaaaaa tcaacgattt cggattggta cacacaaacg caacaatatg aagaaattca    3780
```

```
tatctgatta gatataaaca taaccacgtg tagatacaca gtcaaatcaa caaatttata    3840
gcttctaaac ggatgagatg aacaagataa agatattcac ataaggcata cataagataa    3900
gcagattaac aaactagcaa taatacatac ctaattaaaa caaggaataa cagagagaga    3960
gagagagaga gagatttacc ttgaaaatga agaggagaag agaggatttc ttaaaattgg    4020
gggtagagaa agaaagatga tgaattgtga gaaggagag atagaagggg gggttgtata     4080
tataggctgt agaagattat ttttgtgttt gaggcggtga aggaagaggg gatctgacta    4140
tgacacgttt gcggttacgt atttcgatag gagtctttca acgcttaacg ccgttactct    4200
atatgaccgt ttgggccgta acggggccgt tgttaacgc tgatgttgat tcttttcttt     4260
ctttctttct tcctttttta aagaagcaat tgtacaatcg ttgctagctg tcaaacggat    4320
aattcggata cggatatgcc tatattcata tccgtaattt ttggattcga attgactgcg    4380
atcgccaatt gacgcgtact agtgtacaag cttgcggccg cgaattcggt acatccggcc    4440
agtgaattat caactatgta taataaagtt gccatgatta cgccaagctt gcatgcccat    4500
atgctcgagg cggccgcaga tatcagatct ggtcgaccta aggatcccc gggtaccca     4560
ctttgtacaa gaaagctggg tccatgatta cgccaagctt gcatgcccat atgctcgagg    4620
cggccgcaga tatcagatct ggtcgaccta aggatcccc gggtaccagc ctgcttttt     4680
gtacaaactt gccatgatta cgccaagctt gaattcccga tctagtaaca tagatgacac    4740
cgcgcgcgat aatttatcct agtttgcgcg ctatattttg ttttctatcg cgtattaaat    4800
gtataattgc gggactctaa tcataaaaac ccatctcata aataacgtca tgcattacat    4860
gttaattatt acatgcttaa cgtaattcaa cagaaattat atgataatca tcgcaagacc    4920
ggcaacagga ttcaatctta agaaacttta ttgccaaatg tttgaacgat cggggaaatt    4980
cgagcccata tgctcgaggc ggccttactc ggtagcaatt cccgaggctg tagccgacga    5040
tggtgcgcca ggagagttgt tgattcattg tttgcctccc tgctgcggtt tttcaccgaa    5100
gttcatgcca gtccagcgtt tttgcagcag aaaagccgcc gacttcggtt tgcggtcgcg    5160
agtgaagatc cctttcttgt taccgccaac gcgcaatatg ccttgcgagg tcgcaaaatc    5220
ggcgaaattc catacctgtt caccgacgac ggcgctgacg cgatcaaaga gcggtgata    5280
catatccagc catgcacact gatactcttc actccacatg tcggtgtaca ttgagtgcag    5340
cccggctaac gtatccacgc cgtattcggt gatgataatc ggctgatgca gtttctcctg    5400
ccaggccaga agttcttttt ccagtacctt ctctgccgtt tccaaatcgc cgctttggac    5460
ataccatccg taataacggt tcaggcacag cacatcaaag agatcgctga tggtatcggt    5520
gtgagcgtcg cagaacatta cattgacgca ggtgatcgga cgcgtcgggt cgagtttacg    5580
cgttgcttcc gccagtggcg cgaaatattc ccgtgcacct tgcggacggg tatccggttc    5640
gttggcaata ctccacatca ccacgcttgg gtggtttttg tcacgcgcta tcagctcttt    5700
aatcgcctgt aagtgcgctt gctgagtttc ccgttgact gcctcttcgc tgtacagttc     5760
tttcggcttg ttgcccgctt cgaaaccaat gcctaaagag aggttaaagc cgacagcagc    5820
agtttcatca atcaccacga tgccatgttc atctgcccag tcgagcatct cttcagcgta    5880
agggtaatgc gaggtacggt aggagttggc cccaatccag tccattaatg cgtggtcgtg    5940
caccatcagc acgttatcga atcctttgcc acgcaagtcc gcatcttcat gacgaccaaa    6000
gccagtaaag tagaacggtt tgtggttaat caggaactgt tcgcccttca ctgccactga    6060
ccggatgccg acgcgaagcg ggtagatatc acactctgtc tggcttttgg ctgtgacgca    6120
cagttcatag agataaccctt cacccggttg ccagaggtgc ggattcacca cttgcaaagt   6180
```

```
cccgctagtg ccttgtccag ttgcaaccac ctgttgatcc gcatcacgca gttcaacgct   6240
gacatcacca ttggccacca cctgccagtc aacagacgcg tggttacagt cttgcgcgac   6300
atgcgtcacc acggtgatat cgtccaccca ggtgttcggc gtggtgtaga gcattacgct   6360
gcgatggatt ccggcatagt taaagaaatc atggaagtaa gactgctttt tcttgccgtt   6420
ttcgtcggta atcaccattc ccggcgggat agtctgccag ttcagttcgt tgttcacaca   6480
aacggtgata cctgcacatc aacaaatttt ggtcatatat tagaaaagtt ataaattaaa   6540
atatacacac ttataaacta cagaaaagca attgctatat actacattct tttattttga   6600
aaaaaatatt tgaaatatta tattactact aattaatgat aattattata tatatatcaa   6660
aggtagaagc agaaacttac gtacactttt cccggcaata acatacggcg tgacatcggc   6720
ttcaaatggc gtatagccgc cctgatgctc catcacttcc tgattattga cccacacttt   6780
gccgtaatga gtgaccgcat cgaaacgcag cacgatacgc tggcctgccc aacctttcgg   6840
tataaagact tcgcgctgat accagacgtt gcccgcataa ttacgaatat ctgcatcggc   6900
gaactgatcg ttaaaactgc ctggcacagc aattgcccgg ctttcttgta acgcgctttc   6960
ccaccaacgc tgaccaattc cacagttttc gcgatccaga ctgaatgccc acaggccgtc   7020 gagtttttg atttcacggg ttggggtttc tacaggacgt accatggtta attaatttca   7080
atctctccct ctctatctcc tacgctacac aacacatcac atcaatgatc ttatcttata   7140
cttttttttt ttgtttcctg atactattat gcatgaactg gaaagtacaa tagtttaaga   7200
agaaaagctt accttaacag atggcgaacg gagaattggg aatctaatct gcgacctcga   7260
attgagaccc tacgagcaag tgtagagatt aaataagcag ctgttggatg aggtggcaag   7320
tgttctcctt ttctctatt ttgtttttag tttctacttt tgacgcgaaa tcgtaatgta   7380
atgagaatca atggatctgg attctgaacg ttcacgggaa gaatggggaa acattaaagt   7440
ttcaggcaaa gcccgtgctg agtgctcaac caccaaccaa tattgttgtc ttcaacaacc   7500
ccatgcaaat aaataccatt cgccccatgc aaagtgtaca ataactcaac aactaactac   7560
tggtgtaatc ttcagcgatt ctttcaatta ttctaaaact ggtttagtta cattattatt   7620
ttccttcaat taacatgaaa attgcatcaa tgtattcaac accttgatga cgacatgtct   7680
actagtcaaa tgctttaatc tgaaacgttt ctattgaaat tcttcttctt atagagcaac   7740
attgtagtct tgtgagttta tcatgtcgtt ttaatacttt tgttttgcaa gacgtaaaaa   7800
taaacaagca actcagttga gtttatccat agagcttatc ttttcagcaa aattaaccac   7860
gaacgagtaa ttgactttgt caatggaatg caccgtagac ctttcaacaa caccacattt   7920
ttcatgatac tttcaaataa tatgctcgca ataccattc gtcctatgcg tactgtaact   7980
attggagtag cctttagcaa aaattttata aaaaaaatg gtttgaatct gattattaag   8040
tcattatatg tcgtttcatt gttgattctg gcatactcct cccggcgcgc gttgctatat   8100
gcctcattag tttgtctccc cctccccctc tcttccccaa ccattagatt aaccttatat   8160
ctcccacaac tatagcaacc taaaatgaca tgtttaacag tcaaatgctt caattcgaaa   8220
tatttagatt cattgaaact cttgttctgt ttctggatca tgttatcaca agtaatcccc   8280
aacgaatgtc ttacgagttt ctcgtggtgt gtttaaagtt taatgttttt ccaagacagc   8340
tacatccata atcccacaaa ctacatataa aaagatgatt gattctagga tgggaaagct   8400
catcaaattt cccaccgtga gaaacatatg atacgttaga tatgaatatc ttgtaattaa   8460
tgcactagaa tatattttta taagaaaata aaaaacattg ttcactcgtt cctatcccrt   8520
```

```
cccttccaag cccaactcac cgacccttc tcctaccacc acccgctacc tagctcgacc    8580
ccgctggtgt cctccgtgcc tatcgaagtt gatgttaatt ggcaccatct tctgcttcat    8640
catccgctct atcgtcgcac catacagttg tcgacgccac aagtgaggtg cacattatca    8700
tctttagggt tgccttgttg tcgcactcgc aatgttccaa gatagggagc aatgagattt    8760
tagagcaaca aaattcttgt tatttatt taaattgtgc agaacaaata aaggccttga      8820
ttgagaggta cccaactttt ctatacaaag ttgatagctt ggcgtaatcg atgtaccgat    8880
atcaatttaa attggccggc cgagctccct gcagggggcc cggcgcgcct ctagattaat    8940
taaaggcctt agttactaat cagtgatcag attgtcgttt cccgccttca gtttaaacta    9000
tcagtgtttg acaggatata ttggcgggta aacctaagag aaaagagcgt ttattagaat    9060
aatcggatat ttaaaagggc gtgaaaaggt ttatccgttc gtccatttgt atgtcaatat    9120
ccatgataag tcgcgctgta tgtgtttgtt tgaatattca tggaacgcag tggcggtttt    9180
catggcttgt tatgactgtt tttttggggt acagtctatg cctcgggcat ccaagcagca    9240
agcgcgttac gccgtgggtc gatgtttgat gttatggagc agcaacgatg ttacgcagca    9300
gggcagtcgc cctaaaacaa agttaaacat catgggtgaa gcggtcatcg ccgaggtgtc    9360
cacccagctg tcggaagtcg tgggtgtcat cgagcgccac ctcgaaccga ccctcctcgc    9420
cgtgcatctg tatggtagcg ccgttgacgg cggccttaag ccccattcgg acatcgacct    9480
gcttgtcacc gttaccgtcc gtctcgacga gaccacgcgc cgcgcgctta tcaacgacct    9540
tctggaaacg tccgcctccc ccggcgagag cgaaatcctg cgcgcggttg aggtgacgat    9600
tgtggtgcac gatgacatca tcccctggcg ctatccggcc aaacgcgaac tccagttcgg    9660
cgaatggcag cgtaatgata ttctggcggg tatctttgaa ccggccacca tcgacattga    9720
tctggcgatc ctgctcacca aggcccggga gcatagcgtg gccctcgtcg gccccgcggc    9780
cgaggaactt ttcgacccgg tgccggaaca ggatctgttc gaagcactga acgagacgct    9840
gaccctgtgg aactccccgc cggattgggc gggcgatgag cgcaatgtgg tccttacgct    9900
gagccggatt tggtactcgg cggttaccgg caagatcgcg ccgaaggatg tcgccgccga    9960
ctgggcgatg gagcgccttc cggcgcaata ccagcccgtg atcctcgaag cgcgccaagc    10020
ctatctgggc caagaagaag accgtctcgc gtcccgggcc gaccagctcg aagaatttgt    10080
ccactatgtc aagggcgaga tcacgaaggt cgttggcaaa taatgtctag ctagaaattc    10140
gttcaagccg acgccgcttc gcggcgcggc ttaactcaag cgttagatgc actaagcaca    10200
taattgctca cagccaaact atcgatgagt tgaaggaccc cgtagaaaag atcaaaggat    10260
cttcttgaga tccttttttt ctgcgcgtaa tctgctgctt gcaaacaaaa aaaccaccgc    10320
taccagcggt ggtttgtttg ccggatcaag agctaccaac tcttttccg aaggtaactg    10380
gcttcagcag agcgcagata ccaaatactg tccttctagt gtagccgtag ttaggccacc    10440
acttcaagaa ctctgtagca ccgcctacat acctcgctct gctaatcctg ttaccagtgg    10500
ctgctgccag tggcgataag tcgtgtctta ccgggttgga ctcaagacga tagttaccgg    10560
ataaggcgca gcggtcgggc tgaacggggg gttcgtgcac acagcccagc ttggagcgaa    10620
cgacctacac cgaactgaga tacctacagc gtgagctatg agaaagcgcc acgcttcccg    10680
aagggagaaa ggcggacagg tatccggtaa gcggcagggt cggaacagga gagcgcacga    10740
gggagcttcc agggggaaac gcctggtatc tttatagtcc tgtcgggttt cgccacctct    10800
gacttgagcg tcgatttttg tgatgctcgt caggggggcg gagcctatgg aaaaacgcca    10860
gcaacgcggc cttttacgg ttcctggcct tttgctggcc ttttgctcac atgttctttc    10920
```

```
ctgcgttatc ccctgattct gtggataacc gtattaccgc ctttgagtga gctgataccg    10980
ctcgccgcag ccgaacgacc gagcgcagcg agtcagtgag cgaggaagcg gaagagcgcc    11040
tgatgcggta ttttctcctt acgcatctgt gcggtatttc acaccgcata ggccgcgata    11100
ggccgacgcg aagcggcggg gcgtaggag cgcagcgacc gaagggtagg cgcttttgc      11160
agctcttcgg ctgtgcgctg gccagacagt tatgcacagg ccaggcgggt tttaagagtt    11220
ttaataagtt ttaaagagtt ttaggcggaa aaatcgcctt ttttctcttt tatatcagtc    11280
acttacatgt gtgaccggtt cccaatgtac ggctttgggt tcccaatgta cgggttccgg    11340
ttcccaatgt acggctttgg gttcccaatg tacgtgctat ccacaggaaa gagacctttt    11400
cgacctttt cccctgctag ggcaatttgc cctagcatct gctccgtaca ttaggaaccg    11460
gcggatgctt cgccctcgat caggttgcg tagcgcatga ctaggatcgg ccagcctgc      11520
cccgcctcct ccttcaaatc gtactccggc aggtcatttg acccgatcag cttgcgcacg    11580
gtgaaacaga acttcttgaa ctctccggcg ctgccactgc gttcgtagat cgtcttgaac    11640
aaccatctgg cttctgcctt gcctgcggcg cggcgtgcca ggcggtagag aaaacggccg    11700
atgccggggt cgatcaaaaa gtaatcgggg tgaaccgtca gcacgtccgg gttcttgcct    11760
tctgtgatct cgcggtacat ccaatcagca agctcgatct cgatgtactc cggccgcccg    11820
gtttcgctct ttacgatctt gtagcggcta atcaaggctt cacccctcgga taccgtcacc    11880
aggcggccgt tcttggcctt cttggtacgc tgcatggcaa cgtgcgtggt gtttaaccga    11940
atgcaggttt ctaccaggtc gtctttctgc tttccgccat cggctcgccg gcagaacttg    12000
agtacgtccg caacgtgtgg acggaacacg cggccgggct tgtctcccct cccttcccgg    12060
tatcggttca tggattcggt tagatgggaa accgccatca gtaccaggtc gtaatcccac    12120
acactggcca tgccggcggg gcctgcggaa acctctacgt gcccgtctgg aagctcgtag    12180
cggatcacct cgccagctcg tcggtcacgc ttcgacagac ggaaaacggc cacgtccatg    12240
atgctgcgac tatcgcgggt gcccacgtca tagagcatcg gaacgaaaaa atctggttgc    12300
tcgtcgccct tgggcggctt cctaatcgac ggcgcaccgg ctgccggcgg ttgccgggat    12360
tctttgcgga ttcgatcagc ggccccttgc cacgattcac cggggcgtgc ttctgcctcg    12420
atgcgttgcc gctgggcggc ctgcgcggcc ttcaacttct ccaccaggtc atcacccagc    12480
gccgcgccga tttgtaccgg gccggatggt ttgcgaccgc tcacgccgat tcctcgggct    12540
tggggttcc agtgccattg cagggccggc agacaaccca gccgcttacg cctggccaac    12600
cgcccgttcc tccacacatg gggcattcca cggcgtcggt gcctggttgt tcttgatttt    12660
ccatgccgcc tcctttagcc gctaaaattc atctactcat ttattcattt gctcatttac    12720
tctggtagct gcgcgatgta ttcagatagc agctcggtaa tggtcttgcc ttggcgtacc    12780
gcgtacatct tcagcttggt gtgatcctcc gccggcaact gaaagttgac ccgcttcatg    12840
gctgcgtgt ctgccaggct ggccaacgtt gcagccttgc tgctgcgtgc gctcggacgg    12900
ccggcactta gcgtgtttgt gcttttgctc attttctctt tacctcatta actcaaatga    12960
gttttgattt aatttcagcg gccagcgcct ggacctcgcg ggcagcgtcg ccctcgggtt    13020
ctgattcaag aacggttgtg ccggcggcgg cagtgcctgg gtagctcacg cgctgcgtga    13080
tacgggactc aagaatgggc agctcgtacc cggccagcgc ctcggcaacc tcaccgccga    13140
tgcgcgtgcc tttgatcgcc cgcgacacga caaaggccgc ttgtagcctt ccatccgtga    13200
cctcaatgcg ctgcttaacc agctccacca ggtcggcggt gcccaaatg tcgtaagggc    13260
```

```
ttggctgcac cggaatcagc acgaagtcgg ctgccttgat cgcggacaca gccaagtccg    13320
ccgcctgggg cgctccgtcg atcactacga agtcgcgccg gccgatggcc ttcacgtcgc    13380
ggtcaatcgt cgggcggtcg atgccgacaa cggttagcgg ttgatcttcc cgcacggccg    13440
cccaatcgcg ggcactgccc tgggatcgg aatcgactaa cagaacatcg gccccggcga     13500
gttgcagggc gcgggctaga tgggttgcga tggtcgtctt gcctgacccg cctttctggt    13560
taagtacagc gataaccttc atgcgttccc cttgcgtatt tgtttattta ctcatcgcat    13620
catatacgca gcgaccgcat gacgcaagct gttttactca aatacacatc accttttag     13680 atgatcak                                                              13688

<210> SEQ ID NO 258
<211> LENGTH: 12984
<212> TYPE: DNA
<213> ORGANISM: artificial
<220> FEATURE:
<223> OTHER INFORMATION: vector sequence

<400> SEQUENCE: 258
gtgattttgt gccgagctgc cggtcgggga gctgttggct ggctggtggc aggatatatt      60
gtggtgtaaa caaattgacg cttagacaac ttaataacac attgcggacg tctttaatgt     120
actgaattta gttactgatc actgattaag tctagatatt gttttgtttt cacataaatg     180
tcgttttgga ttattcatgt aatattttaa actaaagtac aatttttgac tactttagtt     240
tactagttaa gcttttattt ttttgactaa ccattgaatg atgaagagat caacgcatca     300
tatttacaac ttacatagtc ttttggaagt gtaaattgct aatactacct aaaatatatc     360
tataattaac taatatttt tcgtcaatta aatagatca attaaaaggc tatcaaaagg       420
aaaaaaatga atccacatc ctgccatcat aacctcatgc tggaaaaaga aatgaaaaaa      480
tataaaaaat ttcttttgtt tattaaattt acaactttaa tactagtttc ttttctattt    540
tttaaaagct tttgtcactt acttaaaaaa aaaaaacttt ttgaaatatt cctacttcca    600
atgtctgatt agtgcttctg gatttccttt ttggatcatg tgaatcctaa atcagaaaaa   660
ttcatataat acccaattca gtatattttc atacttcaat ttacaagagt tctctatgtt    720
tttagcttct ttcttttaag ccaaatgttt taagcatctt ttatacatta aataatttta   780
gtgttgagtt gagattttt ttttttttt ttggatttac ttgttcaaaa tctgaaaaaa    840
tgtttacaga aggttaaaat gaaccaaaag gcatatcaag ctagattttg aattacccta    900
tttcatcgta tacacaaaac tgataatgtg gacacagttg attttacttc tcgatgacat    960 cgtagttta tttaatttgg aaaccacggc ccatatgagc acattcaat taaaaaccaa     1020 tggtaagagc atttccatg caagattcga gagatattaa cccagtgact gttaaaacag    1080
cttagaaccc taataacgaa tttcaattac tcaattacc attcgcattt cgcaataacc    1140
aaactgagcc agtcacaagg agtaaaccga accggattat ttatttataa aatgaaagaa   1200
aggaaaccaa acaacaacag cagtagtagt ctgacgtaaa ccaaaaagca ggcagatcaa    1260
caactaaaag aaactcaaat taccaaaaca aacaggaaat tgcaaactaa gttttttta   1320 catatgcata caaagaccat aaaaggttct gataatcacc ggtttcatct ctcagtattt    1380
aatccggcca tctccttccg ttatgacatc gttgaaagtg ccaccattcg ggatcatcgg   1440
caacacatgt tcttggtgcg acaaatcac atccaacagg taaggtcctg gtgtatccag    1500
cattgtctga atagcttctc ggagatctgc tttcttgtc accctcgccg ctggaatccc   1560
gcaagctgct gcaaacagca acatgttcgg gaatatctcg tcctcctgag ccggatcccc   1620
```

```
gagaaatgtg tgagctcggt tagctttgta gaaccgatct tcccattgca taaccatgcc   1680
aagatgctgg ttgtttaata aaagtacctt cactggaaga ttctctacac gaatagtggc   1740
tagctcttgc acattcatta taaagcttcc atctccgtca atatccacaa ctatcgcatc   1800
agggttagca acagacgctc caatcgcagc aggaagtcca aatcccatag ctccaaggcc   1860
tcctgatgat agccactgcc ttggtttctt gtaattgtag aactgcgccg cccacatttg   1920
atgttgcccg acaccagtac ttattatggc ttttccatca gtcaactcat caaggacctt   1980
aatcgcatac tgtggaggaa tagcttcccc aaacgtctta aagctcaacg gaaacttctg   2040
tttctgtacg ttcaactcat tcctccaaac tccaaaatca agcttaagct cctccgctcg   2100
gttctcaaga accttattca tcccttgcaa agccagctta acatcaccac acacagacac   2160
atgaggagtc ttattcttcc caatctcagc cgagtcaata tcaatatgaa caatcttagc   2220
cctactagca aaagcctcaa gcttacccgt gacacgatca tcaaaccttc ccccaaacgc   2280
caacaacaaa tcactatgct ccacagcgta atttgcatac acagtcccat gcattccaag   2340
catatgtaac gacaactcat catcacaagg ataagatccc agccccatca acgtactcgc   2400
aacagggatc cccgtaagct caacaaacct acccaattca tcgctagaat tcaaacaacc   2460
accaccaaca tacaacacag gcttcttaga ctcagaaatc aacctaacaa tctgctccaa   2520
atgagaatct tccggaggtt taggcatcct agacatataa ccaggtaatc tcatagcctg   2580
ttcccaatta ggaatcgcaa gctgttgttg aatatcttta ggaacatcaa ccaaaacagg   2640
tccaggtcta ccagaagtag ctaaaaagaa agcttcctca ataatcctag ggatatcttc   2700
aacatccatc acaagatagt tatgcttcgt aatcgaacgc gttacctcaa caatcggagt   2760
ctcttgaaac gcatctgtac caatcatacg acgagggact tgtcctgtga ttgctacaag   2820
aggaacacta tctaacaacg catcggctaa tccgctaacg agatttgtag ctccgggacc   2880
tgaagtggct atacagatac ctggtttacc tgaggatcga gcgtatcctt ctgctgcgaa   2940
tacacctcct tgttcgtgac gaggaaggac gttacggatt gaggaagagc gggttaaggc   3000
ttggtgaatc tccattgatg tacctccagg gtaagcgaat acggtttcta cgccttgacg   3060
ttctaaagct tcgacgagga tatcagcgcc tttgcgtggg tgatctggag cgaatcggga   3120
gatgaatgtt tcgggtttgg taggtttggt tggagaggga gtggttgtga cattggtggt   3180
tgtgttgagc acggcggaga tggaggaggg agagctggat ttgataccgc ggcggcggga   3240
ggaggaggat gatttgttgg ggtttaggga gaatgggagg gagaatctgg agattggtaa   3300
tggtgatttg gaggaggaag gagatggttt ggtggagaag gagatcgaag aagatgttgt   3360
tgttgttgtt gttgccgccg ccatggttca gctgcacata cataacatat caagatcaga   3420
acacacatat acacacacaa atacaatcaa gtcaacaact ccaaaaagtc cagatctaca   3480
tatatacata cgtaaataac aaaatcatgt aaataatcac aatcatgtaa tccagatcta   3540
tgcacatata tatatacaca attaataaaa aaaatgatat aacagatcta tatctatgta   3600
tgtaacaaca caatcagatg agagaagtga tgttttcaga tctgtataca tacaaacaca   3660
aacagatgaa caattgatac gtagatccat atgtatacgt acaattagct acacgattaa   3720
atgaaaaaaa tcaacgattt cggattggta cacacaaacg caacaatatg aagaaattca   3780
tatctgatta gatataaaca taaccacgtg tagatacaca gtcaaatcaa caaatttata   3840
gcttctaaac ggatgagatg aacaagataa agatattcac ataaggcata cataagataa   3900
gcagattaac aaactagcaa taatacatac ctaattaaaa caaggaataa cagagagaga   3960
```

```
gagagagaga gagatttacc ttgaaaatga agaggagaag agaggatttc ttaaaattgg    4020
gggtagagaa agaaagatga tgaattgtga gaaaggagag atagaagggg gggttgtata    4080
tataggctgt agaagattat ttttgtgttt gaggcggtga aggaagaggg gatctgacta    4140
tgacacgttt gcggttacgt atttcgatag gagtctttca acgcttaacg ccgttactct    4200
atatgaccgt ttgggccgta acggggccgt ttgttaacgc tgatgttgat tcttttcttt    4260
ctttctttct tcctttttta aagaagcaat tgtacaatcg ttgctagctg tcaaacggat    4320
aattcggata cggatatgcc tatattcata tccgtaattt ttggattcga attgactgcg    4380
atcgccaatt gacgcgtact agtgtacaag cttgcggccg cgaattcggt acatccggcc    4440
agtgaattat caactatgta taataaagtt gccatgatta cgccaagctt gcatgcccat    4500
atgctcgagg cggccgcaga tatcagatct ggtcgaccta aggatccccc gggtacccca    4560
ctttgtacaa gaaagctggg tccatgatta cgccaagctt gcatgcccat atgctcgagg    4620
cggccgcaga tatcagatct ggtcgaccta aggatccccc gggtaccagc ctgctttttt    4680
gtacaaactt gccatgatta cgccaagctt gaattcccga tctagtaaca tagatgacac    4740
cgcgcgcgat aatttatcct agtttgcgcg ctatattttg ttttctatcg cgtattaaat    4800
gtataattgc gggactctaa tcataaaaac ccatctcata ataacgtca tgcattacat    4860
gttaattatt acatgcttaa cgtaattcaa cagaaattat atgataatca tcgcaagacc    4920
ggcaacagga ttcaatctta agaaacttta ttgccaaatg tttgaacgat cggggaaatt    4980
cgagcccata tgctcgaggc ggccttactc ggtagcaatt cccgaggctg tagccgacga    5040
tggtgcgcca ggagagttgt tgattcattg tttgcctccc tgctgcggtt tttcaccgaa    5100
gttcatgcca gtccagcgtt tttgcagcag aaaagccgcc gacttcggtt tgcggtcgcg    5160
agtgaagatc cctttcttgt taccgccaac gcgcaatatg ccttgcgagg tcgcaaaatc    5220
ggcgaaattc catacctgtt caccgacgac ggcgctgacg cgatcaaaga cgcggtgata    5280
catatccagc catgcacact gatactcttc actccacatg tcggtgtaca ttgagtgcag    5340
cccggctaac gtatccacgc cgtattcggt gatgataatc ggctgatgca gtttctcctg    5400
ccaggccaga agttcttttt ccagtacctt ctctgccgtt tccaaatcgc cgcttttggac   5460
ataccatccg taataacggt tcaggcacag cacatcaaag agatcgctga tggtatcggt    5520
gtgagcgtcg cagaacatta cattgacgca ggtgatcgga cgcgtcgggt cgagtttacg    5580
cgttgcttcc gccagtggcg cgaaatattc ccgtgcacct tgcggacggg tatccggttc    5640
gttggcaata ctccacatca ccacgcttgg gtggttttg tcacgcgcta tcagctcttt    5700
aatcgcctgt aagtgcgctt gctgagtttc cccgttgact gcctcttcgc tgtacagttc    5760
tttcggcttt tgcccgctt cgaaaccaat gcctaaagag aggttaaagc cgacagcagc    5820
agtttcatca atcaccacga tgccatgttc atctgcccag tcgagcatct cttcagcgta    5880
agggtaatgc gaggtacggt aggagttggc cccaatccag tccattaatg cgtggtcgtg    5940
caccatcagc acgttatcga atcctttgcc acgcaagtcc gcatcttcat gacgaccaaa    6000
gccagtaaag tagaacggtt tgtggttaat caggaactgt tcgcccttca ctgccactga    6060
ccggatgccg acgcgaagcg ggtagatatc acactctgtc tggcttttgg ctgtgacgca    6120
cagttcatag agataacctt cacccggttg ccagaggtgc ggattcacca cttgcaaagt    6180
cccgctagtg ccttgtccag ttgcaaccac ctgttgatcc gcatcacgca gttcaacgct    6240
gacatcacca ttgccaccac cctgccagtc aacagacgcg tggttacagt cttgcgcgac    6300
atgcgtcacc acggtgatat cgtccaccca ggtgttcggc gtggtgtaga gcattacgct    6360
```

```
gcgatggatt ccggcatagt taaagaaatc atggaagtaa gactgctttt tcttgccgtt    6420
ttcgtcggta atcaccattc ccggcgggat agtctgccag ttcagttcgt tgttcacaca    6480
aacggtgata cctgcacatc aacaaatttt ggtcatatat tagaaaagtt ataaattaaa    6540
atatacacac ttataaacta cagaaaagca attgctatat actacattct tttattttga    6600
aaaaaatatt tgaaatatta tattactact aattaatgat aattattata tatatatcaa    6660
aggtagaagc agaaacttac gtacactttt cccggcaata acatacggcg tgacatcggc    6720
ttcaaatggc gtatagccgc cctgatgctc catcacttcc tgattattga cccacacttt    6780
gccgtaatga gtgaccgcat cgaaacgcag cacgatacgc tggcctgccc aaccttccgg    6840
tataaagact tcgcgctgat accagacgtt gcccgcataa ttacgaatat ctgcatcggc    6900
gaactgatcg ttaaaactgc ctggcacagc aattgcccgg cttcttgta acgcgctttc    6960 ccaccaacgc tgaccaattc cacagttttc gcgatccaga ctgaatgccc acaggccgtc    7020 gagtttttg atttcacggg ttggggtttc tacaggacgt accatggtta attaacaagg    7080
gagtggaata acttgttggc aagagaagct tctttcttt cttgttcaat tttgaaacga    7140
tttttggcag aggagaaatg gacaaagtca caaaggttct tctttcagga aaaccgagaa    7200 agcactttt aatccatttt taatttggtg attgatgaac caacgctgaa gagaggatgg    7260
aacctgaaat cacgtggcag ttatctaaag gcgagagagg agaattcaaa agttattaag    7320
acacacaggg tttgtgagat gtagaacctg catgtgggtc atcaccatt tatgcaacacc    7380 aacaaaaatt aatgcaagga ttttctaag atgctttgcg ctttgccta gccaactttt    7440 ggaacataat ggtccaagcc ttctcttac ctatttacct ctttttctt ttttttccaa     7500 ataatagact tgtcctctaa ctccttcagg gtccccatgt ttttgttata aaagtacat    7560 tcaacgctac attatatata cttcgggaat taaatcttcg tatctctgtg tttacttaat    7620
tagtagtctc aattctcaag catatataca ttcggattac tcgatttgga agagagaatg    7680
gaacgtttat tattacgtac tgcgcgccgc tactagtata atattattaa aagtttaaac    7740
catactcaga gaataattgt taacagtatg tgactactcc atcttgatga atagtgattg    7800
cattagcatt tagctaacat tagattgtcg caatgtcagc tgtaatttc acgaaacaat    7860 acagcttgcc tggaaaaccc atggccgaag gaaagggaga aaacagcaaa gaaatacaat    7920
aaactaaagg aaaataaaac agaaagttag ccataattat agtcatgtaa tgcatattga    7980
aggtgctgga acgtgtgata gcatcacata tgtcacgtga actctttatc ataaaaacca    8040
tcgaatgatt atgttcttca ctttgtgatt aattagtcct tgatcaactt gtcaacttga    8100
ccatgcctta aataaacatc ccggtaccca actttctat acaaagttga tagcttggcg    8160
taatcgatgt accgatatca atttaaattg gccggccgag ctccctgcag ggggccggc    8220 gcgcctctag attaattaaa ggccttagtt actaatcagt gatcagattg tcgtttcccg    8280
ccttcagttt aaactatcag tgtttgacag gatatattgg cgggtaaacc taagagaaaa    8340
gagcgtttat tagaataatc ggatatttaa aagggcgtga aaaggtttat ccgttcgtcc    8400
atttgtatgt caatatccat gataagtcgc gctgtatgtg tttgtttgaa tattcatgga    8460
acgcagtggc ggttttcatg gcttgttatg actgtttttt tggggtacag tctatgcctc    8520
gggcatccaa gcagcaagcg cgttacgccg tgggtcgatg tttgatgtta tggagcagca    8580
acgatgttac gcagcagggc agtcgcccta aacaaagtt aaacatcatg gtgaagcgg    8640 tcatcgccga ggtgtccacc cagctgtcgg aagtcgtggg tgtcatcgag cgccacctcg    8700
```

```
aaccgaccct cctcgccgtg catctgtatg gtagcgccgt tgacggcggc cttaagcccc   8760
attcggacat cgacctgctt gtcaccgtta ccgtccgtct cgacgagacc acgcgccgcg   8820
cgcttatcaa cgaccttctg gaaacgtccg cctcccccgg cgagagcgaa atcctgcgcg   8880
cggttgaggt gacgattgtg gtgcacgatg acatcatccc ctggcgctat ccggccaaac   8940
gcgaactcca gttcggcgaa tggcagcgta atgatattct ggcgggtatc tttgaaccgg   9000
ccaccatcga cattgatctg gcgatcctgc tcaccaaggc ccgggagcat agcgtggccc   9060
tcgtcggccc cgcggccgag gaacttttcg acccggtgcc ggaacaggat ctgttcgaag   9120
cactgaacga gacgctgacc ctgtggaact ccccgccgga ttgggcgggc gatgagcgca   9180
atgtggtcct tacgctgagc cggatttggt actcggcggt taccggcaag atcgcgccga   9240
aggatgtcgc cgccgactgg gcgatggagc gccttccggc gcaataccag cccgtgatcc   9300
tcgaagcgcg ccaagcctat ctgggccaag aagaagaccg tctcgcgtcc cgggccgacc   9360
agctcgaaga atttgtccac tatgtcaagg gcgagatcac gaaggtcgtt ggcaaataat   9420
gtctagctag aaattcgttc aagccgacgc cgcttcgcgg cgcggcttaa ctcaagcgtt   9480
agatgcacta agcacataat tgctcacagc caaactatcg atgagttgaa ggaccccgta   9540
gaaaagatca aaggatcttc ttgagatcct ttttttctgc gcgtaatctg ctgcttgcaa   9600
acaaaaaaac caccgctacc agcggtggtt tgtttgccgg atcaagagct accaactctt   9660
tttccgaagg taactggctt cagcagagcg cagataccaa atactgtcct tctagtgtag   9720
ccgtagttag gccaccactt caagaactct gtagcaccgc ctacatacct cgctctgcta   9780
atcctgttac cagtggctgc tgccagtggc gataagtcgt gtcttaccgg gttggactca   9840
agacgatagt taccggataa ggcgcagcgg tcgggctgaa cggggggttc gtgcacacag   9900
cccagcttgg agcgaacgac ctacaccgaa ctgagatacc tacagcgtga gctatgagaa   9960
agcgccacgc ttcccgaagg gagaaaggcg gacaggtatc cggtaagcgg cagggtcgga  10020
acaggagagc gcacgaggga gcttccaggg ggaaacgcct ggtatcttta tagtcctgtc  10080
gggtttcgcc acctctgact tgagcgtcga ttttttgtgat gctcgtcagg ggggcggagc  10140
ctatggaaaa acgccagcaa cgcggccttt ttacggttcc tggccttttg ctggccttttt  10200 gctcacatgt tctttcctgc gttatcccct gattctgtgg ataaccgtat taccgccttt  10260
gagtgagctg ataccgctcg ccgcagccga acgaccgagc gcagcgagtc agtgagcgag  10320
gaagcggaag agcgcctgat gcggtatttt ctccttacgc atctgtgcgg tatttcacac  10380
cgcataggcc gcgataggcc gacgcgaagc ggcggggcgt agggagcgca gcgaccgaag  10440
ggtaggcgct ttttgcagct cttcggctgt gcgctggcca gacagttatg cacaggccag  10500
gcgggtttta agagttttaa taagttttaa agagttttag gcggaaaaat cgccttttt  10560 ctcttttata tcagtcactt acatgtgtga ccggttccca atgtacggct ttgggttccc  10620
aatgtacggg ttccggttcc caatgtacgg ctttgggttc ccaatgtacg tgctatccac  10680
aggaaagaga cctttttcgac cttttttcccc tgctagggca atttgcccta gcatctgctc  10740
cgtacattag gaaccggcgg atgcttcgcc ctcgatcagg ttgcggtagc gcatgactag  10800
gatcgggcca gcctgccccg cctcctcctt caaatcgtac tccggcaggt catttgaccc  10860
gatcagcttg cgcacggtga aacagaactt cttgaactct ccggcgctgc cactgcgttc  10920
gtagatcgtc ttgaacaacc atctggcttc tgccttgcct gcggcgcggc gtgccaggcg  10980
gtagagaaaa cggccgatgc cggggtcgat caaaaagtaa tcggggtgaa ccgtcagcac  11040
gtccgggttc ttgccttctg tgatctcgcg gtacatccaa tcagcaagct cgatctcgat  11100
```

```
gtactccggc cgcccggttt cgctctttac gatcttgtag cggctaatca aggcttcacc    11160
ctcggatacc gtcaccaggc ggccgttctt ggccttcttg gtacgctgca tggcaacgtg    11220
cgtggtgttt aaccgaatgc aggtttctac caggtcgtct ttctgctttc cgccatcggc    11280
tcgccggcag aacttgagta cgtccgcaac gtgtggacgg aacacgcggc cgggcttgtc    11340
tcccttccct tcccggtatc ggttcatgga ttcggttaga tgggaaaccg ccatcagtac    11400
caggtcgtaa tcccacacac tggccatgcc ggcggggcct gcggaaacct ctacgtgccc    11460
gtctggaagc tcgtagcgga tcacctcgcc agctcgtcgg tcacgcttcg acagacggaa    11520
aacggccacg tccatgatgc tgcgactatc gcggtgcccc acgtcataga gcatcggaac    11580
gaaaaaatct ggttgctcgt cgcccttggg cggcttccta atcgacggcg caccggctgc    11640
cggcggttgc cggattctt tgcggattcg atcagcggcc ccttgccacg attcaccggg    11700
gcgtgcttct gcctcgatgc gttgccgctg ggcggcctgc gcggccttca acttctccac    11760
caggtcatca cccagcgccg cgccgatttg taccggcccg gatggtttgc gaccgctcac    11820
gccgattcct cgggcttggg ggttccagtg ccattgcagg gccggcagac aacccagccg    11880
cttacgcctg gccaaccgcc cgttcctcca cacatggggc attccacggc gtcggtgcct    11940
ggttgttctt gattttccat gccgcctcct ttagccgcta aaattcatct actcatttat    12000
tcatttgctc atttactctg gtagctgcgc gatgtattca gatagcagct cggtaatggt    12060
cttgccttgg cgtaccgcgt acatcttcag cttggtgtga tcctccgccg gcaactgaaa    12120
gttgacccgc ttcatggctg gcgtgtctgc caggctggcc aacgttgcag ccttgctgct    12180
gcgtgcgctc ggacggccgg cacttagcgt gtttgtgctt ttgctcattt tctctttacc    12240
tcattaactc aaatgagttt tgatttaatt tcagcggcca gcgcctggac ctcgcgggca    12300
gcgtcgccct cgggttctga ttcaagaacg gttgtgccgg cggcggcagt gcctgggtag    12360
ctcacgcgct gcgtgatacg ggactcaaga atgggcagct cgtacccggc cagcgcctcg    12420
gcaacctcac cgccgatgcg cgtgcctttg atcgcccgcg acacgacaaa ggccgcttgt    12480
agccttccat ccgtgacctc aatgcgctgc ttaaccagct ccaccaggtc ggcggtggcc    12540
caaatgtcgt aagggcttgg ctgcaccgga atcagcacga agtcggctgc cttgatcgcg    12600
gacacagcca gtccgccgc ctggggcgct ccgtcgatca ctacgaagtc gcgccggccg    12660
atggccttca cgtcgcggtc aatcgtcggg cggtcgatgc cgacaacggt tagcggttga    12720
tcttcccgca cggccgccca atcgcgggca ctgccctggg gatcggaatc gactaacaga    12780
acatcggccc cggcgagttg cagggcgcgg gctagatggg ttgcgatggt cgtcttgcct    12840
gacccgcctt tctggttaag tacagcgata accttcatgc gttccccttg cgtatttgtt    12900
tatttactca tcgcatcata tacgcagcga ccgcatgacg caagctgttt tactcaaata    12960
cacatcacct ttttagatga tcak                                           12984
```

<210> SEQ ID NO 259
<211> LENGTH: 13322
<212> TYPE: DNA
<213> ORGANISM: artificial
<220> FEATURE:
<223> OTHER INFORMATION: vector sequence

<400> SEQUENCE: 259

```
gctagaaatt cgttcaagcc gacgccgctt cgcggcgcgg cttaactcaa gcgttagatg      60
cactaagcac ataattgctc acagccaaac tatcgatgag ttgaaggacc ccgtagaaaa     120
```

-continued

```
gatcaaagga tcttcttgag atcctttttt tctgcgcgta atctgctgct tgcaaacaaa    180
aaaaccaccg ctaccagcgg tggtttgttt gccggatcaa gagctaccaa ctcttttccc    240
gaaggtaact ggcttcagca gagcgcagat accaaatact gtccttctag tgtagccgta    300
gttaggccac cacttcaaga actctgtagc accgcctaca tacctcgctc tgctaatcct    360
gttaccagtg gctgctgcca gtggcgataa gtcgtgtctt accgggttgg actcaagacg    420
atagttaccg gataaggcgc agcggtcggg ctgaacgggg ggttcgtgca cacagcccag    480
cttggagcga acgacctaca ccgaactgag atacctacag cgtgagctat gagaaagcgc    540
cacgcttccc gaagggagaa aggcggacag gtatccggta agcggcaggg tcggaacagg    600
agagcgcacg agggagcttc caggggggaaa cgcctggtat ctttatagtc ctgtcgggtt    660
tcgccacctc tgacttgagc gtcgattttt gtgatgctcg tcaggggggc ggagcctatg    720
gaaaaacgcc agcaacgcgg ccttttttacg gttcctggcc ttttgctggc cttttgctca    780
catgttcttt cctgcgttat ccctgattc tgtggataac cgtattaccg cctttgagtg    840
agctgatacc gctcgccgca gccgaacgac cgagcgcagc gagtcagtga gcgaggaagc    900
ggaagagcgc ctgatgcggt atttctcct tacgcatctg tgcggtattt cacaccgcat    960
aggccgcgat aggccgacgc gaagcggcgg ggcgtaggga gcgcagcgac cgaagggtag    1020 gcgcttttg cagctcttcg gctgtgcgct ggccagacag ttatgcacag gccaggcggg    1080
ttttaagagt tttaataagt tttaaagagt tttaggcgaa aaatcgcct tttttctctt    1140 ttatatcagt cacttacatg tgtgaccggt tcccaatgta cggctttggg ttcccaatgt    1200
acgggttccg gttcccaatg tacgctttg ggttcccaat gtacgtgcta ccacaggaa    1260 agagaccttt tcgaccttt tccctgcta gggcaatttg ccctagcatc tgctccgtac    1320
attaggaacc ggcggatgct tcgccctcga tcaggttgcg gtagcgcatg actaggatcg    1380
ggccagcctg ccccgcctcc tccttcaaat cgtactccgg caggtcattt gacccgatca    1440
gcttgcgcac ggtgaaacag aacttcttga actctccggc gctgccactg cgttcgtaga    1500
tcgtcttgaa caaccatctg gcttctgcct tgcctgcggc gcggcgtgcc aggcggtaga    1560
gaaaacggcc gatgccgggg tcgatcaaaa agtaatcggg gtgaaccgtc agcacgtccg    1620
ggttcttgcc ttctgtgatc tcgcggtaca tccaatcagc aagctcgatc tcgatgtact    1680
ccggccgccc ggtttcgctc tttacgatct tgtagcggct aatcaaggct tcaccctcgg    1740
ataccgtcac caggcggccg ttcttggcct tcttggtacg ctgcatggca acgtgcgtgg    1800
tgtttaaccg aatgcaggtt tctaccaggt cgtctttctg cttccgcca tcggctcgcc    1860 ggcagaactt gagtacgtcc gcaacgtgtg gacggaacac gcggccgggc ttgtctccct    1920
tcccttcccg gtatcggttc atggattcgg ttagatggga aaccgccatc agtaccaggt    1980
cgtaatccca cacactggcc atgccggcgg ggcctgcgga aacctctacg tgcccgtctg    2040
gaagctcgta gcggatcacc tcgccagctc gtcggtcacg cttcgacaga cggaaaacgg    2100
ccacgtccat gatgctgcga ctatcgcggg tgcccacgtc atagagcatc ggaacgaaaa    2160
aatctggttg ctcgtcgccc ttgggcggct tcctaatcga cggcgcaccg gctgccggcg    2220
gttgccggga ttctttgcgg attcgatcag cggcccttg ccacgattca ccggggcgtg    2280
cttctgcctc gatgcgttgc cgctgggcgg cctgcgcggc cttcaacttc tccaccaggt    2340
catcacccag cgccgcgccg atttgtaccg gccggatgg tttgcgaccg ctcacgccga    2400
ttcctcgggc ttgggggttc cagtgccatt gcagggccgg cagacaaccc agccgcttac    2460
gcctggccaa ccgcccgttc ctccacacat ggggcattcc acggcgtcgg tgcctggttg    2520
```

```
ttcttgattt tccatgccgc ctcctttagc cgctaaaatt catctactca tttattcatt   2580
tgctcattta ctctggtagc tgcgcgatgt attcagatag cagctcggta atggtcttgc   2640
cttggcgtac cgcgtacatc ttcagcttgg tgtgatcctc cgccggcaac tgaaagttga   2700
cccgcttcat ggctggcgtg tctgccaggc tggccaacgt tgcagcctcg ctgctgcgtg   2760
cgctcggacg gccggcactt agcgtgtttg tgcttttgct cattttctct ttacctcatt   2820
aactcaaatg agttttgatt taatttcagc ggccagcgcc tggacctcgc gggcagcgtc   2880
gccctcgggt tctgattcaa gaacggttgt gccggcggcg gcagtgcctg ggtagctcac   2940
gcgctgcgtg atacgggact caagaatggg cagctcgtac ccggccagcg cctcggcaac   3000
ctcaccgccg atgcgcgtgc ctttgatcgc ccgcgacacg acaaaggccg cttgtagcct   3060
tccatccgtg acctcaatgc gctgcttaac cagctccacc aggtcggcgg tggcccaaat   3120
gtcgtaaggg cttggctgca ccggaatcag cacgaagtcg gctgccttga tcgcggacac   3180
agccaagtcc gccgcctggg gcgctccgtc gatcactacg aagtcgcgcc ggccgatggc   3240
cttcacgtcg cggtcaatcg tcgggcggtc gatgccgaca acggttagcg gttgatcttc   3300
ccgcacggcc gcccaatcgc gggcactgcc ctggggatcg gaatcgacta acagaacatc   3360
ggccccggcg agttgcaggg cgcgggctag atgggttgcg atggtcgtct tgcctgaccc   3420
gcctttctgg ttaagtacag cgataacctt catgcgttcc ccttgcgtat ttgtttattt   3480
actcatcgca tcatatacgc agcgaccgca tgacgcaagc tgttttactc aaatacacat   3540 cacctttta gatgatcagt gattttgtgc cgagctgccg gtcggggagc tgttggctgg   3600
ctggtggcag gatatattgt ggtgtaaaca aattgacgct tagacaactt aataacacat   3660
tgcggacgtc tttaatgtac tgaatttagt tactgatcac tgattaagtc tagatattgt   3720
ttttgtttca cataaatgtc gttttggatt attcatgtaa tattttaaac taaagtacaa   3780
tttttgacta ctttagttta ctagttaagc tttttatttt ttgactaacc attgaatgat   3840
gaagagatca acgcatcata tttacaactt acatagtctt ttggaagtgt aaattgctaa   3900
tactacctaa aatatatcta taattaacta atatttttc gtcaattata atagatcaat    3960
taaaaggcta tcaaaaggaa aaaaatgaaa tccacatcct gccatcataa cctcatgctg   4020
gaaaaagaaa tgaaaaaata taaaaaattt cttttgttta ttaaatttac aactttaata   4080
ctagtttctt ttctattttt taaaagcttt tgtcacttac ttaaaaaaaa aaactttt    4140 gaaatattcc tacttccaat gtctgattag tgcttctgga tttccttttt ggatcatgtg   4200
aatcctaaat cagaaaaatt catataatac ccaattcagt atattttcat acttcaattt   4260
acaagagttc tctatgtttt tagcttcttt cttttaagcc aaatgtttta agcatctttt   4320
atacattaaa ataatttagt gttgagttga gattttttt tttttttttt ggatttactt    4380
gttcaaaatc tgaaaaaatg tttacagaag gttaaaatga accaaaaggc atatcaagct   4440
agattttgaa ttccctatt tcatcgtata cacaaaactg ataatgtgga cacagttgat     4500
tttacttctc gatgacatcg tagttttatt taatttggaa accacggccc atatgagcac   4560
atttcaatta aaaaccaatg gtaagagcat tttccatgca agattcgaga gatattaacc   4620
cagtgactgt taaaacagct tagaacccta ataacgaatt tcaattactc aatttaccat   4680
tcgcatttcg caataaccaa actgagccag tcacaaggag taaaccgaac cggattatt    4740 atttataaaa tgaagaaag gaaccaaac aacaacagca gtagtagtct gacgtaaacc     4800
aaaaagcagg cagatcaaca actaaaagaa actcaaatta ccaaaacaaa caggaaattg   4860
```

| | |
|---|---|
| caaactaagt tttttacca tatgcataca aagaccataa aaggttctga taatcaccgg | 4920 |
| tttcatctct cagtatttaa tccggccatc tccttccgtt atgacatcgt tgaaagtgcc | 4980 |
| accattcggg atcatcggca acacatgttc ttggtgcgga caaatcacat ccaacaggta | 5040 |
| aggtcctggt gtatccagca ttgtctgaat agcttctcgg agatctgctt tctttgtcac | 5100 |
| cctcgccgct ggaatcccgc aagctgctgc aaacagcaac atgttcggga atatctcgtc | 5160 |
| ctcctgagcc ggatcccga gaaatgtgtg agctcggtta gctttgtaga accgatcttc | 5220 |
| ccattgcata accatgccaa gatgctggtt gtttaataaa agtaccttca ctggaagatt | 5280 |
| ctctacacga atagtggcta gctcttgcac attcattata aagcttccat ctccgtcaat | 5340 |
| atccacaact atcgcatcag ggttagcaac agacgctcca atcgcagcag gaagtccaaa | 5400 |
| tcccatagct ccaaggcctc ctgatgatag ccactgcctt ggtttcttgt aattgtagaa | 5460 |
| ctgcgccgcc cacatttgat gttgcccgac accagtactt attatggctt ttccatcagt | 5520 |
| caactcatca aggaccttaa tcgcatactg tggaggaata gcttccccaa acgtcttaaa | 5580 |
| gctcaacgga aacttctgtt tctgtacgtt caactcattc tccaaactc caaaatcaag | 5640 |
| cttaagctcc tccgctcggt tctcaagaac cttattcatc ccttgcaaag ccagcttaac | 5700 |
| atcaccacac acagacacat gaggagtctt attcttccca atctcagccg agtcaatatc | 5760 |
| aatatgaaca atcttagccc tactagcaaa agcctcaagc ttacccgtga cacgatcatc | 5820 |
| aaaccttacc ccaaacgcca acaacaaatc actatgctcc acagcgtaat ttgcatacac | 5880 |
| agtcccatgc attccaagca tatgtaacga caactcatca tcacaaggat aagatcccag | 5940 |
| ccccatcaac gtactcgcaa cagggatccc cgtaagctca acaaacctac ccaattcatc | 6000 |
| gctagaattc aaacaaccac caccaacata caacacaggc ttcttagact cagaaatcaa | 6060 |
| cctaacaatc tgctccaaat gagaatcttc cggaggttta ggcatcctag acatataacc | 6120 |
| aggtaatctc atagcctgtt cccaattagg aatcgcaagc tgttgttgaa tatctttagg | 6180 |
| aacatcaacc aaaacaggtc caggtctacc agaagtagcc aaaaagaaag cttcctcaat | 6240 |
| aatcctaggg atatcttcaa catccatcac aagatagtta tgcttcgtaa tcgaacgcgt | 6300 |
| tacctcaaca atcggagtct cttgaaacgc atctgtacca atcatacgac gagggacttg | 6360 |
| tcctgtgatt gctacaagag gaacactatc taacaacgca tcggctaatc cgctaacgag | 6420 |
| atttgtagct ccgggacctg aagtggctat acagatacct ggtttacctg aggatcgagc | 6480 |
| gtatccttct gctgcgaata cacctccttg ttcgtgacga ggaaggacgt tacggattga | 6540 |
| ggaagagcgg gttaaggctt ggtgaatctc cattgatgta cctccagggt aagcgaatac | 6600 |
| ggtttctacg ccttgacgtt ctaaagcttc gacgaggata tcagcgcctt tgcggggttg | 6660 |
| atctggagcg aatcgggaga tgaatgtttc gggtttggta ggtttggttg gagagggagt | 6720 |
| ggttgtgaca ttggtggttg tgttgagcac ggcggagatg gaggagggag agctggattt | 6780 |
| gataccgcgg cggcgggagg aggaggatga tttgttgggg tttagggaga atgggaggga | 6840 |
| gaatctggag attggtaatg gtgatttgga ggaggaagga gatggtttgg tggagaagga | 6900 |
| gatcgaagaa gatgttgttg ttgttgttgt tgccgccgcc atggttcagc tgcacataca | 6960 |
| taacatatca agatcagaac acacatatac acacacaaat acaatcaagt caacaactcc | 7020 |
| aaaaagtcca gatctacata tatacatacg taaataacaa aatcatgtaa ataatcacaa | 7080 |
| tcatgtaatc cagatctatg cacatatata tatacacaat taataaaaaa aatgatataa | 7140 |
| cagatctata tctatgtatg taacaacaca atcagatgag agaagtgatg ttttcagatc | 7200 |
| tgtatacata caaacacaaa cagatgaaca attgatacgt agatccatat gtatacgtac | 7260 |

```
aattagctac acgattaaat gaaaaaaatc aacgatttcg gattggtaca cacaaacgca    7320
acaatatgaa gaaattcata tctgattaga tataaacata accacgtgta gatacacagt    7380
caaatcaaca aatttatagc ttctaaacgg atgagatgaa caagataaag atattcacat    7440
aaggcataca taagataagc agattaacaa actagcaata atacatacct aattaaaaca    7500
aggaataaca gagagagaga gagagagaga gatttacctt gaaaatgaag aggagaagag    7560
aggatttctt aaaattgggg gtagagaaag aaagatgatg aattgtgaga aaggagagat    7620 agaaggggggg gttgtatata taggctgtag aagattattt ttgtgtttga ggcggtgaag    7680
gaagagggga tctgactatg acacgtttgc ggttacgtat ttcgatagga gtctttcaac    7740
gcttaacgcc gttactctat atgaccgttt gggccgtaac ggggccgttt gttaacgctg    7800
atgttgattc ttttctttct ttctttcttc cttttttaaa gaagcaattg tacaatcgtt    7860
gctagctgtc aaacggataa ttcggatacg gatatgccta tattcatatc cgtaattttt    7920
ggattcgaat tgactgcgat cgccaattga cgcgtactag tgtacaagct tgcggccgcg    7980
aattcggtac atccggccag tgaattatca actatgtata ataaagttgc catgattacg    8040
ccaagcttgc atgcccatat gctcgaggcg gccgcagata tcagatctgg tcgacctaga    8100
ggatccccgg gtaccccact ttgtacaaga aagctgggtc catgattacg ccaagcttgc    8160
atgcccatat gctcgaggcg gccgcagata tcagatctgg tcgacctaga ggatccccgg    8220
gtaccagcct gcttttttgt acaaacttgc catgattacg ccaagcttga attcccgatc    8280
tagtaacata gatgacaccg cgcgcgataa tttatcctag tttgcgcgct atattttgtt    8340

ttctatcgcg tattaaatgt ataattgcgg gactctaatc ataaaaaccc atctcataaa    8400

taacgtcatg cattacatgt taattattac atgcttaacg taattcaaca gaaattatat    8460
gataatcatc gcaagaccgg caacaggatt caatcttaag aaactttatt gccaaatgtt    8520

tgaacgatcg gggaaattcg agcccatatg ctcgaggcgg ccttactcgg tagcaattcc    8580
cgaggctgta gccgacgatg gtgcgccagg agagttgttg attcattgtt tgcctccctg    8640 ctgcggttt tcaccgaagt tcatgccagt ccagcgtttt tgcagcagaa aagccgccga    8700
cttcggtttg cggtcgcgag tgaagatccc tttcttgtta ccgccaacgc gcaatatgcc    8760

ttgcgaggtc gcaaaatcgg cgaaattcca tacctgttca ccgacgacgg cgctgacgcg    8820

atcaaagacg cggtgataca tatccagcca tgcacactga tactcttcac tccacatgtc    8880
ggtgtacatt gagtgcagcc cggctaacgt atccacgccg tattcggtga tgataatcgg    8940
ctgatgcagt ttctcctgcc aggccagaag ttctttttcc agtaccttct ctgccgtttc    9000
caaatcgccg ctttggacat accatccgta ataacggttc aggcacagca catcaaagag    9060

atcgctgatg gtatcggtgt gagcgtcgca gaacattaca ttgacgcagg tgatcggacg    9120
cgtcgggtcg agtttacgcg ttgcttccgc cagtggcgcg aaatattccc gtgcaccttg    9180
cggacgggta tccggttcgt tggcaatact ccacatcacc acgcttgggt ggtttttgtc    9240
acgcgctatc agctctttaa tcgcctgtaa gtgcgcttgc tgagtttccc cgttgactgc    9300
ctcttcgctg tacagttctt tcggcttgtt gcccgcttcg aaaccaatgc ctaaagagag    9360
gttaaagccg acagcagcag tttcatcaat caccacgatg ccatgttcat ctgcccagtc    9420
gagcatctct tcagcgtaag gtaatgcga ggtacggtag gagttggccc caatccagtc    9480
cattaatgcg tggtcgtgca ccatcagcac gttatcgaat cctttgccac gcaagtccgc    9540

atcttcatga cgaccaaagc cagtaaagta gaacggtttg tggttaatca ggaactgttc    9600
```

```
gcccttcact gccactgacc ggatgccgac gcgaagcggg tagatatcac actctgtctg    9660
gcttttggct gtgacgcaca gttcatagag ataaccttca cccggttgcc agaggtgcgg    9720
attcaccact tgcaaagtcc cgctagtgcc ttgtccagtt gcaaccacct gttgatccgc    9780
atcacgcagt tcaacgctga catcaccatt ggccaccacc tgccagtcaa cagacgcgtg    9840
gttacagtct tgcgcgacat gcgtcaccac ggtgatatcg tccacccagg tgttcggcgt    9900
ggtgtagagc attcgctgc gatggattcc ggcatagtta agaaatcat ggaagtaaga    9960 ctgcttttc ttgccgtttt cgtcggtaat caccattccc ggcgggatag tctgccagtt   10020
cagttcgttg ttcacacaaa cggtgatacc tgcacatcaa caaattttgg tcatatatta   10080
gaaaagttat aaattaaaat atacacactt ataaactaca gaaaagcaat tgctatatac   10140
tacattcttt tattttgaaa aaatatttg aatattata ttactactaa ttaatgataa   10200
ttattatata tatcaaag gtagaagcag aaacttacgt acacttttcc cggcaataac   10260
atacggcgtg acatcggctt caaatggcgt atagccgccc tgatgctcca tcacttcctg   10320
attattgacc cacactttgc cgtaatgagt gaccgcatcg aaacgcagca cgatacgctg   10380
gcctgcccaa cctttcggta taagacttc gcgctgatac cagacgttgc ccgcataatt   10440
acgaatatct gcatcggcga actgatcgtt aaaactgcct ggcacagcaa ttgcccggct   10500
ttcttgtaac gcgctttccc accaacgctg accaattcca cagttttcgc gatccagact   10560
gaatgcccac aggccgtcga gttttttgat ttcacgggtt ggggttttcta caggacgtac   10620 catggttttg tgaggaaatt aaagggttgc aaatgcacca ccctaagtga agtgaaatga   10680
aatgttatac gaaatagata gttaaatttg tgttgaatat gaatataatg tgatgtggag   10740
aaggaattta taaggatggt ttggtcaact tttggagaac tagtaagcaa aatcggcttg   10800
tgcaagtata taataagggt gcatgaagct ggggtcacgt cttttgtcta ctgggatgca   10860
gtgataatgc aaatgattac gcgtaatggg tgcattttgt caagggtgg tgttttctt   10920 ttcattatcc acttccactt gcaataagtg gtgggatatt tctaagaaat gctattgcac   10980
ttggcttgtc acgttcgtag gcgacgaagt tggatgctgc cgcgaaaagt accaaagaac   11040
ttctccagtc tccaccttga gtaaattact aactaagggt gtgcttttgg aagaaaagat   11100
agaaataata ctgaaaaaa aaattatttt tttttatcgt gaaattagca tatattttat   11160
tttattttca tcatcttcat tttcatttc atgtttcttc atttgagata tctctctttt   11220
tgggtgggaa cgaatctcaa cgtgagtcat gtgtctggcc taccgcactt tctttttctaa   11280 aaaatatatc ttttttctgt ggatggaatt tttcgattgt gatgaggttg aaattatata   11340
tcaatatttt aatttagttt atcagaacta agatgaata ttcgttatca taaatattat   11400 gcttttagg aattaagttt cataaaattt aattttccga atttattgtt tgaacgcaag   11460
atatagaatt ttcttttggt tcaaattaga tgcagaattt gaaaataaat caattatgat   11520
cagttctatt aacgtaagag gctaggtaag ggctttcttt ctctttaaat aacattgctg   11580
gtttgaatat tgtgaagaca aaaaaagttc taagagagcg cgcgctagct ttatttctat   11640
aagtgatcga tatgattcga ttatgactca tacatattag ttggattaaa gtgggtagcc   11700
tcaaaaagta aaacctaaga caaaatgatt aattagttat gaatattgtc acgttaaaaa   11760
tatgtttatg atataagcat ttggaatata ataatatttt ttattataaa ataatgattt   11820
aaaaattaat taaaaatgca tattttatta acaatatttt aagtttctta aaattataa   11880 gtggatccaa caaattaaaa taacatggac ataatatata tttgattaaa aaattaaata   11940
tatactttaa ttaaatgggt cctttgagaa tacttttaca ttaaaatttt gaaagtagaa   12000
```

-continued

```
tttttttcacc tataatttgg tacccaactt ttctatacaa agttgatagc ttggcgtaat    12060
cgatgtaccg atatcaattt aaattggccg gccgagctcc ctgcaggggg cccggcgcgc    12120
ctctagatta attaaaggcc ttagttacta atcagtgatc agattgtcgt ttcccgcctt    12180
cagtttaaac tatcagtgtt tgacaggata tattggcggg taaacctaag agaaaagagc    12240
gtttattaga ataatcggat atttaaaagg gcgtgaaaag gtttatccgt tcgtccattt    12300
gtatgtcaat atccatgata agtcgcgctg tatgtgtttg tttgaatatt catgaacgc    12360
agtggcggtt ttcatggctt gttatgactg ttttttttggg gtacagtcta tgcctcgggc    12420
atccaagcag caagcgcgtt acgccgtggg tcgatgtttg atgttatgga gcagcaacga    12480
tgttacgcag cagggcagtc gccctaaaac aaagttaaac atcatgggtg aagcggtcat    12540
cgccgaggtg tccacccagc tgtcggaagt cgtgggtgtc atcgagcgcc acctcgaacc    12600
gaccctcctc gccgtgcatc tgtatggtag cgccgttgac ggcggcctta agccccattc    12660
ggacatcgac ctgcttgtca ccgttaccgt ccgtctcgac gagaccacgc gccgcgcgct    12720
tatcaacgac cttctggaaa cgtccgcctc ccccggcgag agcgaaatcc tgcgcgcggt    12780
tgaggtgacg attgtggtgc acgatgacat catcccctgg cgctatccgg ccaaacgcga    12840
actccagttc ggcgaatggc agcgtaatga tattctggcg ggtatctttg aaccggccac    12900
catcgacatt gatctggcga tcctgctcac caaggcccgg gagcatagcg tggccctcgt    12960
cggccccgcg gccgaggaac ttttcgaccc ggtgccggaa caggatctgt tcgaagcact    13020
gaacgagacg ctgaccctgt ggaactcccc gccggattgg gcgggcgatg agcgcaatgt    13080
ggtccttacg ctgagccgga tttggtactc ggcggttacc ggcaagatcg cgccgaagga    13140
tgtcgccgcc gactgggcga tggagcgcct tccggcgcaa taccagcccg tgatcctcga    13200
agcgcgccaa gcctatctgg gccaagaaga agaccgtctc gcgtcccggg ccgaccagct    13260
cgaagaattt gtccactatg tcaagggcga gatcacgaag gtcgttggca ataatgtct    13320
ak                                                                    13322
```

<210> SEQ ID NO 260
<211> LENGTH: 12497
<212> TYPE: DNA
<213> ORGANISM: artificial
<220> FEATURE:
<223> OTHER INFORMATION: vector sequence

<400> SEQUENCE: 260

```
gtgattttgt gccgagctgc cggtcgggga gctgttggct ggctggtggc aggatatatt      60
gtggtgtaaa caaattgacg cttagacaac ttaataacac attgcggacg tctttaatgt     120
actgaattta gttactgatc actgattaag tctagatatt gtttttgttt cacataaatg     180
tcgttttgga ttattcatgt aatatttaa actaaagtac aatttttgac tactttagtt     240
tactagttaa gcttttattt ttttgactaa ccattgaatg atgaagagat caacgcatca     300
tatttacaac ttacatagtc ttttggaagt gtaaattgct aatactacct aaaatatatc     360
tataattaac taatattttt tcgtcaatta taatagatca attaaaaggc tatcaaaagg     420
aaaaaaatga atccacatc ctgccatcat aacctcatgc tggaaaaaga atgaaaaaa     480
tataaaaaat ttctttttgtt tattaaattt acaactttaa tactagtttc ttttctattt     540
tttaaaagct tttgtcactt acttaaaaaa aaaaaacttt tgaaatatt cctacttcca     600
atgtctgatt agtgcttctg gatttccttt ttggatcatg tgaatcctaa atcagaaaaa     660
```

```
ttcatataat acccaattca gtatattttc atacttcaat ttacaagagt tctctatgtt      720
tttagcttct ttcttttaag ccaaatgttt taagcatctt ttatacatta aaataattta      780
gtgttgagtt gagattttt ttttttttt ttggatttac ttgttcaaaa tctgaaaaaa       840
tgtttacaga aggttaaaat gaaccaaaag gcatatcaag ctagattttg aattaccta      900
tttcatcgta tacacaaaac tgataatgtg gacacagttg attttacttc tcgatgacat     960
cgtagtttta tttaatttgg aaaccacggc ccatatgagc acatttcaat taaaaaccaa    1020
tggtaagagc attttccatg caagattcga gagatattaa cccagtgact gttaaaacag    1080
cttagaaccc taataacgaa tttcaattac tcaatttacc attcgcattt cgcaataacc    1140
aaactgagcc agtcacaagg agtaaaccga accggattat ttatttataa aatgaaagaa    1200
aggaaaccaa acaacaacag cagtagtagt ctgacgtaaa ccaaaaagca ggcagatcaa    1260
caactaaaag aaactcaaat taccaaaaca aacaggaaat tgcaaactaa gtttttttac    1320
catatgcata caaagaccat aaaaggttct gataatcacc ggtttcatct ctcagtattt    1380
aatccggcca tctccttccg ttatgacatc gttgaaagtg ccaccattcg ggatcatcgg    1440
caacacatgt tcttggtgcg gacaaatcac atccaacagg taaggtcctg gtgtatccag    1500
cattgtctga atagcttctc ggagatctgc tttctttgtc accctcgccg ctggaatccc    1560
gcaagctgct gcaaacagca acatgttcgg gaatatctcg tcctcctgag ccggatcccc    1620
gagaaatgtg tgagctcggt tagctttgta gaaccgatct tcccattgca taaccatgcc    1680
aagatgctgg ttgtttaata aaagtacctt cactggaaga ttctctacac gaatagtggc    1740
tagctcttgc acattcatta taaagcttcc atctccgtca atatccacaa ctatcgcatc    1800
agggttagca acagacgctc caatcgcagc aggaagtcca atcccatag ctccaaggcc     1860
tcctgatgat agccactgcc ttggtttctt gtaattgtag aactgcgccg cccacatttg    1920
atgttgcccg acaccagtac ttattatggc ttttccatca gtcaactcat caaggacctt    1980
aatcgcatac tgtggaggaa tagcttcccc aaacgtctta agctcaacg gaaacttctg     2040
tttctgtacg ttcaactcat tcctccaaac tccaaaatca agcttaagct cctccgctcg    2100
gttctcaaga accttattca tcccttgcaa agccagctta acatcaccac acacagacac    2160
atgaggagtc ttattcttcc caatctcagc cgagtcaata tcaatatgaa caatcttagc    2220
cctactagca aaagcctcaa gcttacccgt gacacgatca tcaaacctta ccccaaacgc    2280
caacaacaaa tcactatgct ccacagcgta atttgcatac acagtcccat gcattccaag    2340
catatgtaac gacaactcat catcacaagg ataagatccc agccccatca acgtactcgc    2400
aacagggatc cccgtaagct caacaaacct acccaattca tcgctagaat tcaaacaacc    2460
accaccaaca tacaacacag gcttcttaga ctcagaaatc aacctaacaa tctgctccaa    2520
atgagaatct tccggaggtt taggcatcct agacatataa ccaggtaatc tcatagcctg    2580
ttcccaatta ggaatcgcaa gctgttgttg aatatcttta ggaacatcaa ccaaaacagg    2640
tccaggtcta ccagaagtag ctaaaaagaa agcttcctca ataatcctag ggatatcttc    2700
aacatccatc acaagatagt tatgcttcgt aatcgaacgc gttacctcaa caatcggagt    2760
ctcttgaaac gcatctgtac caatcatacg acgagggact tgtcctgtga ttgctacaag    2820
aggaacacta tctaacaacg catcggctaa tccgctaacg agatttgtag ctccgggacc    2880
tgaagtggct atacagatac ctggtttacc tgaggatcga gcgtatcctt ctgctgcgaa    2940
tacacctcct tgttcgtgac gaggaaggac gttacggatt gaggaagagc gggttaaggc    3000
ttggtgaatc tccattgatg tacctccagg gtaagcgaat acggtttcta cgccttgacg    3060
```

```
ttctaaagct tcgacgagga tatcagcgcc tttgcggggt tgatctggag cgaatcggga    3120
gatgaatgtt tcgggtttgg taggtttggt tggagaggga gtggttgtga cattggtggt    3180
tgtgttgagc acggcggaga tggaggaggg agagctggat ttgataccgc ggcggcggga    3240
ggaggaggat gatttgttgg ggtttaggga gaatgggagg gagaatctgg agattggtaa    3300
tggtgatttg gaggaggaag gagatggttt ggtggagaag gagatcgaag aagatgttgt    3360
tgttgttgtt gttgccgccg ccatggttca gctgcacata cataacatat caagatcaga    3420
acacacatat acacacacaa atacaatcaa gtcaacaact ccaaaaagtc cagatctaca    3480
tatatacata cgtaaataac aaaatcatgt aaataatcac aatcatgtaa tccagatcta    3540
tgcacatata tatatacaca attaataaaa aaaatgatat aacagatcta tatctatgta    3600
tgtaacaaca caatcagatg agagaagtga tgttttcaga tctgtataca tacaaacaca    3660
aacagatgaa caattgatac gtagatccat atgtatacgt acaattagct acacgattaa    3720
atgaaaaaaa tcaacgattt cggattggta cacacaaacg caacaatatg aagaaattca    3780
tatctgatta gatataaaca taaccacgtg tagatacaca gtcaaatcaa caaatttata    3840
gcttctaaac ggatgagatg aacaagataa agatattcac ataaggcata cataagataa    3900
gcagattaac aaactagcaa taatacatac ctaattaaaa caaggaataa cagagagaga    3960
gagagagaga gagatttacc ttgaaaatga agaggagaag agaggatttc ttaaaattgg    4020
gggtagagaa agaaagatga tgaattgtga gaaaggagag atagaagggg gggttgtata    4080
tataggctgt agaagattat ttttgtgttt gaggcggtga aggaagaggg gatctgacta    4140
tgacacgttt gcggttacgt atttcgatag gagtctttca acgcttaacg ccgttactct    4200
atatgaccgt ttgggccgta acggggccgt ttgttaacgc tgatgttgat tcttttcttt    4260 cttctttct tccttttta aagaagcaat tgtacaatcg ttgctagctg tcaaacggat    4320
aattcggata cggatatgcc tatattcata tccgtaattt ttggattcga attgactgcg    4380
atcgccaatt gacgcgtact agtgtacaag cttgcggccg cgaattcggt acatccggcc    4440
agtgaattat caactatgta taataaagtt gccatgatta cgccaagctt cgacggacaa    4500
tcagtaaatt gaacggagaa tattattcat aaaaatacga tagtaacggg tgatatattc    4560
attagaatga accgaaaccg gcggtaagga tctgagctac acatgctcag gttttttaca    4620
acgtgcacaa cagaattgaa agcaaatatc atgcgatcat aggcgtctcg catatctcat    4680
taaagcagga ggcctactag tcaattggcg cgccgcggcc gctcacttgt acagctcatc    4740
catgccgtgg gtgatggcgg cggcggtcac gaagccgaag tagatcatgt gatcgcgctt    4800
ctcgttgggg tccttggaca gggcgctctg ggtggacagg tagtggttat cgggcagcag    4860
cacagggcca tcgccgatgg gggtattctg ctggtagtgg tcggccagct gcacgctgcc    4920
atcctcgatg ttgtggcgga tcttgaagtt caccttgatg ccattcttgg ccttgtcgt    4980 catgatgtac acattgtggg cgttgtagtt gtactccatc ttattgccca ggatgttgcc    5040
atcctccttg aaatcggtgc cggtcagctc gatgcgattc accagggtat cgccctcgaa    5100
cttcacctcg gcgcgcgact tgtagttgcc gtcatcctcg aagaagatgg tgcgctcctg    5160
gatgtagccc tcaggcatgg cgctcttgaa gaagtcgtgc tgcttcatgt gatcgggta    5220 gcgtgagaag cactgcacgc cgtagctcag ggtggtcacc agggtgggcc agggcacagg    5280
cagcttgccg gtggtgcaga tgaacttcag ggtcagcttg cctaggtgg catcgccctc    5340 gccctcgccg ctcacgctga acttgtggcc attcacatcg ccattcagct cgatcaggat    5400
```

-continued

| | |
|---|---|
| gggcacgatg ccggtgaaca gctcggcgcc cttgctcacc atggtttctt agttgattct | 5460 |
| acaaatcttt tattttcttg tgcgatgttt tttttatttt tgtttttgca gttttgtttt | 5520 |
| cctctataca gtctttaaaa tgatttaggc aagaatcatc gtgtggcttt ggcgatcaca | 5580 |
| gaaatggatt ctgtttaggt tacctcttgc tgaggtgtca agtgtctatt ggctgatttc | 5640 |
| aactctggat aagactgtct catcgtcatc acagtgcaga ttttctttca aacctttca | 5700 |
| ttttgggctt catgcaggcc catttatact tatattaaat cttagtacaa atcatggaac | 5760 |
| ttgaatacta tgatcgtgtg gacttcaagc ggtctgattt aaaccaaaca caaattacat | 5820 |
| ttgaaacatt tagtgctcgt ggaaattgga aaaggctcgt gtatactata ggtttagtgg | 5880 |
| tactttcgta gttgtttcaa gagacgaact tgccgtgaag aacactttcg agcttaatta | 5940 |
| gtcaaattct ttacccttt tgtgattaatt tttcaaacc tatcccatct gaattagttg | 6000 |
| atcaatcagt tatctttcat atattaaaca aaagcttaaa ttcgtatcca taatcaactt | 6060 |
| ataaataaac cgcatgaagt gtattttaaa tgcaagttca attgttcgta ttaggttgtt | 6120 |
| aacaaaaact ctaatacaaa aaaatgaat ttttatcgat cgagagtgac accaaaatta | 6180 |
| aagattagtt ttcaccttt aattaatcaa ttaagtcaaa ccatattagt ctgaaatgta | 6240 |
| cgtcaatcat ctacgtccat ttattcaaaa atataatgag atatgtgagt ttctttattt | 6300 |
| gtaagccaag aacaattatt tctgggtgtt tattggattt catgtaaatg ttcttatcca | 6360 |
| aaagtagtaa tatatatttc attagaaaaa gtggacccgt ttattaggag aaagttgga | 6420 |
| gttatataac ctaacgcaaa agccgacaca gtagacgact cttgtaagag ttgattttcc | 6480 |
| taacaaataa tcataattaa tttcattaat atatgttttg tatatagagc agccctaatt | 6540 |
| attcaatcct taagctgcca agaataacta tcatcatggc gtattattat tactttgacc | 6600 |
| aactaaaatc attttgacaa aatgagattg tgttttgact taaacaaaa acctttccaa | 6660 |
| gaggagattt aattagagtt gctggatatg gtttacctga accggaattc tgatttttat | 6720 |
| tagcaacctt cacttcacta ctcgcatata aacctaaac cgtatattat accggtaatt | 6780 |
| aataatcatt cttccgtacc gaacaatgtt ttagtacaag gtcaaacatt tattcttcgt | 6840 |
| caacgcatat gagtatcttc ccagaagcaa catatgcata tgttgcttca tatatataac | 6900 |
| acatagagat ctattccaaa gcatatcgat caattcttgc tacaacacat cacaacttta | 6960 |
| tcatcatcat catcatcacc tcaaaaatta tccgaccgat aaactcagaa atggagaacg | 7020 |
| cattggtcaa aactccactg agaaagctaa gaagaagaag aactaaacgg gtctggagat | 7080 |
| tgaagcagaa gctaaagctt gcatggaaat ctatcaagat ccgggtcaag tcacatcttc | 7140 |
| cgggtttctt gtcaaccaag aaacacctct tccacattaa atcacgaaag gaagaacaag | 7200 |
| atttgtctca agtggcccag aggatctgca aaatctccaa tgactcgacc aaatcactgg | 7260 |
| cgtttctact tcagcttcca aaatactcag ccgacgattt tcttgaccgc ggcgatctga | 7320 |
| tgactccagc tgcgtctcca agggaaaaaa tatccaaaat gtggcgtgag cttcacggta | 7380 |
| gcaacaattg ggagaatctt cttgatcctc tgcatggtac cccactttgt acaagaaagc | 7440 |
| tgggtccatg attacgccaa gcttgcatgc ccatatgctc gaggcggccg cagatatcag | 7500 |
| atctggtcga cctagaggat ccccgggtac cagcctgctt ttttgtacaa acttgccatg | 7560 |
| attacgccaa gcttgcatgc ccatatgctc gaggcggccg cagatatcag atctggtcga | 7620 |
| cctagaggat ccccgggtac ccaactttc tatacaaagt tgatagcttg gcgtaatcga | 7680 |
| tgtaccgata tcaattaaa ttggccggcc gagctccctg caggggccc ggcgcgcctc | 7740 |
| tagattaatt aaaggcctta gttactaatc agtgatcaga ttgtcgtttc ccgccttcag | 7800 |

```
tttaaactat cagtgtttga caggatatat tggcgggtaa acctaagaga aaagagcgtt    7860
tattagaata atcggatatt taaaagggcg tgaaaaggtt tatccgttcg tccatttgta    7920
tgtcaatatc catgataagt cgcgctgtat gtgtttgttt gaatattcat ggaacgcagt    7980
ggcggttttc atggcttgtt atgactgttt ttttggggta cagtctatgc ctcgggcatc    8040
caagcagcaa gcgcgttacg ccgtgggtcg atgtttgatg ttatggagca gcaacgatgt    8100
tacgcagcag ggcagtcgcc ctaaaacaaa gttaaacatc atgggtgaag cggtcatcgc    8160
cgaggtgtcc acccagctgt cggaagtcgt gggtgtcatc gagcgccacc tcgaaccgac    8220
cctcctcgcc gtgcatctgt atggtagcgc cgttgacggc ggccttaagc cccattcgga    8280
catcgacctg cttgtcaccg ttaccgtccg tctcgacgag accacgcgcc gcgcgcttat    8340
caacgacctt ctggaaacgt ccgcctcccc cggcgagagc gaaatcctgc gcgcggttga    8400
ggtgacgatt gtggtgcacg atgacatcat cccctggcgc tatccggcca acgcgaact    8460 ccagttcggc gaatggcagc gtaatgatat tctggcgggt atctttgaac cggccaccat    8520
cgacattgat ctggcgatcc tgctcaccaa ggcccgggag catagcgtgg ccctcgtcgg    8580
ccccgcggcc gaggaacttt tcgacccggt gccggaacag gatctgttcg aagcactgaa    8640
cgagacgctg accctgtgga actccccgcc ggattgggcg ggcgatgagc gcaatgtggt    8700
ccttacgctg agccggattt ggtactcggc ggttaccggc aagatcgcgc cgaaggatgt    8760
cgccgccgac tgggcgatgg agcgccttcc ggcgcaatac cagcccgtga tcctcgaagc    8820
gcgccaagcc tatctgggcc aagaagaaga ccgtctcgcg tcccgggccg accagctcga    8880
agaatttgtc cactatgtca agggcgagat cacgaaggtc gttggcaaat aatgtctagc    8940
tagaaattcg ttcaagccga cgccgcttcg cggcgcggct taactcaagc gttagatgca    9000
ctaagcacat aattgctcac agccaaacta tcgatgagtt gaaggacccc gtagaaaaga    9060
tcaaaggatc ttcttgagat cctttttttc tgcgcgtaat ctgctgcttg caaacaaaaa    9120
aaccaccgct accagcggtg gtttgtttgc cggatcaaga gctaccaact cttttttccga    9180 aggtaactgg cttcagcaga gcgcagatac caaatactgt ccttctagtg tagccgtagt    9240
taggccacca cttcaagaac tctgtagcac cgcctacata cctcgctctg ctaatcctgt    9300
taccagtggc tgctgccagt ggcgataagt cgtgtcttac cgggttggac tcaagacgat    9360
agttaccgga taaggcgcag cggtcgggct gaacggggg ttcgtgcaca cagcccagct    9420
tggagcgaac gacctacacc gaactgagat acctacagcg tgagctatga aaagcgcca    9480 cgcttcccga agggagaaag gcggacaggt atccggtaag cggcagggtc ggaacaggag    9540
agcgcacgag ggagcttcca gggggaaacg cctggtatct ttatagtcct gtcgggtttc    9600
gccacctctg acttgagcgt cgatttttgt gatgctcgtc agggggggcgg agcctatgga    9660 aaaacgccag caacgcggcc tttttacggt tcctggcctt ttgctggcct tttgctcaca    9720
tgttctttcc tgcgttatcc cctgattctg tggataaccg tattaccgcc tttgagtgag    9780
ctgataccgc tcgccgcagc cgaacgaccg agcgcagcga gtcagtgagc gaggaagcgg    9840
aagagcgcct gatgcggtat ttttctcctta cgcatctgtg cggtatttca caccgcatag    9900
gccgcgatag gccgacgcga agcggcgggg cgtagggagc gcagcgaccg aagggtaggc    9960 gcttttttgca gctcttcggc tgtgcgctgg ccagacagtt atgcacaggc caggcgggtt   10020
ttaagagttt taataagttt taaagagttt taggcggaaa aatcgccttt tttctctttt   10080
atatcagtca cttacatgtg tgaccggttc ccaatgtacg ctttgggtt cccaatgtac    10140 gggttccggt tcccaatgta cggctttggg ttcccaatgt acgtgctatc cacaggaaag   10200
```

```
agaccttttc gaccttttc ccctgctagg gcaatttgcc ctagcatctg ctccgtacat    10260
taggaaccgg cggatgcttc gccctcgatc aggttgcggt agcgcatgac taggatcggg    10320
ccagcctgcc ccgcctcctc cttcaaatcg tactccggca ggtcatttga cccgatcagc    10380
ttgcgcacgg tgaaacagaa cttcttgaac tctccggcgc tgccactgcg ttcgtagatc    10440
gtcttgaaca accatctggc ttctgccttg cctgcgcgcg ggcgtgccag gcggtagaga    10500
aaacggccga tgccggggtc gatcaaaaag taatcgggt gaaccgtcag cacgtccggg    10560
ttcttgcctt ctgtgatctc gcggtacatc caatcagcaa gctcgatctc gatgtactcc    10620
ggccgcccgg tttcgctctt tacgatcttg tagcggctaa tcaaggcttc accctcggat    10680
accgtcacca ggcggccgtt cttggccttc ttggtacgct gcatggcaac gtgcgtggtg    10740
tttaaccgaa tgcaggtttc taccaggtcg tctttctgct ttccgccatc ggctcgccgg    10800
cagaacttga gtacgtccgc aacgtgtgga cggaacacgc ggccgggctt gtctcccttc    10860
ccttcccggt atcggttcat ggattcggtt agatgggaaa ccgccatcag taccaggtcg    10920
taatcccaca cactggccat gccggcgggg cctgcgaaa cctctacgtg cccgtctgga    10980
agctcgtagc ggatcacctc gccagctcgt cggtcacgct tcgacagacg gaaaacggcc    11040
acgtccatga tgctgcgact atcgcgggtg cccacgtcat agagcatcgg aacgaaaaaa    11100
tctggttgct cgtcgccctt gggcggcttc ctaatcgacg gcgcaccggc tgccggcggt    11160
tgccgggatt ctttgcggat tcgatcagcg gccccttgcc acgattcacc ggggcgtgct    11220
tctgcctcga tgcgttgccg ctgggcggcc tgcgcggcct tcaacttctc caccaggtca    11280
tcacccagcg ccgcgccgat ttgtaccggg ccggatggtt tgcgaccgct cacgccgatt    11340
cctcgggctt gggggttcca gtgccattgc agggccggca gacaacccag ccgcttacgc    11400
ctggccaacc gcccgttcct ccacacatgg ggcattccac ggcgtcggtg cctggttgtt    11460
cttgattttc catgccgcct cctttagccg ctaaaattca tctactcatt tattcatttg    11520
ctcatttact ctggtagctg cgcgatgtat tcagatagca gctcggtaat ggtcttgcct    11580
tggcgtaccg cgtacatctt cagcttggtg tgatcctccg ccggcaactg aaagttgacc    11640
cgcttcatgg ctggcgtgtc tgccaggctg gccaacgttg cagccttgct gctgcgtgcg    11700
ctcggacggc cggcacttag cgtgtttgtg cttttgctca tttctctttt acctcattaa    11760
ctcaaatgag ttttgattta atttcagcgg ccagcgcctg gacctcgcgg gcagcgtcgc    11820
cctcgggttc tgattcaaga acggttgtgc cggcggcggc agtgcctggg tagctcacgc    11880
gctgcgtgat acgggactca agaatgggca gctcgtaccc ggccagcgcc tcggcaacct    11940
caccgccgat gcgcgtgcct ttgatcgccc gcgacacgac aaaggccgct tgtagccttc    12000
catccgtgac ctcaatgcgc tgcttaacca gctccaccag gtcggcggtg gcccaaatgt    12060
cgtaagggct tggctgcacc ggaatcagca cgaagtcggc tgccttgatc gcggacacag    12120
ccaagtccgc cgcctggggc gctccgtcga tcactacgaa gtcgcgccgg ccgatggcct    12180
tcacgtcgcg gtcaatcgtc gggcggtcga tgccgacaac ggttagcggt tgatcttccc    12240
gcacggccgc ccaatcgcgg gcactgccct ggggatcgga atcgactaac agaacatcgg    12300
ccccggcgag ttgcagggcg cgggctagat ggggttgcgat ggtcgtcttg cctgacccgc    12360
cttttctggtt aagtacagcg ataaccttca tgcgttcccc ttgcgtattt gtttatttac    12420
tcatcgcatc atatacgcag cgaccgcatg acgcaagctg ttttactcaa atacacatca    12480
ccttttttaga tgatcak                                                 12497
```